United States Patent
Somers et al.

(10) Patent No.: US 7,235,367 B2
(45) Date of Patent: Jun. 26, 2007

(54) METHOD USING CRYSTAL STRUCTURE OF ESTROGEN RECEPTOR-β COMPLEX

(75) Inventors: William S. Somers, Cambridge, MA (US); Zhang-Bao Xu, Tewksbury, MA (US); Tatos N. Akopian, West Roxbury, MA (US); Chu-Lai Hsiao, Waltham, MA (US); Rayomand Unwalla, Eagleville, PA (US)

(73) Assignee: Genetics Institute, LLC., Cambridge, MA (US)

( * ) Notice: Subject to any disclaimer, the term of this patent is extended or adjusted under 35 U.S.C. 154(b) by 525 days.

(21) Appl. No.: 09/903,876

(22) Filed: Jul. 11, 2001

(65) Prior Publication Data

US 2002/0072587 A1    Jun. 13, 2002

Related U.S. Application Data

(60) Provisional application No. 60/217,834, filed on Jul. 12, 2000.

(51) Int. Cl.
*G01N 23/20* (2006.01)
*G01N 33/53* (2006.01)

(52) U.S. Cl. .................. 435/7.1; 364/194; 530/402

(58) Field of Classification Search ................. 435/7.1
See application file for complete search history.

(56) References Cited

U.S. PATENT DOCUMENTS

| | | | |
|---|---|---|---|
| 6,228,990 B1 | 5/2001 | Ljunggren et al. | |
| 6,476,196 B1 | 11/2002 | Ljunggren et al. | |
| 2003/0167999 A1* | 9/2003 | Donner et al. ................ | 117/2 |

OTHER PUBLICATIONS

Bourguet, W , et al. *Nature* 1995, 375: 377-382. "Crystal structure of the lingand-binding domain of the human nuclear receptor RXR-α".

Brzozowski, A, et al. *Nature* 1997, 389: 753-758.
Ding, S, et al. *Mol. Endocrinol.* 1998, 12: 302-313. "Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities".
Evans, RM, *Science* 1988, 240:889-895. "The Steroid and Thyroid Hormone Receptor Superfamily."
Glass, CK et al. *Curr. Opin. Cell Biol.* 1997, 9: 222-232. "Nuclear receptor coactivators".
Heery, D, et al. *Nature* 1997, 387: 733-736. "A signature motif in transcriptional co-activators mediates binding to nuclear receptors".
Horwitz, KB, et al. *Mol. Endocrinol.* 1996, 10:1167-1177. "Nuclear Receptor Coactivators and Corepressors".
Kuiper JJGM, et al. *Proc. Natl. Acad. Sci. USA* 1996, 93:5925-5930. "Cloning of a novel estrogen receptor expressed in rat prostate and ovary".
Le Douarin, B, et al. *EMBO J.* 1996 15: 6701-6715. "A possible involvement of TIF1α and TIF1β in the epigenetic control of transcription by nuclear receptors".
Renaud, J, et al. *Nature* 1995, 378: 681-689. "Crystal strucutre of the RAR-γ ligand-binding domain bound to all-*trans* retinoic acid".
Shiau, A, et al. *Cell* 1998, 95: 927-937. "The Structural Basis of Estrogen Receptor/Coactivator Recognition and the Antagonism of This Interaction by Tamoxifen".
Suen, C-S, et al. *J. Biol. Chem.* 1998, 273: 27645-27653. "A Transcriptional Coactivator, Steroid Receptor Coativator-3, Selectively Augments Steroid Receptor Transcriptional Activity".
Tanenbaum, DN, et al. *Proc. Natl. Acad. Sci. USA* 1998, 95: 5998-6003. "Crystallographic comparison of the estrogen and progesterone receptor's ligand binding domain".
Torchia, J, et al. *Nature* 1997, 387: 677-684. "The transcriptional co-activator p/CIP bind CBP and mediates nuclear-receptor function".
Tsai, MJ, et al. *Annu. Rev. Biochem.* 1994, 63:451-486. "Molecular mechanisms of action of steroid/thyroid receptor superfamily members".

* cited by examiner

*Primary Examiner*—Michael Pak
(74) *Attorney, Agent, or Firm*—Fish & Richardson P.C.

(57) ABSTRACT

This invention is directed to the crystal structure of Estrogen Receptor-β (ER-β) complexed with genistein, and to the use of this structure in rational drug design methods to identify agents that may interact with active sites of ER-β, which may be useful as novel chemotherapeutic agents.

9 Claims, 51 Drawing Sheets

```
ER_alpha_LBD  307  ALSLTADQMVSALLDAEPPILYSEYDPTRPFSEASMMGLLTNLADRELVHMINWAKRVPG
ER_beta_LBD   308  LDALSPEQLVLTLLEAEPPHVLISR-PSAPFTEASMMMSLTKLADKELVHMISWAKKIPG ER_alpha_LBD  367  FVDLTLHDQVHLLECAWLEILMIGLVWRSMEHPVKLLFAPNLLLDRNQGKCVEGMVEIFD
ER_beta_LBD   367  FVELSLFDQVRLLESCWMEVLMMGLMWRSIDHPGKLIFAPDLVLDRDEGKCVEGILEIFD ER_alpha_LBD  427  MLLATSSRFRMMNLQGEEFVCLKSIILLNSGVYTFLSSTLKSLEEKDHIHRVLDKITDTL
ER_beta_LBD   427  MLLATTSRFRELKLQHKEYLCVKAMILLNSSMYPLVTATQDADSSRKLAH-LNAVTDAL ER_alpha_LBD  487  IHLMAKAGLTLQQQHQRLAQLLLILSHIRHMSNKGMEHLYSMKCKNVVPLYDLLLEMLDA
ER_beta_LBD   486  VWVIAKSGISSQQQSMRLANLLMLLSHVRHASNKGMEHLLNMKCKNVVPVYDLLLEMLNA ER_alpha_LBD  547  HRL
ER_beta_LBD   546  HVL
```

FIG. 1

The coordinates of ER-beta/Genestein complex X-ray crystal structure

Unit Cell:    53.486   85.207  107.065  90.00  90.00  90.00
Space Group:  P212121

|  | atom type | Res. |  |  | x | y | z |  |  |  |
|---|---|---|---|---|---|---|---|---|---|---|
| ATOM | 1 | N | LEU A | 311 | 0.971 | -5.129 | 37.101 | 1.00 | 55.91 | N |
| ATOM | 2 | CA | LEU A | 311 | 1.453 | -4.204 | 36.024 | 1.00 | 52.91 | C |
| ATOM | 3 | C | LEU A | 311 | 0.411 | -3.151 | 35.699 | 1.00 | 52.76 | C |
| ATOM | 4 | O | LEU A | 311 | 0.662 | -2.238 | 34.911 | 1.00 | 51.43 | O |
| ATOM | 5 | CB | LEU A | 311 | 1.933 | -4.990 | 34.806 | 1.00 | 50.10 | C |
| ATOM | 6 | CG | LEU A | 311 | 3.007 | -6.031 | 35.117 | 1.00 | 51.90 | C |
| ATOM | 7 | CD1 | LEU A | 311 | 3.070 | -7.107 | 34.063 | 1.00 | 55.02 | C |
| ATOM | 8 | CD2 | LEU A | 311 | 4.361 | -5.396 | 35.366 | 1.00 | 50.07 | C |
| ATOM | 9 | N | SER A | 312 | -0.779 | -3.304 | 36.277 | 1.00 | 48.17 | N |
| ATOM | 10 | CA | SER A | 312 | -1.856 | -2.323 | 36.154 | 1.00 | 45.76 | C |
| ATOM | 11 | C | SER A | 312 | -1.257 | -1.024 | 36.704 | 1.00 | 42.54 | C |
| ATOM | 12 | O | SER A | 312 | -0.515 | -1.023 | 37.696 | 1.00 | 40.55 | O |
| ATOM | 13 | CB | SER A | 312 | -3.096 | -2.816 | 36.876 | 1.00 | 42.53 | C |
| ATOM | 14 | OG | SER A | 312 | -3.636 | -1.866 | 37.778 | 1.00 | 44.17 | O |
| ATOM | 15 | N | PRO A | 313 | -1.543 | 0.085 | 36.037 | 1.00 | 39.31 | N |
| ATOM | 16 | CA | PRO A | 313 | -0.943 | 1.365 | 36.364 | 1.00 | 37.98 | C |
| ATOM | 17 | C | PRO A | 313 | -0.958 | 1.765 | 37.812 | 1.00 | 38.63 | C |
| ATOM | 18 | O | PRO A | 313 | 0.140 | 1.992 | 38.375 | 1.00 | 38.34 | O |
| ATOM | 19 | CB | PRO A | 313 | -1.582 | 2.348 | 35.397 | 1.00 | 35.68 | C |
| ATOM | 20 | CG | PRO A | 313 | -2.035 | 1.509 | 34.261 | 1.00 | 40.46 | C |
| ATOM | 21 | CD | PRO A | 313 | -2.427 | 0.172 | 34.651 | 1.00 | 37.34 | C |
| ATOM | 22 | N | GLU A | 314 | -2.111 | 1.866 | 38.474 | 1.00 | 30.67 | N |
| ATOM | 23 | CA | GLU A | 314 | -2.089 | 2.235 | 39.382 | 1.00 | 34.57 | C |
| ATOM | 24 | C | GLU A | 314 | -1.249 | 1.270 | 40.711 | 1.00 | 30.99 | C |
| ATOM | 25 | O | GLU A | 314 | -0.591 | 1.744 | 41.639 | 1.00 | 32.77 | O |
| ATOM | 26 | CB | GLU A | 314 | -3.517 | 2.267 | 40.462 | 1.00 | 38.24 | C |
| ATOM | 27 | CG | GLU A | 314 | -3.503 | 2.626 | 41.948 | 1.00 | 44.67 | C |
| ATOM | 28 | CD | GLU A | 314 | -4.887 | 3.065 | 42.419 | 1.00 | 50.70 | C |
| ATOM | 29 | OE1 | GLU A | 314 | -5.884 | 2.794 | 41.711 | 1.00 | 48.91 | O |
| ATOM | 30 | OE2 | GLU A | 314 | -4.907 | 3.693 | 43.496 | 1.00 | 54.40 | O |
| ATOM | 31 | N | GLN A | 315 | -1.337 | -0.035 | 40.456 | 1.00 | 31.00 | N |
| ATOM | 32 | CA | GLN A | 315 | -0.578 | -0.989 | 41.250 | 1.00 | 37.11 | C |
| ATOM | 33 | C | GLN A | 315 | 0.937 | -0.913 | 41.010 | 1.00 | 36.55 | C |
| ATOM | 34 | O | GLN A | 315 | 1.708 | -0.982 | 41.951 | 1.00 | 33.12 | O |
| ATOM | 35 | CB | GLN A | 315 | -1.014 | -2.441 | 40.956 | 1.00 | 41.80 | C |
| ATOM | 36 | CG | GLN A | 315 | -2.386 | -2.674 | 41.588 | 1.00 | 51.16 | C |
| ATOM | 37 | CD | GLN A | 315 | -3.004 | -4.012 | 41.339 | 1.00 | 56.60 | C |
| ATOM | 38 | OE1 | GLN A | 315 | -4.222 | -4.172 | 41.485 | 1.00 | 60.96 | O |
| ATOM | 39 | NE2 | GLN A | 315 | -2.210 | -5.021 | 40.973 | 1.00 | 61.33 | N |
| ATOM | 40 | N | LEU A | 316 | 1.294 | -0.818 | 39.727 | 1.00 | 34.75 | N |
| ATOM | 41 | CA | LEU A | 316 | 2.730 | -0.721 | 39.378 | 1.00 | 32.58 | C |
| ATOM | 42 | C | LEU A | 316 | 3.327 | 0.491 | 40.058 | 1.00 | 29.66 | C |
| ATOM | 43 | O | LEU A | 316 | 4.414 | 0.401 | 40.654 | 1.00 | 29.13 | O |
| ATOM | 44 | CB | LEU A | 316 | 2.863 | -0.742 | 37.857 | 1.00 | 32.85 | C |
| ATOM | 45 | CG | LEU A | 316 | 4.273 | -0.604 | 37.276 | 1.00 | 36.22 | C |
| ATOM | 46 | CD1 | LEU A | 316 | 5.272 | -1.606 | 37.841 | 1.00 | 36.76 | C |
| ATOM | 47 | CD2 | LEU A | 316 | 4.173 | -0.851 | 35.774 | 1.00 | 32.29 | C |
| ATOM | 48 | N | VAL A | 317 | 2.642 | 1.640 | 40.063 | 1.00 | 29.47 | N |
| ATOM | 49 | CA | VAL A | 317 | 3.131 | 2.817 | 40.754 | 1.00 | 26.29 | C |
| ATOM | 50 | C | VAL A | 317 | 3.263 | 2.588 | 42.253 | 1.00 | 33.46 | C |
| ATOM | 51 | O | VAL A | 317 | 4.239 | 2.996 | 42.865 | 1.00 | 28.60 | O |
| ATOM | 52 | CB | VAL A | 317 | 2.278 | 4.055 | 40.488 | 1.00 | 27.01 | C |
| ATOM | 53 | CG1 | VAL A | 317 | 2.703 | 5.285 | 41.242 | 1.00 | 30.45 | C |
| ATOM | 54 | CG2 | VAL A | 317 | 2.278 | 4.300 | 38.964 | 1.00 | 25.96 | C |
| ATOM | 55 | N | LEU A | 318 | 2.236 | 1.951 | 42.850 | 1.00 | 30.90 | N |
| ATOM | 56 | CA | LEU A | 318 | 2.340 | 1.635 | 44.267 | 1.00 | 32.73 | C |
| ATOM | 57 | C | LEU A | 318 | 3.532 | 0.696 | 44.534 | 1.00 | 25.10 | C |
| ATOM | 58 | O | LEU A | 318 | 4.120 | 0.933 | 45.581 | 1.00 | 28.81 | O |
| ATOM | 59 | CB | LEU A | 318 | 1.051 | 1.062 | 44.813 | 1.00 | 33.80 | C |
| ATOM | 60 | CG | LEU A | 318 | 0.983 | 0.754 | 46.309 | 1.00 | 40.30 | C |
| ATOM | 61 | CD1 | LEU A | 318 | 1.574 | 1.849 | 47.191 | 1.00 | 35.41 | C |
| ATOM | 62 | CD2 | LEU A | 318 | -0.488 | 0.535 | 46.684 | 1.00 | 40.42 | C |
| ATOM | 63 | N | THR A | 319 | 3.845 | -0.268 | 43.727 | 1.00 | 26.05 | N |
| ATOM | 64 | CA | THR A | 319 | 4.970 | -1.153 | 43.868 | 1.00 | 33.78 | C |
| ATOM | 65 | C | THR A | 319 | 6.274 | -0.340 | 43.734 | 1.00 | 32.10 | C |
| ATOM | 66 | O | THR A | 319 | 7.212 | -0.552 | 44.485 | 1.00 | 26.69 | O |
| ATOM | 67 | CB | THR A | 319 | 5.011 | -2.308 | 42.863 | 1.00 | 32.57 | C |
| ATOM | 68 | OG1 | THR A | 319 | 3.894 | -3.206 | 43.075 | 1.00 | 41.02 | O |
| ATOM | 69 | CG2 | THR A | 319 | 6.273 | -3.163 | 43.004 | 1.00 | 34.97 | C |
| ATOM | 70 | N | LEU A | 320 | 6.295 | 0.635 | 42.823 | 1.00 | 33.55 | N |

FIG 2A

| | | | | | | | | | |
|---|---|---|---|---|---|---|---|---|---|
| ATOM | 71 | CA | LEU | A | 320 | 7.508 | 1.473 | 42.689 | 1.00 27.98 | C |
| ATOM | 72 | C | LEU | A | 320 | 7.676 | 2.335 | 43.912 | 1.00 28.44 | C |
| ATOM | 73 | O | LEU | A | 320 | 8.787 | 2.559 | 44.367 | 1.00 24.05 | O |
| ATOM | 74 | CB | LEU | A | 320 | 7.433 | 2.242 | 41.372 | 1.00 26.83 | C |
| ATOM | 75 | CG | LEU | A | 320 | 7.423 | 1.436 | 40.083 | 1.00 26.50 | C |
| ATOM | 76 | CD1 | LEU | A | 320 | 7.291 | 2.422 | 38.915 | 1.00 27.39 | C |
| ATOM | 77 | CD2 | LEU | A | 320 | 8.656 | 0.587 | 39.837 | 1.00 30.76 | C |
| ATOM | 78 | N | LEU | A | 321 | 6.582 | 2.879 | 44.489 | 1.00 27.23 | N |
| ATOM | 79 | CA | LEU | A | 321 | 6.724 | 3.682 | 45.701 | 1.00 28.02 | C |
| ATOM | 80 | C | LEU | A | 321 | 7.271 | 2.823 | 46.840 | 1.00 28.69 | C |
| ATOM | 81 | O | LEU | A | 321 | 8.210 | 3.259 | 47.546 | 1.00 27.56 | O |
| ATOM | 82 | CB | LEU | A | 321 | 5.360 | 4.288 | 46.062 | 1.00 28.80 | C |
| ATOM | 83 | CG | LEU | A | 321 | 5.318 | 5.192 | 47.292 | 1.00 37.72 | C |
| ATOM | 84 | CD1 | LEU | A | 321 | 6.011 | 6.518 | 47.054 | 1.00 38.86 | C |
| ATOM | 85 | CD2 | LEU | A | 321 | 3.853 | 5.423 | 47.666 | 1.00 39.97 | C |
| ATOM | 86 | N | GLU | A | 322 | 6.792 | 1.595 | 47.016 | 1.00 31.64 | N |
| ATOM | 87 | CA | GLU | A | 322 | 7.292 | 0.747 | 48.104 | 1.00 30.94 | C |
| ATOM | 88 | C | GLU | A | 322 | 8.744 | 0.325 | 47.877 | 1.00 31.86 | C |
| ATOM | 89 | O | GLU | A | 322 | 9.429 | 0.024 | 48.861 | 1.00 30.98 | O |
| ATOM | 90 | CB | GLU | A | 322 | 6.504 | -0.561 | 48.235 | 1.00 34.36 | C |
| ATOM | 91 | CG | GLU | A | 322 | 5.000 | -0.329 | 48.246 | 1.00 44.87 | C |
| ATOM | 92 | CD | GLU | A | 322 | 4.194 | -1.612 | 48.152 | 1.00 50.59 | C |
| ATOM | 93 | OE1 | GLU | A | 322 | 4.633 | -2.606 | 47.524 | 1.00 55.23 | O |
| ATOM | 94 | OE2 | GLU | A | 322 | 3.085 | -1.635 | 48.719 | 1.00 53.11 | O |
| ATOM | 95 | N | ALA | A | 323 | 9.186 | 0.251 | 46.621 | 1.00 30.12 | N |
| ATOM | 96 | CA | ALA | A | 323 | 10.557 | -0.167 | 46.332 | 1.00 30.14 | C |
| ATOM | 97 | C | ALA | A | 323 | 11.543 | 0.966 | 46.514 | 1.00 27.90 | C |
| ATOM | 98 | O | ALA | A | 323 | 12.745 | 0.641 | 46.392 | 1.00 26.52 | O |
| ATOM | 99 | CB | ALA | A | 323 | 10.674 | -0.686 | 44.890 | 1.00 30.03 | C |
| ATOM | 100 | N | GLU | A | 324 | 11.124 | 2.190 | 46.841 | 1.00 25.78 | N |
| ATOM | 101 | CA | GLU | A | 324 | 12.108 | 3.269 | 46.888 | 1.00 25.49 | C |
| ATOM | 102 | C | GLU | A | 324 | 13.191 | 2.929 | 47.911 | 1.00 28.63 | C |
| ATOM | 103 | O | GLU | A | 324 | 12.860 | 2.474 | 49.025 | 1.00 30.65 | O |
| ATOM | 104 | CB | GLU | A | 324 | 11.561 | 4.658 | 47.223 | 1.00 23.53 | C |
| ATOM | 105 | CG | GLU | A | 324 | 10.923 | 5.411 | 46.046 | 1.00 26.29 | C |
| ATOM | 106 | CD | GLU | A | 324 | 12.073 | 5.984 | 45.192 | 1.00 27.30 | C |
| ATOM | 107 | OE1 | GLU | A | 324 | 12.478 | 5.247 | 44.305 | 1.00 26.25 | O |
| ATOM | 108 | OE2 | GLU | A | 324 | 12.592 | 7.083 | 45.480 | 1.00 30.19 | O |
| ATOM | 109 | N | PRO | A | 325 | 14.456 | 3.133 | 47.590 | 1.00 25.18 | N |
| ATOM | 110 | CA | PRO | A | 325 | 15.520 | 2.894 | 48.547 | 1.00 26.69 | C |
| ATOM | 111 | C | PRO | A | 325 | 15.429 | 3.769 | 49.775 | 1.00 29.75 | C |
| ATOM | 112 | O | PRO | A | 325 | 14.908 | 4.886 | 49.777 | 1.00 32.58 | O |
| ATOM | 113 | CB | PRO | A | 325 | 16.818 | 3.256 | 47.789 | 1.00 30.40 | C |
| ATOM | 114 | CG | PRO | A | 325 | 16.365 | 4.075 | 46.636 | 1.00 32.28 | C |
| ATOM | 115 | CD | PRO | A | 325 | 14.939 | 3.733 | 46.305 | 1.00 22.13 | C |
| ATOM | 116 | N | PRO | A | 326 | 16.058 | 3.331 | 50.879 | 1.00 33.46 | N |
| ATOM | 117 | CA | PRO | A | 326 | 16.116 | 4.073 | 52.109 | 1.00 36.27 | C |
| ATOM | 118 | C | PRO | A | 326 | 17.047 | 5.260 | 51.951 | 1.00 36.99 | C |
| ATOM | 119 | O | PRO | A | 326 | 17.971 | 5.196 | 51.130 | 1.00 36.32 | O |
| ATOM | 120 | CB | PRO | A | 326 | 16.739 | 3.076 | 53.107 | 1.00 37.47 | C |
| ATOM | 121 | CG | PRO | A | 326 | 17.626 | 2.236 | 52.249 | 1.00 39.51 | C |
| ATOM | 122 | CD | PRO | A | 326 | 16.851 | 2.079 | 50.939 | 1.00 36.10 | C |
| ATOM | 123 | N | HIS | A | 327 | 16.899 | 6.282 | 52.788 | 1.00 38.59 | N |
| ATOM | 124 | CA | HIS | A | 327 | 17.847 | 7.406 | 52.678 | 1.00 40.75 | C |
| ATOM | 125 | C | HIS | A | 327 | 19.230 | 6.940 | 53.079 | 1.00 36.06 | C |
| ATOM | 126 | O | HIS | A | 327 | 19.395 | 6.138 | 54.018 | 1.00 32.5? | O |
| ATOM | 127 | CB | HIS | A | 327 | 17.300 | 8.555 | 53.528 | 1.00 45.? | C |
| ATOM | 128 | CG | HIS | A | 327 | 15.987 | 9.043 | 52.982 | 1.00 53. | C |
| ATOM | 129 | ND1 | HIS | A | 327 | 14.957 | 8.186 | 52.665 | 1.00 59.65 | N |
| ATOM | 130 | CD2 | HIS | A | 327 | 15.530 | 10.278 | 52.688 | 1.00 56.60 | C |
| ATOM | 131 | CE1 | HIS | A | 327 | 13.920 | 8.860 | 52.202 | 1.00 59.43 | C |
| ATOM | 132 | NE2 | HIS | A | 327 | 14.244 | 10.137 | 52.209 | 1.00 60.32 | N |
| ATOM | 133 | N | VAL | A | 328 | 20.282 | 7.369 | 52.404 | 1.00 32.13 | N |
| ATOM | 134 | CA | VAL | A | 328 | 21.657 | 6.980 | 52.751 | 1.00 36.60 | C |
| ATOM | 135 | C | VAL | A | 328 | 22.288 | 8.070 | 53.608 | 1.00 43.74 | C |
| ATOM | 136 | O | VAL | A | 328 | 22.291 | 9.188 | 53.071 | 1.00 51.71 | O |
| ATOM | 137 | CB | VAL | A | 328 | 22.619 | 6.823 | 51.549 | 1.00 35.11 | C |
| ATOM | 138 | CG1 | VAL | A | 328 | 24.068 | 6.722 | 52.020 | 1.00 34.13 | C |
| ATOM | 139 | CG2 | VAL | A | 328 | 22.189 | 5.603 | 50.768 | 1.00 31.62 | C |
| ATOM | 140 | N | LEU | A | 329 | 22.788 | 7.715 | 54.770 | 1.00 44.76 | N |
| ATOM | 141 | CA | LEU | A | 329 | 23.338 | 8.705 | 55.672 | 1.00 49.06 | C |
| ATOM | 142 | C | LEU | A | 329 | 24.833 | 8.942 | 55.562 | 1.00 47.49 | C |
| ATOM | 143 | O | LEU | A | 329 | 25.601 | 8.211 | 56.188 | 1.00 53.01 | O |
| ATOM | 144 | CB | LEU | A | 329 | 23.008 | 8.250 | 57.121 | 1.00 51.57 | C |
| ATOM | 145 | CG | LEU | A | 329 | 21.485 | 7.974 | 57.281 | 1.00 55.29 | C |
| ATOM | 146 | CD1 | LEU | A | 329 | 21.206 | 7.139 | 58.539 | 1.00 56.60 | C |
| ATOM | 147 | CD2 | LEU | A | 329 | 20.781 | 9.337 | 57.445 | 1.00 56.44 | C |

FIG. 2B

| | | | | | | | | | | |
|---|---|---|---|---|---|---|---|---|---|---|
| ATOM | 148 | N | ILE | A | 330 | 25.227 | 9.937 | 54.768 | 1.00 47.68 | N |
| ATOM | 149 | CA | ILE | A | 330 | 26.650 | 10.243 | 54.682 | 1.00 43.16 | C |
| ATOM | 150 | C | ILE | A | 330 | 26.808 | 11.652 | 55.247 | 1.00 44.09 | C |
| ATOM | 151 | O | ILE | A | 330 | 25.993 | 12.531 | 54.992 | 1.00 39.19 | O |
| ATOM | 152 | CB | ILE | A | 330 | 27.268 | 10.097 | 53.297 | 1.00 43.80 | C |
| ATOM | 153 | CG1 | ILE | A | 330 | 28.801 | 10.199 | 53.394 | 1.00 35.76 | C |
| ATOM | 154 | CG2 | ILE | A | 330 | 26.714 | 11.120 | 52.329 | 1.00 37.55 | C |
| ATOM | 155 | CD1 | ILE | A | 330 | 29.485 | 9.364 | 52.319 | 1.00 37.90 | C |
| ATOM | 156 | N | SER | A | 331 | 27.880 | 11.847 | 56.030 | 1.00 46.29 | N |
| ATOM | 157 | CA | SER | A | 331 | 28.030 | 13.202 | 56.563 | 1.00 49.87 | C |
| ATOM | 158 | C | SER | A | 331 | 29.267 | 13.807 | 55.914 | 1.00 52.53 | C |
| ATOM | 159 | O | SER | A | 331 | 30.160 | 13.053 | 55.533 | 1.00 49.80 | O |
| ATOM | 160 | CB | SER | A | 331 | 28.213 | 13.243 | 58.076 | 1.00 48.11 | C |
| ATOM | 161 | OG | SER | A | 331 | 26.912 | 13.454 | 58.596 | 1.00 52.06 | O |
| ATOM | 162 | N | ARG | A | 332 | 29.295 | 15.124 | 55.816 | 1.00 51.02 | N |
| ATOM | 163 | CA | ARG | A | 332 | 30.453 | 15.793 | 55.247 | 1.00 47.44 | C |
| ATOM | 164 | C | ARG | A | 332 | 31.719 | 15.467 | 56.048 | 1.00 46.53 | C |
| ATOM | 165 | O | ARG | A | 332 | 31.584 | 15.127 | 57.211 | 1.00 44.60 | O |
| ATOM | 166 | CB | ARG | A | 332 | 30.312 | 17.307 | 55.395 | 1.00 49.11 | C |
| ATOM | 167 | CG | ARG | A | 332 | 30.002 | 18.071 | 54.130 | 1.00 47.15 | C |
| ATOM | 168 | CD | ARG | A | 332 | 29.914 | 19.560 | 54.480 | 1.00 48.27 | C |
| ATOM | 169 | NE | ARG | A | 332 | 29.062 | 20.225 | 53.493 | 1.00 45.94 | N |
| ATOM | 170 | CZ | ARG | A | 332 | 29.569 | 20.997 | 52.531 | 1.00 44.52 | C |
| ATOM | 171 | NH1 | ARG | A | 332 | 28.715 | 21.538 | 51.674 | 1.00 43.36 | N |
| ATOM | 172 | NH2 | ARG | A | 332 | 30.873 | 21.223 | 52.439 | 1.00 41.93 | N |
| ATOM | 173 | N | PRO | A | 333 | 32.861 | 15.669 | 55.438 | 1.00 46.60 | N |
| ATOM | 174 | CA | PRO | A | 333 | 34.114 | 15.452 | 56.141 | 1.00 50.04 | C |
| ATOM | 175 | C | PRO | A | 333 | 34.378 | 16.619 | 57.093 | 1.00 50.91 | C |
| ATOM | 176 | O | PRO | A | 333 | 33.758 | 17.679 | 56.986 | 1.00 46.07 | O |
| ATOM | 177 | CB | PRO | A | 333 | 35.192 | 15.402 | 55.062 | 1.00 51.24 | C |
| ATOM | 178 | CG | PRO | A | 333 | 34.581 | 16.017 | 53.857 | 1.00 51.07 | C |
| ATOM | 179 | CD | PRO | A | 333 | 33.091 | 16.096 | 54.045 | 1.00 48.89 | C |
| ATOM | 180 | N | SER | A | 334 | 35.273 | 16.359 | 58.036 | 1.00 54.26 | N |
| ATOM | 181 | CA | SER | A | 334 | 35.698 | 17.405 | 58.971 | 1.00 59.74 | C |
| ATOM | 182 | C | SER | A | 334 | 36.973 | 17.950 | 58.320 | 1.00 58.71 | C |
| ATOM | 183 | O | SER | A | 334 | 37.913 | 17.172 | 58.137 | 1.00 61.30 | O |
| ATOM | 184 | CB | SER | A | 334 | 35.976 | 16.884 | 60.365 | 1.00 57.11 | C |
| ATOM | 185 | OG | SER | A | 334 | 35.815 | 17.982 | 61.246 | 1.00 65.66 | O |
| ATOM | 186 | N | ALA | A | 335 | 36.927 | 19.173 | 57.850 | 1.00 57.04 | N |
| ATOM | 187 | CA | ALA | A | 335 | 38.032 | 19.809 | 57.136 | 1.00 57.50 | C |
| ATOM | 188 | C | ALA | A | 335 | 37.420 | 20.176 | 55.781 | 1.00 56.09 | C |
| ATOM | 189 | O | ALA | A | 335 | 36.664 | 19.356 | 55.256 | 1.00 56.58 | O |
| ATOM | 190 | CB | ALA | A | 335 | 39.255 | 18.963 | 56.851 | 1.00 55.12 | C |
| ATOM | 191 | N | PRO | A | 336 | 37.677 | 21.372 | 55.299 | 1.00 55.44 | N |
| ATOM | 192 | CA | PRO | A | 336 | 37.107 | 21.770 | 54.016 | 1.00 47.77 | C |
| ATOM | 193 | C | PRO | A | 336 | 37.465 | 20.746 | 52.949 | 1.00 43.81 | C |
| ATOM | 194 | O | PRO | A | 336 | 38.438 | 19.982 | 53.033 | 1.00 35.36 | O |
| ATOM | 195 | CB | PRO | A | 336 | 37.643 | 23.167 | 53.817 | 1.00 50.74 | C |
| ATOM | 196 | CG | PRO | A | 336 | 38.306 | 23.605 | 55.069 | 1.00 51.78 | C |
| ATOM | 197 | CD | PRO | A | 336 | 38.561 | 22.389 | 55.913 | 1.00 52.02 | C |
| ATOM | 198 | N | PHE | A | 337 | 36.688 | 20.667 | 51.872 | 1.00 38.45 | N |
| ATOM | 199 | CA | PHE | A | 337 | 36.930 | 19.690 | 50.829 | 1.00 38.41 | C |
| ATOM | 200 | C | PHE | A | 337 | 38.188 | 19.870 | 50.003 | 1.00 36.62 | C |
| ATOM | 201 | O | PHE | A | 337 | 38.535 | 21.009 | 49.768 | 1.00 37.09 | O |
| ATOM | 202 | CB | PHE | A | 337 | 35.767 | 19.748 | 49.808 | 1.00 34.49 | C |
| ATOM | 203 | CG | PHE | A | 337 | 34.594 | 18.891 | 50.176 | 1.00 29.83 | C |
| ATOM | 204 | CD1 | PHE | A | 337 | 34.797 | 17.520 | 50.284 | 1.00 26.36 | C |
| ATOM | 205 | CD2 | PHE | A | 337 | 33.337 | 19.405 | 50.381 | 1.00 33.91 | C |
| ATOM | 206 | CE1 | PHE | A | 337 | 33.783 | 16.653 | 50.608 | 1.00 30.38 | C |
| ATOM | 207 | CE2 | PHE | A | 337 | 32.304 | 18.537 | 50.729 | 1.00 33.76 | C |
| ATOM | 208 | CZ | PHE | A | 337 | 32.524 | 17.176 | 50.818 | 1.00 30.40 | C |
| ATOM | 209 | N | THR | A | 338 | 38.822 | 18.764 | 49.605 | 1.00 35.69 | N |
| ATOM | 210 | CA | THR | A | 338 | 39.931 | 18.850 | 48.667 | 1.00 34.49 | C |
| ATOM | 211 | C | THR | A | 338 | 39.521 | 18.042 | 47.428 | 1.00 36.55 | C |
| ATOM | 212 | O | THR | A | 338 | 38.489 | 17.354 | 47.471 | 1.00 33.13 | O |
| ATOM | 213 | CB | THR | A | 338 | 41.227 | 18.242 | 49.174 | 1.00 37.42 | C |
| ATOM | 214 | OG1 | THR | A | 338 | 40.992 | 16.847 | 49.378 | 1.00 34.86 | O |
| ATOM | 215 | CG2 | THR | A | 338 | 41.695 | 18.905 | 50.466 | 1.00 39.82 | C |
| ATOM | 216 | N | GLU | A | 339 | 40.299 | 18.060 | 46.356 | 1.00 38.20 | N |
| ATOM | 217 | CA | GLU | A | 339 | 39.939 | 17.245 | 45.182 | 1.00 31.68 | C |
| ATOM | 218 | C | GLU | A | 339 | 39.804 | 15.784 | 45.602 | 1.00 34.71 | C |
| ATOM | 219 | O | GLU | A | 339 | 38.782 | 15.149 | 45.344 | 1.00 29.59 | O |
| ATOM | 220 | CB | GLU | A | 339 | 40.948 | 17.416 | 44.063 | 1.00 33.81 | C |
| ATOM | 221 | CG | GLU | A | 339 | 40.500 | 16.717 | 42.776 | 1.00 34.94 | C |
| ATOM | 222 | CD | GLU | A | 339 | 41.430 | 17.024 | 41.627 | 1.00 35.71 | C |
| ATOM | 223 | OE1 | GLU | A | 339 | 42.466 | 16.332 | 41.550 | 1.00 40.73 | O |
| ATOM | 224 | OE2 | GLU | A | 339 | 41.125 | 17.947 | 40.853 | 1.00 39.23 | O |

FIG. 2C

```
ATOM  225  N    ALA A 340    40.740  15.237  46.384  1.00  30.70    N
ATOM  226  CA   ALA A 340    40.665  13.863  46.831  1.00  27.77    C
ATOM  227  C    ALA A 340    39.502  13.519  47.748  1.00  25.62    C
ATOM  228  O    ALA A 340    38.927  12.448  47.552  1.00  27.51    O
ATOM  229  CB   ALA A 340    41.931  13.448  47.601  1.00  29.10    C
ATOM  230  N    SER A 341    39.226  14.388  48.720  1.00  26.84    N
ATOM  231  CA   SER A 341    38.196  14.096  49.708  1.00  29.79    C
ATOM  232  C    SER A 341    36.803  14.291  49.100  1.00  28.43    C
ATOM  233  O    SER A 341    35.920  13.514  49.464  1.00  26.98    O
ATOM  234  CB   SER A 341    38.420  14.894  51.001  1.00  26.89    C
ATOM  235  OG   SER A 341    38.028  16.252  50.905  1.00  30.59    O
ATOM  236  N    MET A 342    36.644  15.260  48.188  1.00  26.89    N
ATOM  237  CA   MET A 342    35.292  15.347  47.551  1.00  23.72    C
ATOM  238  C    MET A 342    35.145  14.123  46.629  1.00  28.77    C
ATOM  239  O    MET A 342    34.075  13.509  46.708  1.00  26.04    O
ATOM  240  CB   MET A 342    35.126  16.618  46.749  1.00  25.36    C
ATOM  241  CG   MET A 342    33.749  16.704  46.050  1.00  28.37    C
ATOM  242  SD   MET A 342    33.464  18.319  45.306  1.00  28.56    S
ATOM  243  CE   MET A 342    33.156  19.429  46.631  1.00  33.24    C
ATOM  244  N    MET A 343    36.180  13.703  45.885  1.00  25.81    N
ATOM  245  CA   MET A 343    36.015  12.491  45.066  1.00  25.62    C
ATOM  246  C    MET A 343    35.803  11.283  45.963  1.00  28.46    C
ATOM  247  O    MET A 343    34.998  10.391  45.669  1.00  24.46    O
ATOM  248  CB   MET A 343    37.130  12.226  44.064  1.00  18.08    C
ATOM  249  CG   MET A 343    37.256  13.268  42.943  1.00  22.77    C
ATOM  250  SD   MET A 343    35.660  13.268  41.976  1.00  24.43    S
ATOM  251  CE   MET A 343    35.546  11.509  41.690  1.00  24.64    C
ATOM  252  N    MET A 344    36.401  11.204  47.163  1.00  23.55    N
ATOM  253  CA   MET A 344    36.150  10.057  48.034  1.00  21.04    C
ATOM  254  C    MET A 344    34.727  10.018  48.589  1.00  22.36    C
ATOM  255  O    MET A 344    34.109   8.962  48.755  1.00  22.72    O
ATOM  256  CB   MET A 344    37.106  10.117  49.236  1.00  28.70    C
ATOM  257  CG   MET A 344    36.782   9.085  50.305  1.00  39.38    C
ATOM  258  SD   MET A 344    38.017   9.192  51.632  1.00  46.12    S
ATOM  259  CE   MET A 344    39.321   8.239  50.809  1.00  47.00    C
ATOM  260  N    SER A 345    34.189  11.164  48.919  1.00  22.84    N
ATOM  261  CA   SER A 345    32.839  11.285  49.427  1.00  22.70    C
ATOM  262  C    SER A 345    31.804  10.862  48.332  1.00  21.50    C
ATOM  263  O    SER A 345    30.891  10.084  48.632  1.00  21.09    O
ATOM  264  CB   SER A 345    32.520  12.718  49.846  1.00  26.69    C
ATOM  265  OG   SER A 345    33.175  12.967  51.105  1.00  26.93    O
ATOM  266  N    LEU A 346    32.043  11.312  47.136  1.00  20.73    N
ATOM  267  CA   LEU A 346    31.063  10.950  46.059  1.00  21.78    C
ATOM  268  C    LEU A 346    31.140   9.484  45.733  1.00  19.80    C
ATOM  269  O    LEU A 346    30.092   8.886  45.524  1.00  20.97    O
ATOM  270  CB   LEU A 346    31.316  11.808  44.825  1.00  20.76    C
ATOM  271  CG   LEU A 346    31.072  13.318  44.954  1.00  24.44    C
ATOM  272  CD1  LEU A 346    31.454  14.028  43.664  1.00  27.57    C
ATOM  273  CD2  LEU A 346    29.603  13.613  45.260  1.00  24.42    C
ATOM  274  N    THR A 347    32.338   8.877  45.732  1.00  18.51    N
ATOM  275  CA   THR A 347    32.414   7.450  45.373  1.00  21.98    C
ATOM  276  C    THR A 347    31.983   6.573  46.524  1.00  24.51    C
ATOM  277  O    THR A 347    31.368   5.529  46.275  1.00  23.87    O
ATOM  278  CB   THR A 347    33.796   7.089  44.809  1.00  25.39    C
ATOM  279  OG1  THR A 347    34.738   7.391  45.842  1.00  21.99    O
ATOM  280  CG2  THR A 347    34.123   7.889  43.565  1.00  25.92    C
ATOM  281  N    LYS A 348    32.185   6.947  47.799  1.00  24.27    N
ATOM  282  CA   LYS A 348    31.650   6.172  48.913  1.00  22.75    C
ATOM  283  C    LYS A 348    30.115   6.236  48.952  1.00  20.19    C
ATOM  284  O    LYS A 348    29.438   5.260  49.278  1.00  20.54    O
ATOM  285  CB   LYS A 348    32.116   6.807  50.258  1.00  30.65    C
ATOM  286  CG   LYS A 348    31.525   6.139  51.484  1.00  38.85    C
ATOM  287  CD   LYS A 348    32.566   5.870  52.566  1.00  51.23    C
ATOM  288  CE   LYS A 348    32.062   4.767  53.515  1.00  53.45    C
ATOM  289  NZ   LYS A 348    33.152   4.400  54.471  1.00  61.29    N
ATOM  290  N    LEU A 349    29.568   7.436  48.668  1.00  21.35    N
ATOM  291  CA   LEU A 349    28.098   7.606  48.692  1.00  20.62    C
ATOM  292  C    LEU A 349    27.531   6.728  47.554  1.00  20.65    C
ATOM  293  O    LEU A 349    26.554   6.036  47.757  1.00  18.64    O
ATOM  294  CB   LEU A 349    27.658   9.049  48.459  1.00  20.47    C
ATOM  295  CG   LEU A 349    26.159   9.320  48.202  1.00  24.04    C
ATOM  296  CD1  LEU A 349    25.303   8.888  49.386  1.00  23.46    C
ATOM  297  CD2  LEU A 349    25.830  10.812  48.019  1.00  22.26    C
ATOM  298  N    ALA A 350    28.198   6.787  46.386  1.00  19.00    N
ATOM  299  CA   ALA A 350    27.723   5.962  45.252  1.00  21.07    C
ATOM  300  C    ALA A 350    27.733   4.475  45.613  1.00  19.81    C
ATOM  301  O    ALA A 350    26.784   3.733  45.385  1.00  18.86    O
```

FIG. 2D

| | | | | | | | | | | |
|---|---|---|---|---|---|---|---|---|---|---|
| ATOM | 302 | CB | ALA | A | 350 | 28.558 | 6.162 | 43.988 | 1.00 20.94 | C |
| ATOM | 303 | N | ASP | A | 351 | 28.807 | 4.047 | 46.335 | 1.00 23.60 | N |
| ATOM | 304 | CA | ASP | A | 351 | 28.879 | 2.611 | 46.709 | 1.00 23.15 | C |
| ATOM | 305 | C | ASP | A | 351 | 27.698 | 2.216 | 47.569 | 1.00 21.31 | C |
| ATOM | 306 | O | ASP | A | 351 | 26.994 | 1.228 | 47.345 | 1.00 22.54 | O |
| ATOM | 307 | CB | ASP | A | 351 | 30.222 | 2.317 | 47.405 | 1.00 24.66 | C |
| ATOM | 308 | CG | ASP | A | 351 | 30.369 | 0.831 | 47.750 | 1.00 24.20 | C |
| ATOM | 309 | OD1 | ASP | A | 351 | 30.751 | 0.016 | 46.881 | 1.00 22.60 | O |
| ATOM | 310 | OD2 | ASP | A | 351 | 30.083 | 0.368 | 48.854 | 1.00 27.97 | O |
| ATOM | 311 | N | LYS | A | 352 | 27.319 | 3.080 | 48.505 | 1.00 18.89 | N |
| ATOM | 312 | CA | LYS | A | 352 | 26.231 | 2.812 | 49.429 | 1.00 25.83 | C |
| ATOM | 313 | C | LYS | A | 352 | 24.908 | 2.730 | 48.660 | 1.00 23.96 | C |
| ATOM | 314 | O | LYS | A | 352 | 24.066 | 1.863 | 48.897 | 1.00 23.98 | O |
| ATOM | 315 | CB | LYS | A | 352 | 26.165 | 3.884 | 50.514 | 1.00 29.24 | C |
| ATOM | 316 | CG | LYS | A | 352 | 27.383 | 3.864 | 51.460 | 1.00 37.75 | C |
| ATOM | 317 | CD | LYS | A | 352 | 27.337 | 5.094 | 52.366 | 1.00 41.30 | C |
| ATOM | 318 | CE | LYS | A | 352 | 28.428 | 5.141 | 53.406 | 1.00 47.71 | C |
| ATOM | 319 | NZ | LYS | A | 352 | 28.383 | 6.407 | 54.191 | 1.00 57.64 | N |
| ATOM | 320 | N | GLU | A | 353 | 24.728 | 3.733 | 47.785 | 1.00 18.65 | N |
| ATOM | 321 | CA | GLU | A | 353 | 23.473 | 3.732 | 47.012 | 1.00 19.52 | C |
| ATOM | 322 | C | GLU | A | 353 | 23.422 | 2.552 | 46.054 | 1.00 19.13 | C |
| ATOM | 323 | O | GLU | A | 353 | 22.313 | 2.097 | 45.724 | 1.00 21.39 | O |
| ATOM | 324 | CB | GLU | A | 353 | 23.330 | 5.038 | 46.198 | 1.00 22.06 | C |
| ATOM | 325 | CG | GLU | A | 353 | 23.214 | 6.231 | 47.159 | 1.00 21.74 | C |
| ATOM | 326 | CD | GLU | A | 353 | 22.893 | 7.495 | 46.368 | 1.00 24.03 | C |
| ATOM | 327 | OE1 | GLU | A | 353 | 21.699 | 7.700 | 46.076 | 1.00 23.53 | O |
| ATOM | 328 | OE2 | GLU | A | 353 | 23.754 | 8.285 | 46.001 | 1.00 23.99 | O |
| ATOM | 329 | N | LEU | A | 354 | 24.577 | 2.155 | 45.504 | 1.00 16.94 | N |
| ATOM | 330 | CA | LEU | A | 354 | 24.568 | 1.032 | 44.534 | 1.00 20.92 | C |
| ATOM | 331 | C | LEU | A | 354 | 24.138 | -0.261 | 45.217 | 1.00 20.96 | C |
| ATOM | 332 | O | LEU | A | 354 | 23.455 | -1.036 | 44.517 | 1.00 21.13 | O |
| ATOM | 333 | CB | LEU | A | 354 | 25.922 | 0.856 | 43.824 | 1.00 19.93 | C |
| ATOM | 334 | CG | LEU | A | 354 | 26.275 | 1.921 | 42.787 | 1.00 17.91 | C |
| ATOM | 335 | CD1 | LEU | A | 354 | 27.778 | 1.969 | 42.528 | 1.00 18.30 | C |
| ATOM | 336 | CD2 | LEU | A | 354 | 25.567 | 1.655 | 41.478 | 1.00 22.25 | C |
| ATOM | 337 | N | VAL | A | 355 | 24.454 | -0.450 | 46.503 | 1.00 24.62 | N |
| ATOM | 338 | CA | VAL | A | 355 | 23.931 | -1.679 | 47.168 | 1.00 24.78 | C |
| ATOM | 339 | C | VAL | A | 355 | 22.415 | -1.611 | 47.189 | 1.00 22.47 | C |
| ATOM | 340 | O | VAL | A | 355 | 21.745 | -2.574 | 46.806 | 1.00 24.58 | O |
| ATOM | 341 | CB | VAL | A | 355 | 24.375 | -1.768 | 48.649 | 1.00 27.79 | C |
| ATOM | 342 | CG1 | VAL | A | 355 | 23.758 | -2.998 | 49.293 | 1.00 28.19 | C |
| ATOM | 343 | CG2 | VAL | A | 355 | 25.902 | -1.767 | 48.678 | 1.00 29.07 | C |
| ATOM | 344 | N | HIS | A | 356 | 21.817 | -0.473 | 47.556 | 1.00 22.33 | N |
| ATOM | 345 | CA | HIS | A | 356 | 20.366 | -0.318 | 47.555 | 1.00 23.50 | C |
| ATOM | 346 | C | HIS | A | 356 | 19.747 | -0.390 | 46.156 | 1.00 25.98 | C |
| ATOM | 347 | O | HIS | A | 356 | 18.603 | -0.823 | 45.985 | 1.00 20.85 | O |
| ATOM | 348 | CB | HIS | A | 356 | 19.973 | 1.059 | 48.154 | 1.00 25.64 | C |
| ATOM | 349 | CG | HIS | A | 356 | 20.417 | 1.150 | 49.594 | 1.00 30.50 | C |
| ATOM | 350 | ND1 | HIS | A | 356 | 20.380 | 0.032 | 50.404 | 1.00 36.00 | N |
| ATOM | 351 | CD2 | HIS | A | 356 | 20.901 | 2.131 | 50.348 | 1.00 33.71 | C |
| ATOM | 352 | CE1 | HIS | A | 356 | 20.836 | 0.334 | 51.603 | 1.00 38.33 | C |
| ATOM | 353 | NE2 | HIS | A | 356 | 21.149 | 1.608 | 51.614 | 1.00 35.34 | N |
| ATOM | 354 | N | MET | A | 357 | 20.475 | 0.096 | 45.141 | 1.00 22.11 | N |
| ATOM | 355 | CA | MET | A | 357 | 19.922 | 0.085 | 43.760 | 1.00 23.05 | C |
| ATOM | 356 | C | MET | A | 357 | 19.671 | -1.353 | 43.318 | 1.00 22.29 | C |
| ATOM | 357 | O | MET | A | 357 | 18.676 | -1.604 | 42.647 | 1.00 22.13 | O |
| ATOM | 358 | CB | MET | A | 357 | 20.869 | 0.761 | 42.761 | 1.00 20.67 | C |
| ATOM | 359 | CG | MET | A | 357 | 20.200 | 1.079 | 41.381 | 1.00 17.48 | C |
| ATOM | 360 | SD | MET | A | 357 | 21.487 | 1.628 | 40.215 | 1.00 18.70 | S |
| ATOM | 361 | CE | MET | A | 357 | 21.975 | 3.188 | 40.968 | 1.00 21.32 | C |
| ATOM | 362 | N | ILE | A | 358 | 20.563 | -2.306 | 43.693 | 1.00 19.95 | N |
| ATOM | 363 | CA | ILE | A | 358 | 20.278 | -3.705 | 43.318 | 1.00 23.22 | C |
| ATOM | 364 | C | ILE | A | 358 | 18.954 | -4.180 | 43.932 | 1.00 26.07 | C |
| ATOM | 365 | O | ILE | A | 358 | 18.170 | -4.859 | 43.261 | 1.00 26.53 | O |
| ATOM | 366 | CB | ILE | A | 358 | 21.371 | -4.633 | 43.891 | 1.00 24.88 | C |
| ATOM | 367 | CG1 | ILE | A | 358 | 22.731 | -4.358 | 43.262 | 1.00 31.03 | C |
| ATOM | 368 | CG2 | ILE | A | 358 | 21.074 | -6.125 | 43.773 | 1.00 33.68 | C |
| ATOM | 369 | CD1 | ILE | A | 358 | 22.836 | -4.417 | 41.769 | 1.00 32.41 | C |
| ATOM | 370 | N | SER | A | 359 | 18.749 | -3.920 | 45.215 | 1.00 23.68 | N |
| ATOM | 371 | CA | SER | A | 359 | 17.524 | -4.297 | 45.906 | 1.00 27.31 | C |
| ATOM | 372 | C | SER | A | 359 | 16.307 | -3.645 | 45.281 | 1.00 26.81 | C |
| ATOM | 373 | O | SER | A | 359 | 15.259 | -4.304 | 45.149 | 1.00 24.44 | O |
| ATOM | 374 | CB | SER | A | 359 | 17.526 | -3.949 | 47.422 | 1.00 26.99 | C |
| ATOM | 375 | OG | SER | A | 359 | 18.585 | -4.728 | 47.964 | 1.00 38.36 | O |
| ATOM | 376 | N | TRP | A | 360 | 16.440 | -2.402 | 44.872 | 1.00 20.43 | N |
| ATOM | 377 | CA | TRP | A | 360 | 15.336 | -1.654 | 44.241 | 1.00 20.64 | C |
| ATOM | 378 | C | TRP | A | 360 | 14.948 | -2.256 | 42.910 | 1.00 21.97 | C |

FIG. 2E

| | | | | | | | | | |
|---|---|---|---|---|---|---|---|---|---|
| ATOM | 379 | O | TRP | A | 360 | 13.758 | -2.569 | 42.651 | 1.00 23.85 | O |
| ATOM | 380 | CB | TRP | A | 360 | 15.787 | -0.183 | 44.026 | 1.00 22.61 | C |
| ATOM | 381 | CG | TRP | A | 360 | 14.982 | 0.581 | 43.022 | 1.00 22.58 | C |
| ATOM | 382 | CD1 | TRP | A | 360 | 13.724 | 1.108 | 43.219 | 1.00 24.32 | C |
| ATOM | 383 | CD2 | TRP | A | 360 | 15.352 | 0.891 | 41.666 | 1.00 21.14 | C |
| ATOM | 384 | NE1 | TRP | A | 360 | 13.302 | 1.741 | 42.050 | 1.00 22.74 | N |
| ATOM | 385 | CE2 | TRP | A | 360 | 14.278 | 1.619 | 41.098 | 1.00 22.86 | C |
| ATOM | 386 | CE3 | TRP | A | 360 | 16.492 | 0.703 | 40.922 | 1.00 16.31 | C |
| ATOM | 387 | CZ2 | TRP | A | 360 | 14.321 | 2.172 | 39.807 | 1.00 22.60 | C |
| ATOM | 388 | CZ3 | TRP | A | 360 | 16.550 | 1.216 | 39.616 | 1.00 21.78 | C |
| ATOM | 389 | CH2 | TRP | A | 360 | 15.477 | 1.930 | 39.084 | 1.00 18.56 | C |
| ATOM | 390 | N | ALA | A | 361 | 15.953 | -2.554 | 42.082 | 1.00 20.48 | N |
| ATOM | 391 | CA | ALA | A | 361 | 15.724 | -3.136 | 40.771 | 1.00 24.14 | C |
| ATOM | 392 | C | ALA | A | 361 | 15.009 | -4.478 | 40.913 | 1.00 26.60 | C |
| ATOM | 393 | O | ALA | A | 361 | 14.137 | -4.799 | 40.095 | 1.00 27.72 | O |
| ATOM | 394 | CB | ALA | A | 361 | 17.037 | -3.312 | 40.014 | 1.00 23.41 | C |
| ATOM | 395 | N | LYS | A | 362 | 15.357 | -5.249 | 41.958 | 1.00 26.22 | N |
| ATOM | 396 | CA | LYS | A | 362 | 14.708 | -6.564 | 42.127 | 1.00 26.09 | C |
| ATOM | 397 | C | LYS | A | 362 | 13.273 | -6.438 | 42.572 | 1.00 27.56 | C |
| ATOM | 398 | O | LYS | A | 362 | 12.486 | -7.396 | 42.492 | 1.00 28.56 | O |
| ATOM | 399 | CB | LYS | A | 362 | 15.609 | -7.446 | 43.018 | 1.00 31.05 | C |
| ATOM | 400 | CG | LYS | A | 362 | 16.947 | -7.716 | 42.322 | 1.00 33.04 | C |
| ATOM | 401 | CD | LYS | A | 362 | 17.809 | -8.604 | 43.227 | 1.00 39.64 | C |
| ATOM | 402 | CE | LYS | A | 362 | 18.966 | -9.239 | 42.480 | 1.00 41.35 | C |
| ATOM | 403 | NZ | LYS | A | 362 | 19.957 | -9.851 | 43.441 | 1.00 44.61 | N |
| ATOM | 404 | N | LYS | A | 363 | 12.818 | -5.284 | 43.041 | 1.00 29.47 | N |
| ATOM | 405 | CA | LYS | A | 363 | 11.444 | -5.081 | 43.441 | 1.00 29.52 | C |
| ATOM | 406 | C | LYS | A | 363 | 10.513 | -4.591 | 42.331 | 1.00 36.08 | C |
| ATOM | 407 | O | LYS | A | 363 | 9.292 | -4.506 | 42.590 | 1.00 31.07 | O |
| ATOM | 408 | CB | LYS | A | 363 | 11.329 | -4.144 | 44.611 | 1.00 30.07 | C |
| ATOM | 409 | CG | LYS | A | 363 | 11.820 | -4.650 | 45.939 | 1.00 33.52 | C |
| ATOM | 410 | CD | LYS | A | 363 | 11.809 | -3.501 | 46.942 | 1.00 35.99 | C |
| ATOM | 411 | CE | LYS | A | 363 | 12.392 | -3.957 | 48.275 | 1.00 40.38 | C |
| ATOM | 412 | NZ | LYS | A | 363 | 13.862 | -4.097 | 48.227 | 1.00 43.85 | N |
| ATOM | 413 | N | ILE | A | 364 | 11.033 | -4.284 | 41.164 | 1.00 30.49 | N |
| ATOM | 414 | CA | ILE | A | 364 | 10.245 | -3.884 | 40.013 | 1.00 36.46 | C |
| ATOM | 415 | C | ILE | A | 364 | 9.684 | -5.159 | 39.377 | 1.00 37.50 | C |
| ATOM | 416 | O | ILE | A | 364 | 10.438 | -6.022 | 38.937 | 1.00 33.78 | O |
| ATOM | 417 | CB | ILE | A | 364 | 11.099 | -3.127 | 38.995 | 1.00 33.25 | C |
| ATOM | 418 | CG1 | ILE | A | 364 | 11.618 | -1.828 | 39.650 | 1.00 33.92 | C |
| ATOM | 419 | CG2 | ILE | A | 364 | 10.359 | -2.830 | 37.703 | 1.00 37.49 | C |
| ATOM | 420 | CD1 | ILE | A | 364 | 12.686 | -1.134 | 38.838 | 1.00 29.17 | C |
| ATOM | 421 | N | PRO | A | 365 | 8.363 | -5.269 | 39.351 | 1.00 40.37 | N |
| ATOM | 422 | CA | PRO | A | 365 | 7.691 | -6.449 | 38.834 | 1.00 40.35 | C |
| ATOM | 423 | C | PRO | A | 365 | 8.279 | -6.909 | 37.527 | 1.00 38.24 | C |
| ATOM | 424 | O | PRO | A | 365 | 8.500 | -6.088 | 36.655 | 1.00 36.01 | O |
| ATOM | 425 | CB | PRO | A | 365 | 6.220 | -6.019 | 38.708 | 1.00 39.06 | C |
| ATOM | 426 | CG | PRO | A | 365 | 6.103 | -5.098 | 39.901 | 1.00 39.95 | C |
| ATOM | 427 | CD | PRO | A | 365 | 7.379 | -4.275 | 39.835 | 1.00 41.03 | C |
| ATOM | 428 | N | GLY | A | 366 | 8.650 | -8.190 | 37.442 | 1.00 39.52 | N |
| ATOM | 429 | CA | GLY | A | 366 | 9.192 | -8.725 | 36.216 | 1.00 39.49 | C |
| ATOM | 430 | C | GLY | A | 366 | 10.687 | -8.686 | 36.054 | 1.00 35.99 | C |
| ATOM | 431 | O | GLY | A | 366 | 11.234 | -9.500 | 35.322 | 1.00 34.12 | O |
| ATOM | 432 | N | PHE | A | 367 | 11.361 | -7.787 | 36.785 | 1.00 35.43 | N |
| ATOM | 433 | CA | PHE | A | 367 | 12.806 | -7.698 | 36.677 | 1.00 34.62 | C |
| ATOM | 434 | C | PHE | A | 367 | 13.529 | -9.009 | 37.030 | 1.00 27.50 | C |
| ATOM | 435 | O | PHE | A | 367 | 14.385 | -9.403 | 36.245 | 1.00 29.96 | O |
| ATOM | 436 | CB | PHE | A | 367 | 13.354 | -6.572 | 37.552 | 1.00 32.50 | C |
| ATOM | 437 | CG | PHE | A | 367 | 14.805 | -6.279 | 37.261 | 1.00 32.90 | C |
| ATOM | 438 | CD1 | PHE | A | 367 | 15.144 | -5.390 | 36.251 | 1.00 31.40 | C |
| ATOM | 439 | CD2 | PHE | A | 367 | 15.815 | -6.869 | 37.988 | 1.00 30.54 | C |
| ATOM | 440 | CE1 | PHE | A | 367 | 16.468 | -5.134 | 35.986 | 1.00 24.88 | C |
| ATOM | 441 | CE2 | PHE | A | 367 | 17.152 | -6.598 | 37.722 | 1.00 27.58 | C |
| ATOM | 442 | CZ | PHE | A | 367 | 17.476 | -5.704 | 36.716 | 1.00 26.84 | C |
| ATOM | 443 | N | VAL | A | 368 | 13.172 | -9.684 | 38.100 | 1.00 32.49 | N |
| ATOM | 444 | CA | VAL | A | 368 | 13.883 | -10.923 | 38.447 | 1.00 32.31 | C |
| ATOM | 445 | C | VAL | A | 368 | 13.578 | -12.051 | 37.478 | 1.00 36.24 | C |
| ATOM | 446 | O | VAL | A | 368 | 14.321 | -13.046 | 37.437 | 1.00 33.42 | O |
| ATOM | 447 | CB | VAL | A | 368 | 13.680 | -11.377 | 39.901 | 1.00 35.22 | C |
| ATOM | 448 | CG1 | VAL | A | 368 | 14.393 | -10.440 | 40.889 | 1.00 35.30 | C |
| ATOM | 449 | CG2 | VAL | A | 368 | 12.202 | -11.506 | 40.251 | 1.00 39.26 | C |
| ATOM | 450 | N | GLU | A | 369 | 12.554 | -11.897 | 36.643 | 1.00 41.05 | N |
| ATOM | 451 | CA | GLU | A | 369 | 12.216 | -12.899 | 35.627 | 1.00 43.35 | C |
| ATOM | 452 | C | GLU | A | 369 | 13.059 | -12.766 | 34.378 | 1.00 43.93 | C |
| ATOM | 453 | O | GLU | A | 369 | 13.077 | -13.642 | 33.500 | 1.00 43.51 | O |
| ATOM | 454 | CB | GLU | A | 369 | 10.718 | -12.789 | 35.299 | 1.00 44.22 | C |
| ATOM | 455 | CG | GLU | A | 369 | 9.861 | -13.359 | 36.425 | 1.00 53.77 | C |

FIG. 2F

```
ATOM    456  CD  GLU A 369       8.375 -13.179  36.203  1.00 58.72           C
ATOM    457  OE1 GLU A 369       7.974 -12.735  35.104  1.00 61.35           O
ATOM    458  OE2 GLU A 369       7.559 -13.460  37.111  1.00 63.00           O
ATOM    459  N   LEU A 370      13.752 -11.636  34.229  1.00 42.33           N
ATOM    460  CA  LEU A 370      14.641 -11.430  33.093  1.00 39.24           C
ATOM    461  C   LEU A 370      15.821 -12.375  33.255  1.00 38.86           C
ATOM    462  O   LEU A 370      16.080 -12.782  34.396  1.00 43.46           O
ATOM    463  CB  LEU A 370      15.169  -9.992  33.024  1.00 38.90           C
ATOM    464  CG  LEU A 370      14.069  -8.932  32.855  1.00 36.26           C
ATOM    465  CD1 LEU A 370      14.661  -7.526  32.880  1.00 38.31           C
ATOM    466  CD2 LEU A 370      13.335  -9.131  31.534  1.00 41.34           C
ATOM    467  N   SER A 371      16.502 -12.715  32.176  1.00 41.52           N
ATOM    468  CA  SER A 371      17.658 -13.594  32.332  1.00 39.96           C
ATOM    469  C   SER A 371      18.720 -12.862  33.148  1.00 43.04           C
ATOM    470  O   SER A 371      18.730 -11.620  33.243  1.00 39.51           O
ATOM    471  CB  SER A 371      18.255 -13.899  30.955  1.00 43.12           C
ATOM    472  OG  SER A 371      18.677 -12.649  30.419  1.00 38.32           O
ATOM    473  N   LEU A 372      19.675 -13.612  33.675  1.00 31.82           N
ATOM    474  CA  LEU A 372      20.754 -13.028  34.452  1.00 32.28           C
ATOM    475  C   LEU A 372      21.563 -12.049  33.611  1.00 34.87           C
ATOM    476  O   LEU A 372      22.098 -11.009  34.047  1.00 33.17           O
ATOM    477  CB  LEU A 372      21.640 -14.147  34.974  1.00 38.05           C
ATOM    478  CG  LEU A 372      22.793 -13.858  35.916  1.00 39.95           C
ATOM    479  CD1 LEU A 372      22.273 -13.117  37.149  1.00 44.82           C
ATOM    480  CD2 LEU A 372      23.410 -15.187  36.387  1.00 42.80           C
ATOM    481  N   PHE A 373      21.787 -12.417  32.333  1.00 31.42           N
ATOM    482  CA  PHE A 373      22.547 -11.511  31.483  1.00 31.42           C
ATOM    483  C   PHE A 373      21.782 -10.220  31.250  1.00 24.19           C
ATOM    484  O   PHE A 373      22.455  -9.193  31.101  1.00 29.66           O
ATOM    485  CB  PHE A 373      22.926 -12.143  30.138  1.00 36.67           C
ATOM    486  CG  PHE A 373      23.950 -13.236  30.303  1.00 43.12           C
ATOM    487  CD1 PHE A 373      24.689 -13.358  31.467  1.00 45.48           C
ATOM    488  CD2 PHE A 373      24.170 -14.146  29.273  1.00 46.57           C
ATOM    489  CE1 PHE A 373      25.611 -14.378  31.619  1.00 52.03           C
ATOM    490  CE2 PHE A 373      25.101 -15.162  29.416  1.00 49.07           C
ATOM    491  CZ  PHE A 373      25.820 -15.266  30.584  1.00 49.72           C
ATOM    492  N   ASP A 374      20.468 -10.304  31.152  1.00 26.27           N
ATOM    493  CA  ASP A 374      19.704  -9.061  30.891  1.00 29.02           C
ATOM    494  C   ASP A 374      19.705  -8.212  32.177  1.00 33.83           C
ATOM    495  O   ASP A 374      19.921  -6.991  32.125  1.00 28.99           O
ATOM    496  CB  ASP A 374      18.300  -9.313  30.398  1.00 32.07           C
ATOM    497  CG  ASP A 374      18.189  -9.669  28.906  1.00 41.32           C
ATOM    498  OD1 ASP A 374      19.188  -9.555  28.161  1.00 40.18           O
ATOM    499  OD2 ASP A 374      17.086 -10.089  28.467  1.00 39.38           O
ATOM    500  N   GLN A 375      19.591  -8.865  33.347  1.00 32.60           N
ATOM    501  CA  GLN A 375      19.608  -8.071  34.583  1.00 31.64           C
ATOM    502  C   GLN A 375      20.916  -7.333  34.726  1.00 30.67           C
ATOM    503  O   GLN A 375      20.870  -6.138  35.028  1.00 25.21           O
ATOM    504  CB  GLN A 375      19.352  -8.889  35.868  1.00 32.73           C
ATOM    505  CG  GLN A 375      17.995  -9.549  35.848  1.00 26.43           C
ATOM    506  CD  GLN A 375      17.776 -10.429  37.077  1.00 37.35           C
ATOM    507  OE1 GLN A 375      18.178 -10.067  38.176  1.00 37.23           O
ATOM    508  NE2 GLN A 375      17.123 -11.571  36.895  1.00 32.94           N
ATOM    509  N   VAL A 376      22.037  -8.009  34.515  1.00 26.87           N
ATOM    510  CA  VAL A 376      23.342  -7.387  34.620  1.00 29.51           C
ATOM    511  C   VAL A 376      23.603  -6.347  33.546  1.00 28.83           C
ATOM    512  O   VAL A 376      24.160  -5.246  33.774  1.00 27.40           O
ATOM    513  CB  VAL A 376      24.406  -8.503  34.672  1.00 32.02           C
ATOM    514  CG1 VAL A 376      25.813  -7.968  34.697  1.00 26.56           C
ATOM    515  CG2 VAL A 376      24.140  -9.362  35.927  1.00 35.02           C
ATOM    516  N   ARG A 377      23.206  -6.612  32.296  1.00 25.73           N
ATOM    517  CA  ARG A 377      23.455  -5.585  31.270  1.00 27.53           C
ATOM    518  C   ARG A 377      22.663  -4.309  31.596  1.00 23.06           C
ATOM    519  O   ARG A 377      23.199  -3.217  31.349  1.00 25.17           O
ATOM    520  CB  ARG A 377      23.134  -6.117  29.895  1.00 34.14           C
ATOM    521  CG  ARG A 377      21.735  -5.910  29.433  1.00 40.47           C
ATOM    522  CD  ARG A 377      21.572  -5.937  27.920  1.00 48.13           C
ATOM    523  NE  ARG A 377      20.220  -6.455  27.686  1.00 45.66           N
ATOM    524  CZ  ARG A 377      19.401  -5.929  26.796  1.00 53.53           C
ATOM    525  NH1 ARG A 377      18.208  -6.486  26.676  1.00 51.20           N
ATOM    526  NH2 ARG A 377      19.793  -4.873  26.093  1.00 55.56           N
ATOM    527  N   LEU A 378      21.418  -4.443  31.991  1.00 22.82           N
ATOM    528  CA  LEU A 378      20.599  -3.260  32.361  1.00 22.74           C
ATOM    529  C   LEU A 378      21.273  -2.443  33.483  1.00 20.13           C
ATOM    530  O   LEU A 378      21.502  -1.230  33.334  1.00 24.01           O
ATOM    531  CB  LEU A 378      19.172  -3.599  32.766  1.00 21.48           C
ATOM    532  CG  LEU A 378      18.322  -4.303  31.691  1.00 26.61           C
```

FIG. 2G

```
ATOM    533  CD1 LEU A 378      16.974  -4.747  32.179  1.00 25.18           C
ATOM    534  CD2 LEU A 378      18.156  -3.326  30.516  1.00 26.44           C
ATOM    535  N   LEU A 379      21.623  -3.098  34.582  1.00 23.21           N
ATOM    536  CA  LEU A 379      22.258  -2.379  35.694  1.00 23.26           C
ATOM    537  C   LEU A 379      23.589  -1.746  35.352  1.00 24.40           C
ATOM    538  O   LEU A 379      23.889  -0.596  35.669  1.00 21.75           O
ATOM    539  CB  LEU A 379      22.463  -3.314  36.893  1.00 20.84           C
ATOM    540  CG  LEU A 379      21.188  -3.651  37.669  1.00 24.99           C
ATOM    541  CD1 LEU A 379      21.460  -4.962  38.405  1.00 24.61           C
ATOM    542  CD2 LEU A 379      20.694  -2.570  38.597  1.00 27.69           C
ATOM    543  N   GLU A 380      24.415  -2.461  34.539  1.00 24.06           N
ATOM    544  CA  GLU A 380      25.714  -1.922  34.173  1.00 25.95           C
ATOM    545  C   GLU A 380      25.571  -0.678  33.311  1.00 25.00           C
ATOM    546  O   GLU A 380      26.337   0.267  33.415  1.00 27.21           O
ATOM    547  CB  GLU A 380      26.467  -3.046  33.416  1.00 35.58           C
ATOM    548  CG  GLU A 380      27.815  -2.632  32.866  1.00 43.85           C
ATOM    549  CD  GLU A 380      28.719  -2.197  34.012  1.00 50.26           C
ATOM    550  OE1 GLU A 380      29.012  -2.992  34.923  1.00 50.00           O
ATOM    551  OE2 GLU A 380      29.079  -1.015  33.949  1.00 52.17           O
ATOM    552  N   SER A 381      24.559  -0.692  32.421  1.00 22.96           N
ATOM    553  CA  SER A 381      24.391   0.472  31.597  1.00 20.93           C
ATOM    554  C   SER A 381      23.796   1.718  32.260  1.00 22.00           C
ATOM    555  O   SER A 381      24.076   2.802  31.757  1.00 25.94           O
ATOM    556  CB  SER A 381      23.427   0.135  30.443  1.00 26.35           C
ATOM    557  OG  SER A 381      23.369   1.319  29.665  1.00 41.12           O
ATOM    558  N   CYS A 382      22.991   1.574  33.279  1.00 19.49           N
ATOM    559  CA  CYS A 382      22.268   2.746  33.789  1.00 20.72           C
ATOM    560  C   CYS A 382      22.649   3.184  35.179  1.00 20.55           C
ATOM    561  O   CYS A 382      22.032   4.173  35.591  1.00 18.26           O
ATOM    562  CB  CYS A 382      20.784   2.232  33.926  1.00 20.19           C
ATOM    563  SG  CYS A 382      20.419   1.235  35.363  1.00 23.70           S
ATOM    564  N   TRP A 383      23.692   2.615  35.831  1.00 16.62           N
ATOM    565  CA  TRP A 383      23.714   2.980  37.265  1.00 17.45           C
ATOM    566  C   TRP A 383      24.047   4.435  37.510  1.00 17.92           C
ATOM    567  O   TRP A 383      23.395   5.063  38.383  1.00 17.80           O
ATOM    568  CB  TRP A 383      24.667   2.020  38.033  1.00 18.03           C
ATOM    569  CG  TRP A 383      26.081   2.031  37.564  1.00 20.65           C
ATOM    570  CD1 TRP A 383      26.642   1.181  36.616  1.00 18.50           C
ATOM    571  CD2 TRP A 383      27.125   2.928  37.985  1.00 18.96           C
ATOM    572  NE1 TRP A 383      27.979   1.540  36.470  1.00 19.72           N
ATOM    573  CE2 TRP A 383      28.293   2.585  37.289  1.00 22.08           C
ATOM    574  CE3 TRP A 383      27.160   4.002  38.915  1.00 18.46           C
ATOM    575  CZ2 TRP A 383      29.484   3.321  37.430  1.00 22.38           C
ATOM    576  CZ3 TRP A 383      28.309   4.725  39.045  1.00 22.44           C
ATOM    577  CH2 TRP A 383      29.483   4.358  38.328  1.00 23.23           C
ATOM    578  N   MET A 384      24.955   5.020  36.711  1.00 14.97           N
ATOM    579  CA  MET A 384      25.254   6.450  37.001  1.00 15.11           C
ATOM    580  C   MET A 384      24.024   7.290  36.691  1.00 16.51           C
ATOM    581  O   MET A 384      23.729   8.291  37.354  1.00 14.18           O
ATOM    582  CB  MET A 384      26.519   6.912  36.267  1.00 20.28           C
ATOM    583  CG  MET A 384      26.749   8.399  36.546  1.00 19.66           C
ATOM    584  SD  MET A 384      27.340   8.718  38.232  1.00 19.34           S
ATOM    585  CE  MET A 384      29.061   8.231  38.081  1.00 19.18           C
ATOM    586  N   GLU A 385      23.271   6.910  35.638  1.00 14.74           N
ATOM    587  CA  GLU A 385      22.051   7.674  35.297  1.00 15.30           C
ATOM    588  C   GLU A 385      20.996   7.593  36.411  1.00 15.06           C
ATOM    589  O   GLU A 385      20.308   8.573  36.682  1.00 16.82           O
ATOM    590  CB  GLU A 385      21.445   7.258  33.915  1.00 18.49           C
ATOM    591  CG  GLU A 385      20.565   8.409  33.347  1.00 21.96           C
ATOM    592  CD  GLU A 385      19.946   8.069  32.000  1.00 29.86           C
ATOM    593  OE1 GLU A 385      20.470   7.169  31.267  1.00 21.88           O
ATOM    594  OE2 GLU A 385      18.913   8.711  31.676  1.00 30.28           O
ATOM    595  N   VAL A 386      20.846   6.400  36.972  1.00 16.06           N
ATOM    596  CA  VAL A 386      19.838   6.276  38.070  1.00 15.50           C
ATOM    597  C   VAL A 386      20.265   7.075  39.250  1.00 16.51           C
ATOM    598  O   VAL A 386      19.470   7.747  39.926  1.00 17.88           O
ATOM    599  CB  VAL A 386      19.719   4.793  38.408  1.00 15.13           C
ATOM    600  CG1 VAL A 386      18.872   4.559  39.647  1.00 17.57           C
ATOM    601  CG2 VAL A 386      19.005   4.159  37.192  1.00 20.15           C
ATOM    602  N   LEU A 387      21.573   6.938  39.608  1.00 14.70           N
ATOM    603  CA  LEU A 387      22.059   7.752  40.744  1.00 15.55           C
ATOM    604  C   LEU A 387      21.773   9.225  40.466  1.00 15.84           C
ATOM    605  O   LEU A 387      21.360   9.916  41.401  1.00 19.29           O
ATOM    606  CB  LEU A 387      23.592   7.579  40.850  1.00 14.14           C
ATOM    607  CG  LEU A 387      24.058   6.259  41.474  1.00 15.59           C
ATOM    608  CD1 LEU A 387      25.617   6.319  41.591  1.00 16.49           C
ATOM    609  CD2 LEU A 387      23.356   5.939  42.802  1.00 19.80           C
```

FIG. 2H

| ATOM | 610 | N | MET A 388 | 22.057 | 9.734 | 39.250 | 1.00 | 14.43 | N |
|------|-----|-----|-----------|--------|--------|--------|------|-------|---|
| ATOM | 611 | CA | MET A 388 | 21.900 | 11.185 | 39.015 | 1.00 | 15.37 | C |
| ATOM | 612 | C | MET A 388 | 20.447 | 11.530 | 38.940 | 1.00 | 15.03 | C |
| ATOM | 613 | O | MET A 388 | 20.058 | 12.648 | 39.466 | 1.00 | 16.31 | O |
| ATOM | 614 | CB | MET A 388 | 22.598 | 11.558 | 37.691 | 1.00 | 13.28 | C |
| ATOM | 615 | CG | MET A 388 | 24.134 | 11.508 | 37.914 | 1.00 | 16.22 | C |
| ATOM | 616 | SD | MET A 388 | 24.930 | 12.007 | 36.345 | 1.00 | 15.49 | S |
| ATOM | 617 | CE | MET A 388 | 26.537 | 12.485 | 36.996 | 1.00 | 17.90 | C |
| ATOM | 618 | N | MET A 389 | 19.617 | 10.631 | 38.473 | 1.00 | 12.07 | N |
| ATOM | 619 | CA | MET A 389 | 18.131 | 10.977 | 38.496 | 1.00 | 16.42 | C |
| ATOM | 620 | C | MET A 389 | 17.675 | 11.200 | 39.947 | 1.00 | 18.92 | C |
| ATOM | 621 | O | MET A 389 | 16.902 | 12.135 | 40.261 | 1.00 | 17.10 | O |
| ATOM | 622 | CB | MET A 389 | 17.327 | 9.898 | 37.804 | 1.00 | 16.48 | C |
| ATOM | 623 | CG | MET A 389 | 15.804 | 10.185 | 37.609 | 1.00 | 20.74 | C |
| ATOM | 624 | SD | MET A 389 | 15.549 | 11.620 | 36.521 | 1.00 | 21.26 | S |
| ATOM | 625 | CE | MET A 389 | 14.006 | 12.304 | 37.143 | 1.00 | 31.58 | C |
| ATOM | 626 | N | GLY A 390 | 18.124 | 10.306 | 40.839 | 1.00 | 19.95 | N |
| ATOM | 627 | CA | GLY A 390 | 17.755 | 10.442 | 42.274 | 1.00 | 19.62 | C |
| ATOM | 628 | C | GLY A 390 | 18.298 | 11.763 | 42.831 | 1.00 | 24.49 | C |
| ATOM | 629 | O | GLY A 390 | 17.603 | 12.480 | 43.574 | 1.00 | 21.09 | O |
| ATOM | 630 | N | LEU A 391 | 19.539 | 12.120 | 42.484 | 1.00 | 17.24 | N |
| ATOM | 631 | CA | LEU A 391 | 20.106 | 13.363 | 42.942 | 1.00 | 18.33 | C |
| ATOM | 632 | C | LEU A 391 | 19.252 | 14.546 | 42.476 | 1.00 | 18.46 | C |
| ATOM | 633 | O | LEU A 391 | 19.054 | 15.541 | 43.203 | 1.00 | 19.59 | O |
| ATOM | 634 | CB | LEU A 391 | 21.505 | 13.511 | 42.329 | 1.00 | 15.42 | C |
| ATOM | 635 | CG | LEU A 391 | 22.244 | 14.833 | 42.480 | 1.00 | 15.46 | C |
| ATOM | 636 | CD1 | LEU A 391 | 22.499 | 15.155 | 43.968 | 1.00 | 23.19 | C |
| ATOM | 637 | CD2 | LEU A 391 | 23.600 | 14.728 | 41.777 | 1.00 | 17.31 | C |
| ATOM | 638 | N | MET A 392 | 18.862 | 14.513 | 41.199 | 1.00 | 15.68 | N |
| ATOM | 639 | CA | MET A 392 | 18.091 | 15.642 | 40.650 | 1.00 | 18.68 | C |
| ATOM | 640 | C | MET A 392 | 16.770 | 15.763 | 41.383 | 1.00 | 20.62 | C |
| ATOM | 641 | O | MET A 392 | 16.405 | 16.876 | 41.784 | 1.00 | 19.69 | O |
| ATOM | 642 | CB | MET A 392 | 17.873 | 15.414 | 39.153 | 1.00 | 19.75 | C |
| ATOM | 643 | CG | MET A 392 | 19.179 | 15.445 | 38.372 | 1.00 | 22.97 | C |
| ATOM | 644 | SD | MET A 392 | 18.739 | 15.196 | 36.596 | 1.00 | 24.98 | S |
| ATOM | 645 | CE | MET A 392 | 20.397 | 15.422 | 35.940 | 1.00 | 25.59 | C |
| ATOM | 646 | N | TRP A 393 | 16.113 | 14.616 | 41.589 | 1.00 | 18.58 | N |
| ATOM | 647 | CA | TRP A 393 | 14.877 | 14.673 | 42.386 | 1.00 | 24.71 | C |
| ATOM | 648 | C | TRP A 393 | 15.124 | 15.209 | 43.802 | 1.00 | 26.53 | C |
| ATOM | 649 | O | TRP A 393 | 14.279 | 16.016 | 44.283 | 1.00 | 25.74 | O |
| ATOM | 650 | CB | TRP A 393 | 14.243 | 13.287 | 42.476 | 1.00 | 21.18 | C |
| ATOM | 651 | CG | TRP A 393 | 13.059 | 13.235 | 43.404 | 1.00 | 24.40 | C |
| ATOM | 652 | CD1 | TRP A 393 | 13.005 | 12.632 | 44.621 | 1.00 | 27.20 | C |
| ATOM | 653 | CD2 | TRP A 393 | 11.776 | 13.838 | 43.164 | 1.00 | 25.32 | C |
| ATOM | 654 | NE1 | TRP A 393 | 11.746 | 12.830 | 45.186 | 1.00 | 26.36 | N |
| ATOM | 655 | CE2 | TRP A 393 | 10.993 | 13.572 | 44.304 | 1.00 | 26.02 | C |
| ATOM | 656 | CE3 | TRP A 393 | 11.232 | 14.584 | 42.116 | 1.00 | 24.98 | C |
| ATOM | 657 | CZ2 | TRP A 393 | 9.671 | 14.005 | 44.408 | 1.00 | 26.15 | C |
| ATOM | 658 | CZ3 | TRP A 393 | 9.879 | 15.004 | 42.195 | 1.00 | 26.45 | C |
| ATOM | 659 | CH2 | TRP A 393 | 9.148 | 14.720 | 43.368 | 1.00 | 28.96 | C |
| ATOM | 660 | N | ARG A 394 | 16.175 | 14.790 | 44.508 | 1.00 | 21.62 | N |
| ATOM | 661 | CA | ARG A 394 | 16.427 | 15.299 | 45.869 | 1.00 | 20.86 | C |
| ATOM | 662 | C | ARG A 394 | 16.740 | 16.786 | 45.833 | 1.00 | 24.67 | C |
| ATOM | 663 | O | ARG A 394 | 16.496 | 17.528 | 46.796 | 1.00 | 23.01 | O |
| ATOM | 664 | CB | ARG A 394 | 17.623 | 14.563 | 46.533 | 1.00 | 18.23 | C |
| ATOM | 665 | CG | ARG A 394 | 17.184 | 13.127 | 46.915 | 1.00 | 22.23 | C |
| ATOM | 666 | CD | ARG A 394 | 18.268 | 12.424 | 47.731 | 1.00 | 21.34 | C |
| ATOM | 667 | NE | ARG A 394 | 19.583 | 12.406 | 47.096 | 1.00 | 22.33 | N |
| ATOM | 668 | CZ | ARG A 394 | 19.990 | 11.465 | 46.204 | 1.00 | 18.45 | C |
| ATOM | 669 | NH1 | ARG A 394 | 19.128 | 10.506 | 45.872 | 1.00 | 19.75 | N |
| ATOM | 670 | NH2 | ARG A 394 | 21.240 | 11.562 | 45.776 | 1.00 | 19.94 | N |
| ATOM | 671 | N | SER A 395 | 17.255 | 17.320 | 44.742 | 1.00 | 21.15 | N |
| ATOM | 672 | CA | SER A 395 | 17.635 | 18.714 | 44.635 | 1.00 | 21.44 | C |
| ATOM | 673 | C | SER A 395 | 16.584 | 19.641 | 44.025 | 1.00 | 19.15 | C |
| ATOM | 674 | O | SER A 395 | 16.879 | 20.820 | 43.832 | 1.00 | 23.10 | O |
| ATOM | 675 | CB | SER A 395 | 18.892 | 18.684 | 43.718 | 1.00 | 18.04 | C |
| ATOM | 676 | OG | SER A 395 | 19.875 | 17.836 | 44.335 | 1.00 | 18.21 | O |
| ATOM | 677 | N | ILE A 396 | 15.440 | 19.141 | 43.684 | 1.00 | 19.81 | N |
| ATOM | 678 | CA | ILE A 396 | 14.453 | 19.950 | 42.942 | 1.00 | 24.62 | C |
| ATOM | 679 | C | ILE A 396 | 14.005 | 21.237 | 43.614 | 1.00 | 27.35 | C |
| ATOM | 680 | O | ILE A 396 | 13.937 | 22.268 | 42.954 | 1.00 | 28.08 | O |
| ATOM | 681 | CB | ILE A 396 | 13.332 | 18.975 | 42.576 | 1.00 | 31.97 | C |
| ATOM | 682 | CG1 | ILE A 396 | 12.714 | 19.384 | 41.243 | 1.00 | 35.67 | C |
| ATOM | 683 | CG2 | ILE A 396 | 12.331 | 18.782 | 43.701 | 1.00 | 34.39 | C |
| ATOM | 684 | CD1 | ILE A 396 | 11.807 | 18.343 | 40.594 | 1.00 | 31.62 | C |
| ATOM | 685 | N | ASP A 397 | 13.775 | 21.172 | 44.899 | 1.00 | 27.38 | N |
| ATOM | 686 | CA | ASP A 397 | 13.317 | 22.305 | 45.726 | 1.00 | 30.34 | C |

FIG. 21

| | | | | | | | | | | |
|---|---|---|---|---|---|---|---|---|---|---|
| ATOM | 687 | C | ASP | A | 397 | 14.452 | 23.046 | 46.363 | 1.00 33.09 | C |
| ATOM | 688 | O | ASP | A | 397 | 14.280 | 23.798 | 47.336 | 1.00 33.75 | O |
| ATOM | 689 | CB | ASP | A | 397 | 12.426 | 21.706 | 46.827 | 1.00 31.40 | C |
| ATOM | 690 | CG | ASP | A | 397 | 11.165 | 21.107 | 46.262 | 1.00 34.81 | C |
| ATOM | 691 | OD1 | ASP | A | 397 | 10.711 | 21.642 | 45.238 | 1.00 36.72 | O |
| ATOM | 692 | OD2 | ASP | A | 397 | 10.636 | 20.123 | 46.799 | 1.00 42.07 | O |
| ATOM | 693 | N | HIS | A | 398 | 15.690 | 22.885 | 45.876 | 1.00 26.91 | N |
| ATOM | 694 | CA | HIS | A | 398 | 16.869 | 23.510 | 46.427 | 1.00 31.70 | C |
| ATOM | 695 | C | HIS | A | 398 | 17.772 | 24.132 | 45.405 | 1.00 27.69 | C |
| ATOM | 696 | O | HIS | A | 398 | 18.930 | 23.699 | 45.195 | 1.00 31.30 | O |
| ATOM | 697 | CB | HIS | A | 398 | 17.627 | 22.505 | 47.331 | 1.00 32.19 | C |
| ATOM | 698 | CG | HIS | A | 398 | 16.875 | 21.918 | 48.488 | 1.00 35.05 | C |
| ATOM | 699 | ND1 | HIS | A | 398 | 16.304 | 20.677 | 48.504 | 1.00 33.32 | N |
| ATOM | 700 | CD2 | HIS | A | 398 | 16.575 | 22.452 | 49.696 | 1.00 30.34 | C |
| ATOM | 701 | CE1 | HIS | A | 398 | 15.690 | 20.447 | 49.661 | 1.00 34.45 | C |
| ATOM | 702 | NE2 | HIS | A | 398 | 15.853 | 21.527 | 50.409 | 1.00 37.51 | N |
| ATOM | 703 | N | PRO | A | 399 | 17.345 | 25.183 | 44.713 | 1.00 33.73 | N |
| ATOM | 704 | CA | PRO | A | 399 | 18.144 | 25.898 | 43.752 | 1.00 29.82 | C |
| ATOM | 705 | C | PRO | A | 399 | 19.549 | 26.216 | 44.223 | 1.00 33.25 | C |
| ATOM | 706 | O | PRO | A | 399 | 19.766 | 26.630 | 45.365 | 1.00 33.94 | O |
| ATOM | 707 | CB | PRO | A | 399 | 17.431 | 27.225 | 43.481 | 1.00 34.26 | C |
| ATOM | 708 | CG | PRO | A | 399 | 16.273 | 27.257 | 44.391 | 1.00 34.08 | C |
| ATOM | 709 | CD | PRO | A | 399 | 16.032 | 25.857 | 44.891 | 1.00 33.97 | C |
| ATOM | 710 | N | GLY | A | 400 | 20.500 | 25.996 | 43.336 | 1.00 28.90 | N |
| ATOM | 711 | CA | GLY | A | 400 | 21.921 | 26.254 | 43.561 | 1.00 29.24 | C |
| ATOM | 712 | C | GLY | A | 400 | 22.590 | 25.173 | 44.418 | 1.00 25.18 | C |
| ATOM | 713 | O | GLY | A | 400 | 23.787 | 25.298 | 44.704 | 1.00 27.24 | O |
| ATOM | 714 | N | LYS | A | 401 | 21.860 | 24.150 | 44.863 | 1.00 25.56 | N |
| ATOM | 715 | CA | LYS | A | 401 | 22.470 | 23.122 | 45.672 | 1.00 26.68 | C |
| ATOM | 716 | C | LYS | A | 401 | 22.286 | 21.688 | 45.064 | 1.00 20.20 | C |
| ATOM | 717 | O | LYS | A | 401 | 21.296 | 21.465 | 44.391 | 1.00 24.95 | O |
| ATOM | 718 | CB | LYS | A | 401 | 21.635 | 22.912 | 46.955 | 1.00 30.94 | C |
| ATOM | 719 | CG | LYS | A | 401 | 21.844 | 23.694 | 48.203 | 1.00 43.57 | C |
| ATOM | 720 | CD | LYS | A | 401 | 22.115 | 25.154 | 48.045 | 1.00 45.37 | C |
| ATOM | 721 | CE | LYS | A | 401 | 22.201 | 25.882 | 49.389 | 1.00 48.67 | C |
| ATOM | 722 | NZ | LYS | A | 401 | 20.883 | 26.446 | 49.784 | 1.00 51.08 | N |
| ATOM | 723 | N | LEU | A | 402 | 23.267 | 20.878 | 45.374 | 1.00 20.86 | N |
| ATOM | 724 | CA | LEU | A | 402 | 23.112 | 19.446 | 44.987 | 1.00 22.31 | C |
| ATOM | 725 | C | LEU | A | 402 | 22.957 | 18.664 | 46.275 | 1.00 21.03 | C |
| ATOM | 726 | O | LEU | A | 402 | 23.914 | 18.555 | 47.078 | 1.00 19.36 | O |
| ATOM | 727 | CB | LEU | A | 402 | 24.288 | 19.025 | 44.112 | 1.00 18.88 | C |
| ATOM | 728 | CG | LEU | A | 402 | 24.207 | 19.596 | 42.679 | 1.00 20.75 | C |
| ATOM | 729 | CD1 | LEU | A | 402 | 25.487 | 19.208 | 41.954 | 1.00 23.26 | C |
| ATOM | 730 | CD2 | LEU | A | 402 | 23.011 | 19.057 | 41.840 | 1.00 22.84 | C |
| ATOM | 731 | N | ILE | A | 403 | 21.760 | 18.072 | 46.414 | 1.00 19.33 | N |
| ATOM | 732 | CA | ILE | A | 403 | 21.468 | 17.280 | 47.619 | 1.00 19.55 | C |
| ATOM | 733 | C | ILE | A | 403 | 21.916 | 15.809 | 47.407 | 1.00 20.88 | C |
| ATOM | 734 | O | ILE | A | 403 | 21.112 | 14.947 | 47.151 | 1.00 20.74 | O |
| ATOM | 735 | CB | ILE | A | 403 | 20.006 | 17.287 | 48.022 | 1.00 20.45 | C |
| ATOM | 736 | CG1 | ILE | A | 403 | 19.419 | 18.695 | 48.148 | 1.00 28.69 | C |
| ATOM | 737 | CG2 | ILE | A | 403 | 19.785 | 16.535 | 49.355 | 1.00 25.33 | C |
| ATOM | 738 | CD1 | ILE | A | 403 | 20.234 | 19.713 | 48.883 | 1.00 32.71 | C |
| ATOM | 739 | N | PHE | A | 404 | 23.216 | 15.587 | 47.603 | 1.00 22.57 | N |
| ATOM | 740 | CA | PHE | A | 404 | 23.745 | 14.250 | 47.395 | 1.00 23.38 | C |
| ATOM | 741 | C | PHE | A | 404 | 23.132 | 13.275 | 48.383 | 1.00 23.34 | C |
| ATOM | 742 | O | PHE | A | 404 | 22.779 | 12.120 | 48.095 | 1.00 23.60 | O |
| ATOM | 743 | CB | PHE | A | 404 | 25.284 | 14.338 | 47.413 | 1.00 21.32 | C |
| ATOM | 744 | CG | PHE | A | 404 | 25.845 | 14.745 | 46.053 | 1.00 22.32 | C |
| ATOM | 745 | CD1 | PHE | A | 404 | 26.195 | 16.065 | 45.825 | 1.00 20.75 | C |
| ATOM | 746 | CD2 | PHE | A | 404 | 26.003 | 13.816 | 45.024 | 1.00 21.33 | C |
| ATOM | 747 | CE1 | PHE | A | 404 | 26.704 | 16.480 | 44.603 | 1.00 19.07 | C |
| ATOM | 748 | CE2 | PHE | A | 404 | 26.479 | 14.227 | 43.802 | 1.00 20.69 | C |
| ATOM | 749 | CZ | PHE | A | 404 | 26.871 | 15.550 | 43.573 | 1.00 20.96 | C |
| ATOM | 750 | N | ALA | A | 405 | 23.051 | 13.741 | 49.614 | 1.00 23.85 | N |
| ATOM | 751 | CA | ALA | A | 405 | 22.409 | 13.027 | 50.715 | 1.00 26.71 | C |
| ATOM | 752 | C | ALA | A | 405 | 21.900 | 14.100 | 51.676 | 1.00 28.50 | C |
| ATOM | 753 | O | ALA | A | 405 | 22.384 | 15.235 | 51.720 | 1.00 25.10 | O |
| ATOM | 754 | CB | ALA | A | 405 | 23.337 | 12.063 | 51.417 | 1.00 25.68 | C |
| ATOM | 755 | N | PRO | A | 406 | 20.986 | 13.724 | 52.568 | 1.00 32.52 | N |
| ATOM | 756 | CA | PRO | A | 406 | 20.427 | 14.651 | 53.539 | 1.00 37.50 | C |
| ATOM | 757 | C | PRO | A | 406 | 21.459 | 15.439 | 54.322 | 1.00 34.45 | C |
| ATOM | 758 | O | PRO | A | 406 | 21.222 | 16.618 | 54.615 | 1.00 34.95 | O |
| ATOM | 759 | CB | PRO | A | 406 | 19.464 | 13.803 | 54.362 | 1.00 37.05 | C |
| ATOM | 760 | CG | PRO | A | 406 | 19.075 | 12.711 | 53.424 | 1.00 35.58 | C |
| ATOM | 761 | CD | PRO | A | 406 | 20.321 | 12.409 | 52.623 | 1.00 35.62 | C |
| ATOM | 762 | N | ASP | A | 407 | 22.589 | 14.836 | 54.642 | 1.00 36.25 | N |
| ATOM | 763 | CA | ASP | A | 407 | 23.669 | 15.532 | 55.325 | 1.00 37.74 | C |

FIG. 2J

```
ATOM    764  C   ASP A 407      24.942  15.713  54.485  1.00 35.68           C
ATOM    765  O   ASP A 407      26.067  15.939  54.972  1.00 35.16           O
ATOM    766  CB  ASP A 407      23.951  14.837  56.658  1.00 45.22           C
ATOM    767  CG  ASP A 407      24.683  15.756  57.615  1.00 51.47           C
ATOM    768  OD1 ASP A 407      24.752  16.972  57.337  1.00 53.42           O
ATOM    769  OD2 ASP A 407      25.206  15.264  58.640  1.00 56.11           O
ATOM    770  N   LEU A 408      24.780  15.623  53.155  1.00 31.91           N
ATOM    771  CA  LEU A 408      25.846  15.841  52.181  1.00 28.65           C
ATOM    772  C   LEU A 408      25.291  16.787  51.117  1.00 33.12           C
ATOM    773  O   LEU A 408      24.960  16.416  49.990  1.00 29.33           O
ATOM    774  CB  LEU A 408      26.393  14.590  51.522  1.00 31.43           C
ATOM    775  CG  LEU A 408      27.607  14.813  50.592  1.00 33.95           C
ATOM    776  CD1 LEU A 408      28.719  15.544  51.340  1.00 38.24           C
ATOM    777  CD2 LEU A 408      28.093  13.493  50.021  1.00 35.82           C
ATOM    778  N   VAL A 409      25.111  18.046  51.500  1.00 28.59           N
ATOM    779  CA  VAL A 409      24.521  19.044  50.608  1.00 29.53           C
ATOM    780  C   VAL A 409      25.595  19.925  50.021  1.00 35.26           C
ATOM    781  O   VAL A 409      26.304  20.606  50.769  1.00 37.91           O
ATOM    782  CB  VAL A 409      23.498  19.864  51.412  1.00 32.96           C
ATOM    783  CG1 VAL A 409      22.890  20.993  50.603  1.00 31.95           C
ATOM    784  CG2 VAL A 409      22.430  18.950  51.974  1.00 30.22           C
ATOM    785  N   LEU A 410      25.821  19.922  48.706  1.00 27.77           N
ATOM    786  CA  LEU A 410      26.842  20.773  48.118  1.00 28.83           C
ATOM    787  C   LEU A 410      26.298  22.004  47.435  1.00 36.39           C
ATOM    788  O   LEU A 410      25.299  21.967  46.711  1.00 30.29           O
ATOM    789  CB  LEU A 410      27.768  20.016  47.156  1.00 32.95           C
ATOM    790  CG  LEU A 410      28.396  18.710  47.612  1.00 36.56           C
ATOM    791  CD1 LEU A 410      29.505  18.242  46.683  1.00 34.98           C
ATOM    792  CD2 LEU A 410      28.902  18.749  49.045  1.00 41.39           C
ATOM    793  N   ASP A 411      26.938  23.164  47.686  1.00 33.11           N
ATOM    794  CA  ASP A 411      26.539  24.350  46.933  1.00 34.05           C
ATOM    795  C   ASP A 411      27.299  24.255  45.600  1.00 29.65           C
ATOM    796  O   ASP A 411      28.419  23.727  45.543  1.00 30.84           O
ATOM    797  CB  ASP A 411      26.884  25.698  47.590  1.00 41.04           C
ATOM    798  CG  ASP A 411      25.865  26.016  48.674  1.00 49.46           C
ATOM    799  OD1 ASP A 411      25.986  25.474  49.792  1.00 56.56           O
ATOM    800  OD2 ASP A 411      24.919  26.778  48.410  1.00 55.40           O
ATOM    801  N   ARG A 412      26.745  24.819  44.558  1.00 31.76           N
ATOM    802  CA  ARG A 412      27.345  24.827  43.227  1.00 29.21           C
ATOM    803  C   ARG A 412      28.814  25.148  43.185  1.00 32.15           C
ATOM    804  O   ARG A 412      29.634  24.412  42.643  1.00 31.27           O
ATOM    805  CB  ARG A 412      26.552  25.852  42.363  1.00 32.70           C
ATOM    806  CG  ARG A 412      27.039  25.878  40.919  1.00 36.94           C
ATOM    807  CD  ARG A 412      28.132  26.912  40.680  1.00 42.09           C
ATOM    808  NE  ARG A 412      28.493  26.982  39.276  1.00 40.17           N
ATOM    809  CZ  ARG A 412      29.542  27.671  38.812  1.00 45.07           C
ATOM    810  NH1 ARG A 412      29.784  27.654  37.497  1.00 38.97           N
ATOM    811  NH2 ARG A 412      30.303  28.339  39.683  1.00 37.08           N
ATOM    812  N   ASP A 413      29.233  26.262  43.809  1.00 34.93           N
ATOM    813  CA  ASP A 413      30.622  26.701  43.828  1.00 40.84           C
ATOM    814  C   ASP A 413      31.593  25.749  44.469  1.00 36.09           C
ATOM    815  O   ASP A 413      32.796  25.792  44.201  1.00 37.87           O
ATOM    816  CB  ASP A 413      30.740  28.092  44.465  1.00 46.18           C
ATOM    817  CG  ASP A 413      30.199  29.197  43.580  1.00 51.56           C
ATOM    818  OD1 ASP A 413      30.090  29.017  42.345  1.00 54.10           O
ATOM    819  OD2 ASP A 413      29.872  30.278  44.130  1.00 53.78           O
ATOM    820  N   GLU A 414      31.171  24.776  45.271  1.00 36.43           N
ATOM    821  CA  GLU A 414      32.096  23.800  45.838  1.00 33.20           C
ATOM    822  C   GLU A 414      32.628  22.891  44.742  1.00 35.36           C
ATOM    823  O   GLU A 414      33.644  22.235  44.932  1.00 40.36           O
ATOM    824  CB  GLU A 414      31.491  23.040  46.993  1.00 38.12           C
ATOM    825  CG  GLU A 414      30.691  24.000  47.892  1.00 41.60           C
ATOM    826  CD  GLU A 414      30.377  23.195  49.151  1.00 42.56           C
ATOM    827  OE1 GLU A 414      29.182  23.012  49.394  1.00 39.90           O
ATOM    828  OE2 GLU A 414      31.360  22.790  49.793  1.00 44.66           O
ATOM    829  N   GLY A 415      32.085  22.926  43.536  1.00 34.58           N
ATOM    830  CA  GLY A 415      32.610  22.195  42.395  1.00 35.34           C
ATOM    831  C   GLY A 415      34.002  22.657  41.995  1.00 36.70           C
ATOM    832  O   GLY A 415      34.711  22.005  41.201  1.00 32.74           O
ATOM    833  N   LYS A 416      34.448  23.846  42.442  1.00 35.48           N
ATOM    834  CA  LYS A 416      35.776  24.340  42.108  1.00 35.85           C
ATOM    835  C   LYS A 416      36.869  23.525  42.794  1.00 37.60           C
ATOM    836  O   LYS A 416      38.023  23.520  42.370  1.00 35.22           O
ATOM    837  CB  LYS A 416      35.874  25.827  42.441  1.00 38.97           C
ATOM    838  CG  LYS A 416      34.861  26.691  41.670  1.00 47.16           C
ATOM    839  CD  LYS A 416      34.985  28.160  42.065  1.00 52.82           C
ATOM    840  CE  LYS A 416      33.891  29.049  41.509  1.00 54.67           C
```

FIG. 2K

```
ATOM    841  NZ   LYS A 416      34.253  29.728  40.235  1.00 61.17           N
ATOM    842  N    CYS A 417      36.549  22.700  43.777  1.00 37.57           N
ATOM    843  CA   CYS A 417      37.456  21.852  44.507  1.00 39.44           C
ATOM    844  C    CYS A 417      38.026  20.726  43.662  1.00 39.18           C
ATOM    845  O    CYS A 417      39.158  20.251  43.845  1.00 40.72           O
ATOM    846  CB   CYS A 417      36.732  21.280  45.758  1.00 41.41           C
ATOM    847  SG   CYS A 417      35.889  22.509  46.822  1.00 49.13           S
ATOM    848  N    VAL A 418      37.259  20.203  42.698  1.00 36.06           N
ATOM    849  CA   VAL A 418      37.639  19.067  41.878  1.00 31.96           C
ATOM    850  C    VAL A 418      37.823  19.509  40.426  1.00 29.98           C
ATOM    851  O    VAL A 418      36.963  20.136  39.835  1.00 29.54           O
ATOM    852  CB   VAL A 418      36.607  17.916  41.954  1.00 24.72           C
ATOM    853  CG1  VAL A 418      37.056  16.721  41.120  1.00 28.34           C
ATOM    854  CG2  VAL A 418      36.491  17.385  43.376  1.00 27.69           C
ATOM    855  N    GLU A 419      38.996  19.260  39.852  1.00 30.53           N
ATOM    856  CA   GLU A 419      39.222  19.705  38.486  1.00 27.70           C
ATOM    857  C    GLU A 419      38.127  19.138  37.565  1.00 28.75           C
ATOM    858  O    GLU A 419      37.973  17.920  37.644  1.00 25.87           O
ATOM    859  CB   GLU A 419      40.567  19.171  38.008  1.00 32.23           C
ATOM    860  CG   GLU A 419      40.880  19.646  36.586  1.00 40.70           C
ATOM    861  CD   GLU A 419      42.378  19.766  36.390  1.00 49.13           C
ATOM    862  OE1  GLU A 419      43.197  19.569  37.319  1.00 54.26           O
ATOM    863  OE2  GLU A 419      42.768  20.087  35.253  1.00 53.59           O
ATOM    864  N    GLY A 420      37.466  19.950  36.778  1.00 31.18           N
ATOM    865  CA   GLY A 420      36.492  19.450  35.807  1.00 27.93           C
ATOM    866  C    GLY A 420      35.122  19.080  36.355  1.00 33.09           C
ATOM    867  O    GLY A 420      34.249  18.794  35.504  1.00 28.63           O
ATOM    868  N    ILE A 421      34.902  19.073  37.666  1.00 24.94           N
ATOM    869  CA   ILE A 421      33.550  18.669  38.126  1.00 29.80           C
ATOM    870  C    ILE A 421      32.517  19.771  38.086  1.00 28.97           C
ATOM    871  O    ILE A 421      31.279  19.623  38.123  1.00 25.14           O
ATOM    872  CB   ILE A 421      33.628  18.004  39.500  1.00 27.62           C
ATOM    873  CG1  ILE A 421      32.670  16.788  39.594  1.00 24.09           C
ATOM    874  CG2  ILE A 421      33.307  19.021  40.589  1.00 25.66           C
ATOM    875  CD1  ILE A 421      32.796  16.062  40.920  1.00 26.64           C
ATOM    876  N    LEU A 422      32.974  21.033  38.058  1.00 29.20           N
ATOM    877  CA   LEU A 422      32.064  22.151  37.994  1.00 29.02           C
ATOM    878  C    LEU A 422      31.130  22.047  36.786  1.00 28.10           C
ATOM    879  O    LEU A 422      29.936  22.370  36.938  1.00 26.46           O
ATOM    880  CB   LEU A 422      32.832  23.474  37.990  1.00 34.57           C
ATOM    881  CG   LEU A 422      32.019  24.681  38.416  1.00 40.29           C
ATOM    882  CD1  LEU A 422      31.516  24.495  39.849  1.00 31.88           C
ATOM    883  CD2  LEU A 422      32.838  25.975  38.252  1.00 39.46           C
ATOM    884  N    GLU A 423      31.671  21.647  35.639  1.00 25.58           N
ATOM    885  CA   GLU A 423      30.835  21.486  34.431  1.00 29.62           C
ATOM    886  C    GLU A 423      29.725  20.452  34.679  1.00 28.25           C
ATOM    887  O    GLU A 423      28.595  20.664  34.252  1.00 27.19           O
ATOM    888  CB   GLU A 423      31.726  20.974  33.267  1.00 34.04           C
ATOM    889  CG   GLU A 423      31.029  20.644  31.973  1.00 44.60           C
ATOM    890  CD   GLU A 423      31.782  19.973  30.850  1.00 50.42           C
ATOM    891  OE1  GLU A 423      32.943  19.506  30.965  1.00 51.43           O
ATOM    892  OE2  GLU A 423      31.182  19.846  29.747  1.00 55.11           O
ATOM    893  N    ILE A 424      30.100  19.371  35.348  1.00 22.70           N
ATOM    894  CA   ILE A 424      29.183  18.289  35.705  1.00 20.28           C
ATOM    895  C    ILE A 424      28.161  18.831  36.706  1.00 20.01           C
ATOM    896  O    ILE A 424      26.968  18.612  36.533  1.00 18.93           O
ATOM    897  CB   ILE A 424      29.908  17.079  36.296  1.00 20.86           C
ATOM    898  CG1  ILE A 424      31.091  16.538  35.477  1.00 26.56           C
ATOM    899  CG2  ILE A 424      28.909  15.958  36.559  1.00 19.58           C
ATOM    900  CD1  ILE A 424      30.837  16.382  34.004  1.00 32.30           C
ATOM    901  N    PHE A 425      28.572  19.625  37.705  1.00 21.17           N
ATOM    902  CA   PHE A 425      27.563  20.165  38.618  1.00 22.12           C
ATOM    903  C    PHE A 425      26.562  21.060  37.921  1.00 23.84           C
ATOM    904  O    PHE A 425      25.358  21.088  38.232  1.00 20.50           O
ATOM    905  CB   PHE A 425      28.265  20.943  39.744  1.00 22.81           C
ATOM    906  CG   PHE A 425      28.866  20.061  40.816  1.00 24.91           C
ATOM    907  CD1  PHE A 425      28.974  18.689  40.724  1.00 20.45           C
ATOM    908  CD2  PHE A 425      29.312  20.649  41.986  1.00 24.78           C
ATOM    909  CE1  PHE A 425      29.536  17.906  41.701  1.00 22.48           C
ATOM    910  CE2  PHE A 425      29.849  19.888  42.999  1.00 26.28           C
ATOM    911  CZ   PHE A 425      29.958  18.527  42.866  1.00 28.92           C
ATOM    912  N    ASP A 426      27.088  21.901  37.013  1.00 24.52           N
ATOM    913  CA   ASP A 426      26.215  22.841  36.274  1.00 24.95           C
ATOM    914  C    ASP A 426      25.206  22.084  35.406  1.00 24.85           C
ATOM    915  O    ASP A 426      24.035  22.490  35.318  1.00 26.21           O
ATOM    916  CB   ASP A 426      27.115  23.764  35.443  1.00 24.42           C
ATOM    917  CG   ASP A 426      27.712  24.875  36.299  1.00 31.66           C
```

FIG. 2L

| ATOM | 918 | OD1 | ASP A 426 | 27.244 | 25.208 | 37.405 | 1.00 | 32.79 | O |
|------|-----|-----|-----------|--------|--------|--------|------|-------|---|
| ATOM | 919 | OD2 | ASP A 426 | 28.716 | 25.431 | 35.813 | 1.00 | 32.76 | O |
| ATOM | 920 | N | MET A 427 | 25.653 | 21.005 | 34.757 | 1.00 | 22.59 | N |
| ATOM | 921 | CA | MET A 427 | 24.719 | 20.177 | 33.979 | 1.00 | 23.55 | C |
| ATOM | 922 | C | MET A 427 | 23.619 | 19.572 | 34.871 | 1.00 | 22.77 | C |
| ATOM | 923 | O | MET A 427 | 22.426 | 19.571 | 34.511 | 1.00 | 22.13 | O |
| ATOM | 924 | CB | MET A 427 | 25.382 | 18.953 | 33.318 | 1.00 | 23.77 | C |
| ATOM | 925 | CG | MET A 427 | 26.166 | 19.216 | 32.058 | 1.00 | 39.26 | C |
| ATOM | 926 | SD | MET A 427 | 27.097 | 17.719 | 31.652 | 1.00 | 33.49 | S |
| ATOM | 927 | CE | MET A 427 | 28.487 | 18.460 | 30.795 | 1.00 | 41.30 | C |
| ATOM | 928 | N | LEU A 428 | 24.041 | 19.061 | 36.022 | 1.00 | 18.69 | N |
| ATOM | 929 | CA | LEU A 428 | 23.120 | 18.480 | 36.982 | 1.00 | 18.97 | C |
| ATOM | 930 | C | LEU A 428 | 22.129 | 19.543 | 37.489 | 1.00 | 22.36 | C |
| ATOM | 931 | O | LEU A 428 | 20.945 | 19.276 | 37.539 | 1.00 | 20.87 | O |
| ATOM | 932 | CB | LEU A 428 | 23.827 | 17.857 | 38.196 | 1.00 | 21.39 | C |
| ATOM | 933 | CG | LEU A 428 | 24.649 | 16.599 | 37.827 | 1.00 | 22.33 | C |
| ATOM | 934 | CD1 | LEU A 428 | 25.693 | 16.260 | 38.887 | 1.00 | 20.04 | C |
| ATOM | 935 | CD2 | LEU A 428 | 23.682 | 15.441 | 37.588 | 1.00 | 19.44 | C |
| ATOM | 936 | N | LEU A 429 | 22.616 | 20.730 | 37.858 | 1.00 | 20.75 | N |
| ATOM | 937 | CA | LEU A 429 | 21.684 | 21.752 | 38.345 | 1.00 | 21.34 | C |
| ATOM | 938 | C | LEU A 429 | 20.771 | 22.255 | 37.222 | 1.00 | 21.01 | C |
| ATOM | 939 | O | LEU A 429 | 19.608 | 22.572 | 37.484 | 1.00 | 22.84 | O |
| ATOM | 940 | CB | LEU A 429 | 22.576 | 22.910 | 38.843 | 1.00 | 22.26 | C |
| ATOM | 941 | CG | LEU A 429 | 23.274 | 22.672 | 40.180 | 1.00 | 28.42 | C |
| ATOM | 942 | CD1 | LEU A 429 | 24.433 | 23.668 | 40.299 | 1.00 | 25.07 | C |
| ATOM | 943 | CD2 | LEU A 429 | 22.287 | 22.730 | 41.331 | 1.00 | 29.09 | C |
| ATOM | 944 | N | ALA A 430 | 21.330 | 22.398 | 36.022 | 1.00 | 22.61 | N |
| ATOM | 945 | CA | ALA A 430 | 20.459 | 22.904 | 34.935 | 1.00 | 23.01 | C |
| ATOM | 946 | C | ALA A 430 | 19.324 | 21.949 | 34.623 | 1.00 | 22.28 | C |
| ATOM | 947 | O | ALA A 430 | 18.143 | 22.234 | 34.415 | 1.00 | 21.97 | O |
| ATOM | 948 | CB | ALA A 430 | 21.351 | 23.146 | 33.718 | 1.00 | 24.63 | C |
| ATOM | 949 | N | THR A 431 | 19.626 | 20.616 | 34.677 | 1.00 | 22.30 | N |
| ATOM | 950 | CA | THR A 431 | 18.598 | 19.631 | 34.408 | 1.00 | 19.73 | C |
| ATOM | 951 | C | THR A 431 | 17.553 | 19.549 | 35.498 | 1.00 | 20.90 | C |
| ATOM | 952 | O | THR A 431 | 16.355 | 19.408 | 35.286 | 1.00 | 21.68 | O |
| ATOM | 953 | CB | THR A 431 | 19.270 | 18.273 | 34.091 | 1.00 | 23.86 | C |
| ATOM | 954 | OG1 | THR A 431 | 20.179 | 18.438 | 33.003 | 1.00 | 22.73 | O |
| ATOM | 955 | CG2 | THR A 431 | 18.173 | 17.291 | 33.763 | 1.00 | 25.40 | C |
| ATOM | 956 | N | THR A 432 | 18.044 | 19.673 | 36.746 | 1.00 | 22.30 | N |
| ATOM | 957 | CA | THR A 432 | 17.171 | 19.702 | 37.910 | 1.00 | 21.09 | C |
| ATOM | 958 | C | THR A 432 | 16.233 | 20.907 | 37.751 | 1.00 | 22.21 | C |
| ATOM | 959 | O | THR A 432 | 15.047 | 20.780 | 38.056 | 1.00 | 21.87 | O |
| ATOM | 960 | CB | THR A 432 | 17.967 | 19.863 | 39.205 | 1.00 | 20.58 | C |
| ATOM | 961 | OG1 | THR A 432 | 18.805 | 18.708 | 39.393 | 1.00 | 19.56 | O |
| ATOM | 962 | CG2 | THR A 432 | 17.000 | 19.978 | 40.401 | 1.00 | 20.00 | C |
| ATOM | 963 | N | SER A 433 | 16.810 | 22.022 | 37.252 | 1.00 | 23.81 | N |
| ATOM | 964 | CA | SER A 433 | 15.898 | 23.187 | 37.068 | 1.00 | 24.78 | C |
| ATOM | 965 | C | SER A 433 | 14.819 | 22.920 | 36.033 | 1.00 | 27.00 | C |
| ATOM | 966 | O | SER A 433 | 13.665 | 23.358 | 36.191 | 1.00 | 33.54 | O |
| ATOM | 967 | CB | SER A 433 | 16.709 | 24.424 | 36.654 | 1.00 | 29.38 | C |
| ATOM | 968 | OG | SER A 433 | 17.674 | 24.752 | 37.647 | 1.00 | 29.98 | O |
| ATOM | 969 | N | ARG A 434 | 15.148 | 22.167 | 34.984 | 1.00 | 26.97 | N |
| ATOM | 970 | CA | ARG A 434 | 14.097 | 21.842 | 33.990 | 1.00 | 26.97 | C |
| ATOM | 971 | C | ARG A 434 | 13.009 | 20.996 | 34.615 | 1.00 | 30.42 | C |
| ATOM | 972 | O | ARG A 434 | 11.823 | 21.204 | 34.328 | 1.00 | 27.41 | O |
| ATOM | 973 | CB | ARG A 434 | 14.752 | 21.167 | 32.801 | 1.00 | 25.33 | C |
| ATOM | 974 | CG | ARG A 434 | 13.708 | 20.721 | 31.827 | 1.00 | 42.33 | C |
| ATOM | 975 | CD | ARG A 434 | 12.817 | 21.554 | 31.010 | 1.00 | 49.31 | C |
| ATOM | 976 | NE | ARG A 434 | 11.713 | 22.346 | 31.491 | 1.00 | 46.14 | N |
| ATOM | 977 | CZ | ARG A 434 | 10.568 | 22.425 | 30.807 | 1.00 | 58.17 | C |
| ATOM | 978 | NH1 | ARG A 434 | 10.399 | 21.741 | 29.673 | 1.00 | 57.71 | N |
| ATOM | 979 | NH2 | ARG A 434 | 9.588 | 23.206 | 31.266 | 1.00 | 58.73 | N |
| ATOM | 980 | N | PHE A 435 | 13.341 | 20.066 | 35.543 | 1.00 | 22.36 | N |
| ATOM | 981 | CA | PHE A 435 | 12.293 | 19.277 | 36.179 | 1.00 | 25.31 | C |
| ATOM | 982 | C | PHE A 435 | 11.524 | 20.205 | 37.144 | 1.00 | 22.12 | C |
| ATOM | 983 | O | PHE A 435 | 10.294 | 20.007 | 37.311 | 1.00 | 24.29 | O |
| ATOM | 984 | CB | PHE A 435 | 12.909 | 18.077 | 36.894 | 1.00 | 20.35 | C |
| ATOM | 985 | CG | PHE A 435 | 13.318 | 16.946 | 35.972 | 1.00 | 23.24 | C |
| ATOM | 986 | CD1 | PHE A 435 | 12.380 | 16.302 | 35.170 | 1.00 | 25.28 | C |
| ATOM | 987 | CD2 | PHE A 435 | 14.634 | 16.508 | 35.910 | 1.00 | 25.71 | C |
| ATOM | 988 | CE1 | PHE A 435 | 12.767 | 15.255 | 34.343 | 1.00 | 29.66 | C |
| ATOM | 989 | CE2 | PHE A 435 | 15.004 | 15.490 | 35.079 | 1.00 | 25.15 | C |
| ATOM | 990 | CZ | PHE A 435 | 14.095 | 14.853 | 34.287 | 1.00 | 25.57 | C |
| ATOM | 991 | N | ARG A 436 | 12.161 | 21.138 | 37.805 | 1.00 | 21.91 | N |
| ATOM | 992 | CA | ARG A 436 | 11.422 | 22.028 | 38.727 | 1.00 | 23.44 | C |
| ATOM | 993 | C | ARG A 436 | 10.433 | 22.864 | 37.894 | 1.00 | 26.42 | C |
| ATOM | 994 | O | ARG A 436 | 9.242 | 22.945 | 38.249 | 1.00 | 27.86 | O |

FIG. 2M

```
ATOM    995  CB  ARG A 436      12.368  22.967  39.489  1.00 23.65           C
ATOM    996  CG  ARG A 436      11.670  23.942  40.483  1.00 29.31           C
ATOM    997  CD  ARG A 436      12.636  25.141  40.739  1.00 30.70           C
ATOM    998  NE  ARG A 436      13.845  24.503  41.263  1.00 34.92           N
ATOM    999  CZ  ARG A 436      15.097  24.584  40.859  1.00 36.96           C
ATOM   1000  NH1 ARG A 436      15.522  25.354  39.866  1.00 32.94           N
ATOM   1001  NH2 ARG A 436      15.982  23.795  41.483  1.00 34.07           N
ATOM   1002  N   GLU A 437      10.904  23.400  36.792  1.00 25.27           N
ATOM   1003  CA  GLU A 437      10.005  24.217  35.935  1.00 32.74           C
ATOM   1004  C   GLU A 437       8.817  23.413  35.448  1.00 32.08           C
ATOM   1005  O   GLU A 437       7.668  23.875  35.338  1.00 27.72           O
ATOM   1006  CB  GLU A 437      10.767  24.809  34.765  1.00 33.92           C
ATOM   1007  CG  GLU A 437      11.831  25.799  35.161  1.00 40.07           C
ATOM   1008  CD  GLU A 437      12.911  26.078  34.141  1.00 50.46           C
ATOM   1009  OE1 GLU A 437      12.797  25.709  32.943  1.00 51.91           O
ATOM   1010  OE2 GLU A 437      13.916  26.722  34.561  1.00 53.95           O
ATOM   1011  N   LEU A 438       9.020  22.146  35.090  1.00 27.00           N
ATOM   1012  CA  LEU A 438       7.921  21.269  34.681  1.00 27.50           C
ATOM   1013  C   LEU A 438       7.122  20.813  35.882  1.00 23.14           C
ATOM   1014  O   LEU A 438       6.119  20.121  35.729  1.00 25.79           O
ATOM   1015  CB  LEU A 438       8.482  19.998  33.993  1.00 31.41           C
ATOM   1016  CG  LEU A 438       8.842  20.132  32.526  1.00 40.32           C
ATOM   1017  CD1 LEU A 438       9.491  18.860  31.987  1.00 41.08           C
ATOM   1018  CD2 LEU A 438       7.614  20.452  31.675  1.00 39.10           C
ATOM   1019  N   LYS A 439       7.498  21.129  37.130  1.00 24.41           N
ATOM   1020  CA  LYS A 439       6.850  20.706  38.331  1.00 25.43           C
ATOM   1021  C   LYS A 439       6.634  19.197  38.406  1.00 27.06           C
ATOM   1022  O   LYS A 439       5.572  18.619  38.637  1.00 24.32           O
ATOM   1023  CB  LYS A 439       5.500  21.405  38.605  1.00 33.10           C
ATOM   1024  CG  LYS A 439       5.617  22.924  38.646  1.00 33.57           C
ATOM   1025  CD  LYS A 439       4.307  23.503  39.237  1.00 42.76           C
ATOM   1026  CE  LYS A 439       4.111  24.919  38.704  1.00 47.35           C
ATOM   1027  NZ  LYS A 439       2.797  25.501  39.101  1.00 53.11           N
ATOM   1028  N   LEU A 440       7.713  18.479  38.105  1.00 22.41           N
ATOM   1029  CA  LEU A 440       7.745  17.019  38.154  1.00 19.51           C
ATOM   1030  C   LEU A 440       7.205  16.500  39.479  1.00 20.02           C
ATOM   1031  O   LEU A 440       7.514  17.037  40.524  1.00 20.61           O
ATOM   1032  CB  LEU A 440       9.257  16.635  38.077  1.00 19.19           C
ATOM   1033  CG  LEU A 440       9.491  15.126  38.152  1.00 23.27           C
ATOM   1034  CD1 LEU A 440       8.999  14.476  36.869  1.00 20.04           C
ATOM   1035  CD2 LEU A 440      10.973  14.766  38.354  1.00 23.57           C
ATOM   1036  N   GLN A 441       6.261  15.572  39.391  1.00 21.24           N
ATOM   1037  CA  GLN A 441       5.631  14.957  40.541  1.00 27.68           C
ATOM   1038  C   GLN A 441       6.343  13.693  40.980  1.00 25.36           C
ATOM   1039  O   GLN A 441       6.956  12.969  40.193  1.00 24.49           O
ATOM   1040  CB  GLN A 441       4.168  14.650  40.088  1.00 26.49           C
ATOM   1041  CG  GLN A 441       3.538  16.013  39.645  1.00 27.50           C
ATOM   1042  CD  GLN A 441       3.371  16.910  40.870  1.00 38.48           C
ATOM   1043  OE1 GLN A 441       2.720  16.500  41.851  1.00 44.82           O
ATOM   1044  NE2 GLN A 441       3.926  18.107  40.916  1.00 40.95           N
ATOM   1045  N   HIS A 442       6.263  13.394  42.274  1.00 26.03           N
ATOM   1046  CA  HIS A 442       6.911  12.181  42.787  1.00 26.55           C
ATOM   1047  C   HIS A 442       6.558  10.937  42.009  1.00 24.66           C
ATOM   1048  O   HIS A 442       7.472  10.187  41.610  1.00 23.31           O
ATOM   1049  CB  HIS A 442       6.603  12.052  44.276  1.00 27.31           C
ATOM   1050  CG  HIS A 442       7.278  10.914  44.955  1.00 28.31           C
ATOM   1051  ND1 HIS A 442       8.666  10.898  45.111  1.00 35.26           N
ATOM   1052  CD2 HIS A 442       6.817   9.788  45.551  1.00 27.34           C
ATOM   1053  CE1 HIS A 442       9.004   9.810  45.796  1.00 30.99           C
ATOM   1054  NE2 HIS A 442       7.915   9.118  46.071  1.00 34.85           N
ATOM   1055  N   LYS A 443       5.288  10.626  41.696  1.00 22.61           N
ATOM   1056  CA  LYS A 443       5.004   9.421  40.939  1.00 22.02           C
ATOM   1057  C   LYS A 443       5.508   9.465  39.490  1.00 20.78           C
ATOM   1058  O   LYS A 443       5.660   8.400  38.883  1.00 21.28           O
ATOM   1059  CB  LYS A 443       3.494   9.093  40.933  1.00 25.46           C
ATOM   1060  CG  LYS A 443       3.045   8.904  42.433  1.00 29.15           C
ATOM   1061  CD  LYS A 443       1.527   8.662  42.419  1.00 35.81           C
ATOM   1062  CE  LYS A 443       0.973   8.749  43.842  1.00 50.19           C
ATOM   1063  NZ  LYS A 443      -0.512   8.923  43.885  1.00 49.05           N
ATOM   1064  N   GLU A 444       5.621  10.629  38.862  1.00 21.19           N
ATOM   1065  CA  GLU A 444       6.194  10.712  37.520  1.00 21.16           C
ATOM   1066  C   GLU A 444       7.704  10.362  37.666  1.00 19.76           C
ATOM   1067  O   GLU A 444       8.215   9.621  36.854  1.00 20.88           O
ATOM   1068  CB  GLU A 444       6.115  12.170  37.043  1.00 23.14           C
ATOM   1069  CG  GLU A 444       4.686  12.479  36.566  1.00 26.05           C
ATOM   1070  CD  GLU A 444       4.491  13.951  36.334  1.00 24.40           C
ATOM   1071  OE1 GLU A 444       5.237  14.852  36.759  1.00 24.79           O
```

FIG. 2N

```
ATOM   1072  OE2 GLU A 444       3.508  14.272  35.614  1.00 27.56           O
ATOM   1073  N   TYR A 445       8.319  10.868  38.714  1.00 19.97           N
ATOM   1074  CA  TYR A 445       9.741  10.551  38.960  1.00 22.26           C
ATOM   1075  C   TYR A 445       9.921   9.048  39.128  1.00 19.04           C
ATOM   1076  O   TYR A 445      10.875   8.469  38.622  1.00 20.97           O
ATOM   1077  CB  TYR A 445      10.224  11.291  40.206  1.00 20.96           C
ATOM   1078  CG  TYR A 445      11.366  10.659  40.969  1.00 24.17           C
ATOM   1079  CD1 TYR A 445      12.643  10.727  40.420  1.00 26.90           C
ATOM   1080  CD2 TYR A 445      11.166  10.029  42.192  1.00 22.07           C
ATOM   1081  CE1 TYR A 445      13.727  10.156  41.087  1.00 22.98           C
ATOM   1082  CE2 TYR A 445      12.249   9.453  42.829  1.00 26.07           C
ATOM   1083  CZ  TYR A 445      13.491   9.528  42.285  1.00 25.04           C
ATOM   1084  OH  TYR A 445      14.586   8.970  42.950  1.00 33.42           O
ATOM   1085  N   LEU A 446       9.105   8.389  39.995  1.00 18.03           N
ATOM   1086  CA  LEU A 446       9.240   6.938  40.102  1.00 24.19           C
ATOM   1087  C   LEU A 446       9.232   6.239  38.755  1.00 18.83           C
ATOM   1088  O   LEU A 446      10.038   5.315  38.475  1.00 20.62           O
ATOM   1089  CB  LEU A 446       8.090   6.364  40.975  1.00 23.00           C
ATOM   1090  CG  LEU A 446       8.104   7.007  42.394  1.00 27.50           C
ATOM   1091  CD1 LEU A 446       6.864   6.568  43.165  1.00 30.48           C
ATOM   1092  CD2 LEU A 446       9.360   6.584  43.147  1.00 27.81           C
ATOM   1093  N   CYS A 447       8.256   6.568  37.863  1.00 19.93           N
ATOM   1094  CA  CYS A 447       8.172   5.920  36.591  1.00 21.27           C
ATOM   1095  C   CYS A 447       9.414   6.235  35.722  1.00 18.48           C
ATOM   1096  O   CYS A 447       9.908   5.341  35.061  1.00 19.17           O
ATOM   1097  CB  CYS A 447       6.956   6.313  35.775  1.00 20.29           C
ATOM   1098  SG  CYS A 447       5.415   5.811  36.632  1.00 21.69           S
ATOM   1099  N   VAL A 448       9.811   7.509  35.655  1.00 18.45           N
ATOM   1100  CA  VAL A 448      10.988   7.806  34.826  1.00 20.08           C
ATOM   1101  C   VAL A 448      12.245   7.095  35.280  1.00 21.79           C
ATOM   1102  O   VAL A 448      13.002   6.560  34.466  1.00 19.53           O
ATOM   1103  CB  VAL A 448      11.152   9.358  34.853  1.00 24.07           C
ATOM   1104  CG1 VAL A 448      12.507   9.721  34.360  1.00 28.67           C
ATOM   1105  CG2 VAL A 448      10.025   9.856  33.907  1.00 29.43           C
ATOM   1106  N   LYS A 449      12.452   7.021  36.602  1.00 18.71           N
ATOM   1107  CA  LYS A 449      13.626   6.290  37.101  1.00 17.39           C
ATOM   1108  C   LYS A 449      13.652   4.857  36.649  1.00 23.94           C
ATOM   1109  O   LYS A 449      14.646   4.251  36.178  1.00 18.35           O
ATOM   1110  CB  LYS A 449      13.698   6.454  38.640  1.00 21.62           C
ATOM   1111  CG  LYS A 449      15.080   5.973  39.135  1.00 23.58           C
ATOM   1112  CD  LYS A 449      15.285   6.410  40.580  1.00 26.52           C
ATOM   1113  CE  LYS A 449      14.188   5.858  41.501  1.00 25.87           C
ATOM   1114  NZ  LYS A 449      14.611   5.765  42.945  1.00 26.92           N
ATOM   1115  N   ALA A 450      12.478   4.190  36.703  1.00 18.50           N
ATOM   1116  CA  ALA A 450      12.323   2.831  36.260  1.00 21.41           C
ATOM   1117  C   ALA A 450      12.563   2.711  34.783  1.00 20.13           C
ATOM   1118  O   ALA A 450      13.206   1.738  34.329  1.00 18.60           O
ATOM   1119  CB  ALA A 450      10.985   2.198  36.684  1.00 20.44           C
ATOM   1120  N   MET A 451      12.139   3.721  33.968  1.00 18.77           N
ATOM   1121  CA  MET A 451      12.358   3.655  32.570  1.00 18.14           C
ATOM   1122  C   MET A 451      13.877   3.727  32.260  1.00 17.57           C
ATOM   1123  O   MET A 451      14.311   3.045  31.322  1.00 20.73           O
ATOM   1124  CB  MET A 451      11.633   4.842  31.842  1.00 21.77           C
ATOM   1125  CG  MET A 451      10.131   4.584  32.084  1.00 27.69           C
ATOM   1126  SD  MET A 451       9.016   5.929  31.603  1.00 34.64           S
ATOM   1127  CE  MET A 451       9.857   6.385  30.106  1.00 35.01           C
ATOM   1128  N   ILE A 452      14.588   4.498  33.024  1.00 16.50           N
ATOM   1129  CA  ILE A 452      16.037   4.640  32.828  1.00 17.08           C
ATOM   1130  C   ILE A 452      16.654   3.246  32.962  1.00 20.78           C
ATOM   1131  O   ILE A 452      17.508   2.878  32.158  1.00 19.75           O
ATOM   1132  CB  ILE A 452      16.625   5.638  33.802  1.00 19.19           C
ATOM   1133  CG1 ILE A 452      16.292   7.107  33.388  1.00 17.81           C
ATOM   1134  CG2 ILE A 452      18.162   5.500  33.943  1.00 20.76           C
ATOM   1135  CD1 ILE A 452      16.477   8.045  34.585  1.00 21.82           C
ATOM   1136  N   LEU A 453      16.259   2.506  33.992  1.00 19.70           N
ATOM   1137  CA  LEU A 453      16.809   1.164  34.201  1.00 21.38           C
ATOM   1138  C   LEU A 453      16.452   0.220  33.063  1.00 22.74           C
ATOM   1139  O   LEU A 453      17.339  -0.447  32.508  1.00 23.04           O
ATOM   1140  CB  LEU A 453      16.272   0.592  35.526  1.00 20.23           C
ATOM   1141  CG  LEU A 453      16.436  -0.933  35.734  1.00 23.99           C
ATOM   1142  CD1 LEU A 453      17.861  -1.311  35.991  1.00 24.30           C
ATOM   1143  CD2 LEU A 453      15.585  -1.366  36.938  1.00 30.09           C
ATOM   1144  N   LEU A 454      15.173   0.257  32.658  1.00 18.55           N
ATOM   1145  CA  LEU A 454      14.763  -0.675  31.599  1.00 20.55           C
ATOM   1146  C   LEU A 454      15.129  -0.287  30.191  1.00 22.40           C
ATOM   1147  O   LEU A 454      15.126  -1.229  29.347  1.00 25.90           O
ATOM   1148  CB  LEU A 454      13.230  -0.867  31.745  1.00 21.21           C
```

FIG. 20

```
ATOM   1149  CG   LEU A 454      12.728  -1.319  33.126  1.00 24.00           C
ATOM   1150  CD1  LEU A 454      11.213  -1.146  33.221  1.00 23.17           C
ATOM   1151  CD2  LEU A 454      13.163  -2.762  33.390  1.00 24.11           C
ATOM   1152  N    ASN A 455      15.439   0.969  29.912  1.00 20.57           N
ATOM   1153  CA   ASN A 455      15.704   1.437  28.552  1.00 26.20           C
ATOM   1154  C    ASN A 455      17.175   1.744  28.246  1.00 27.11           C
ATOM   1155  O    ASN A 455      17.552   1.762  27.088  1.00 33.65           O
ATOM   1156  CB   ASN A 455      14.976   2.798  28.371  1.00 31.10           C
ATOM   1157  CG   ASN A 455      15.173   3.511  27.043  1.00 38.22           C
ATOM   1158  OD1  ASN A 455      15.592   4.701  26.960  1.00 37.37           O
ATOM   1159  ND2  ASN A 455      14.858   2.842  25.935  1.00 34.72           N
ATOM   1160  N    SER A 456      17.997   1.775  29.258  1.00 30.24           N
ATOM   1161  CA   SER A 456      19.382   2.119  29.231  1.00 36.00           C
ATOM   1162  C    SER A 456      20.311   1.573  28.153  1.00 36.83           C
ATOM   1163  O    SER A 456      21.062   2.288  27.473  1.00 33.20           O
ATOM   1164  CB   SER A 456      20.038   1.689  30.582  1.00 39.77           C
ATOM   1165  OG   SER A 456      19.588   0.394  31.044  1.00 37.99           O
ATOM   1166  N    ALA A 457      20.318   0.245  28.192  1.00 35.54           N
ATOM   1167  CA   ALA A 457      21.274  -0.464  27.352  1.00 42.47           C
ATOM   1168  C    ALA A 457      21.142  -0.038  25.896  1.00 41.31           C
ATOM   1169  O    ALA A 457      20.080   0.110  25.316  1.00 44.55           O
ATOM   1170  CB   ALA A 457      21.235  -1.963  27.524  1.00 40.51           C
ATOM   1171  N    MET A 458      22.311   0.172  25.315  1.00 46.24           N
ATOM   1172  CA   MET A 458      22.508   0.547  23.933  1.00 48.76           C
ATOM   1173  C    MET A 458      22.623  -0.689  23.027  1.00 53.25           C
ATOM   1174  O    MET A 458      22.945  -1.782  23.501  1.00 58.48           O
ATOM   1175  CB   MET A 458      23.841   1.294  23.819  1.00 47.06           C
ATOM   1176  CG   MET A 458      23.888   2.585  24.618  1.00 44.75           C
ATOM   1177  SD   MET A 458      22.827   3.882  23.950  1.00 37.82           S
ATOM   1178  CE   MET A 458      23.515   4.064  22.295  1.00 37.93           C
ATOM   1179  N    ALA A 469      12.316 -14.119  24.676  1.00 60.19           N
ATOM   1180  CA   ALA A 469      11.449 -14.316  25.833  1.00 60.72           C
ATOM   1181  C    ALA A 469      11.881 -13.355  26.943  1.00 60.69           C
ATOM   1182  O    ALA A 469      11.014 -12.627  27.414  1.00 63.87           O
ATOM   1183  CB   ALA A 469      11.405 -15.721  26.368  1.00 61.18           C
ATOM   1184  N    SER A 470      13.153 -13.392  27.347  1.00 59.40           N
ATOM   1185  CA   SER A 470      13.620 -12.423  28.348  1.00 57.12           C
ATOM   1186  C    SER A 470      13.440 -11.061  27.661  1.00 58.67           C
ATOM   1187  O    SER A 470      12.743 -10.174  28.142  1.00 57.72           O
ATOM   1188  CB   SER A 470      15.066 -12.641  28.751  1.00 56.65           C
ATOM   1189  OG   SER A 470      15.454 -11.735  29.774  1.00 53.66           O
ATOM   1190  N    SER A 471      13.997 -10.972  26.450  1.00 60.93           N
ATOM   1191  CA   SER A 471      13.866  -9.803  25.607  1.00 60.15           C
ATOM   1192  C    SER A 471      12.387  -9.446  25.460  1.00 61.94           C
ATOM   1193  O    SER A 471      12.018  -8.291  25.674  1.00 59.07           O
ATOM   1194  CB   SER A 471      14.458 -10.007  24.210  1.00 60.90           C
ATOM   1195  OG   SER A 471      13.824  -9.104  23.313  1.00 63.44           O
ATOM   1196  N    ARG A 472      11.523 -10.412  25.150  1.00 61.18           N
ATOM   1197  CA   ARG A 472      10.091 -10.111  25.031  1.00 61.86           C
ATOM   1198  C    ARG A 472       9.455  -9.705  26.351  1.00 55.71           C
ATOM   1199  O    ARG A 472       8.492  -8.942  26.430  1.00 55.98           O
ATOM   1200  CB   ARG A 472       9.415 -11.346  24.439  1.00 66.43           C
ATOM   1201  CG   ARG A 472       7.896 -11.320  24.439  1.00 71.44           C
ATOM   1202  CD   ARG A 472       7.339 -12.571  23.765  1.00 75.25           C
ATOM   1203  NE   ARG A 472       8.268 -13.690  23.790  1.00 77.23           N
ATOM   1204  CZ   ARG A 472       8.229 -14.781  23.045  1.00 79.57           C
ATOM   1205  NH1  ARG A 472       7.268 -14.977  22.145  1.00 80.41           N
ATOM   1206  NH2  ARG A 472       9.174 -15.705  23.192  1.00 79.36           N
ATOM   1207  N    LYS A 473       9.959 -10.212  27.461  1.00 52.42           N
ATOM   1208  CA   LYS A 473       9.497  -9.883  28.804  1.00 52.83           C
ATOM   1209  C    LYS A 473       9.945  -8.463  29.166  1.00 48.89           C
ATOM   1210  O    LYS A 473       9.187  -7.725  29.794  1.00 51.86           O
ATOM   1211  CB   LYS A 473      10.047 -10.914  29.790  1.00 56.33           C
ATOM   1212  CG   LYS A 473       8.988 -11.534  30.696  1.00 59.83           C
ATOM   1213  CD   LYS A 473       9.414 -12.925  31.140  1.00 61.94           C
ATOM   1214  CE   LYS A 473       8.378 -13.586  32.024  1.00 63.15           C
ATOM   1215  NZ   LYS A 473       8.870 -14.867  32.606  1.00 65.28           N
ATOM   1216  N    LEU A 474      11.144  -8.065  28.738  1.00 45.57           N
ATOM   1217  CA   LEU A 474      11.679  -6.734  28.989  1.00 43.81           C
ATOM   1218  C    LEU A 474      10.823  -5.675  28.309  1.00 45.51           C
ATOM   1219  O    LEU A 474      10.280  -4.751  28.917  1.00 40.26           O
ATOM   1220  CB   LEU A 474      13.135  -6.592  28.503  1.00 42.11           C
ATOM   1221  CG   LEU A 474      13.753  -5.187  28.638  1.00 39.15           C
ATOM   1222  CD1  LEU A 474      13.670  -4.693  30.088  1.00 34.72           C
ATOM   1223  CD2  LEU A 474      15.201  -5.159  28.185  1.00 34.37           C
ATOM   1224  N    ALA A 475      10.584  -5.830  27.004  1.00 42.52           N
ATOM   1225  CA   ALA A 475       9.787  -4.953  26.164  1.00 41.94           C
```

FIG. 2P

```
ATOM   1226  C    ALA A 475       8.452   -4.581  26.793  1.00 41.48           C
ATOM   1227  O    ALA A 475       7.891   -3.490  26.828  1.00 45.13           O
ATOM   1228  CB   ALA A 475       9.517   -5.761  24.884  1.00 41.45           C
ATOM   1229  N    HIS A 476       7.859   -5.612  27.354  1.00 44.24           N
ATOM   1230  CA   HIS A 476       6.609   -5.656  28.053  1.00 48.12           C
ATOM   1231  C    HIS A 476       6.640   -4.990  29.425  1.00 42.60           C
ATOM   1232  O    HIS A 476       5.672   -4.359  29.830  1.00 39.37           O
ATOM   1233  CB   HIS A 476       6.243   -7.140  28.168  1.00 54.04           C
ATOM   1234  CG   HIS A 476       5.008   -7.310  28.990  1.00 55.91           C
ATOM   1235  ND1  HIS A 476       5.063   -7.803  30.275  1.00 59.64           N
ATOM   1236  CD2  HIS A 476       3.716   -7.013  28.733  1.00 58.19           C
ATOM   1237  CE1  HIS A 476       3.835   -7.821  30.770  1.00 60.13           C
ATOM   1238  NE2  HIS A 476       2.996   -7.351  29.856  1.00 58.29           N
ATOM   1239  N    LEU A 477       7.757   -5.132  30.124  1.00 41.27           N
ATOM   1240  CA   LEU A 477       7.937   -4.489  31.425  1.00 38.48           C
ATOM   1241  C    LEU A 477       8.000   -2.966  31.201  1.00 30.49           C
ATOM   1242  O    LEU A 477       7.353   -2.117  31.820  1.00 31.42           O
ATOM   1243  CB   LEU A 477       9.229   -4.994  32.078  1.00 37.51           C
ATOM   1244  CG   LEU A 477       9.565   -4.461  33.471  1.00 44.59           C
ATOM   1245  CD1  LEU A 477       8.323   -4.147  34.302  1.00 42.81           C
ATOM   1246  CD2  LEU A 477      10.487   -5.429  34.227  1.00 40.95           C
ATOM   1247  N    LEU A 478       8.786   -2.632  30.194  1.00 31.48           N
ATOM   1248  CA   LEU A 478       8.993   -1.262  29.749  1.00 33.28           C
ATOM   1249  C    LEU A 478       7.676   -0.674  29.290  1.00 33.35           C
ATOM   1250  O    LEU A 478       7.328    0.441  29.722  1.00 30.92           O
ATOM   1251  CB   LEU A 478      10.130   -1.139  28.730  1.00 31.10           C
ATOM   1252  CG   LEU A 478      10.375    0.295  28.241  1.00 34.76           C
ATOM   1253  CD1  LEU A 478      10.866    1.210  29.382  1.00 32.74           C
ATOM   1254  CD2  LEU A 478      11.333    0.415  27.084  1.00 33.23           C
ATOM   1255  N    ASN A 479       6.888   -1.392  28.480  1.00 34.95           N
ATOM   1256  CA   ASN A 479       5.578   -0.880  28.099  1.00 35.98           C
ATOM   1257  C    ASN A 479       4.662   -0.638  29.299  1.00 28.84           C
ATOM   1258  O    ASN A 479       3.970    0.359  29.338  1.00 29.63           O
ATOM   1259  CB   ASN A 479       4.908   -1.837  27.092  1.00 42.20           C
ATOM   1260  CG   ASN A 479       5.611   -1.804  25.735  1.00 48.35           C
ATOM   1261  OD1  ASN A 479       5.951   -0.721  25.237  1.00 47.39           O
ATOM   1262  ND2  ASN A 479       5.801   -3.025  25.210  1.00 50.10           N
ATOM   1263  N    ALA A 480       4.651   -1.498  30.311  1.00 33.47           N
ATOM   1264  CA   ALA A 480       3.829   -1.276  31.503  1.00 30.90           C
ATOM   1265  C    ALA A 480       4.228   -0.030  32.259  1.00 23.64           C
ATOM   1266  O    ALA A 480       3.352    0.665  32.801  1.00 26.15           O
ATOM   1267  CB   ALA A 480       3.908   -2.526  32.390  1.00 34.69           C
ATOM   1268  N    VAL A 481       5.553    0.298  32.353  1.00 23.24           N
ATOM   1269  CA   VAL A 481       5.960    1.470  33.122  1.00 22.74           C
ATOM   1270  C    VAL A 481       5.517    2.722  32.351  1.00 18.06           C
ATOM   1271  O    VAL A 481       5.153    3.729  32.942  1.00 26.87           O
ATOM   1272  CB   VAL A 481       7.469    1.529  33.436  1.00 27.05           C
ATOM   1273  CG1  VAL A 481       7.838    2.847  34.155  1.00 23.49           C
ATOM   1274  CG2  VAL A 481       7.910    0.314  34.266  1.00 28.60           C
ATOM   1275  N    THR A 482       5.655    2.689  31.030  1.00 23.57           N
ATOM   1276  CA   THR A 482       5.220    3.783  30.154  1.00 26.39           C
ATOM   1277  C    THR A 482       3.721    4.017  30.327  1.00 22.53           C
ATOM   1278  O    THR A 482       3.225    5.112  30.645  1.00 23.67           O
ATOM   1279  CB   THR A 482       5.588    3.436  28.695  1.00 31.20           C
ATOM   1280  OG1  THR A 482       6.974    3.215  28.498  1.00 32.83           O
ATOM   1281  CG2  THR A 482       5.230    4.522  27.698  1.00 33.29           C
ATOM   1282  N    ASP A 483       2.917    2.922  30.355  1.00 27.94           N
ATOM   1283  CA   ASP A 483       1.471    3.068  30.599  1.00 29.23           C
ATOM   1284  C    ASP A 483       1.177    3.699  31.933  1.00 25.55           C
ATOM   1285  O    ASP A 483       0.289    4.539  32.087  1.00 31.75           O
ATOM   1286  CB   ASP A 483       0.689    1.742  30.578  1.00 33.31           C
ATOM   1287  CG   ASP A 483       0.420    1.189  29.200  1.00 37.11           C
ATOM   1288  OD1  ASP A 483       0.338    1.935  28.199  1.00 38.37           O
ATOM   1289  OD2  ASP A 483       0.243   -0.048  29.064  1.00 40.00           O
ATOM   1290  N    ALA A 484       1.984    3.364  32.957  1.00 25.28           N
ATOM   1291  CA   ALA A 484       1.859    3.856  34.306  1.00 23.57           C
ATOM   1292  C    ALA A 484       2.129    5.346  34.356  1.00 22.08           C
ATOM   1293  O    ALA A 484       1.476    6.126  35.054  1.00 26.22           O
ATOM   1294  CB   ALA A 484       2.811    3.100  35.251  1.00 22.07           C
ATOM   1295  N    LEU A 485       3.192    5.769  33.625  1.00 26.30           N
ATOM   1296  CA   LEU A 485       3.525    7.206  33.576  1.00 20.03           C
ATOM   1297  C    LEU A 485       2.364    7.896  32.849  1.00 22.17           C
ATOM   1298  O    LEU A 485       1.940    8.956  33.304  1.00 26.47           O
ATOM   1299  CB   LEU A 485       4.842    7.395  32.776  1.00 20.92           C
ATOM   1300  CG   LEU A 485       5.232    8.863  32.522  1.00 21.92           C
ATOM   1301  CD1  LEU A 485       5.387    9.644  33.822  1.00 23.10           C
ATOM   1302  CD2  LEU A 485       6.554    8.878  31.721  1.00 22.61           C
```

FIG. 2Q

```
ATOM   1303  N    VAL A 486       1.882   7.319  31.775  1.00 27.15           N
ATOM   1304  CA   VAL A 486       0.750   7.946  31.037  1.00 27.86           C
ATOM   1305  C    VAL A 486      -0.459   8.062  31.975  1.00 27.38           C
ATOM   1306  O    VAL A 486      -1.137   9.081  32.037  1.00 30.67           O
ATOM   1307  CB   VAL A 486       0.450   7.134  29.781  1.00 31.08           C
ATOM   1308  CG1  VAL A 486      -0.889   7.515  29.131  1.00 34.82           C
ATOM   1309  CG2  VAL A 486       1.555   7.198  28.723  1.00 29.27           C
ATOM   1310  N    TRP A 487      -0.704   7.032  32.786  1.00 29.86           N
ATOM   1311  CA   TRP A 487      -1.813   7.029  33.747  1.00 33.05           C
ATOM   1312  C    TRP A 487      -1.595   8.089  34.799  1.00 36.27           C
ATOM   1313  O    TRP A 487      -2.490   8.869  35.094  1.00 33.38           O
ATOM   1314  CB   TRP A 487      -1.961   5.661  34.390  1.00 32.60           C
ATOM   1315  CG   TRP A 487      -2.952   5.586  35.502  1.00 37.95           C
ATOM   1316  CD1  TRP A 487      -4.312   5.400  35.367  1.00 43.97           C
ATOM   1317  CD2  TRP A 487      -2.695   5.681  36.900  1.00 35.97           C
ATOM   1318  NE1  TRP A 487      -4.915   5.354  36.603  1.00 37.38           N
ATOM   1319  CE2  TRP A 487      -3.942   5.503  37.560  1.00 41.60           C
ATOM   1320  CE3  TRP A 487      -1.551   5.845  37.670  1.00 36.56           C
ATOM   1321  CZ2  TRP A 487      -4.056   5.521  38.947  1.00 40.06           C
ATOM   1322  CZ3  TRP A 487      -1.675   5.863  39.047  1.00 42.43           C
ATOM   1323  CH2  TRP A 487      -2.925   5.715  39.689  1.00 39.24           C
ATOM   1324  N    VAL A 488      -0.324   8.225  35.293  1.00 33.25           N
ATOM   1325  CA   VAL A 488      -0.071   9.273  36.250  1.00 24.32           C
ATOM   1326  C    VAL A 488      -0.300  10.651  35.669  1.00 23.44           C
ATOM   1327  O    VAL A 488      -0.775  11.526  36.380  1.00 28.37           O
ATOM   1328  CB   VAL A 488       1.404   9.226  36.805  1.00 25.91           C
ATOM   1329  CG1  VAL A 488       1.675  10.401  37.711  1.00 26.73           C
ATOM   1330  CG2  VAL A 488       1.628   7.908  37.545  1.00 26.12           C
ATOM   1331  N    ILE A 489       0.120  10.908  34.411  1.00 24.14           N
ATOM   1332  CA   ILE A 489      -0.044  12.233  33.849  1.00 21.86           C
ATOM   1333  C    ILE A 489      -1.572  12.521  33.604  1.00 24.17           C
ATOM   1334  O    ILE A 489      -2.028  13.610  33.910  1.00 27.18           O
ATOM   1335  CB   ILE A 489       0.659  12.310  32.501  1.00 27.91           C
ATOM   1336  CG1  ILE A 489       2.205  12.283  32.756  1.00 23.18           C
ATOM   1337  CG2  ILE A 489       0.349  13.603  31.762  1.00 24.36           C
ATOM   1338  CD1  ILE A 489       2.871  11.911  31.416  1.00 23.22           C
ATOM   1339  N    ALA A 490      -2.197  11.421  33.241  1.00 27.97           N
ATOM   1340  CA   ALA A 490      -3.661  11.609  32.971  1.00 38.05           C
ATOM   1341  C    ALA A 490      -4.468  12.018  34.168  1.00 40.03           C
ATOM   1342  O    ALA A 490      -5.461  12.758  34.028  1.00 44.53           O
ATOM   1343  CB   ALA A 490      -4.193  10.347  32.324  1.00 32.57           C
ATOM   1344  N    LYS A 491      -4.053  11.710  35.395  1.00 41.28           N
ATOM   1345  CA   LYS A 491      -4.770  12.013  36.608  1.00 39.88           C
ATOM   1346  C    LYS A 491      -4.714  13.450  37.049  1.00 41.63           C
ATOM   1347  O    LYS A 491      -5.514  13.839  37.904  1.00 40.95           O
ATOM   1348  CB   LYS A 491      -4.423  10.983  37.665  1.00 46.07           C
ATOM   1349  CG   LYS A 491      -3.555  11.300  38.854  1.00 46.19           C
ATOM   1350  CD   LYS A 491      -3.467  10.033  39.711  1.00 49.83           C
ATOM   1351  CE   LYS A 491      -2.668  10.278  40.973  1.00 53.59           C
ATOM   1352  NZ   LYS A 491      -2.631   9.101  41.881  1.00 55.67           N
ATOM   1353  N    SER A 492      -3.923  14.308  36.410  1.00 34.55           N
ATOM   1354  CA   SER A 492      -3.912  15.741  36.672  1.00 36.18           C
ATOM   1355  C    SER A 492      -5.139  16.352  35.960  1.00 37.48           C
ATOM   1356  O    SER A 492      -5.478  17.525  36.050  1.00 40.92           O
ATOM   1357  CB   SER A 492      -2.639  16.378  36.086  1.00 35.10           C
ATOM   1358  OG   SER A 492      -2.727  16.210  34.657  1.00 35.62           O
ATOM   1359  N    GLY A 493      -5.740  15.560  35.084  1.00 38.75           N
ATOM   1360  CA   GLY A 493      -6.895  15.878  34.283  1.00 42.90           C
ATOM   1361  C    GLY A 493      -6.682  16.956  33.240  1.00 43.44           C
ATOM   1362  O    GLY A 493      -7.654  17.652  32.910  1.00 40.48           O
ATOM   1363  N    ILE A 494      -5.456  17.078  32.727  1.00 35.87           N
ATOM   1364  CA   ILE A 494      -5.212  18.106  31.690  1.00 33.56           C
ATOM   1365  C    ILE A 494      -5.691  17.494  30.391  1.00 30.12           C
ATOM   1366  O    ILE A 494      -5.950  16.286  30.309  1.00 32.80           O
ATOM   1367  CB   ILE A 494      -3.734  18.543  31.664  1.00 36.79           C
ATOM   1368  CG1  ILE A 494      -2.877  17.319  31.371  1.00 31.42           C
ATOM   1369  CG2  ILE A 494      -3.387  19.189  33.002  1.00 37.06           C
ATOM   1370  CD1  ILE A 494      -1.378  17.458  31.570  1.00 31.81           C
ATOM   1371  N    SER A 495      -5.889  18.311  29.352  1.00 32.65           N
ATOM   1372  CA   SER A 495      -6.414  17.762  28.115  1.00 35.83           C
ATOM   1373  C    SER A 495      -5.440  16.781  27.479  1.00 41.15           C
ATOM   1374  O    SER A 495      -4.258  16.704  27.857  1.00 35.53           O
ATOM   1375  CB   SER A 495      -6.712  18.859  27.106  1.00 39.81           C
ATOM   1376  OG   SER A 495      -5.497  19.492  26.741  1.00 41.83           O
ATOM   1377  N    SER A 496      -6.019  16.067  26.511  1.00 38.77           N
ATOM   1378  CA   SER A 496      -5.253  15.104  25.744  1.00 40.43           C
ATOM   1379  C    SER A 496      -4.047  15.740  25.068  1.00 39.16           C
```

FIG. 2R

```
ATOM  1380  O    SER A 496    -2.997  15.075  25.065  1.00 32.27           O
ATOM  1381  CB   SER A 496    -6.165  14.425  24.705  1.00 45.71           C
ATOM  1382  OG   SER A 496    -6.874  15.475  24.036  1.00 58.28           O
ATOM  1383  N    GLN A 497    -4.163  16.920  24.486  1.00 33.62           N
ATOM  1384  CA   GLN A 497    -3.013  17.537  23.846  1.00 30.60           C
ATOM  1385  C    GLN A 497    -1.903  17.799  24.866  1.00 27.01           C
ATOM  1386  O    GLN A 497    -0.712  17.722  24.566  1.00 25.03           O
ATOM  1387  CB   GLN A 497    -3.450  18.912  23.304  1.00 29.67           C
ATOM  1388  CG   GLN A 497    -2.408  19.547  22.388  1.00 27.55           C
ATOM  1389  CD   GLN A 497    -1.449  20.438  23.130  1.00 34.92           C
ATOM  1390  OE1  GLN A 497    -1.807  20.960  24.189  1.00 40.14           O
ATOM  1391  NE2  GLN A 497    -0.228  20.613  22.652  1.00 32.44           N
ATOM  1392  N    GLN A 498    -2.270  18.326  26.042  1.00 26.37           N
ATOM  1393  CA   GLN A 498    -1.342  18.677  27.107  1.00 28.55           C
ATOM  1394  C    GLN A 498    -0.738  17.413  27.727  1.00 26.58           C
ATOM  1395  O    GLN A 498     0.435  17.482  28.207  1.00 26.30           O
ATOM  1396  CB   GLN A 498    -1.952  19.578  28.196  1.00 33.52           C
ATOM  1397  CG   GLN A 498    -2.140  21.027  27.725  1.00 38.85           C
ATOM  1398  CD   GLN A 498    -0.799  21.708  27.516  1.00 44.43           C
ATOM  1399  OE1  GLN A 498    -0.054  21.850  28.497  1.00 49.42           O
ATOM  1400  NE2  GLN A 498    -0.496  22.141  26.294  1.00 39.08           N
ATOM  1401  N    GLN A 499    -1.450  16.296  27.726  1.00 26.16           N
ATOM  1402  CA   GLN A 499    -0.911  15.050  28.276  1.00 26.49           C
ATOM  1403  C    GLN A 499     0.242  14.556  27.407  1.00 31.44           C
ATOM  1404  O    GLN A 499     1.226  14.057  27.933  1.00 26.52           O
ATOM  1405  CB   GLN A 499    -1.931  13.910  28.339  1.00 30.42           C
ATOM  1406  CG   GLN A 499    -2.997  14.113  29.400  1.00 31.96           C
ATOM  1407  CD   GLN A 499    -3.974  12.950  29.393  1.00 41.30           C
ATOM  1408  OE1  GLN A 499    -3.628  11.776  29.317  1.00 40.19           O
ATOM  1409  NE2  GLN A 499    -5.267  13.267  29.460  1.00 41.59           N
ATOM  1410  N    SER A 500     0.064  14.631  26.086  1.00 25.27           N
ATOM  1411  CA   SER A 500     1.083  14.229  25.133  1.00 29.39           C
ATOM  1412  C    SER A 500     2.292  15.157  25.229  1.00 25.24           C
ATOM  1413  O    SER A 500     3.425  14.688  25.136  1.00 24.41           O
ATOM  1414  CB   SER A 500     0.574  14.277  23.690  1.00 28.59           C
ATOM  1415  OG   SER A 500    -0.409  13.240  23.513  1.00 34.11           O
ATOM  1416  N    MET A 501     2.048  16.461  25.413  1.00 24.36           N
ATOM  1417  CA   MET A 501     3.145  17.410  25.539  1.00 25.98           C
ATOM  1418  C    MET A 501     3.920  17.119  26.823  1.00 26.81           C
ATOM  1419  O    MET A 501     5.158  17.203  26.791  1.00 23.19           O
ATOM  1420  CB   MET A 501     2.697  18.890  25.502  1.00 30.80           C
ATOM  1421  CG   MET A 501     3.552  19.758  24.600  1.00 46.15           C
ATOM  1422  SD   MET A 501     3.103  19.769  22.874  1.00 47.15           S
ATOM  1423  CE   MET A 501     2.464  18.152  22.499  1.00 52.53           C
ATOM  1424  N    ARG A 502     3.230  16.759  27.895  1.00 20.36           N
ATOM  1425  CA   ARG A 502     3.927  16.549  29.173  1.00 22.08           C
ATOM  1426  C    ARG A 502     4.758  15.264  29.102  1.00 21.26           C
ATOM  1427  O    ARG A 502     5.910  15.222  29.533  1.00 22.71           O
ATOM  1428  CB   ARG A 502     2.897  16.497  30.329  1.00 23.98           C
ATOM  1429  CG   ARG A 502     3.628  16.378  31.664  1.00 24.01           C
ATOM  1430  CD   ARG A 502     2.730  16.533  32.892  1.00 27.06           C
ATOM  1431  NE   ARG A 502     3.540  16.593  34.105  1.00 23.61           N
ATOM  1432  CZ   ARG A 502     4.211  17.635  34.552  1.00 22.53           C
ATOM  1433  NH1  ARG A 502     4.895  17.470  35.711  1.00 26.82           N
ATOM  1434  NH2  ARG A 502     4.218  18.780  33.907  1.00 22.56           N
ATOM  1435  N    LEU A 503     4.162  14.232  28.466  1.00 19.02           N
ATOM  1436  CA   LEU A 503     4.925  12.986  28.284  1.00 21.30           C
ATOM  1437  C    LEU A 503     6.138  13.260  27.421  1.00 23.43           C
ATOM  1438  O    LEU A 503     7.292  12.886  27.742  1.00 19.06           O
ATOM  1439  CB   LEU A 503     3.966  11.989  27.615  1.00 25.98           C
ATOM  1440  CG   LEU A 503     4.535  10.636  27.243  1.00 22.62           C
ATOM  1441  CD1  LEU A 503     5.053   9.898  28.501  1.00 21.09           C
ATOM  1442  CD2  LEU A 503     3.433   9.776  26.604  1.00 23.95           C
ATOM  1443  N    ALA A 504     5.963  14.019  26.321  1.00 18.94           N
ATOM  1444  CA   ALA A 504     7.116  14.256  25.459  1.00 20.93           C
ATOM  1445  C    ALA A 504     8.182  15.057  26.200  1.00 22.24           C
ATOM  1446  O    ALA A 504     9.386  14.873  26.026  1.00 22.41           O
ATOM  1447  CB   ALA A 504     6.684  15.142  24.288  1.00 26.47           C
ATOM  1448  N    ASN A 505     7.748  16.098  26.956  1.00 19.01           N
ATOM  1449  CA   ASN A 505     8.708  16.944  27.653  1.00 24.23           C
ATOM  1450  C    ASN A 505     9.551  16.177  28.690  1.00 24.35           C
ATOM  1451  O    ASN A 505    10.755  16.445  28.839  1.00 22.02           O
ATOM  1452  CB   ASN A 505     8.055  18.097  28.416  1.00 25.76           C
ATOM  1453  CG   ASN A 505     7.840  19.266  27.443  1.00 36.96           C
ATOM  1454  OD1  ASN A 505     8.741  19.470  26.630  1.00 38.16           O
ATOM  1455  ND2  ASN A 505     6.676  19.872  27.650  1.00 36.08           N
ATOM  1456  N    LEU A 506     8.859  15.309  29.406  1.00 20.34           N
```

FIG. 2S

```
ATOM   1457  CA  LEU A 506       9.539  14.516  30.450  1.00 20.82           C
ATOM   1458  C   LEU A 506      10.539  13.552  29.784  1.00 20.11           C
ATOM   1459  O   LEU A 506      11.696  13.419  30.231  1.00 21.17           O
ATOM   1460  CB  LEU A 506       8.592  13.707  31.278  1.00 19.79           C
ATOM   1461  CG  LEU A 506       7.680  14.476  32.230  1.00 22.72           C
ATOM   1462  CD1 LEU A 506       6.606  13.555  32.781  1.00 23.93           C
ATOM   1463  CD2 LEU A 506       8.442  15.065  33.422  1.00 26.30           C
ATOM   1464  N   LEU A 507      10.084  12.890  28.683  1.00 19.88           N
ATOM   1465  CA  LEU A 507      10.988  11.929  28.063  1.00 21.64           C
ATOM   1466  C   LEU A 507      12.076  12.613  27.268  1.00 22.05           C
ATOM   1467  O   LEU A 507      13.121  11.940  27.163  1.00 25.18           O
ATOM   1468  CB  LEU A 507      10.181  10.891  27.265  1.00 19.48           C
ATOM   1469  CG  LEU A 507       9.165  10.148  28.158  1.00 26.42           C
ATOM   1470  CD1 LEU A 507       8.420   9.135  27.311  1.00 28.63           C
ATOM   1471  CD2 LEU A 507       9.853   9.479  29.339  1.00 25.64           C
ATOM   1472  N   MET A 508      11.877  13.849  26.818  1.00 16.93           N
ATOM   1473  CA  MET A 508      12.986  14.496  26.123  1.00 23.08           C
ATOM   1474  C   MET A 508      14.076  14.811  27.154  1.00 28.54           C
ATOM   1475  O   MET A 508      15.265  14.820  26.855  1.00 23.86           O
ATOM   1476  CB  MET A 508      12.603  15.865  25.438  1.00 26.46           C
ATOM   1477  CG  MET A 508      12.016  15.450  24.036  1.00 23.87           C
ATOM   1478  SD  MET A 508      11.715  17.040  23.204  1.00 27.80           S
ATOM   1479  CE  MET A 508      10.678  17.924  24.359  1.00 30.56           C
ATOM   1480  N   LEU A 509      13.694  15.107  28.395  1.00 25.05           N
ATOM   1481  CA  LEU A 509      14.653  15.377  29.477  1.00 27.05           C
ATOM   1482  C   LEU A 509      15.476  14.184  29.885  1.00 22.15           C
ATOM   1483  O   LEU A 509      16.562  14.328  30.484  1.00 26.84           O
ATOM   1484  CB  LEU A 509      13.929  15.907  30.716  1.00 28.80           C
ATOM   1485  CG  LEU A 509      13.620  17.398  30.651  1.00 35.21           C
ATOM   1486  CD1 LEU A 509      12.905  17.767  31.920  1.00 32.29           C
ATOM   1487  CD2 LEU A 509      14.902  18.188  30.394  1.00 36.14           C
ATOM   1488  N   LEU A 510      15.101  12.954  29.602  1.00 22.10           N
ATOM   1489  CA  LEU A 510      15.847  11.731  29.817  1.00 31.30           C
ATOM   1490  C   LEU A 510      17.152  11.661  29.004  1.00 27.86           C
ATOM   1491  O   LEU A 510      18.184  11.107  29.461  1.00 25.83           O
ATOM   1492  CB  LEU A 510      15.009  10.509  29.533  1.00 32.50           C
ATOM   1493  CG  LEU A 510      14.041  10.070  30.659  1.00 37.86           C
ATOM   1494  CD1 LEU A 510      14.036   8.558  30.650  1.00 33.60           C
ATOM   1495  CD2 LEU A 510      14.409  10.625  32.030  1.00 41.89           C
ATOM   1496  N   SER A 511      17.164  12.332  27.846  1.00 21.01           N
ATOM   1497  CA  SER A 511      18.407  12.412  27.088  1.00 19.52           C
ATOM   1498  C   SER A 511      19.356  13.350  27.853  1.00 20.33           C
ATOM   1499  O   SER A 511      20.578  13.174  27.756  1.00 19.80           O
ATOM   1500  CB  SER A 511      18.054  13.094  25.749  1.00 21.91           C
ATOM   1501  OG  SER A 511      17.353  12.110  24.988  1.00 27.19           O
ATOM   1502  N   HIS A 512      18.820  14.337  28.598  1.00 17.00           N
ATOM   1503  CA  HIS A 512      19.675  15.265  29.350  1.00 17.20           C
ATOM   1504  C   HIS A 512      20.310  14.488  30.520  1.00 18.30           C
ATOM   1505  O   HIS A 512      21.462  14.726  30.897  1.00 18.47           O
ATOM   1506  CB  HIS A 512      18.901  16.482  29.781  1.00 22.31           C
ATOM   1507  CG  HIS A 512      18.468  17.393  28.645  1.00 27.23           C
ATOM   1508  ND1 HIS A 512      18.601  18.755  28.801  1.00 30.72           N
ATOM   1509  CD2 HIS A 512      17.899  17.200  27.450  1.00 32.28           C
ATOM   1510  CE1 HIS A 512      18.129  19.363  27.717  1.00 33.98           C
ATOM   1511  NE2 HIS A 512      17.705  18.450  26.873  1.00 27.65           N
ATOM   1512  N   VAL A 513      19.477  13.666  31.181  1.00 18.12           N
ATOM   1513  CA  VAL A 513      19.990  12.851  32.290  1.00 22.72           C
ATOM   1514  C   VAL A 513      21.030  11.881  31.730  1.00 20.91           C
ATOM   1515  O   VAL A 513      22.097  11.700  32.335  1.00 20.66           O
ATOM   1516  CB  VAL A 513      18.847  12.145  33.064  1.00 22.88           C
ATOM   1517  CG1 VAL A 513      19.459  11.526  34.341  1.00 23.18           C
ATOM   1518  CG2 VAL A 513      17.778  13.131  33.458  1.00 20.14           C
ATOM   1519  N   ARG A 514      20.876  11.298  30.545  1.00 19.00           N
ATOM   1520  CA  ARG A 514      21.899  10.441  29.925  1.00 20.34           C
ATOM   1521  C   ARG A 514      23.173  11.232  29.640  1.00 20.91           C
ATOM   1522  O   ARG A 514      24.289  10.721  29.911  1.00 18.76           O
ATOM   1523  CB  ARG A 514      21.354   9.808  28.623  1.00 18.63           C
ATOM   1524  CG  ARG A 514      22.254   8.874  27.840  1.00 22.80           C
ATOM   1525  CD  ARG A 514      22.365   7.479  28.524  1.00 30.40           C
ATOM   1526  NE  ARG A 514      21.077   6.785  28.263  1.00 34.94           N
ATOM   1527  CZ  ARG A 514      20.885   5.873  27.310  1.00 36.49           C
ATOM   1528  NH1 ARG A 514      21.890   5.517  26.538  1.00 35.79           N
ATOM   1529  NH2 ARG A 514      19.683   5.346  27.147  1.00 41.59           N
ATOM   1530  N   HIS A 515      23.056  12.440  29.151  1.00 18.76           N
ATOM   1531  CA  HIS A 515      24.205  13.313  28.810  1.00 21.44           C
ATOM   1532  C   HIS A 515      25.011  13.540  30.105  1.00 18.96           C
ATOM   1533  O   HIS A 515      26.244  13.432  30.147  1.00 17.34           O
```

FIG. 2T

```
ATOM   1534  CB   HIS A 515      23.755  14.646  28.186  1.00 20.53           C
ATOM   1535  CG   HIS A 515      24.880  15.556  27.748  1.00 25.29           C
ATOM   1536  ND1  HIS A 515      25.296  16.581  28.585  1.00 35.84           N
ATOM   1537  CD2  HIS A 515      25.726  15.642  26.703  1.00 29.95           C
ATOM   1538  CE1  HIS A 515      26.312  17.249  28.046  1.00 32.66           C
ATOM   1539  NE2  HIS A 515      26.606  16.696  26.909  1.00 26.95           N
ATOM   1540  N    ALA A 516      24.275  13.854  31.185  1.00 18.30           N
ATOM   1541  CA   ALA A 516      24.996  14.120  32.445  1.00 18.51           C
ATOM   1542  C    ALA A 516      25.711  12.871  32.896  1.00 16.96           C
ATOM   1543  O    ALA A 516      26.824  12.971  33.458  1.00 17.97           O
ATOM   1544  CB   ALA A 516      23.976  14.626  33.499  1.00 17.16           C
ATOM   1545  N    SER A 517      25.037  11.721  32.775  1.00 13.23           N
ATOM   1546  CA   SER A 517      25.702  10.469  33.226  1.00 15.19           C
ATOM   1547  C    SER A 517      26.931  10.196  32.386  1.00 19.61           C
ATOM   1548  O    SER A 517      27.959   9.748  32.898  1.00 16.73           O
ATOM   1549  CB   SER A 517      24.651   9.355  33.164  1.00 20.28           C
ATOM   1550  OG   SER A 517      24.221   8.924  31.883  1.00 35.94           O
ATOM   1551  N    ASN A 518      26.850  10.393  31.069  1.00 15.58           N
ATOM   1552  CA   ASN A 518      28.059  10.099  30.252  1.00 17.67           C
ATOM   1553  C    ASN A 518      29.163  11.108  30.623  1.00 19.64           C
ATOM   1554  O    ASN A 518      30.335  10.742  30.682  1.00 18.53           O
ATOM   1555  CB   ASN A 518      27.733  10.366  28.774  1.00 19.79           C
ATOM   1556  CG   ASN A 518      26.808   9.340  28.118  1.00 29.86           C
ATOM   1557  OD1  ASN A 518      26.142   9.822  27.189  1.00 31.32           O
ATOM   1558  ND2  ASN A 518      26.903   8.120  28.634  1.00 29.79           N
ATOM   1559  N    LYS A 519      28.774  12.388  30.869  1.00 18.99           N
ATOM   1560  CA   LYS A 519      29.861  13.324  31.222  1.00 19.79           C
ATOM   1561  C    LYS A 519      30.474  12.933  32.560  1.00 22.35           C
ATOM   1562  O    LYS A 519      31.692  13.041  32.810  1.00 19.90           O
ATOM   1563  CB   LYS A 519      29.351  14.774  31.166  1.00 20.32           C
ATOM   1564  CG   LYS A 519      28.748  15.191  29.831  1.00 29.40           C
ATOM   1565  CD   LYS A 519      29.562  14.820  28.603  1.00 40.46           C
ATOM   1566  CE   LYS A 519      30.943  15.429  28.663  1.00 43.73           C
ATOM   1567  NZ   LYS A 519      30.945  16.821  29.190  1.00 52.15           N
ATOM   1568  N    GLY A 520      29.640  12.570  33.550  1.00 19.78           N
ATOM   1569  CA   GLY A 520      30.068  12.129  34.849  1.00 21.87           C
ATOM   1570  C    GLY A 520      30.951  10.892  34.772  1.00 20.42           C
ATOM   1571  O    GLY A 520      31.990  10.889  35.452  1.00 20.49           O
ATOM   1572  N    MET A 521      30.641   9.931  33.866  1.00 17.39           N
ATOM   1573  CA   MET A 521      31.494   8.751  33.761  1.00 20.77           C
ATOM   1574  C    MET A 521      32.854   9.090  33.132  1.00 22.09           C
ATOM   1575  O    MET A 521      33.874   8.495  33.496  1.00 25.57           O
ATOM   1576  CB   MET A 521      30.859   7.661  32.894  1.00 21.70           C
ATOM   1577  CG   MET A 521      29.597   7.087  33.542  1.00 22.12           C
ATOM   1578  SD   MET A 521      29.941   6.202  35.059  1.00 25.78           S
ATOM   1579  CE   MET A 521      30.966   4.858  34.483  1.00 34.57           C
ATOM   1580  N    GLU A 522      32.821  10.026  32.210  1.00 19.77           N
ATOM   1581  CA   GLU A 522      34.082  10.475  31.567  1.00 25.22           C
ATOM   1582  C    GLU A 522      34.992  11.125  32.617  1.00 27.04           C
ATOM   1583  O    GLU A 522      36.222  10.925  32.674  1.00 25.63           O
ATOM   1584  CB   GLU A 522      33.737  11.549  30.540  1.00 28.85           C
ATOM   1585  CG   GLU A 522      34.963  11.924  29.709  1.00 38.45           C
ATOM   1586  CD   GLU A 522      34.586  12.775  28.502  1.00 42.28           C
ATOM   1587  OE1  GLU A 522      33.522  13.439  28.455  1.00 42.42           O
ATOM   1588  OE2  GLU A 522      35.398  12.792  27.558  1.00 44.02           O
ATOM   1589  N    HIS A 523      34.365  11.986  33.411  1.00 25.50           N
ATOM   1590  CA   HIS A 523      35.072  12.655  34.496  1.00 25.58           C
ATOM   1591  C    HIS A 523      35.612  11.652  35.497  1.00 27.34           C
ATOM   1592  O    HIS A 523      36.771  11.815  35.999  1.00 26.33           O
ATOM   1593  CB   HIS A 523      34.136  13.679  35.140  1.00 21.63           C
ATOM   1594  CG   HIS A 523      34.806  14.412  36.272  1.00 24.67           C
ATOM   1595  ND1  HIS A 523      34.739  14.029  37.579  1.00 29.47           N
ATOM   1596  CD2  HIS A 523      35.574  15.543  36.198  1.00 29.20           C
ATOM   1597  CE1  HIS A 523      35.458  14.901  38.312  1.00 29.69           C
ATOM   1598  NE2  HIS A 523      35.964  15.828  37.492  1.00 28.98           N
ATOM   1599  N    LEU A 524      34.832  10.630  35.885  1.00 23.61           N
ATOM   1600  CA   LEU A 524      35.316   9.624  36.806  1.00 25.30           C
ATOM   1601  C    LEU A 524      36.493   8.821  36.262  1.00 29.29           C
ATOM   1602  O    LEU A 524      37.517   8.568  36.943  1.00 25.59           O
ATOM   1603  CB   LEU A 524      34.121   8.699  37.151  1.00 22.60           C
ATOM   1604  CG   LEU A 524      34.407   7.594  38.141  1.00 26.13           C
ATOM   1605  CD1  LEU A 524      35.007   8.077  39.469  1.00 23.83           C
ATOM   1606  CD2  LEU A 524      33.118   6.810  38.416  1.00 26.40           C
ATOM   1607  N    LEU A 525      36.388   8.450  34.978  1.00 26.41           N
ATOM   1608  CA   LEU A 525      37.508   7.752  34.317  1.00 29.31           C
ATOM   1609  C    LEU A 525      38.733   8.665  34.330  1.00 26.40           C
ATOM   1610  O    LEU A 525      39.855   8.175  34.538  1.00 33.34           O
```

FIG. 2U

| | | | | | | | | | |
|---|---|---|---|---|---|---|---|---|---|
| ATOM | 1611 | CB | LEU | A | 525 | 37.125 | 7.485 | 32.859 | 1.00 30.24 | C |
| ATOM | 1612 | CG | LEU | A | 525 | 38.261 | 6.885 | 32.008 | 1.00 35.53 | C |
| ATOM | 1613 | CD1 | LEU | A | 525 | 38.603 | 5.515 | 32.560 | 1.00 33.00 | C |
| ATOM | 1614 | CD2 | LEU | A | 525 | 37.813 | 6.926 | 30.556 | 1.00 38.35 | C |
| ATOM | 1615 | N | ASN | A | 526 | 38.585 | 9.964 | 34.173 | 1.00 28.04 | N |
| ATOM | 1616 | CA | ASN | A | 526 | 39.739 | 10.879 | 34.195 | 1.00 32.60 | C |
| ATOM | 1617 | C | ASN | A | 526 | 40.314 | 10.939 | 35.601 | 1.00 37.85 | C |
| ATOM | 1618 | O | ASN | A | 526 | 41.544 | 10.831 | 35.827 | 1.00 32.78 | O |
| ATOM | 1619 | CB | ASN | A | 526 | 39.404 | 12.184 | 33.509 | 1.00 41.07 | C |
| ATOM | 1620 | CG | ASN | A | 526 | 39.453 | 12.066 | 31.989 | 1.00 49.96 | C |
| ATOM | 1621 | OD1 | ASN | A | 526 | 40.312 | 11.382 | 31.400 | 1.00 47.80 | O |
| ATOM | 1622 | ND2 | ASN | A | 526 | 38.548 | 12.701 | 31.238 | 1.00 52.37 | N |
| ATOM | 1623 | N | MET | A | 527 | 39.459 | 10.912 | 36.620 | 1.00 28.88 | N |
| ATOM | 1624 | CA | MET | A | 527 | 39.892 | 10.932 | 38.016 | 1.00 31.09 | C |
| ATOM | 1625 | C | MET | A | 527 | 40.665 | 9.681 | 38.371 | 1.00 29.41 | C |
| ATOM | 1626 | O | MET | A | 527 | 41.583 | 9.730 | 39.228 | 1.00 31.63 | O |
| ATOM | 1627 | CB | MET | A | 527 | 38.737 | 11.111 | 38.996 | 1.00 30.94 | C |
| ATOM | 1628 | CG | MET | A | 527 | 38.123 | 12.480 | 39.050 | 1.00 32.25 | C |
| ATOM | 1629 | SD | MET | A | 527 | 39.273 | 13.812 | 39.490 | 1.00 38.32 | S |
| ATOM | 1630 | CE | MET | A | 527 | 39.552 | 14.517 | 37.876 | 1.00 42.34 | C |
| ATOM | 1631 | N | LYS | A | 528 | 40.260 | 8.580 | 37.788 | 1.00 29.65 | N |
| ATOM | 1632 | CA | LYS | A | 528 | 40.898 | 7.290 | 37.996 | 1.00 33.35 | C |
| ATOM | 1633 | C | LYS | A | 528 | 42.250 | 7.321 | 37.261 | 1.00 40.21 | C |
| ATOM | 1634 | O | LYS | A | 528 | 43.214 | 6.736 | 37.778 | 1.00 35.78 | O |
| ATOM | 1635 | CB | LYS | A | 528 | 40.042 | 6.128 | 37.542 | 1.00 33.72 | C |
| ATOM | 1636 | CG | LYS | A | 528 | 40.665 | 4.749 | 37.628 | 1.00 43.74 | C |
| ATOM | 1637 | CD | LYS | A | 528 | 41.195 | 4.294 | 36.273 | 1.00 46.75 | C |
| ATOM | 1638 | CE | LYS | A | 528 | 41.618 | 2.830 | 36.366 | 1.00 53.32 | C |
| ATOM | 1639 | NZ | LYS | A | 528 | 41.249 | 2.097 | 35.117 | 1.00 59.40 | N |
| ATOM | 1640 | N | CYS | A | 529 | 42.290 | 7.989 | 36.107 | 1.00 36.42 | N |
| ATOM | 1641 | CA | CYS | A | 529 | 43.556 | 8.114 | 35.386 | 1.00 45.49 | C |
| ATOM | 1642 | C | CYS | A | 529 | 44.505 | 9.085 | 36.089 | 1.00 44.41 | C |
| ATOM | 1643 | O | CYS | A | 529 | 45.739 | 8.956 | 35.943 | 1.00 46.54 | O |
| ATOM | 1644 | CB | CYS | A | 529 | 43.361 | 8.551 | 33.933 | 1.00 45.99 | C |
| ATOM | 1645 | SG | CYS | A | 529 | 42.538 | 7.282 | 32.929 | 1.00 54.11 | S |
| ATOM | 1646 | N | LYS | A | 530 | 44.020 | 10.057 | 36.840 | 1.00 41.40 | N |
| ATOM | 1647 | CA | LYS | A | 530 | 44.865 | 10.985 | 37.583 | 1.00 42.22 | C |
| ATOM | 1648 | C | LYS | A | 530 | 45.317 | 10.356 | 38.907 | 1.00 41.34 | C |
| ATOM | 1649 | O | LYS | A | 530 | 45.983 | 10.964 | 39.741 | 1.00 42.74 | O |
| ATOM | 1650 | CB | LYS | A | 530 | 44.181 | 12.315 | 37.843 | 1.00 47.78 | C |
| ATOM | 1651 | CG | LYS | A | 530 | 44.062 | 13.248 | 36.639 | 1.00 54.93 | C |
| ATOM | 1652 | CD | LYS | A | 530 | 43.608 | 14.622 | 37.112 | 1.00 59.63 | C |
| ATOM | 1653 | CE | LYS | A | 530 | 42.681 | 15.306 | 36.131 | 1.00 62.07 | C |
| ATOM | 1654 | NZ | LYS | A | 530 | 41.996 | 16.471 | 36.772 | 1.00 66.71 | N |
| ATOM | 1655 | N | ASN | A | 531 | 44.862 | 9.159 | 39.207 | 1.00 33.96 | N |
| ATOM | 1656 | CA | ASN | A | 531 | 45.071 | 8.329 | 40.356 | 1.00 36.95 | C |
| ATOM | 1657 | C | ASN | A | 531 | 44.447 | 8.962 | 41.597 | 1.00 37.21 | C |
| ATOM | 1658 | O | ASN | A | 531 | 44.861 | 8.759 | 42.729 | 1.00 34.97 | O |
| ATOM | 1659 | CB | ASN | A | 531 | 46.555 | 8.010 | 40.595 | 1.00 41.21 | C |
| ATOM | 1660 | CG | ASN | A | 531 | 46.755 | 6.889 | 41.590 | 1.00 42.51 | C |
| ATOM | 1661 | OD1 | ASN | A | 531 | 46.222 | 5.783 | 41.548 | 1.00 44.47 | O |
| ATOM | 1662 | ND2 | ASN | A | 531 | 47.618 | 7.161 | 42.564 | 1.00 45.94 | N |
| ATOM | 1663 | N | VAL | A | 532 | 43.380 | 9.713 | 41.376 | 1.00 33.14 | N |
| ATOM | 1664 | CA | VAL | A | 532 | 42.609 | 10.393 | 42.420 | 1.00 33.52 | C |
| ATOM | 1665 | C | VAL | A | 532 | 41.657 | 9.407 | 43.078 | 1.00 30.82 | C |
| ATOM | 1666 | O | VAL | A | 532 | 41.314 | 9.513 | 44.269 | 1.00 32.78 | O |
| ATOM | 1667 | CB | VAL | A | 532 | 41.893 | 11.631 | 41.888 | 1.00 30.67 | C |
| ATOM | 1668 | CG1 | VAL | A | 532 | 41.012 | 12.351 | 42.894 | 1.00 30.77 | C |
| ATOM | 1669 | CG2 | VAL | A | 532 | 42.905 | 12.624 | 41.305 | 1.00 33.95 | C |
| ATOM | 1670 | N | VAL | A | 533 | 41.163 | 8.425 | 42.334 | 1.00 28.16 | N |
| ATOM | 1671 | CA | VAL | A | 533 | 40.301 | 7.405 | 42.880 | 1.00 28.57 | C |
| ATOM | 1672 | C | VAL | A | 533 | 40.833 | 6.084 | 42.358 | 1.00 30.48 | C |
| ATOM | 1673 | O | VAL | A | 533 | 41.461 | 6.090 | 41.297 | 1.00 34.29 | O |
| ATOM | 1674 | CB | VAL | A | 533 | 38.796 | 7.497 | 42.507 | 1.00 26.23 | C |
| ATOM | 1675 | CG1 | VAL | A | 533 | 38.190 | 8.771 | 43.058 | 1.00 25.81 | C |
| ATOM | 1676 | CG2 | VAL | A | 533 | 38.655 | 7.456 | 40.990 | 1.00 27.14 | C |
| ATOM | 1677 | N | PRO | A | 534 | 40.532 | 4.992 | 43.030 | 1.00 33.55 | N |
| ATOM | 1678 | CA | PRO | A | 534 | 40.998 | 3.686 | 42.641 | 1.00 34.79 | C |
| ATOM | 1679 | C | PRO | A | 534 | 40.315 | 2.988 | 41.494 | 1.00 40.51 | C |
| ATOM | 1680 | O | PRO | A | 534 | 40.942 | 2.279 | 40.685 | 1.00 40.19 | O |
| ATOM | 1681 | CB | PRO | A | 534 | 40.796 | 2.868 | 43.926 | 1.00 38.33 | C |
| ATOM | 1682 | CG | PRO | A | 534 | 39.740 | 3.556 | 44.711 | 1.00 35.85 | C |
| ATOM | 1683 | CD | PRO | A | 534 | 39.829 | 5.017 | 44.357 | 1.00 35.36 | C |
| ATOM | 1684 | N | VAL | A | 535 | 38.971 | 3.074 | 41.407 | 1.00 31.84 | N |
| ATOM | 1685 | CA | VAL | A | 535 | 38.265 | 2.375 | 40.373 | 1.00 34.53 | C |
| ATOM | 1686 | C | VAL | A | 535 | 37.284 | 3.306 | 39.646 | 1.00 35.56 | C |
| ATOM | 1687 | O | VAL | A | 535 | 36.844 | 4.334 | 40.129 | 1.00 32.66 | O |

FIG. 2V

```
ATOM  1688  CB   VAL A 535    37.472   1.166  40.914  1.00 42.03      C
ATOM  1689  CG1  VAL A 535    38.378   0.016  41.335  1.00 41.96      C
ATOM  1690  CG2  VAL A 535    36.618   1.636  42.077  1.00 41.40      C
ATOM  1691  N    TYR A 536    37.031   2.914  38.422  1.00 38.81      N
ATOM  1692  CA   TYR A 536    36.127   3.630  37.526  1.00 37.76      C
ATOM  1693  C    TYR A 536    34.753   2.987  37.622  1.00 33.11      C
ATOM  1694  O    TYR A 536    33.713   3.680  37.734  1.00 30.18      O
ATOM  1695  CB   TYR A 536    36.730   3.510  36.113  1.00 39.43      C
ATOM  1696  CG   TYR A 536    35.776   3.844  34.993  1.00 36.84      C
ATOM  1697  CD1  TYR A 536    35.249   5.129  34.853  1.00 40.40      C
ATOM  1698  CD2  TYR A 536    35.390   2.860  34.093  1.00 37.43      C
ATOM  1699  CE1  TYR A 536    34.367   5.418  33.812  1.00 37.67      C
ATOM  1700  CE2  TYR A 536    34.509   3.147  33.062  1.00 36.97      C
ATOM  1701  CZ   TYR A 536    34.025   4.430  32.910  1.00 41.30      C
ATOM  1702  OH   TYR A 536    33.141   4.693  31.877  1.00 41.15      O
ATOM  1703  N    ASP A 537    34.752   1.656  37.547  1.00 28.09      N
ATOM  1704  CA   ASP A 537    33.513   0.889  37.580  1.00 31.30      C
ATOM  1705  C    ASP A 537    33.048   0.696  39.012  1.00 29.04      C
ATOM  1706  O    ASP A 537    33.279  -0.344  39.625  1.00 25.67      O
ATOM  1707  CB   ASP A 537    33.576  -0.430  36.807  1.00 35.55      C
ATOM  1708  CG   ASP A 537    32.198  -1.027  36.548  1.00 42.06      C
ATOM  1709  OD1  ASP A 537    31.230  -0.697  37.278  1.00 35.88      O
ATOM  1710  OD2  ASP A 537    32.045  -1.830  35.593  1.00 44.18      O
ATOM  1711  N    LEU A 538    32.285   1.690  39.496  1.00 27.09      N
ATOM  1712  CA   LEU A 538    31.736   1.612  40.853  1.00 25.60      C
ATOM  1713  C    LEU A 538    30.744   0.503  41.053  1.00 23.74      C
ATOM  1714  O    LEU A 538    30.667   0.038  42.199  1.00 24.81      O
ATOM  1715  CB   LEU A 538    31.116   2.942  41.272  1.00 24.14      C
ATOM  1716  CG   LEU A 538    32.055   4.155  41.069  1.00 23.55      C
ATOM  1717  CD1  LEU A 538    31.387   5.388  41.650  1.00 22.07      C
ATOM  1718  CD2  LEU A 538    33.417   3.877  41.706  1.00 25.28      C
ATOM  1719  N    LEU A 539    29.991   0.086  40.044  1.00 24.40      N
ATOM  1720  CA   LEU A 539    29.082  -1.035  40.197  1.00 25.24      C
ATOM  1721  C    LEU A 539    29.907  -2.329  40.450  1.00 21.34      C
ATOM  1722  O    LEU A 539    29.600  -3.010  41.403  1.00 27.46      O
ATOM  1723  CB   LEU A 539    28.165  -1.180  38.970  1.00 22.82      C
ATOM  1724  CG   LEU A 539    27.298  -2.427  38.999  1.00 25.22      C
ATOM  1725  CD1  LEU A 539    26.383  -2.463  40.212  1.00 23.54      C
ATOM  1726  CD2  LEU A 539    26.489  -2.512  37.687  1.00 26.32      C
ATOM  1727  N    LEU A 540    30.889  -2.564  39.616  1.00 24.92      N
ATOM  1728  CA   LEU A 540    31.808  -3.717  39.812  1.00 31.88      C
ATOM  1729  C    LEU A 540    32.518  -3.655  41.163  1.00 30.52      C
ATOM  1730  O    LEU A 540    32.598  -4.650  41.875  1.00 33.31      O
ATOM  1731  CB   LEU A 540    32.829  -3.697  38.666  1.00 29.45      C
ATOM  1732  CG   LEU A 540    33.861  -4.865  38.710  1.00 37.60      C
ATOM  1733  CD1  LEU A 540    33.184  -6.206  38.876  1.00 36.10      C
ATOM  1734  CD2  LEU A 540    34.700  -4.809  37.449  1.00 39.88      C
ATOM  1735  N    GLU A 541    33.018  -2.494  41.579  1.00 32.71      N
ATOM  1736  CA   GLU A 541    33.658  -2.334  42.881  1.00 31.44      C
ATOM  1737  C    GLU A 541    32.698  -2.709  44.015  1.00 30.48      C
ATOM  1738  O    GLU A 541    33.067  -3.302  45.012  1.00 33.64      O
ATOM  1739  CB   GLU A 541    34.190  -0.926  43.146  1.00 35.85      C
ATOM  1740  CG   GLU A 541    35.058  -0.841  44.410  1.00 42.38      C
ATOM  1741  CD   GLU A 541    36.133  -1.934  44.373  1.00 47.06      C
ATOM  1742  OE1  GLU A 541    36.994  -1.908  43.484  1.00 46.54      O
ATOM  1743  OE2  GLU A 541    36.120  -2.860  45.210  1.00 53.26      O
ATOM  1744  N    MET A 542    31.440  -2.244  43.953  1.00 25.53      N
ATOM  1745  CA   MET A 542    30.427  -2.556  44.905  1.00 25.12      C
ATOM  1746  C    MET A 542    30.201  -4.072  45.019  1.00 28.01      C
ATOM  1747  O    MET A 542    30.232  -4.626  46.114  1.00 29.02      O
ATOM  1748  CB   MET A 542    29.074  -1.863  44.632  1.00 23.97      C
ATOM  1749  CG   MET A 542    28.085  -2.113  45.753  1.00 22.61      C
ATOM  1750  SD   MET A 542    27.112  -3.597  45.520  1.00 27.90      S
ATOM  1751  CE   MET A 542    26.106  -3.241  44.082  1.00 26.51      C
ATOM  1752  N    LEU A 543    29.975  -4.730  43.893  1.00 27.93      N
ATOM  1753  CA   LEU A 543    29.789  -6.177  43.882  1.00 37.51      C
ATOM  1754  C    LEU A 543    31.077  -6.907  44.305  1.00 29.24      C
ATOM  1755  O    LEU A 543    30.992  -8.002  44.851  1.00 40.69      O
ATOM  1756  CB   LEU A 543    29.394  -6.592  42.468  1.00 35.84      C
ATOM  1757  CG   LEU A 543    27.999  -6.116  42.022  1.00 39.20      C
ATOM  1758  CD1  LEU A 543    27.844  -6.273  40.513  1.00 37.50      C
ATOM  1759  CD2  LEU A 543    26.964  -6.890  42.819  1.00 39.03      C
ATOM  1760  N    ASN A 544    32.251  -6.388  44.020  1.00 36.39      N
ATOM  1761  CA   ASN A 544    33.450  -7.147  44.460  1.00 38.48      C
ATOM  1762  C    ASN A 544    33.631  -7.064  45.960  1.00 43.50      C
ATOM  1763  O    ASN A 544    33.883  -8.067  46.657  1.00 42.84      O
ATOM  1764  CB   ASN A 544    34.624  -6.686  43.612  1.00 45.08      C
```

FIG. 2W

```
ATOM   1765  CG   ASN A 544      34.582  -7.357  42.246  1.00 44.51           C
ATOM   1766  OD1  ASN A 544      35.290  -6.838  41.385  1.00 51.67           O
ATOM   1767  ND2  ASN A 544      33.838  -8.437  42.089  1.00 51.31           N
ATOM   1768  N    ALA A 545      33.361  -5.926  46.585  1.00 40.45           N
ATOM   1769  CA   ALA A 545      33.453  -5.756  48.021  1.00 38.08           C
ATOM   1770  C    ALA A 545      32.268  -6.193  48.848  1.00 37.95           C
ATOM   1771  O    ALA A 545      32.444  -6.329  50.078  1.00 47.01           O
ATOM   1772  CB   ALA A 545      33.672  -4.257  48.315  1.00 36.01           C
ATOM   1773  N    HIS A 546      31.048  -6.361  48.386  1.00 31.25           N
ATOM   1774  CA   HIS A 546      29.911  -6.714  49.206  1.00 32.20           C
ATOM   1775  C    HIS A 546      29.653  -8.214  49.109  1.00 38.99           C
ATOM   1776  O    HIS A 546      29.988  -8.799  48.073  1.00 34.48           O
ATOM   1777  CB   HIS A 546      28.664  -5.875  48.914  1.00 35.48           C
ATOM   1778  CG   HIS A 546      28.866  -4.431  49.329  1.00 30.08           C
ATOM   1779  ND1  HIS A 546      28.295  -3.939  50.481  1.00 37.29           N
ATOM   1780  CD2  HIS A 546      29.565  -3.435  48.771  1.00 34.54           C
ATOM   1781  CE1  HIS A 546      28.660  -2.660  50.619  1.00 35.68           C
ATOM   1782  NE2  HIS A 546      29.411  -2.339  49.593  1.00 33.94           N
ATOM   1783  N    VAL A 547      29.150  -8.824  50.174  1.00 40.87           N
ATOM   1784  CA   VAL A 547      28.935 -10.273  50.130  1.00 45.83           C
ATOM   1785  C    VAL A 547      27.450 -10.597  50.207  1.00 48.59           C
ATOM   1786  O    VAL A 547      26.638  -9.875  50.786  1.00 45.34           O
ATOM   1787  CB   VAL A 547      29.786 -11.039  51.161  1.00 49.80           C
ATOM   1788  CG1  VAL A 547      30.307 -10.158  52.287  1.00 51.09           C
ATOM   1789  CG2  VAL A 547      29.123 -12.243  51.823  1.00 53.46           C
ATOM   1790  N    LEU A 548      27.114 -11.681  49.496  1.00 43.35           N
ATOM   1791  CA   LEU A 548      25.729 -12.160  49.515  1.00 47.89           C
ATOM   1792  C    LEU A 548      25.376 -12.566  50.937  1.00 46.50           C
ATOM   1793  O    LEU A 548      26.222 -13.151  51.608  1.00 45.59           O
ATOM   1794  CB   LEU A 548      25.612 -13.387  48.594  1.00 45.45           C
ATOM   1795  CG   LEU A 548      25.824 -13.036  47.118  1.00 49.38           C
ATOM   1796  CD1  LEU A 548      26.029 -14.264  46.249  1.00 47.84           C
ATOM   1797  CD2  LEU A 548      24.627 -12.232  46.615  1.00 48.16           C
ATOM   1798  N    ALA A 549      24.188 -12.232  51.402  1.00 54.13           N
ATOM   1799  CA   ALA A 549      23.752 -12.624  52.744  1.00 57.06           C
ATOM   1800  C    ALA A 549      22.623 -13.653  52.585  1.00 56.83           C
ATOM   1801  O    ALA A 549      22.740 -14.402  51.568  1.00 56.96           O
ATOM   1802  CB   ALA A 549      23.319 -11.460  53.602  1.00 58.43           C
ATOM   1803  N    LEU B 311       2.997  26.939  11.936  1.00 28.08           N
ATOM   1804  CA   LEU B 311       3.288  25.890  12.956  1.00 33.81           C
ATOM   1805  C    LEU B 311       2.220  24.823  13.099  1.00 36.64           C
ATOM   1806  O    LEU B 311       2.422  23.943  13.941  1.00 35.73           O
ATOM   1807  CB   LEU B 311       3.595  26.539  14.293  1.00 32.95           C
ATOM   1808  CG   LEU B 311       4.849  27.406  14.305  1.00 33.74           C
ATOM   1809  CD1  LEU B 311       4.950  28.130  15.644  1.00 36.98           C
ATOM   1810  CD2  LEU B 311       6.095  26.598  14.019  1.00 34.94           C
ATOM   1811  N    SER B 312       1.144  24.868  12.322  1.00 33.54           N
ATOM   1812  CA   SER B 312       0.128  23.810  12.449  1.00 35.91           C
ATOM   1813  C    SER B 312       0.830  22.540  11.976  1.00 31.76           C
ATOM   1814  O    SER B 312       1.699  22.603  11.127  1.00 28.79           O
ATOM   1815  CB   SER B 312      -1.113  24.179  11.641  1.00 37.81           C
ATOM   1816  OG   SER B 312      -0.946  23.904  10.268  1.00 44.53           O
ATOM   1817  N    PRO B 313       0.472  21.378  12.505  1.00 33.20           N
ATOM   1818  CA   PRO B 313       1.160  20.130  12.176  1.00 29.36           C
ATOM   1819  C    PRO B 313       1.374  19.809  10.726  1.00 30.45           C
ATOM   1820  O    PRO B 313       2.500  19.515  10.291  1.00 28.30           O
ATOM   1821  CB   PRO B 313       0.272  19.093  12.871  1.00 28.85           C
ATOM   1822  CG   PRO B 313      -0.357  19.811  14.029  1.00 30.58           C
ATOM   1823  CD   PRO B 313      -0.571  21.235  13.545  1.00 32.44           C
ATOM   1824  N    GLU B 314       0.350  19.829   9.859  1.00 26.68           N
ATOM   1825  CA   GLU B 314       0.570  19.471   8.458  1.00 28.47           C
ATOM   1826  C    GLU B 314       1.575  20.360   7.714  1.00 26.99           C
ATOM   1827  O    GLU B 314       2.441  19.927   6.942  1.00 30.41           O
ATOM   1828  CB   GLU B 314      -0.788  19.492   7.734  1.00 35.34           C
ATOM   1829  CG   GLU B 314      -0.667  19.284   6.226  1.00 39.69           C
ATOM   1830  CD   GLU B 314      -2.047  18.819   5.717  1.00 47.00           C
ATOM   1831  OE1  GLU B 314      -3.053  19.421   6.148  1.00 48.55           O
ATOM   1832  OE2  GLU B 314      -2.071  17.867   4.941  1.00 44.66           O
ATOM   1833  N    GLN B 315       1.475  21.643   7.937  1.00 26.38           N
ATOM   1834  CA   GLN B 315       2.343  22.653   7.352  1.00 29.68           C
ATOM   1835  C    GLN B 315       3.763  22.592   7.945  1.00 31.40           C
ATOM   1836  O    GLN B 315       4.698  22.770   7.183  1.00 27.97           O
ATOM   1837  CB   GLN B 315       1.778  24.030   7.722  1.00 34.22           C
ATOM   1838  CG   GLN B 315       2.781  25.134   7.527  1.00 45.77           C
ATOM   1839  CD   GLN B 315       2.388  26.515   7.980  1.00 56.80           C
ATOM   1840  OE1  GLN B 315       3.047  27.482   7.546  1.00 61.06           O
ATOM   1841  NE2  GLN B 315       1.343  26.636   8.806  1.00 59.90           N
```

FIG. 2X

```
ATOM   1842  N    LEU B 316      3.844  22.320   9.266  1.00 26.87           N
ATOM   1843  CA   LEU B 316      5.164  22.225   9.893  1.00 30.02           C
ATOM   1844  C    LEU B 316      5.953  21.060   9.307  1.00 24.87           C
ATOM   1845  O    LEU B 316      7.087  21.168   8.853  1.00 21.60           O
ATOM   1846  CB   LEU B 316      5.082  22.171  11.419  1.00 30.22           C
ATOM   1847  CG   LEU B 316      6.448  22.132  12.151  1.00 29.83           C
ATOM   1848  CD1  LEU B 316      7.407  23.196  11.647  1.00 36.85           C
ATOM   1849  CD2  LEU B 316      6.214  22.305  13.649  1.00 31.20           C
ATOM   1850  N    VAL B 317      5.290  19.911   9.164  1.00 26.19           N
ATOM   1851  CA   VAL B 317      5.910  18.754   8.555  1.00 25.93           C
ATOM   1852  C    VAL B 317      6.283  19.026   7.095  1.00 26.19           C
ATOM   1853  O    VAL B 317      7.335  18.608   6.592  1.00 26.56           O
ATOM   1854  CB   VAL B 317      4.963  17.536   8.651  1.00 23.20           C
ATOM   1855  CG1  VAL B 317      5.602  16.338   7.965  1.00 29.83           C
ATOM   1856  CG2  VAL B 317      4.725  17.198  10.129  1.00 24.89           C
ATOM   1857  N    LEU B 318      5.366  19.711   6.374  1.00 26.44           N
ATOM   1858  CA   LEU B 318      5.715  20.004   4.961  1.00 25.87           C
ATOM   1859  C    LEU B 318      6.993  20.864   4.939  1.00 21.42           C
ATOM   1860  O    LEU B 318      7.871  20.601   4.105  1.00 26.99           O
ATOM   1861  CB   LEU B 318      4.557  20.676   4.227  1.00 34.23           C
ATOM   1862  CG   LEU B 318      4.729  20.919   2.721  1.00 43.62           C
ATOM   1863  CD1  LEU B 318      5.709  19.980   2.035  1.00 43.77           C
ATOM   1864  CD2  LEU B 318      3.321  20.817   2.110  1.00 50.90           C
ATOM   1865  N    THR B 319      7.102  21.869   5.750  1.00 22.65           N
ATOM   1866  CA   THR B 319      8.304  22.714   5.845  1.00 23.19           C
ATOM   1867  C    THR B 319      9.527  21.880   6.190  1.00 24.51           C
ATOM   1868  O    THR B 319     10.600  22.022   5.587  1.00 22.04           O
ATOM   1869  CB   THR B 319      8.050  23.836   6.857  1.00 29.56           C
ATOM   1870  OG1  THR B 319      6.938  24.585   6.281  1.00 31.39           O
ATOM   1871  CG2  THR B 319      9.245  24.756   7.064  1.00 29.89           C
ATOM   1872  N    LEU B 320      9.341  20.936   7.148  1.00 23.26           N
ATOM   1873  CA   LEU B 320     10.491  20.067   7.476  1.00 21.50           C
ATOM   1874  C    LEU B 320     10.894  19.211   6.299  1.00 22.15           C
ATOM   1875  O    LEU B 320     12.092  19.033   6.062  1.00 24.21           O
ATOM   1876  CB   LEU B 320     10.196  19.210   8.717  1.00 20.38           C
ATOM   1877  CG   LEU B 320      9.900  19.993   9.996  1.00 23.03           C
ATOM   1878  CD1  LEU B 320      9.548  19.072  11.165  1.00 25.32           C
ATOM   1879  CD2  LEU B 320     11.194  20.775  10.338  1.00 27.97           C
ATOM   1880  N    LEU B 321      9.926  18.679   5.537  1.00 23.98           N
ATOM   1881  CA   LEU B 321     10.193  17.885   4.347  1.00 27.88           C
ATOM   1882  C    LEU B 321     10.950  18.700   3.297  1.00 24.23           C
ATOM   1883  O    LEU B 321     12.004  18.297   2.834  1.00 28.05           O
ATOM   1884  CB   LEU B 321      8.953  17.279   3.665  1.00 32.25           C
ATOM   1885  CG   LEU B 321      9.444  16.095   2.797  1.00 42.62           C
ATOM   1886  CD1  LEU B 321      9.195  14.790   3.529  1.00 40.89           C
ATOM   1887  CD2  LEU B 321      8.963  16.136   1.372  1.00 44.42           C
ATOM   1888  N    GLU B 322     10.584  19.962   3.117  1.00 26.19           N
ATOM   1889  CA   GLU B 322     11.273  20.866   2.204  1.00 33.17           C
ATOM   1890  C    GLU B 322     12.650  21.304   2.681  1.00 37.53           C
ATOM   1891  O    GLU B 322     13.557  21.573   1.874  1.00 34.01           O
ATOM   1892  CB   GLU B 322     10.419  22.129   1.971  1.00 31.87           C
ATOM   1893  CG   GLU B 322      9.136  21.886   1.212  1.00 45.26           C
ATOM   1894  CD   GLU B 322      7.960  22.821   1.391  1.00 50.64           C
ATOM   1895  OE1  GLU B 322      8.076  23.889   2.029  1.00 55.44           O
ATOM   1896  OE2  GLU B 322      6.862  22.498   0.866  1.00 53.60           O
ATOM   1897  N    ALA B 323     12.918  21.323   3.985  1.00 28.29           N
ATOM   1898  CA   ALA B 323     14.165  21.776   4.551  1.00 28.43           C
ATOM   1899  C    ALA B 323     15.262  20.723   4.563  1.00 23.34           C
ATOM   1900  O    ALA B 323     16.407  21.056   4.918  1.00 23.98           O
ATOM   1901  CB   ALA B 323     13.897  22.348   5.942  1.00 29.41           C
ATOM   1902  N    GLU B 324     14.960  19.516   4.168  1.00 23.45           N
ATOM   1903  CA   GLU B 324     15.866  18.397   4.182  1.00 23.91           C
ATOM   1904  C    GLU B 324     17.077  18.646   3.323  1.00 27.63           C
ATOM   1905  O    GLU B 324     16.940  19.001   2.143  1.00 25.43           O
ATOM   1906  CB   GLU B 324     15.176  17.118   3.748  1.00 26.75           C
ATOM   1907  CG   GLU B 324     14.482  16.319   4.833  1.00 30.12           C
ATOM   1908  CD   GLU B 324     15.459  15.784   5.884  1.00 27.37           C
ATOM   1909  OE1  GLU B 324     15.687  16.472   6.899  1.00 27.33           O
ATOM   1910  OE2  GLU B 324     15.984  14.678   5.715  1.00 32.31           O
ATOM   1911  N    PRO B 325     18.260  18.474   3.861  1.00 27.81           N
ATOM   1912  CA   PRO B 325     19.459  18.676   3.077  1.00 30.04           C
ATOM   1913  C    PRO B 325     19.550  17.819   1.827  1.00 27.05           C
ATOM   1914  O    PRO B 325     19.174  16.649   1.832  1.00 30.82           O
ATOM   1915  CB   PRO B 325     20.579  18.211   4.025  1.00 33.29           C
ATOM   1916  CG   PRO B 325     20.014  18.290   5.394  1.00 32.61           C
ATOM   1917  CD   PRO B 325     18.528  18.063   5.279  1.00 26.80           C
ATOM   1918  N    PRO B 326     20.333  18.312   0.858  1.00 31.94           N
```

FIG. 2Y

```
ATOM   1919  CA  PRO B 326      20.577  17.563  -0.370  1.00 34.47           C
ATOM   1920  C   PRO B 326      21.499  16.404  -0.021  1.00 36.74           C
ATOM   1921  O   PRO B 326      22.182  16.514   1.023  1.00 28.88           O
ATOM   1922  CB  PRO B 326      21.322  18.603  -1.220  1.00 33.99           C
ATOM   1923  CG  PRO B 326      21.992  19.512  -0.229  1.00 36.09           C
ATOM   1924  CD  PRO B 326      20.811  19.708   0.745  1.00 31.99           C
ATOM   1925  N   HIS B 327      21.672  15.369  -0.845  1.00 33.12           N
ATOM   1926  CA  HIS B 327      22.639  14.326  -0.519  1.00 35.27           C
ATOM   1927  C   HIS B 327      24.059  14.891  -0.698  1.00 34.67           C
ATOM   1928  O   HIS B 327      24.280  15.813  -1.510  1.00 30.20           O
ATOM   1929  CB  HIS B 327      22.500  13.130  -1.458  1.00 44.84           C
ATOM   1930  CG  HIS B 327      21.173  12.440  -1.478  1.00 52.21           C
ATOM   1931  ND1 HIS B 327      20.053  13.005  -2.048  1.00 56.60           N
ATOM   1932  CD2 HIS B 327      20.780  11.225  -1.026  1.00 53.45           C
ATOM   1933  CE1 HIS B 327      19.026  12.173  -1.943  1.00 58.32           C
ATOM   1934  NE2 HIS B 327      19.450  11.084  -1.326  1.00 55.20           N
ATOM   1935  N   VAL B 328      24.998  14.343   0.058  1.00 26.84           N
ATOM   1936  CA  VAL B 328      26.407  14.756  -0.017  1.00 29.87           C
ATOM   1937  C   VAL B 328      27.150  13.684  -0.834  1.00 35.70           C
ATOM   1938  O   VAL B 328      26.920  12.470  -0.768  1.00 37.59           O
ATOM   1939  CB  VAL B 328      27.102  14.983   1.329  1.00 38.42           C
ATOM   1940  CG1 VAL B 328      28.608  15.126   1.202  1.00 40.42           C
ATOM   1941  CG2 VAL B 328      26.570  16.241   2.013  1.00 36.69           C
ATOM   1942  N   LEU B 329      28.108  14.161  -1.629  1.00 31.23           N
ATOM   1943  CA  LEU B 329      28.901  13.208  -2.428  1.00 36.50           C
ATOM   1944  C   LEU B 329      30.317  13.139  -1.856  1.00 33.10           C
ATOM   1945  O   LEU B 329      30.967  14.166  -1.773  1.00 27.72           O
ATOM   1946  CB  LEU B 329      29.040  13.675  -3.866  1.00 39.45           C
ATOM   1947  CG  LEU B 329      27.970  14.691  -4.259  1.00 45.22           C
ATOM   1948  CD1 LEU B 329      28.564  15.941  -4.921  1.00 51.61           C
ATOM   1949  CD2 LEU B 329      26.920  14.056  -5.142  1.00 48.87           C
ATOM   1950  N   ILE B 330      30.704  11.973  -1.413  1.00 32.02           N
ATOM   1951  CA  ILE B 330      32.040  11.727  -0.878  1.00 31.90           C
ATOM   1952  C   ILE B 330      32.277  10.263  -1.213  1.00 30.64           C
ATOM   1953  O   ILE B 330      31.317   9.475  -1.174  1.00 29.62           O
ATOM   1954  CB  ILE B 330      32.173  12.091   0.599  1.00 31.89           C
ATOM   1955  CG1 ILE B 330      33.622  12.184   1.039  1.00 38.77           C
ATOM   1956  CG2 ILE B 330      31.427  11.097   1.485  1.00 34.48           C
ATOM   1957  CD1 ILE B 330      33.898  12.836   2.371  1.00 36.86           C
ATOM   1958  N   SER B 331      33.481   9.916  -1.636  1.00 30.39           N
ATOM   1959  CA  SER B 331      33.763   8.514  -1.991  1.00 30.31           C
ATOM   1960  C   SER B 331      34.935   8.017  -1.147  1.00 28.82           C
ATOM   1961  O   SER B 331      35.624   8.891  -0.621  1.00 33.08           O
ATOM   1962  CB  SER B 331      34.269   8.445  -3.451  1.00 36.40           C
ATOM   1963  OG  SER B 331      33.205   8.676  -4.372  1.00 44.06           O
ATOM   1964  N   ARG B 332      35.193   6.727  -1.123  1.00 34.39           N
ATOM   1965  CA  ARG B 332      36.381   6.242  -0.407  1.00 39.40           C
ATOM   1966  C   ARG B 332      37.630   6.760  -1.111  1.00 40.89           C
ATOM   1967  O   ARG B 332      37.532   7.090  -2.301  1.00 37.21           O
ATOM   1968  CB  ARG B 332      36.419   4.737  -0.540  1.00 41.47           C
ATOM   1969  CG  ARG B 332      35.191   4.031  -0.039  1.00 35.40           C
ATOM   1970  CD  ARG B 332      35.310   2.524  -0.298  1.00 36.04           C
ATOM   1971  NE  ARG B 332      34.175   1.914   0.457  1.00 32.43           N
ATOM   1972  CZ  ARG B 332      34.484   1.239   1.581  1.00 32.86           C
ATOM   1973  NH1 ARG B 332      33.409   0.729   2.207  1.00 31.12           N
ATOM   1974  NH2 ARG B 332      35.717   1.083   2.019  1.00 32.26           N
ATOM   1975  N   PRO B 333      38.740   6.812  -0.404  1.00 40.15           N
ATOM   1976  CA  PRO B 333      39.982   7.270  -0.991  1.00 42.44           C
ATOM   1977  C   PRO B 333      40.526   6.211  -1.943  1.00 44.51           C
ATOM   1978  O   PRO B 333      40.051   5.063  -1.909  1.00 35.65           O
ATOM   1979  CB  PRO B 333      40.896   7.440   0.226  1.00 43.67           C
ATOM   1980  CG  PRO B 333      40.351   6.524   1.268  1.00 43.95           C
ATOM   1981  CD  PRO B 333      38.860   6.418   1.019  1.00 40.70           C
ATOM   1982  N   SER B 334      41.467   6.565  -2.811  1.00 47.81           N
ATOM   1983  CA  SER B 334      42.086   5.532  -3.662  1.00 53.70           C
ATOM   1984  C   SER B 334      43.193   4.987  -2.730  1.00 54.54           C
ATOM   1985  O   SER B 334      44.018   5.795  -2.305  1.00 57.51           O
ATOM   1986  CB  SER B 334      42.770   6.035  -4.912  1.00 59.20           C
ATOM   1987  OG  SER B 334      41.981   6.749  -5.830  1.00 62.84           O
ATOM   1988  N   ALA B 335      43.218   3.740  -2.366  1.00 57.13           N
ATOM   1989  CA  ALA B 335      44.189   3.118  -1.471  1.00 57.19           C
ATOM   1990  C   ALA B 335      43.368   2.447  -0.371  1.00 56.88           C
ATOM   1991  O   ALA B 335      42.285   2.954  -0.070  1.00 59.11           O
ATOM   1992  CB  ALA B 335      45.256   4.037  -0.895  1.00 51.31           C
ATOM   1993  N   PRO B 336      43.786   1.320   0.173  1.00 57.85           N
ATOM   1994  CA  PRO B 336      43.002   0.675   1.230  1.00 50.78           C
ATOM   1995  C   PRO B 336      42.779   1.635   2.383  1.00 44.37           C
```

FIG. 2Z

```
ATOM  1996  O    PRO B 336    43.612   2.549   2.492  1.00 37.84          O
ATOM  1997  CB   PRO B 336    43.846  -0.531   1.585  1.00 53.06          C
ATOM  1998  CG   PRO B 336    44.980  -0.609   0.642  1.00 56.37          C
ATOM  1999  CD   PRO B 336    45.082   0.674  -0.133  1.00 56.75          C
ATOM  2000  N    PHE B 337    41.748   1.638   3.226  1.00 40.95          N
ATOM  2001  CA   PHE B 337    41.676   2.607   4.310  1.00 36.23          C
ATOM  2002  C    PHE B 337    42.762   2.434   5.383  1.00 36.84          C
ATOM  2003  O    PHE B 337    43.269   1.361   5.701  1.00 35.34          O
ATOM  2004  CB   PHE B 337    40.390   2.499   5.159  1.00 31.96          C
ATOM  2005  CG   PHE B 337    39.263   3.377   4.699  1.00 34.87          C
ATOM  2006  CD1  PHE B 337    39.363   4.749   4.738  1.00 32.24          C
ATOM  2007  CD2  PHE B 337    38.079   2.834   4.253  1.00 31.52          C
ATOM  2008  CE1  PHE B 337    38.325   5.530   4.307  1.00 28.75          C
ATOM  2009  CE2  PHE B 337    37.038   3.613   3.811  1.00 32.01          C
ATOM  2010  CZ   PHE B 337    37.155   4.997   3.818  1.00 27.84          C
ATOM  2011  N    THR B 338    43.131   3.544   6.012  1.00 33.30          N
ATOM  2012  CA   THR B 338    44.013   3.534   7.156  1.00 29.45          C
ATOM  2013  C    THR B 338    43.306   4.290   8.309  1.00 28.52          C
ATOM  2014  O    THR B 338    42.339   4.992   8.067  1.00 26.68          O
ATOM  2015  CB   THR B 338    45.368   4.221   6.987  1.00 32.68          C
ATOM  2016  OG1  THR B 338    45.197   5.623   6.727  1.00 30.26          O
ATOM  2017  CG2  THR B 338    46.145   3.553   5.846  1.00 29.51          C
ATOM  2018  N    GLU B 339    43.924   4.256   9.484  1.00 28.92          N
ATOM  2019  CA   GLU B 339    43.297   5.026  10.582  1.00 32.61          C
ATOM  2020  C    GLU B 339    43.169   6.490  10.160  1.00 28.51          C
ATOM  2021  O    GLU B 339    42.105   7.088  10.330  1.00 31.42          O
ATOM  2022  CB   GLU B 339    44.151   4.892  11.848  1.00 28.29          C
ATOM  2023  CG   GLU B 339    43.556   5.721  12.990  1.00 26.60          C
ATOM  2024  CD   GLU B 339    44.224   5.307  14.295  1.00 33.99          C
ATOM  2025  OE1  GLU B 339    45.146   6.015  14.724  1.00 36.37          O
ATOM  2026  OE2  GLU B 339    43.792   4.279  14.845  1.00 34.15          O
ATOM  2027  N    ALA B 340    44.255   7.107   9.675  1.00 29.47          N
ATOM  2028  CA   ALA B 340    44.177   8.500   9.231  1.00 27.20          C
ATOM  2029  C    ALA B 340    43.163   8.788   8.129  1.00 27.59          C
ATOM  2030  O    ALA B 340    42.413   9.778   8.200  1.00 25.16          O
ATOM  2031  CB   ALA B 340    45.549   8.937   8.663  1.00 28.39          C
ATOM  2032  N    SER B 341    43.122   7.985   7.064  1.00 27.38          N
ATOM  2033  CA   SER B 341    42.258   8.206   5.930  1.00 29.36          C
ATOM  2034  C    SER B 341    40.800   7.917   6.248  1.00 29.72          C
ATOM  2035  O    SER B 341    39.924   8.573   5.662  1.00 29.01          O
ATOM  2036  CB   SER B 341    42.714   7.502   4.645  1.00 26.99          C
ATOM  2037  OG   SER B 341    42.474   6.115   4.739  1.00 27.11          O
ATOM  2038  N    MET B 342    40.529   6.985   7.166  1.00 24.98          N
ATOM  2039  CA   MET B 342    39.150   6.743   7.561  1.00 23.68          C
ATOM  2040  C    MET B 342    38.673   7.939   8.414  1.00 23.31          C
ATOM  2041  O    MET B 342    37.523   8.386   8.206  1.00 25.29          O
ATOM  2042  CB   MET B 342    38.896   5.487   8.386  1.00 27.55          C
ATOM  2043  CG   MET B 342    37.397   5.215   8.550  1.00 27.66          C
ATOM  2044  SD   MET B 342    37.090   3.656   9.380  1.00 29.65          S
ATOM  2045  CE   MET B 342    35.507   3.104   8.974  1.00 44.03          C
ATOM  2046  N    MET B 343    39.548   8.422   9.265  1.00 21.82          N
ATOM  2047  CA   MET B 343    39.185   9.589  10.107  1.00 22.48          C
ATOM  2048  C    MET B 343    39.016  10.811   9.212  1.00 24.67          C
ATOM  2049  O    MET B 343    38.115  11.634   9.360  1.00 21.01          O
ATOM  2050  CB   MET B 343    40.149   9.859  11.247  1.00 24.43          C
ATOM  2051  CG   MET B 343    39.976   8.774  12.342  1.00 22.35          C
ATOM  2052  SD   MET B 343    38.316   8.829  13.096  1.00 21.63          S
ATOM  2053  CE   MET B 343    38.164  10.583  13.402  1.00 25.68          C
ATOM  2054  N    MET B 344    39.885  10.922   8.218  1.00 24.93          N
ATOM  2055  CA   MET B 344    39.791  12.034   7.260  1.00 25.48          C
ATOM  2056  C    MET B 344    38.474  11.976   6.502  1.00 22.31          C
ATOM  2057  O    MET B 344    37.846  13.025   6.324  1.00 23.67          O
ATOM  2058  CB   MET B 344    40.955  11.930   6.239  1.00 29.94          C
ATOM  2059  CG   MET B 344    40.791  13.025   5.182  1.00 37.21          C
ATOM  2060  SD   MET B 344    42.354  13.368   4.341  1.00 40.57          S
ATOM  2061  CE   MET B 344    42.937  14.787   5.241  1.00 35.41          C
ATOM  2062  N    SER B 345    38.043  10.785   6.034  1.00 21.31          N
ATOM  2063  CA   SER B 345    36.777  10.731   5.342  1.00 23.23          C
ATOM  2064  C    SER B 345    35.615  11.153   6.253  1.00 22.08          C
ATOM  2065  O    SER B 345    34.690  11.845   5.801  1.00 22.12          O
ATOM  2066  CB   SER B 345    36.481   9.333   4.793  1.00 26.82          C
ATOM  2067  OG   SER B 345    37.488   9.025   3.814  1.00 27.51          O
ATOM  2068  N    LEU B 346    35.606  10.660   7.497  1.00 22.10          N
ATOM  2069  CA   LEU B 346    34.441  11.013   8.332  1.00 21.15          C
ATOM  2070  C    LEU B 346    34.404  12.485   8.686  1.00 18.81          C
ATOM  2071  O    LEU B 346    33.298  13.099   8.724  1.00 22.67          O
ATOM  2072  CB   LEU B 346    34.502  10.131   9.599  1.00 19.43          C
```

FIG. 2AA

| | | | | | | | | | |
|---|---|---|---|---|---|---|---|---|---|
| ATOM | 2073 | CG | LEU | B | 346 | 34.427 | 8.639 | 9.369 | 1.00 24.42 | C |
| ATOM | 2074 | CD1 | LEU | B | 346 | 34.561 | 7.966 | 10.740 | 1.00 28.57 | C |
| ATOM | 2075 | CD2 | LEU | B | 346 | 33.157 | 8.187 | 8.655 | 1.00 29.99 | C |
| ATOM | 2076 | N | THR | B | 347 | 35.546 | 13.087 | 8.986 | 1.00 19.93 | N |
| ATOM | 2077 | CA | THR | B | 347 | 35.528 | 14.507 | 9.342 | 1.00 19.84 | C |
| ATOM | 2078 | C | THR | B | 347 | 35.308 | 15.411 | 8.124 | 1.00 24.67 | C |
| ATOM | 2079 | O | THR | B | 347 | 34.717 | 16.475 | 8.227 | 1.00 22.92 | O |
| ATOM | 2080 | CB | THR | B | 347 | 36.838 | 14.910 | 10.037 | 1.00 23.31 | C |
| ATOM | 2081 | OG1 | THR | B | 347 | 37.991 | 14.605 | 9.228 | 1.00 24.67 | O |
| ATOM | 2082 | CG2 | THR | B | 347 | 36.890 | 14.105 | 11.334 | 1.00 24.77 | C |
| ATOM | 2083 | N | LYS | B | 348 | 35.811 | 14.974 | 6.958 | 1.00 22.52 | N |
| ATOM | 2084 | CA | LYS | B | 348 | 35.551 | 15.788 | 5.765 | 1.00 23.61 | C |
| ATOM | 2085 | C | LYS | B | 348 | 34.059 | 15.717 | 5.428 | 1.00 24.49 | C |
| ATOM | 2086 | O | LYS | B | 348 | 33.456 | 16.725 | 5.062 | 1.00 22.74 | O |
| ATOM | 2087 | CB | LYS | B | 348 | 36.403 | 15.342 | 4.563 | 1.00 24.18 | C |
| ATOM | 2088 | CG | LYS | B | 348 | 36.053 | 16.197 | 3.334 | 1.00 37.16 | C |
| ATOM | 2089 | CD | LYS | B | 348 | 37.153 | 16.043 | 2.284 | 1.00 46.82 | C |
| ATOM | 2090 | CE | LYS | B | 348 | 36.641 | 16.262 | 0.860 | 1.00 55.26 | C |
| ATOM | 2091 | NZ | LYS | B | 348 | 37.815 | 16.235 | -0.085 | 1.00 55.79 | N |
| ATOM | 2092 | N | LEU | B | 349 | 33.472 | 14.539 | 5.550 | 1.00 23.04 | N |
| ATOM | 2093 | CA | LEU | B | 349 | 32.029 | 14.391 | 5.307 | 1.00 23.65 | C |
| ATOM | 2094 | C | LEU | B | 349 | 31.203 | 15.243 | 6.270 | 1.00 20.57 | C |
| ATOM | 2095 | O | LEU | B | 349 | 30.243 | 15.901 | 5.846 | 1.00 19.40 | O |
| ATOM | 2096 | CB | LEU | B | 349 | 31.580 | 12.953 | 5.470 | 1.00 21.30 | C |
| ATOM | 2097 | CG | LEU | B | 349 | 30.095 | 12.610 | 5.442 | 1.00 19.13 | C |
| ATOM | 2098 | CD1 | LEU | B | 349 | 29.501 | 13.108 | 4.100 | 1.00 24.56 | C |
| ATOM | 2099 | CD2 | LEU | B | 349 | 29.844 | 11.135 | 5.672 | 1.00 19.63 | C |
| ATOM | 2100 | N | ALA | B | 350 | 31.613 | 15.152 | 7.561 | 1.00 16.98 | N |
| ATOM | 2101 | CA | ALA | B | 350 | 30.858 | 15.982 | 8.544 | 1.00 16.28 | C |
| ATOM | 2102 | C | ALA | B | 350 | 30.952 | 17.454 | 8.186 | 1.00 19.41 | C |
| ATOM | 2103 | O | ALA | B | 350 | 29.939 | 18.204 | 8.257 | 1.00 21.18 | O |
| ATOM | 2104 | CB | ALA | B | 350 | 31.472 | 15.773 | 9.941 | 1.00 22.64 | C |
| ATOM | 2105 | N | ASP | B | 351 | 32.101 | 17.948 | 7.738 | 1.00 23.16 | N |
| ATOM | 2106 | CA | ASP | B | 351 | 32.224 | 19.365 | 7.361 | 1.00 21.48 | C |
| ATOM | 2107 | C | ASP | B | 351 | 31.238 | 19.737 | 6.251 | 1.00 23.62 | C |
| ATOM | 2108 | O | ASP | B | 351 | 30.570 | 20.774 | 6.396 | 1.00 21.75 | O |
| ATOM | 2109 | CB | ASP | B | 351 | 33.665 | 19.593 | 6.857 | 1.00 25.15 | C |
| ATOM | 2110 | CG | ASP | B | 351 | 33.915 | 21.092 | 6.619 | 1.00 29.55 | C |
| ATOM | 2111 | OD1 | ASP | B | 351 | 34.094 | 21.878 | 7.552 | 1.00 24.38 | O |
| ATOM | 2112 | OD2 | ASP | B | 351 | 33.910 | 21.397 | 5.421 | 1.00 29.71 | O |
| ATOM | 2113 | N | LYS | B | 352 | 31.108 | 18.838 | 5.245 | 1.00 23.19 | N |
| ATOM | 2114 | CA | LYS | B | 352 | 30.201 | 19.124 | 4.157 | 1.00 20.51 | C |
| ATOM | 2115 | C | LYS | B | 352 | 28.758 | 19.109 | 4.667 | 1.00 24.27 | C |
| ATOM | 2116 | O | LYS | B | 352 | 27.947 | 19.974 | 4.327 | 1.00 21.67 | O |
| ATOM | 2117 | CB | LYS | B | 352 | 30.382 | 18.082 | 3.038 | 1.00 24.81 | C |
| ATOM | 2118 | CG | LYS | B | 352 | 31.877 | 17.933 | 2.601 | 1.00 30.93 | C |
| ATOM | 2119 | CD | LYS | B | 352 | 31.877 | 17.094 | 1.313 | 1.00 34.26 | C |
| ATOM | 2120 | CE | LYS | B | 352 | 33.301 | 17.013 | 0.763 | 1.00 41.29 | C |
| ATOM | 2121 | NZ | LYS | B | 352 | 33.509 | 15.899 | -0.201 | 1.00 45.08 | N |
| ATOM | 2122 | N | GLU | B | 353 | 28.428 | 18.140 | 5.526 | 1.00 17.32 | N |
| ATOM | 2123 | CA | GLU | B | 353 | 27.046 | 18.100 | 6.066 | 1.00 16.22 | C |
| ATOM | 2124 | C | GLU | B | 353 | 26.782 | 19.277 | 7.021 | 1.00 16.23 | C |
| ATOM | 2125 | O | GLU | B | 353 | 25.612 | 19.734 | 7.097 | 1.00 19.91 | O |
| ATOM | 2126 | CB | GLU | B | 353 | 26.853 | 16.785 | 6.831 | 1.00 19.85 | C |
| ATOM | 2127 | CG | GLU | B | 353 | 26.755 | 15.616 | 5.849 | 1.00 19.59 | C |
| ATOM | 2128 | CD | GLU | B | 353 | 26.332 | 14.342 | 6.575 | 1.00 24.45 | C |
| ATOM | 2129 | OE1 | GLU | B | 353 | 25.117 | 14.127 | 6.692 | 1.00 23.64 | O |
| ATOM | 2130 | OE2 | GLU | B | 353 | 27.224 | 13.602 | 7.037 | 1.00 22.60 | O |
| ATOM | 2131 | N | LEU | B | 354 | 27.762 | 19.710 | 7.764 | 1.00 16.03 | N |
| ATOM | 2132 | CA | LEU | B | 354 | 27.579 | 20.814 | 8.704 | 1.00 17.28 | C |
| ATOM | 2133 | C | LEU | B | 354 | 27.244 | 22.116 | 7.957 | 1.00 22.35 | C |
| ATOM | 2134 | O | LEU | B | 354 | 26.380 | 22.849 | 8.466 | 1.00 20.33 | O |
| ATOM | 2135 | CB | LEU | B | 354 | 28.857 | 21.001 | 9.560 | 1.00 20.38 | C |
| ATOM | 2136 | CG | LEU | B | 354 | 29.000 | 19.896 | 10.630 | 1.00 20.09 | C |
| ATOM | 2137 | CD1 | LEU | B | 354 | 30.374 | 20.090 | 11.265 | 1.00 17.36 | C |
| ATOM | 2138 | CD2 | LEU | B | 354 | 27.921 | 20.070 | 11.703 | 1.00 20.87 | C |
| ATOM | 2139 | N | VAL | B | 355 | 27.823 | 22.335 | 6.779 | 1.00 19.23 | N |
| ATOM | 2140 | CA | VAL | B | 355 | 27.379 | 23.565 | 6.039 | 1.00 21.68 | C |
| ATOM | 2141 | C | VAL | B | 355 | 25.888 | 23.480 | 5.746 | 1.00 24.26 | C |
| ATOM | 2142 | O | VAL | B | 355 | 25.072 | 24.395 | 5.890 | 1.00 24.15 | O |
| ATOM | 2143 | CB | VAL | B | 355 | 28.129 | 23.625 | 4.686 | 1.00 27.74 | C |
| ATOM | 2144 | CG1 | VAL | B | 355 | 27.656 | 24.778 | 3.790 | 1.00 26.81 | C |
| ATOM | 2145 | CG2 | VAL | B | 355 | 29.647 | 23.727 | 4.865 | 1.00 27.16 | C |
| ATOM | 2146 | N | HIS | B | 356 | 25.415 | 22.304 | 5.323 | 1.00 23.49 | N |
| ATOM | 2147 | CA | HIS | B | 356 | 23.998 | 22.087 | 5.018 | 1.00 23.21 | C |
| ATOM | 2148 | C | HIS | B | 356 | 23.154 | 22.102 | 6.271 | 1.00 22.92 | C |
| ATOM | 2149 | O | HIS | B | 356 | 21.981 | 22.450 | 6.206 | 1.00 21.28 | O |

FIG. 2BB

```
ATOM  2150  CB   HIS B 356    23.798  20.750   4.290  1.00 22.36           C
ATOM  2151  CG   HIS B 356    24.325  20.826   2.886  1.00 34.11           C
ATOM  2152  ND1  HIS B 356    23.899  21.870   2.082  1.00 37.17           N
ATOM  2153  CD2  HIS B 356    25.144  20.064   2.136  1.00 35.97           C
ATOM  2154  CE1  HIS B 356    24.458  21.758   0.892  1.00 41.58           C
ATOM  2155  NE2  HIS B 356    25.197  20.667   0.903  1.00 38.16           N
ATOM  2156  N    MET B 357    23.731  21.675   7.431  1.00 20.58           N
ATOM  2157  CA   MET B 357    22.903  21.723   8.643  1.00 22.73           C
ATOM  2158  C    MET B 357    22.497  23.152   8.985  1.00 24.13           C
ATOM  2159  O    MET B 357    21.409  23.360   9.509  1.00 21.21           O
ATOM  2160  CB   MET B 357    23.662  21.090   9.825  1.00 20.64           C
ATOM  2161  CG   MET B 357    22.815  20.946  11.072  1.00 22.76           C
ATOM  2162  SD   MET B 357    23.835  20.185  12.386  1.00 19.26           S
ATOM  2163  CE   MET B 357    24.212  18.588  11.655  1.00 23.13           C
ATOM  2164  N    ILE B 358    23.412  24.115   8.842  1.00 22.55           N
ATOM  2165  CA   ILE B 358    23.064  25.523   9.127  1.00 22.86           C
ATOM  2166  C    ILE B 358    21.879  25.934   8.260  1.00 20.28           C
ATOM  2167  O    ILE B 358    20.931  26.538   8.795  1.00 23.07           O
ATOM  2168  CB   ILE B 358    24.241  26.456   8.781  1.00 25.27           C
ATOM  2169  CG1  ILE B 358    25.478  26.169   9.603  1.00 23.65           C
ATOM  2170  CG2  ILE B 358    23.830  27.946   9.041  1.00 24.03           C
ATOM  2171  CD1  ILE B 358    25.384  26.213  11.077  1.00 23.64           C
ATOM  2172  N    SER B 359    21.972  25.693   6.950  1.00 22.49           N
ATOM  2173  CA   SER B 359    20.842  26.052   6.068  1.00 24.30           C
ATOM  2174  C    SER B 359    19.550  25.362   6.492  1.00 23.34           C
ATOM  2175  O    SER B 359    18.511  26.007   6.473  1.00 23.51           O
ATOM  2176  CB   SER B 359    21.031  25.794   4.560  1.00 30.58           C
ATOM  2177  OG   SER B 359    22.272  26.354   4.169  1.00 37.98           O
ATOM  2178  N    TRP B 360    19.559  24.067   6.810  1.00 19.52           N
ATOM  2179  CA   TRP B 360    18.403  23.362   7.307  1.00 19.34           C
ATOM  2180  C    TRP B 360    17.853  24.045   8.542  1.00 21.70           C
ATOM  2181  O    TRP B 360    16.636  24.272   8.688  1.00 23.01           O
ATOM  2182  CB   TRP B 360    18.754  21.889   7.625  1.00 21.40           C
ATOM  2183  CG   TRP B 360    17.855  21.145   8.551  1.00 21.72           C
ATOM  2184  CD1  TRP B 360    16.645  20.604   8.179  1.00 23.33           C
ATOM  2185  CD2  TRP B 360    18.032  20.823   9.939  1.00 19.39           C
ATOM  2186  NE1  TRP B 360    16.043  19.988   9.280  1.00 21.79           N
ATOM  2187  CE2  TRP B 360    16.885  20.113  10.352  1.00 21.03           C
ATOM  2188  CE3  TRP B 360    19.033  21.075  10.873  1.00 19.08           C
ATOM  2189  CZ2  TRP B 360    16.711  19.580  11.641  1.00 18.45           C
ATOM  2190  CZ3  TRP B 360    18.880  20.573  12.184  1.00 19.70           C
ATOM  2191  CH2  TRP B 360    17.725  19.859  12.534  1.00 18.29           C
ATOM  2192  N    ALA B 361    18.711  24.302   9.535  1.00 19.80           N
ATOM  2193  CA   ALA B 361    18.209  24.862  10.782  1.00 19.54           C
ATOM  2194  C    ALA B 361    17.544  26.215  10.542  1.00 24.20           C
ATOM  2195  O    ALA B 361    16.518  26.490  11.134  1.00 22.57           O
ATOM  2196  CB   ALA B 361    19.298  24.976  11.820  1.00 19.50           C
ATOM  2197  N    LYS B 362    18.144  27.014   9.638  1.00 21.91           N
ATOM  2198  CA   LYS B 362    17.525  28.297   9.321  1.00 26.89           C
ATOM  2199  C    LYS B 362    16.166  28.178   8.665  1.00 26.81           C
ATOM  2200  O    LYS B 362    15.389  29.173   8.663  1.00 28.44           O
ATOM  2201  CB   LYS B 362    18.501  29.050   8.378  1.00 26.95           C
ATOM  2202  CG   LYS B 362    19.611  29.591   9.321  1.00 31.89           C
ATOM  2203  CD   LYS B 362    20.665  30.388   8.556  1.00 36.74           C
ATOM  2204  CE   LYS B 362    20.241  31.816   8.263  1.00 38.32           C
ATOM  2205  NZ   LYS B 362    21.058  32.445   7.174  1.00 40.64           N
ATOM  2206  N    LYS B 363    15.821  27.028   8.119  1.00 21.94           N
ATOM  2207  CA   LYS B 363    14.518  26.860   7.486  1.00 25.35           C
ATOM  2208  C    LYS B 363    13.451  26.373   8.469  1.00 29.06           C
ATOM  2209  O    LYS B 363    12.281  26.308   8.042  1.00 29.31           O
ATOM  2210  CB   LYS B 363    14.619  25.913   6.297  1.00 22.51           C
ATOM  2211  CG   LYS B 363    15.615  26.489   5.273  1.00 25.76           C
ATOM  2212  CD   LYS B 363    15.698  25.515   4.094  1.00 32.07           C
ATOM  2213  CE   LYS B 363    16.603  26.053   3.000  1.00 34.68           C
ATOM  2214  NZ   LYS B 363    16.953  24.999   2.007  1.00 44.70           N
ATOM  2215  N    ILE B 364    13.808  26.069   9.684  1.00 27.38           N
ATOM  2216  CA   ILE B 364    12.773  25.623  10.671  1.00 29.33           C
ATOM  2217  C    ILE B 364    12.047  26.864  11.142  1.00 30.86           C
ATOM  2218  O    ILE B 364    12.650  27.796  11.673  1.00 29.37           O
ATOM  2219  CB   ILE B 364    13.395  24.857  11.834  1.00 27.92           C
ATOM  2220  CG1  ILE B 364    13.941  23.545  11.255  1.00 35.56           C
ATOM  2221  CG2  ILE B 364    12.345  24.497  12.901  1.00 31.49           C
ATOM  2222  CD1  ILE B 364    14.792  22.804  12.242  1.00 32.74           C
ATOM  2223  N    PRO B 365    10.733  26.896  10.963  1.00 34.82           N
ATOM  2224  CA   PRO B 365     9.941  28.056  11.322  1.00 36.62           C
ATOM  2225  C    PRO B 365    10.292  28.581  12.695  1.00 31.74           C
ATOM  2226  O    PRO B 365    10.314  27.858  13.686  1.00 32.94           O
```

FIG. 2CC

```
ATOM   2227  CB  PRO B 365       8.495  27.578  11.208  1.00 34.89           C
ATOM   2228  CG  PRO B 365       8.540  26.408  10.293  1.00 37.43           C
ATOM   2229  CD  PRO B 365       9.903  25.808  10.380  1.00 36.52           C
ATOM   2230  N   GLY B 366      10.626  29.867  12.731  1.00 35.19           N
ATOM   2231  CA  GLY B 366      10.960  30.546  13.971  1.00 35.04           C
ATOM   2232  C   GLY B 366      12.397  30.406  14.442  1.00 36.83           C
ATOM   2233  O   GLY B 366      12.818  31.122  15.344  1.00 32.74           O
ATOM   2234  N   PHE B 367      13.209  29.505  13.848  1.00 31.04           N
ATOM   2235  CA  PHE B 367      14.576  29.367  14.330  1.00 28.81           C
ATOM   2236  C   PHE B 367      15.347  30.679  14.151  1.00 27.63           C
ATOM   2237  O   PHE B 367      16.041  31.071  15.087  1.00 29.57           O
ATOM   2238  CB  PHE B 367      15.320  28.235  13.611  1.00 29.68           C
ATOM   2239  CG  PHE B 367      16.726  28.000  14.123  1.00 27.93           C
ATOM   2240  CD1 PHE B 367      16.930  27.180  15.194  1.00 28.07           C
ATOM   2241  CD2 PHE B 367      17.821  28.601  13.513  1.00 26.67           C
ATOM   2242  CE1 PHE B 367      18.209  26.951  15.704  1.00 29.07           C
ATOM   2243  CE2 PHE B 367      19.097  28.356  13.981  1.00 24.62           C
ATOM   2244  CZ  PHE B 367      19.315  27.524  15.089  1.00 24.18           C
ATOM   2245  N   VAL B 368      15.198  31.350  13.010  1.00 31.59           N
ATOM   2246  CA  VAL B 368      15.932  32.593  12.778  1.00 33.70           C
ATOM   2247  C   VAL B 368      15.405  33.752  13.626  1.00 36.58           C
ATOM   2248  O   VAL B 368      16.049  34.803  13.614  1.00 37.80           O
ATOM   2249  CB  VAL B 368      15.910  33.003  11.301  1.00 32.36           C
ATOM   2250  CG1 VAL B 368      16.690  32.000  10.443  1.00 34.27           C
ATOM   2251  CG2 VAL B 368      14.475  33.098  10.777  1.00 38.21           C
ATOM   2252  N   GLU B 369      14.302  33.609  14.325  1.00 38.63           N
ATOM   2253  CA  GLU B 369      13.715  34.607  15.203  1.00 43.96           C
ATOM   2254  C   GLU B 369      14.224  34.433  16.625  1.00 45.39           C
ATOM   2255  O   GLU B 369      13.893  35.211  17.524  1.00 43.91           O
ATOM   2256  CB  GLU B 369      12.190  34.521  15.182  1.00 50.15           C
ATOM   2257  CG  GLU B 369      11.644  34.939  13.823  1.00 56.65           C
ATOM   2258  CD  GLU B 369      10.217  34.475  13.615  1.00 60.83           C
ATOM   2259  OE1 GLU B 369       9.519  34.182  14.605  1.00 62.32           O
ATOM   2260  OE2 GLU B 369       9.811  34.400  12.434  1.00 63.35           O
ATOM   2261  N   LEU B 370      14.973  33.349  16.842  1.00 38.98           N
ATOM   2262  CA  LEU B 370      15.622  33.121  18.115  1.00 35.51           C
ATOM   2263  C   LEU B 370      16.828  34.093  18.159  1.00 34.78           C
ATOM   2264  O   LEU B 370      17.353  34.493  17.120  1.00 36.72           O
ATOM   2265  CB  LEU B 370      16.152  31.688  18.280  1.00 33.38           C
ATOM   2266  CG  LEU B 370      15.046  30.619  18.367  1.00 33.47           C
ATOM   2267  CD1 LEU B 370      15.690  29.241  18.490  1.00 33.96           C
ATOM   2268  CD2 LEU B 370      14.042  30.909  19.489  1.00 31.83           C
ATOM   2269  N   SER B 371      17.257  34.414  19.362  1.00 36.47           N
ATOM   2270  CA  SER B 371      18.406  35.290  19.526  1.00 36.59           C
ATOM   2271  C   SER B 371      19.642  34.602  18.968  1.00 38.96           C
ATOM   2272  O   SER B 371      19.671  33.352  18.929  1.00 33.42           O
ATOM   2273  CB  SER B 371      18.660  35.563  21.010  1.00 36.21           C
ATOM   2274  OG  SER B 371      19.276  34.476  21.679  1.00 34.10           O
ATOM   2275  N   LEU B 372      20.661  35.404  18.625  1.00 32.71           N
ATOM   2276  CA  LEU B 372      21.898  34.838  18.130  1.00 29.93           C
ATOM   2277  C   LEU B 372      22.467  33.829  19.087  1.00 29.34           C
ATOM   2278  O   LEU B 372      23.071  32.823  18.709  1.00 32.54           O
ATOM   2279  CB  LEU B 372      22.919  35.966  17.938  1.00 34.52           C
ATOM   2280  CG  LEU B 372      24.270  35.675  17.321  1.00 37.48           C
ATOM   2281  CD1 LEU B 372      24.186  34.767  16.098  1.00 37.75           C
ATOM   2282  CD2 LEU B 372      24.881  37.017  16.879  1.00 43.32           C
ATOM   2283  N   PHE B 373      22.498  34.206  20.393  1.00 28.95           N
ATOM   2284  CA  PHE B 373      23.087  33.272  21.358  1.00 33.97           C
ATOM   2285  C   PHE B 373      22.304  31.967  21.429  1.00 29.91           C
ATOM   2286  O   PHE B 373      22.960  30.926  21.545  1.00 29.72           O
ATOM   2287  CB  PHE B 373      23.265  33.954  22.720  1.00 37.52           C
ATOM   2288  CG  PHE B 373      24.325  35.046  22.637  1.00 41.67           C
ATOM   2289  CD1 PHE B 373      25.146  35.196  21.539  1.00 46.80           C
ATOM   2290  CD2 PHE B 373      24.528  35.901  23.707  1.00 46.96           C
ATOM   2291  CE1 PHE B 373      26.109  36.176  21.462  1.00 49.01           C
ATOM   2292  CE2 PHE B 373      25.492  36.899  23.645  1.00 46.70           C
ATOM   2293  CZ  PHE B 373      26.278  37.025  22.527  1.00 46.90           C
ATOM   2294  N   ASP B 374      20.973  32.044  21.348  1.00 31.02           N
ATOM   2295  CA  ASP B 374      20.191  30.812  21.427  1.00 31.49           C
ATOM   2296  C   ASP B 374      20.446  29.964  20.153  1.00 33.16           C
ATOM   2297  O   ASP B 374      20.678  28.765  20.260  1.00 28.96           O
ATOM   2298  CB  ASP B 374      18.706  31.023  21.603  1.00 31.44           C
ATOM   2299  CG  ASP B 374      18.273  31.344  23.033  1.00 36.83           C
ATOM   2300  OD1 ASP B 374      19.090  31.228  23.962  1.00 43.81           O
ATOM   2301  OD2 ASP B 374      17.094  31.748  23.160  1.00 39.45           O
ATOM   2302  N   GLN B 375      20.495  30.611  19.008  1.00 29.43           N
ATOM   2303  CA  GLN B 375      20.774  29.839  17.775  1.00 28.70           C
```

FIG. 2DD

```
ATOM   2304  C   GLN B 375      22.083  29.093  17.902  1.00 28.91           C
ATOM   2305  O   GLN B 375      22.174  27.926  17.537  1.00 24.32           O
ATOM   2306  CB  GLN B 375      20.768  30.768  16.555  1.00 25.04           C
ATOM   2307  CG  GLN B 375      19.398  31.276  16.157  1.00 26.15           C
ATOM   2308  CD  GLN B 375      19.409  32.132  14.909  1.00 31.28           C
ATOM   2309  OE1 GLN B 375      20.055  31.841  13.902  1.00 33.19           O
ATOM   2310  NE2 GLN B 375      18.679  33.254  14.933  1.00 34.93           N
ATOM   2311  N   VAL B 376      23.156  29.788  18.273  1.00 26.24           N
ATOM   2312  CA  VAL B 376      24.475  29.229  18.402  1.00 24.06           C
ATOM   2313  C   VAL B 376      24.563  28.156  19.479  1.00 24.86           C
ATOM   2314  O   VAL B 376      25.224  27.136  19.230  1.00 27.38           O
ATOM   2315  CB  VAL B 376      25.541  30.309  18.686  1.00 28.98           C
ATOM   2316  CG1 VAL B 376      26.921  29.701  18.752  1.00 32.68           C
ATOM   2317  CG2 VAL B 376      25.523  31.331  17.536  1.00 30.22           C
ATOM   2318  N   ARG B 377      23.908  28.345  20.632  1.00 24.35           N
ATOM   2319  CA  ARG B 377      24.042  27.277  21.626  1.00 25.87           C
ATOM   2320  C   ARG B 377      23.297  26.014  21.143  1.00 21.79           C
ATOM   2321  O   ARG B 377      23.788  24.893  21.450  1.00 25.08           O
ATOM   2322  CB  ARG B 377      23.560  27.650  23.028  1.00 33.86           C
ATOM   2323  CG  ARG B 377      22.067  27.918  23.037  1.00 34.88           C
ATOM   2324  CD  ARG B 377      21.449  27.510  24.366  1.00 47.44           C
ATOM   2325  NE  ARG B 377      20.176  28.117  24.596  1.00 49.34           N
ATOM   2326  CZ  ARG B 377      19.171  27.713  25.323  1.00 51.60           C
ATOM   2327  NH1 ARG B 377      18.060  28.424  25.451  1.00 52.27           N
ATOM   2328  NH2 ARG B 377      19.257  26.509  25.900  1.00 53.69           N
ATOM   2329  N   LEU B 378      22.163  26.167  20.499  1.00 21.68           N
ATOM   2330  CA  LEU B 378      21.460  24.947  20.012  1.00 20.41           C
ATOM   2331  C   LEU B 378      22.314  24.160  19.032  1.00 21.16           C
ATOM   2332  O   LEU B 378      22.467  22.933  19.106  1.00 20.81           O
ATOM   2333  CB  LEU B 378      20.113  25.303  19.394  1.00 24.70           C
ATOM   2334  CG  LEU B 378      19.087  25.959  20.354  1.00 27.24           C
ATOM   2335  CD1 LEU B 378      17.809  26.231  19.595  1.00 31.14           C
ATOM   2336  CD2 LEU B 378      18.810  25.096  21.555  1.00 27.64           C
ATOM   2337  N   LEU B 379      22.898  24.882  18.050  1.00 24.82           N
ATOM   2338  CA  LEU B 379      23.728  24.202  17.033  1.00 20.15           C
ATOM   2339  C   LEU B 379      24.979  23.625  17.606  1.00 20.62           C
ATOM   2340  O   LEU B 379      25.339  22.469  17.307  1.00 20.65           O
ATOM   2341  CB  LEU B 379      24.073  25.249  15.953  1.00 23.91           C
ATOM   2342  CG  LEU B 379      22.907  25.518  14.998  1.00 27.86           C
ATOM   2343  CD1 LEU B 379      23.168  26.790  14.196  1.00 26.74           C
ATOM   2344  CD2 LEU B 379      22.716  24.332  14.054  1.00 30.30           C
ATOM   2345  N   GLU B 380      25.609  24.340  18.583  1.00 20.83           N
ATOM   2346  CA  GLU B 380      26.837  23.816  19.195  1.00 27.24           C
ATOM   2347  C   GLU B 380      26.566  22.557  19.997  1.00 25.34           C
ATOM   2348  O   GLU B 380      27.398  21.656  20.096  1.00 28.66           O
ATOM   2349  CB  GLU B 380      27.454  24.857  20.156  1.00 35.51           C
ATOM   2350  CG  GLU B 380      28.304  24.298  21.268  1.00 45.36           C
ATOM   2351  CD  GLU B 380      27.717  23.925  22.601  1.00 52.55           C
ATOM   2352  OE1 GLU B 380      26.687  24.467  23.075  1.00 55.73           O
ATOM   2353  OE2 GLU B 380      28.296  23.028  23.260  1.00 58.84           O
ATOM   2354  N   SER B 381      25.400  22.493  20.619  1.00 19.01           N
ATOM   2355  CA  SER B 381      25.074  21.322  21.439  1.00 23.22           C
ATOM   2356  C   SER B 381      24.624  20.084  20.669  1.00 24.76           C
ATOM   2357  O   SER B 381      24.823  18.963  21.145  1.00 27.36           O
ATOM   2358  CB  SER B 381      23.905  21.791  22.336  1.00 28.20           C
ATOM   2359  OG  SER B 381      23.489  20.648  23.074  1.00 38.79           O
ATOM   2360  N   CYS B 382      23.990  20.220  19.529  1.00 23.25           N
ATOM   2361  CA  CYS B 382      23.404  19.066  18.844  1.00 22.65           C
ATOM   2362  C   CYS B 382      24.073  18.600  17.567  1.00 20.33           C
ATOM   2363  O   CYS B 382      23.538  17.569  17.123  1.00 17.89           O
ATOM   2364  CB  CYS B 382      21.960  19.551  18.367  1.00 21.13           C
ATOM   2365  SG  CYS B 382      21.899  20.543  16.890  1.00 23.58           S
ATOM   2366  N   TRP B 383      25.182  19.230  17.120  1.00 20.02           N
ATOM   2367  CA  TRP B 383      25.567  18.848  15.756  1.00 20.25           C
ATOM   2368  C   TRP B 383      25.893  17.398  15.544  1.00 18.10           C
ATOM   2369  O   TRP B 383      25.465  16.824  14.535  1.00 16.94           O
ATOM   2370  CB  TRP B 383      26.621  19.831  15.176  1.00 15.50           C
ATOM   2371  CG  TRP B 383      27.931  19.774  15.903  1.00 21.30           C
ATOM   2372  CD1 TRP B 383      28.297  20.590  16.947  1.00 22.04           C
ATOM   2373  CD2 TRP B 383      29.040  18.897  15.667  1.00 21.19           C
ATOM   2374  NE1 TRP B 383      29.577  20.278  17.340  1.00 23.74           N
ATOM   2375  CE2 TRP B 383      30.039  19.223  16.606  1.00 24.97           C
ATOM   2376  CE3 TRP B 383      29.270  17.851  14.766  1.00 20.19           C
ATOM   2377  CZ2 TRP B 383      31.274  18.571  16.630  1.00 20.39           C
ATOM   2378  CZ3 TRP B 383      30.499  17.160  14.825  1.00 21.36           C
ATOM   2379  CH2 TRP B 383      31.458  17.535  15.771  1.00 21.33           C
ATOM   2380  N   MET B 384      26.697  16.818  16.461  1.00 14.48           N
```

FIG. 2EE

```
ATOM   2381  CA  MET B 384      27.004  15.391  16.204  1.00 14.60           C
ATOM   2382  C   MET B 384      25.723  14.554  16.309  1.00 13.50           C
ATOM   2383  O   MET B 384      25.586  13.590  15.552  1.00 14.76           O
ATOM   2384  CB  MET B 384      28.076  14.944  17.205  1.00 18.83           C
ATOM   2385  CG  MET B 384      28.416  13.468  16.921  1.00 18.80           C
ATOM   2386  SD  MET B 384      29.317  13.154  15.378  1.00 21.33           S
ATOM   2387  CE  MET B 384      30.967  13.601  15.920  1.00 23.47           C
ATOM   2388  N   GLU B 385      24.841  14.861  17.239  1.00 15.97           N
ATOM   2389  CA  GLU B 385      23.603  14.096  17.375  1.00 15.88           C
ATOM   2390  C   GLU B 385      22.800  14.180  16.053  1.00 17.29           C
ATOM   2391  O   GLU B 385      22.252  13.187  15.627  1.00 16.01           O
ATOM   2392  CB  GLU B 385      22.771  14.484  18.620  1.00 17.76           C
ATOM   2393  CG  GLU B 385      21.809  13.374  19.058  1.00 24.52           C
ATOM   2394  CD  GLU B 385      20.950  13.711  20.264  1.00 26.25           C
ATOM   2395  OE1 GLU B 385      21.287  14.670  21.028  1.00 22.77           O
ATOM   2396  OE2 GLU B 385      19.912  13.009  20.370  1.00 29.33           O
ATOM   2397  N   VAL B 386      22.686  15.386  15.517  1.00 14.08           N
ATOM   2398  CA  VAL B 386      21.948  15.518  14.231  1.00 16.32           C
ATOM   2399  C   VAL B 386      22.635  14.769  13.091  1.00 16.83           C
ATOM   2400  O   VAL B 386      21.963  14.085  12.304  1.00 19.89           O
ATOM   2401  CB  VAL B 386      21.759  16.989  13.868  1.00 17.16           C
ATOM   2402  CG1 VAL B 386      21.078  17.126  12.493  1.00 18.55           C
ATOM   2403  CG2 VAL B 386      20.831  17.639  14.899  1.00 19.24           C
ATOM   2404  N   LEU B 387      23.950  14.819  13.024  1.00 15.69           N
ATOM   2405  CA  LEU B 387      24.632  14.051  11.988  1.00 14.03           C
ATOM   2406  C   LEU B 387      24.304  12.553  12.172  1.00 18.05           C
ATOM   2407  O   LEU B 387      24.032  11.850  11.171  1.00 17.52           O
ATOM   2408  CB  LEU B 387      26.147  14.161  12.110  1.00 14.39           C
ATOM   2409  CG  LEU B 387      26.684  15.512  11.597  1.00 21.48           C
ATOM   2410  CD1 LEU B 387      28.223  15.484  11.684  1.00 17.40           C
ATOM   2411  CD2 LEU B 387      26.219  15.869  10.180  1.00 23.01           C
ATOM   2412  N   MET B 388      24.426  12.102  13.447  1.00 17.21           N
ATOM   2413  CA  MET B 388      24.204  10.641  13.637  1.00 15.95           C
ATOM   2414  C   MET B 388      22.776  10.262  13.407  1.00 21.51           C
ATOM   2415  O   MET B 388      22.538   9.135  12.961  1.00 16.11           O
ATOM   2416  CB  MET B 388      24.684  10.247  15.053  1.00 14.53           C
ATOM   2417  CG  MET B 388      26.216  10.335  15.089  1.00 17.68           C
ATOM   2418  SD  MET B 388      26.703   9.858  16.808  1.00 16.78           S
ATOM   2419  CE  MET B 388      28.434   9.539  16.435  1.00 17.17           C
ATOM   2420  N   MET B 389      21.760  11.053  13.738  1.00 17.83           N
ATOM   2421  CA  MET B 389      20.368  10.687  13.470  1.00 19.28           C
ATOM   2422  C   MET B 389      20.181  10.547  11.948  1.00 20.51           C
ATOM   2423  O   MET B 389      19.564   9.597  11.434  1.00 20.84           O
ATOM   2424  CB  MET B 389      19.417  11.761  14.052  1.00 21.16           C
ATOM   2425  CG  MET B 389      17.931  11.408  13.836  1.00 25.05           C
ATOM   2426  SD  MET B 389      17.528  10.080  15.014  1.00 23.55           S
ATOM   2427  CE  MET B 389      16.196   9.227  14.208  1.00 30.08           C
ATOM   2428  N   GLY B 390      20.779  11.421  11.147  1.00 16.73           N
ATOM   2429  CA  GLY B 390      20.738  11.345   9.678  1.00 18.39           C
ATOM   2430  C   GLY B 390      21.392  10.039   9.195  1.00 23.35           C
ATOM   2431  O   GLY B 390      20.834   9.346   8.340  1.00 21.62           O
ATOM   2432  N   LEU B 391      22.525   9.700   9.795  1.00 21.91           N
ATOM   2433  CA  LEU B 391      23.183   8.413   9.465  1.00 22.72           C
ATOM   2434  C   LEU B 391      22.302   7.209   9.769  1.00 20.25           C
ATOM   2435  O   LEU B 391      22.250   6.183   9.027  1.00 23.27           O
ATOM   2436  CB  LEU B 391      24.496   8.326  10.207  1.00 21.80           C
ATOM   2437  CG  LEU B 391      25.207   6.966  10.253  1.00 22.44           C
ATOM   2438  CD1 LEU B 391      25.705   6.605   8.831  1.00 21.14           C
ATOM   2439  CD2 LEU B 391      26.375   7.025  11.212  1.00 21.16           C
ATOM   2440  N   MET B 392      21.655   7.214  10.935  1.00 20.70           N
ATOM   2441  CA  MET B 392      20.773   6.122  11.304  1.00 20.15           C
ATOM   2442  C   MET B 392      19.598   5.983  10.367  1.00 24.21           C
ATOM   2443  O   MET B 392      19.317   4.873   9.923  1.00 22.83           O
ATOM   2444  CB  MET B 392      20.246   6.277  12.746  1.00 23.62           C
ATOM   2445  CG  MET B 392      21.386   6.151  13.732  1.00 24.52           C
ATOM   2446  SD  MET B 392      20.748   6.520  15.414  1.00 28.58           S
ATOM   2447  CE  MET B 392      22.377   6.498  16.202  1.00 28.75           C
ATOM   2448  N   TRP B 393      18.950   7.099   9.981  1.00 22.28           N
ATOM   2449  CA  TRP B 393      17.847   6.961   9.029  1.00 20.61           C
ATOM   2450  C   TRP B 393      18.365   6.485   7.681  1.00 24.48           C
ATOM   2451  O   TRP B 393      17.723   5.623   7.059  1.00 28.06           O
ATOM   2452  CB  TRP B 393      17.227   8.374   8.916  1.00 23.80           C
ATOM   2453  CG  TRP B 393      16.260   8.471   7.766  1.00 24.50           C
ATOM   2454  CD1 TRP B 393      16.431   9.098   6.579  1.00 24.58           C
ATOM   2455  CD2 TRP B 393      14.972   7.840   7.738  1.00 21.38           C
ATOM   2456  NE1 TRP B 393      15.290   8.917   5.796  1.00 27.40           N
ATOM   2457  CE2 TRP B 393      14.391   8.154   6.503  1.00 28.66           C
```

FIG. 2FF

```
ATOM  2458  CE3  TRP B 393   14.267   7.037   8.657  1.00 24.75      C
ATOM  2459  CZ2  TRP B 393   13.124   7.673   6.163  1.00 28.29      C
ATOM  2460  CZ3  TRP B 393   13.010   6.566   8.295  1.00 27.11      C
ATOM  2461  CH2  TRP B 393   12.460   6.901   7.048  1.00 27.45      C
ATOM  2462  N    ARG B 394   19.505   6.966   7.186  1.00 23.13      N
ATOM  2463  CA   ARG B 394   20.018   6.491   5.889  1.00 24.56      C
ATOM  2464  C    ARG B 394   20.358   5.007   5.979  1.00 26.56      C
ATOM  2465  O    ARG B 394   20.390   4.287   4.973  1.00 29.56      O
ATOM  2466  CB   ARG B 394   21.306   7.218   5.445  1.00 23.42      C
ATOM  2467  CG   ARG B 394   21.074   8.645   4.950  1.00 23.53      C
ATOM  2468  CD   ARG B 394   22.315   9.317   4.420  1.00 26.61      C
ATOM  2469  NE   ARG B 394   23.421   9.413   5.344  1.00 23.76      N
ATOM  2470  CZ   ARG B 394   23.630  10.344   6.297  1.00 25.92      C
ATOM  2471  NH1  ARG B 394   22.726  11.331   6.457  1.00 22.67      N
ATOM  2472  NH2  ARG B 394   24.719  10.304   7.022  1.00 22.50      N
ATOM  2473  N    SER B 395   20.764   4.502   7.115  1.00 23.85      N
ATOM  2474  CA   SER B 395   21.176   3.121   7.281  1.00 23.86      C
ATOM  2475  C    SER B 395   20.068   2.181   7.720  1.00 24.73      C
ATOM  2476  O    SER B 395   20.347   1.019   7.877  1.00 30.38      O
ATOM  2477  CB   SER B 395   22.242   3.119   8.389  1.00 25.71      C
ATOM  2478  OG   SER B 395   23.323   3.973   8.015  1.00 27.34      O
ATOM  2479  N    ILE B 396   18.834   2.641   7.857  1.00 26.38      N
ATOM  2480  CA   ILE B 396   17.781   1.858   8.483  1.00 28.13      C
ATOM  2481  C    ILE B 396   17.402   0.603   7.714  1.00 34.05      C
ATOM  2482  O    ILE B 396   17.107  -0.388   8.375  1.00 36.61      O
ATOM  2483  CB   ILE B 396   16.621   2.803   8.794  1.00 31.52      C
ATOM  2484  CG1  ILE B 396   15.694   2.324   9.911  1.00 35.64      C
ATOM  2485  CG2  ILE B 396   15.806   3.086   7.517  1.00 35.73      C
ATOM  2486  CD1  ILE B 396   14.689   3.407  10.306  1.00 34.63      C
ATOM  2487  N    ASP B 397   17.500   0.642   6.395  1.00 30.79      N
ATOM  2488  CA   ASP B 397   17.150  -0.561   5.623  1.00 35.31      C
ATOM  2489  C    ASP B 397   18.390  -1.323   5.207  1.00 39.39      C
ATOM  2490  O    ASP B 397   18.306  -2.164   4.290  1.00 41.34      O
ATOM  2491  CB   ASP B 397   16.327  -0.097   4.413  1.00 36.48      C
ATOM  2492  CG   ASP B 397   14.950   0.392   4.797  1.00 38.41      C
ATOM  2493  OD1  ASP B 397   14.307  -0.118   5.739  1.00 42.42      O
ATOM  2494  OD2  ASP B 397   14.411   1.326   4.186  1.00 43.72      O
ATOM  2495  N    HIS B 398   19.565  -1.140   5.795  1.00 34.30      N
ATOM  2496  CA   HIS B 398   20.800  -1.831   5.448  1.00 33.99      C
ATOM  2497  C    HIS B 398   21.512  -2.367   6.666  1.00 32.82      C
ATOM  2498  O    HIS B 398   22.577  -1.931   7.129  1.00 31.78      O
ATOM  2499  CB   HIS B 398   21.773  -0.937   4.621  1.00 32.15      C
ATOM  2500  CG   HIS B 398   21.111  -0.344   3.416  1.00 39.99      C
ATOM  2501  ND1  HIS B 398   20.631   0.946   3.405  1.00 47.14      N
ATOM  2502  CD2  HIS B 398   20.791  -0.849   2.203  1.00 40.00      C
ATOM  2503  CE1  HIS B 398   20.049   1.222   2.255  1.00 45.76      C
ATOM  2504  NE2  HIS B 398   20.127   0.138   1.505  1.00 45.33      N
ATOM  2505  N    PRO B 399   20.997  -3.480   7.213  1.00 32.19      N
ATOM  2506  CA   PRO B 399   21.603  -4.117   8.377  1.00 31.87      C
ATOM  2507  C    PRO B 399   23.046  -4.448   8.135  1.00 29.07      C
ATOM  2508  O    PRO B 399   23.508  -4.725   7.021  1.00 34.53      O
ATOM  2509  CB   PRO B 399   20.694  -5.275   8.753  1.00 35.73      C
ATOM  2510  CG   PRO B 399   19.681  -5.366   7.687  1.00 34.94      C
ATOM  2511  CD   PRO B 399   19.797  -4.199   6.757  1.00 34.15      C
ATOM  2512  N    GLY B 400   23.871  -4.247   9.145  1.00 24.75      N
ATOM  2513  CA   GLY B 400   25.300  -4.470   9.167  1.00 31.04      C
ATOM  2514  C    GLY B 400   26.084  -3.377   8.472  1.00 26.14      C
ATOM  2515  O    GLY B 400   27.310  -3.481   8.447  1.00 33.44      O
ATOM  2516  N    LYS B 401   25.464  -2.344   7.923  1.00 27.98      N
ATOM  2517  CA   LYS B 401   26.215  -1.291   7.249  1.00 27.46      C
ATOM  2518  C    LYS B 401   25.856   0.115   7.788  1.00 27.45      C
ATOM  2519  O    LYS B 401   24.718   0.303   8.222  1.00 24.43      O
ATOM  2520  CB   LYS B 401   25.821  -1.148   5.776  1.00 27.97      C
ATOM  2521  CG   LYS B 401   26.773  -1.932   4.848  1.00 40.85      C
ATOM  2522  CD   LYS B 401   26.112  -3.245   4.546  1.00 44.41      C
ATOM  2523  CE   LYS B 401   26.659  -3.895   3.278  1.00 47.73      C
ATOM  2524  NZ   LYS B 401   25.668  -4.872   2.737  1.00 52.90      N
ATOM  2525  N    LEU B 402   26.821   1.008   7.581  1.00 26.26      N
ATOM  2526  CA   LEU B 402   26.566   2.427   7.952  1.00 24.76      C
ATOM  2527  C    LEU B 402   26.626   3.231   6.668  1.00 21.76      C
ATOM  2528  O    LEU B 402   27.723   3.311   6.078  1.00 25.19      O
ATOM  2529  CB   LEU B 402   27.563   2.905   9.012  1.00 25.71      C
ATOM  2530  CG   LEU B 402   27.398   2.307  10.426  1.00 24.37      C
ATOM  2531  CD1  LEU B 402   28.525   2.816  11.330  1.00 26.93      C
ATOM  2532  CD2  LEU B 402   26.031   2.617  11.052  1.00 27.97      C
ATOM  2533  N    ILE B 403   25.500   3.763   6.196  1.00 21.80      N
ATOM  2534  CA   ILE B 403   25.509   4.564   4.969  1.00 22.69      C
```

FIG. 2GG

```
ATOM   2535  C    ILE B 403      25.895   6.009   5.309  1.00 23.32           C
ATOM   2536  O    ILE B 403      25.026   6.891   5.417  1.00 23.36           O
ATOM   2537  CB   ILE B 403      24.097   4.548   4.338  1.00 24.13           C
ATOM   2538  CG1  ILE B 403      23.581   3.119   4.187  1.00 32.41           C
ATOM   2539  CG2  ILE B 403      24.026   5.326   3.049  1.00 24.82           C
ATOM   2540  CD1  ILE B 403      24.551   2.152   3.559  1.00 38.99           C
ATOM   2541  N    PHE B 404      27.176   6.294   5.453  1.00 25.16           N
ATOM   2542  CA   PHE B 404      27.584   7.683   5.787  1.00 22.64           C
ATOM   2543  C    PHE B 404      27.182   8.616   4.666  1.00 24.43           C
ATOM   2544  O    PHE B 404      26.742   9.749   4.825  1.00 24.33.          O
ATOM   2545  CB   PHE B 404      29.081   7.725   6.047  1.00 20.55           C
ATOM   2546  CG   PHE B 404      29.441   7.288   7.436  1.00 21.35           C
ATOM   2547  CD1  PHE B 404      29.764   5.968   7.693  1.00 22.55           C
ATOM   2548  CD2  PHE B 404      29.344   8.164   8.521  1.00 18.14           C
ATOM   2549  CE1  PHE B 404      30.054   5.542   8.971  1.00 22.47           C
ATOM   2550  CE2  PHE B 404      29.650   7.710   9.792  1.00 20.41           C
ATOM   2551  CZ   PHE B 404      29.989   6.406  10.037  1.00 23.05           C
ATOM   2552  N    ALA B 405      27.352   8.116   3.432  1.00 21.86           N
ATOM   2553  CA   ALA B 405      26.933   8.855   2.229  1.00 29.53           C
ATOM   2554  C    ALA B 405      26.589   7.823   1.170  1.00 29.06           C
ATOM   2555  O    ALA B 405      27.088   6.694   1.257  1.00 29.31           O
ATOM   2556  CB   ALA B 405      28.056   9.769   1.776  1.00 30.10           C
ATOM   2557  N    PRO B 406      25.908   8.200   0.102  1.00 32.86           N
ATOM   2558  CA   PRO B 406      25.507   7.243  -0.932  1.00 34.92           C
ATOM   2559  C    PRO B 406      26.686   6.453  -1.442  1.00 33.76           C
ATOM   2560  O    PRO B 406      26.578   5.239  -1.718  1.00 30.44           O
ATOM   2561  CB   PRO B 406      24.815   8.126  -1.979  1.00 37.23           C
ATOM   2562  CG   PRO B 406      24.140   9.155  -1.108  1.00 38.70           C
ATOM   2563  CD   PRO B 406      25.224   9.508  -0.090  1.00 32.36           C
ATOM   2564  N    ASP B 407      27.861   7.059  -1.609  1.00 32.30           N
ATOM   2565  CA   ASP B 407      29.049   6.341  -2.059  1.00 33.54           C
ATOM   2566  C    ASP B 407      30.052   6.082  -0.947  1.00 31.74           C
ATOM   2567  O    ASP B 407      31.198   5.716  -1.205  1.00 28.74           O
ATOM   2568  CB   ASP B 407      29.683   7.099  -3.231  1.00 40.47           C
ATOM   2569  CG   ASP B 407      30.508   6.255  -4.174  1.00 48.65           C
ATOM   2570  OD1  ASP B 407      30.218   5.039  -4.303  1.00 51.06           O
ATOM   2571  OD2  ASP B 407      31.459   6.821  -4.779  1.00 47.04           O
ATOM   2572  N    LEU B 408      29.675   6.252   0.333  1.00 29.67           N
ATOM   2573  CA   LEU B 408      30.615   5.993   1.448  1.00 24.21           C
ATOM   2574  C    LEU B 408      29.831   5.074   2.398  1.00 27.05           C
ATOM   2575  O    LEU B 408      29.170   5.478   3.366  1.00 28.32           O
ATOM   2576  CB   LEU B 408      31.020   7.259   2.189  1.00 25.91           C
ATOM   2577  CG   LEU B 408      32.085   7.094   3.287  1.00 24.69           C
ATOM   2578  CD1  LEU B 408      33.332   6.409   2.725  1.00 31.78           C
ATOM   2579  CD2  LEU B 408      32.461   8.417   3.938  1.00 28.24           C
ATOM   2580  N    VAL B 409      29.791   3.801   2.020  1.00 27.88           N
ATOM   2581  CA   VAL B 409      29.012   2.803   2.773  1.00 26.77           C
ATOM   2582  C    VAL B 409      29.998   1.872   3.455  1.00 30.15           C
ATOM   2583  O    VAL B 409      30.763   1.161   2.787  1.00 30.60           O
ATOM   2584  CB   VAL B 409      28.159   1.992   1.775  1.00 31.29           C
ATOM   2585  CG1  VAL B 409      27.482   0.811   2.453  1.00 29.21           C
ATOM   2586  CG2  VAL B 409      27.139   2.874   1.070  1.00 27.53           C
ATOM   2587  N    LEU B 410      30.037   1.887   4.763  1.00 27.22           N
ATOM   2588  CA   LEU B 410      30.973   1.134   5.549  1.00 27.72           C
ATOM   2589  C    LEU B 410      30.376  -0.077   6.252  1.00 32.86           C
ATOM   2590  O    LEU B 410      29.347  -0.047   6.917  1.00 30.92           O
ATOM   2591  CB   LEU B 410      31.704   1.959   6.625  1.00 27.54           C
ATOM   2592  CG   LEU B 410      32.422   3.213   6.106  1.00 30.97           C
ATOM   2593  CD1  LEU B 410      33.120   3.953   7.234  1.00 31.37           C
ATOM   2594  CD2  LEU B 410      33.403   2.827   4.982  1.00 27.37           C
ATOM   2595  N    ASP B 411      31.076  -1.196   6.010  1.00 30.35           N
ATOM   2596  CA   ASP B 411      30.653  -2.412   6.717  1.00 33.84           C
ATOM   2597  C    ASP B 411      31.102  -2.276   8.164  1.00 30.61           C
ATOM   2598  O    ASP B 411      32.149  -1.691   8.457  1.00 30.55           O
ATOM   2599  CB   ASP B 411      31.307  -3.645   6.059  1.00 39.46           C
ATOM   2600  CG   ASP B 411      30.415  -4.056   4.899  1.00 47.55           C
ATOM   2601  OD1  ASP B 411      30.302  -3.357   3.883  1.00 52.15           O
ATOM   2602  OD2  ASP B 411      29.773  -5.106   5.083  1.00 58.50           O
ATOM   2603  N    ARG B 412      30.311  -2.868   9.050  1.00 29.95           N
ATOM   2604  CA   ARG B 412      30.622  -2.877  10.474  1.00 33.26           C
ATOM   2605  C    ARG B 412      32.082  -3.177  10.738  1.00 35.75           C
ATOM   2606  O    ARG B 412      32.791  -2.445  11.412  1.00 34.51           O
ATOM   2607  CB   ARG B 412      29.688  -3.891  11.142  1.00 32.44           C
ATOM   2608  CG   ARG B 412      29.783  -3.893  12.664  1.00 37.89           C
ATOM   2609  CD   ARG B 412      30.653  -5.027  13.176  1.00 44.63           C
ATOM   2610  NE   ARG B 412      30.821  -5.015  14.633  1.00 44.43           N
ATOM   2611  CZ   ARG B 412      31.756  -5.775  15.205  1.00 47.95           C
```

FIG. 2HH

| | | | | | | | | | |
|---|---|---|---|---|---|---|---|---|---|
| ATOM | 2612 | NH1 | ARG | B | 412 | 31.941 | -5.791 | 16.516 | 1.00 47.65 | N |
| ATOM | 2613 | NH2 | ARG | B | 412 | 32.507 | -6.553 | 14.425 | 1.00 48.50 | N |
| ATOM | 2614 | N | ASP | B | 413 | 32.629 | -4.265 | 10.155 | 1.00 34.38 | N |
| ATOM | 2615 | CA | ASP | B | 413 | 33.995 | -4.708 | 10.311 | 1.00 37.43 | C |
| ATOM | 2616 | C | ASP | B | 413 | 35.067 | -3.763 | 9.852 | 1.00 35.77 | C |
| ATOM | 2617 | O | ASP | B | 413 | 36.216 | -3.738 | 10.383 | 1.00 34.32 | O |
| ATOM | 2618 | CB | ASP | B | 413 | 34.161 | -6.089 | 9.610 | 1.00 40.66 | C |
| ATOM | 2619 | CG | ASP | B | 413 | 33.536 | -7.189 | 10.460 | 1.00 48.67 | C |
| ATOM | 2620 | OD1 | ASP | B | 413 | 33.368 | -7.006 | 11.691 | 1.00 47.59 | O |
| ATOM | 2621 | OD2 | ASP | B | 413 | 33.192 | -8.253 | 9.876 | 1.00 51.36 | O |
| ATOM | 2622 | N | GLU | B | 414 | 34.720 | -2.781 | 8.992 | 1.00 35.67 | N |
| ATOM | 2623 | CA | GLU | B | 414 | 35.764 | -1.812 | 8.612 | 1.00 34.95 | C |
| ATOM | 2624 | C | GLU | B | 414 | 36.070 | -0.879 | 9.769 | 1.00 39.07 | C |
| ATOM | 2625 | O | GLU | B | 414 | 37.039 | -0.107 | 9.723 | 1.00 35.84 | O |
| ATOM | 2626 | CB | GLU | B | 414 | 35.471 | -1.117 | 7.306 | 1.00 35.06 | C |
| ATOM | 2627 | CG | GLU | B | 414 | 35.025 | -1.983 | 6.129 | 1.00 35.23 | C |
| ATOM | 2628 | CD | GLU | B | 414 | 34.667 | -1.067 | 4.959 | 1.00 38.62 | C |
| ATOM | 2629 | OE1 | GLU | B | 414 | 33.472 | -0.896 | 4.675 | 1.00 36.28 | O |
| ATOM | 2630 | OE2 | GLU | B | 414 | 35.637 | -0.530 | 4.369 | 1.00 42.35 | O |
| ATOM | 2631 | N | GLY | B | 415 | 35.355 | -0.973 | 10.889 | 1.00 37.63 | N |
| ATOM | 2632 | CA | GLY | B | 415 | 35.596 | -0.212 | 12.090 | 1.00 42.19 | C |
| ATOM | 2633 | C | GLY | B | 415 | 36.892 | -0.655 | 12.772 | 1.00 39.93 | C |
| ATOM | 2634 | O | GLY | B | 415 | 37.534 | 0.065 | 13.534 | 1.00 36.09 | O |
| ATOM | 2635 | N | LYS | B | 416 | 37.442 | -1.834 | 12.419 | 1.00 40.99 | N |
| ATOM | 2636 | CA | LYS | B | 416 | 38.725 | -2.262 | 12.965 | 1.00 39.11 | C |
| ATOM | 2637 | C | LYS | B | 416 | 39.867 | -1.387 | 12.507 | 1.00 39.37 | C |
| ATOM | 2638 | O | LYS | B | 416 | 40.933 | -1.353 | 13.131 | 1.00 37.86 | O |
| ATOM | 2639 | CB | LYS | B | 416 | 38.996 | -3.731 | 12.591 | 1.00 45.05 | C |
| ATOM | 2640 | CG | LYS | B | 416 | 38.051 | -4.656 | 13.358 | 1.00 46.63 | C |
| ATOM | 2641 | CD | LYS | B | 416 | 38.112 | -6.062 | 12.770 | 1.00 50.30 | C |
| ATOM | 2642 | CE | LYS | B | 416 | 37.255 | -7.010 | 13.607 | 1.00 55.85 | C |
| ATOM | 2643 | NZ | LYS | B | 416 | 37.618 | -6.901 | 15.056 | 1.00 57.31 | N |
| ATOM | 2644 | N | CYS | B | 417 | 39.673 | -0.609 | 11.441 | 1.00 42.91 | N |
| ATOM | 2645 | CA | CYS | B | 417 | 40.649 | 0.299 | 10.915 | 1.00 38.32 | C |
| ATOM | 2646 | C | CYS | B | 417 | 41.041 | 1.434 | 11.844 | 1.00 38.44 | C |
| ATOM | 2647 | O | CYS | B | 417 | 42.143 | 1.931 | 11.609 | 1.00 36.80 | O |
| ATOM | 2648 | CB | CYS | B | 417 | 40.175 | 0.938 | 9.589 | 1.00 44.73 | C |
| ATOM | 2649 | SG | CYS | B | 417 | 39.633 | -0.209 | 8.291 | 1.00 49.95 | S |
| ATOM | 2650 | N | VAL | B | 418 | 40.239 | 1.960 | 12.775 | 1.00 28.66 | N |
| ATOM | 2651 | CA | VAL | B | 418 | 40.670 | 3.094 | 13.606 | 1.00 25.58 | C |
| ATOM | 2652 | C | VAL | B | 418 | 40.658 | 2.691 | 15.095 | 1.00 23.05 | C |
| ATOM | 2653 | O | VAL | B | 418 | 39.612 | 2.113 | 15.416 | 1.00 27.29 | O |
| ATOM | 2654 | CB | VAL | B | 418 | 39.598 | 4.212 | 13.406 | 1.00 28.69 | C |
| ATOM | 2655 | CG1 | VAL | B | 418 | 39.790 | 5.412 | 14.295 | 1.00 29.09 | C |
| ATOM | 2656 | CG2 | VAL | B | 418 | 39.626 | 4.666 | 11.935 | 1.00 24.25 | C |
| ATOM | 2657 | N | GLU | B | 419 | 41.631 | 3.069 | 15.872 | 1.00 28.15 | N |
| ATOM | 2658 | CA | GLU | B | 419 | 41.604 | 2.736 | 17.304 | 1.00 31.89 | C |
| ATOM | 2659 | C | GLU | B | 419 | 40.285 | 3.190 | 17.969 | 1.00 33.35 | C |
| ATOM | 2660 | O | GLU | B | 419 | 39.950 | 4.368 | 17.887 | 1.00 28.30 | O |
| ATOM | 2661 | CB | GLU | B | 419 | 42.779 | 3.421 | 17.983 | 1.00 37.11 | C |
| ATOM | 2662 | CG | GLU | B | 419 | 43.069 | 2.956 | 19.406 | 1.00 40.40 | C |
| ATOM | 2663 | CD | GLU | B | 419 | 44.152 | 3.719 | 20.136 | 1.00 49.85 | C |
| ATOM | 2664 | OE1 | GLU | B | 419 | 44.530 | 4.850 | 19.758 | 1.00 53.97 | O |
| ATOM | 2665 | OE2 | GLU | B | 419 | 44.661 | 3.211 | 21.160 | 1.00 52.13 | O |
| ATOM | 2666 | N | GLY | B | 420 | 39.552 | 2.281 | 18.583 | 1.00 29.93 | N |
| ATOM | 2667 | CA | GLY | B | 420 | 38.334 | 2.499 | 19.315 | 1.00 35.47 | C |
| ATOM | 2668 | C | GLY | B | 420 | 37.061 | 2.865 | 18.598 | 1.00 33.37 | C |
| ATOM | 2669 | O | GLY | B | 420 | 35.982 | 3.059 | 19.214 | 1.00 28.93 | O |
| ATOM | 2670 | N | ILE | B | 421 | 37.097 | 2.945 | 17.248 | 1.00 27.21 | N |
| ATOM | 2671 | CA | ILE | B | 421 | 35.871 | 3.377 | 16.566 | 1.00 27.21 | C |
| ATOM | 2672 | C | ILE | B | 421 | 34.832 | 2.295 | 16.473 | 1.00 28.34 | C |
| ATOM | 2673 | O | ILE | B | 421 | 33.631 | 2.452 | 16.301 | 1.00 26.36 | O |
| ATOM | 2674 | CB | ILE | B | 421 | 36.197 | 3.956 | 15.177 | 1.00 26.54 | C |
| ATOM | 2675 | CG1 | ILE | B | 421 | 35.169 | 5.104 | 14.907 | 1.00 22.99 | C |
| ATOM | 2676 | CG2 | ILE | B | 421 | 36.146 | 2.861 | 14.124 | 1.00 28.24 | C |
| ATOM | 2677 | CD1 | ILE | B | 421 | 35.566 | 5.887 | 13.638 | 1.00 20.02 | C |
| ATOM | 2678 | N | LEU | B | 422 | 35.319 | 1.030 | 16.567 | 1.00 30.64 | N |
| ATOM | 2679 | CA | LEU | B | 422 | 34.437 | -0.125 | 16.473 | 1.00 26.65 | C |
| ATOM | 2680 | C | LEU | B | 422 | 33.300 | -0.064 | 17.501 | 1.00 28.98 | C |
| ATOM | 2681 | O | LEU | B | 422 | 32.160 | -0.392 | 17.176 | 1.00 32.01 | O |
| ATOM | 2682 | CB | LEU | B | 422 | 35.253 | -1.426 | 16.541 | 1.00 33.58 | C |
| ATOM | 2683 | CG | LEU | B | 422 | 34.523 | -2.640 | 15.946 | 1.00 38.34 | C |
| ATOM | 2684 | CD1 | LEU | B | 422 | 34.221 | -2.456 | 14.475 | 1.00 36.28 | C |
| ATOM | 2685 | CD2 | LEU | B | 422 | 35.363 | -3.917 | 16.121 | 1.00 38.73 | C |
| ATOM | 2686 | N | GLU | B | 423 | 33.538 | 0.370 | 18.702 | 1.00 28.85 | N |
| ATOM | 2687 | CA | GLU | B | 423 | 32.522 | 0.549 | 19.732 | 1.00 32.02 | C |
| ATOM | 2688 | C | GLU | B | 423 | 31.482 | 1.582 | 19.233 | 1.00 28.01 | C |

FIG. 2II

| ATOM | 2689 | O | GLU | B | 423 | 30.311 | 1.306 | 19.357 | 1.00 | 29.37 | O |
|------|------|-----|-----|---|-----|--------|--------|--------|------|-------|---|
| ATOM | 2690 | CB | GLU | B | 423 | 33.167 | 1.072 | 21.005 | 1.00 | 37.08 | C |
| ATOM | 2691 | CG | GLU | B | 423 | 32.212 | 1.673 | 22.018 | 1.00 | 50.36 | C |
| ATOM | 2692 | CD | GLU | B | 423 | 32.890 | 1.780 | 23.375 | 1.00 | 59.51 | C |
| ATOM | 2693 | OE1 | GLU | B | 423 | 33.922 | 2.477 | 23.432 | 1.00 | 60.42 | O |
| ATOM | 2694 | OE2 | GLU | B | 423 | 32.376 | 1.149 | 24.324 | 1.00 | 63.97 | O |
| ATOM | 2695 | N | ILE | B | 424 | 31.944 | 2.676 | 18.640 | 1.00 | 27.62 | N |
| ATOM | 2696 | CA | ILE | B | 424 | 30.998 | 3.704 | 18.153 | 1.00 | 26.62 | C |
| ATOM | 2697 | C | ILE | B | 424 | 30.143 | 3.121 | 17.042 | 1.00 | 25.97 | C |
| ATOM | 2698 | O | ILE | B | 424 | 28.900 | 3.176 | 17.017 | 1.00 | 23.96 | O |
| ATOM | 2699 | CB | ILE | B | 424 | 31.725 | 4.968 | 17.692 | 1.00 | 26.20 | C |
| ATOM | 2700 | CG1 | ILE | B | 424 | 32.722 | 5.559 | 18.712 | 1.00 | 31.88 | C |
| ATOM | 2701 | CG2 | ILE | B | 424 | 30.778 | 6.086 | 17.268 | 1.00 | 27.72 | C |
| ATOM | 2702 | CD1 | ILE | B | 424 | 32.350 | 5.412 | 20.158 | 1.00 | 34.17 | C |
| ATOM | 2703 | N | PHE | B | 425 | 30.766 | 2.416 | 16.063 | 1.00 | 25.62 | N |
| ATOM | 2704 | CA | PHE | B | 425 | 29.957 | 1.847 | 14.997 | 1.00 | 21.95 | C |
| ATOM | 2705 | C | PHE | B | 425 | 28.914 | 0.868 | 15.521 | 1.00 | 26.08 | C |
| ATOM | 2706 | O | PHE | B | 425 | 27.790 | 0.763 | 15.034 | 1.00 | 24.27 | O |
| ATOM | 2707 | CB | PHE | B | 425 | 30.826 | 1.075 | 13.983 | 1.00 | 26.92 | C |
| ATOM | 2708 | CG | PHE | B | 425 | 31.634 | 1.932 | 13.044 | 1.00 | 27.06 | C |
| ATOM | 2709 | CD1 | PHE | B | 425 | 31.806 | 3.294 | 13.258 | 1.00 | 25.62 | C |
| ATOM | 2710 | CD2 | PHE | B | 425 | 32.263 | 1.340 | 11.972 | 1.00 | 28.77 | C |
| ATOM | 2711 | CE1 | PHE | B | 425 | 32.558 | 4.078 | 12.405 | 1.00 | 27.33 | C |
| ATOM | 2712 | CE2 | PHE | B | 425 | 33.036 | 2.130 | 11.108 | 1.00 | 32.05 | C |
| ATOM | 2713 | CZ | PHE | B | 425 | 33.183 | 3.479 | 11.331 | 1.00 | 29.20 | C |
| ATOM | 2714 | N | ASP | B | 426 | 29.320 | 0.056 | 16.542 | 1.00 | 25.65 | N |
| ATOM | 2715 | CA | ASP | B | 426 | 28.333 | -0.901 | 17.050 | 1.00 | 27.00 | C |
| ATOM | 2716 | C | ASP | B | 426 | 27.169 | -0.187 | 17.746 | 1.00 | 27.33 | C |
| ATOM | 2717 | O | ASP | B | 426 | 26.058 | -0.669 | 17.623 | 1.00 | 26.00 | O |
| ATOM | 2718 | CB | ASP | B | 426 | 29.012 | -1.873 | 18.040 | 1.00 | 28.08 | C |
| ATOM | 2719 | CG | ASP | B | 426 | 29.802 | -2.966 | 17.334 | 1.00 | 32.25 | C |
| ATOM | 2720 | OD1 | ASP | B | 426 | 29.491 | -3.324 | 16.188 | 1.00 | 38.16 | O |
| ATOM | 2721 | OD2 | ASP | B | 426 | 30.761 | -3.474 | 17.971 | 1.00 | 35.77 | O |
| ATOM | 2722 | N | MET | B | 427 | 27.404 | 0.925 | 18.430 | 1.00 | 28.31 | N |
| ATOM | 2723 | CA | MET | B | 427 | 26.269 | 1.631 | 19.062 | 1.00 | 28.00 | C |
| ATOM | 2724 | C | MET | B | 427 | 25.357 | 2.226 | 17.979 | 1.00 | 25.62 | C |
| ATOM | 2725 | O | MET | B | 427 | 24.142 | 2.282 | 18.161 | 1.00 | 25.62 | O |
| ATOM | 2726 | CB | MET | B | 427 | 26.681 | 2.796 | 19.918 | 1.00 | 29.81 | C |
| ATOM | 2727 | CG | MET | B | 427 | 27.634 | 2.578 | 21.042 | 1.00 | 37.26 | C |
| ATOM | 2728 | SD | MET | B | 427 | 28.151 | 4.195 | 21.708 | 1.00 | 34.12 | S |
| ATOM | 2729 | CE | MET | B | 427 | 29.288 | 3.514 | 22.936 | 1.00 | 43.31 | C |
| ATOM | 2730 | N | LEU | B | 428 | 26.004 | 2.737 | 16.913 | 1.00 | 22.88 | N |
| ATOM | 2731 | CA | LEU | B | 428 | 25.254 | 3.340 | 15.816 | 1.00 | 23.53 | C |
| ATOM | 2732 | C | LEU | B | 428 | 24.379 | 2.312 | 15.135 | 1.00 | 23.97 | C |
| ATOM | 2733 | O | LEU | B | 428 | 23.174 | 2.458 | 14.914 | 1.00 | 23.39 | O |
| ATOM | 2734 | CB | LEU | B | 428 | 26.225 | 4.054 | 14.944 | 1.00 | 19.14 | C |
| ATOM | 2735 | CG | LEU | B | 428 | 26.870 | 5.340 | 15.366 | 1.00 | 20.66 | C |
| ATOM | 2736 | CD1 | LEU | B | 428 | 28.092 | 5.656 | 14.471 | 1.00 | 23.34 | C |
| ATOM | 2737 | CD2 | LEU | B | 428 | 25.857 | 6.485 | 15.509 | 1.00 | 19.84 | C |
| ATOM | 2738 | N | LEU | B | 429 | 24.942 | 1.116 | 14.863 | 1.00 | 25.45 | N |
| ATOM | 2739 | CA | LEU | B | 429 | 24.136 | 0.050 | 14.231 | 1.00 | 26.68 | C |
| ATOM | 2740 | C | LEU | B | 429 | 23.025 | -0.498 | 15.122 | 1.00 | 24.43 | C |
| ATOM | 2741 | O | LEU | B | 429 | 21.920 | -0.832 | 14.676 | 1.00 | 26.67 | O |
| ATOM | 2742 | CB | LEU | B | 429 | 25.060 | -1.141 | 13.852 | 1.00 | 26.02 | C |
| ATOM | 2743 | CG | LEU | B | 429 | 25.945 | -0.808 | 12.624 | 1.00 | 29.17 | C |
| ATOM | 2744 | CD1 | LEU | B | 429 | 27.103 | -1.786 | 12.580 | 1.00 | 27.09 | C |
| ATOM | 2745 | CD2 | LEU | B | 429 | 25.074 | -0.793 | 11.394 | 1.00 | 22.87 | C |
| ATOM | 2746 | N | ALA | B | 430 | 23.282 | -0.586 | 16.405 | 1.00 | 26.72 | N |
| ATOM | 2747 | CA | ALA | B | 430 | 22.295 | -1.104 | 17.364 | 1.00 | 29.50 | C |
| ATOM | 2748 | C | ALA | B | 430 | 21.126 | -0.148 | 17.507 | 1.00 | 29.75 | C |
| ATOM | 2749 | O | ALA | B | 430 | 19.964 | -0.536 | 17.409 | 1.00 | 23.47 | O |
| ATOM | 2750 | CB | ALA | B | 430 | 22.972 | -1.390 | 18.715 | 1.00 | 27.79 | C |
| ATOM | 2751 | N | THR | B | 431 | 21.416 | 1.167 | 17.562 | 1.00 | 29.22 | N |
| ATOM | 2752 | CA | THR | B | 431 | 20.314 | 2.136 | 17.631 | 1.00 | 31.78 | C |
| ATOM | 2753 | C | THR | B | 431 | 19.545 | 2.182 | 16.320 | 1.00 | 27.18 | C |
| ATOM | 2754 | O | THR | B | 431 | 18.306 | 2.273 | 16.230 | 1.00 | 24.27 | O |
| ATOM | 2755 | CB | THR | B | 431 | 20.930 | 3.480 | 18.065 | 1.00 | 25.05 | C |
| ATOM | 2756 | OG1 | THR | B | 431 | 21.794 | 3.282 | 19.200 | 1.00 | 29.32 | O |
| ATOM | 2757 | CG2 | THR | B | 431 | 19.789 | 4.449 | 18.369 | 1.00 | 29.50 | C |
| ATOM | 2758 | N | THR | B | 432 | 20.253 | 2.060 | 15.176 | 1.00 | 24.95 | N |
| ATOM | 2759 | CA | THR | B | 432 | 19.608 | 2.011 | 13.880 | 1.00 | 25.81 | C |
| ATOM | 2760 | C | THR | B | 432 | 18.652 | 0.807 | 13.882 | 1.00 | 27.63 | C |
| ATOM | 2761 | O | THR | B | 432 | 17.530 | 0.895 | 13.396 | 1.00 | 25.14 | O |
| ATOM | 2762 | CB | THR | B | 432 | 20.600 | 1.774 | 12.727 | 1.00 | 26.18 | C |
| ATOM | 2763 | OG1 | THR | B | 432 | 21.520 | 2.903 | 12.755 | 1.00 | 23.04 | O |
| ATOM | 2764 | CG2 | THR | B | 432 | 19.956 | 1.648 | 11.351 | 1.00 | 26.93 | C |
| ATOM | 2765 | N | SER | B | 433 | 19.157 | -0.324 | 14.394 | 1.00 | 29.09 | N |

FIG. 2JJ

```
ATOM   2766  CA   SER B 433      18.269   -1.504   14.469  1.00 29.37           C
ATOM   2767  C    SER B 433      17.002   -1.256   15.252  1.00 28.81           C
ATOM   2768  O    SER B 433      15.971   -1.823   14.883  1.00 32.18           O
ATOM   2769  CB   SER B 433      18.990   -2.672   15.172  1.00 31.10           C
ATOM   2770  OG   SER B 433      20.020   -3.015   14.264  1.00 27.47           O
ATOM   2771  N    ARG B 434      17.085   -0.514   16.358  1.00 29.90           N
ATOM   2772  CA   ARG B 434      15.871   -0.260   17.147  1.00 34.41           C
ATOM   2773  C    ARG B 434      14.859    0.554   16.363  1.00 35.22           C
ATOM   2774  O    ARG B 434      13.636    0.377   16.433  1.00 31.25           O
ATOM   2775  CB   ARG B 434      16.264    0.421   18.463  1.00 32.44           C
ATOM   2776  CG   ARG B 434      15.008    0.863   19.162  1.00 45.34           C
ATOM   2777  CD   ARG B 434      14.064    0.035   19.924  1.00 48.18           C
ATOM   2778  NE   ARG B 434      13.120   -0.900   19.363  1.00 48.77           N
ATOM   2779  CZ   ARG B 434      11.922   -1.055   19.948  1.00 56.45           C
ATOM   2780  NH1  ARG B 434      11.626   -0.316   21.025  1.00 59.27           N
ATOM   2781  NH2  ARG B 434      11.041   -1.928   19.478  1.00 58.02           N
ATOM   2782  N    PHE B 435      15.369    1.546   15.604  1.00 32.09           N
ATOM   2783  CA   PHE B 435      14.458    2.349   14.785  1.00 28.44           C
ATOM   2784  C    PHE B 435      13.872    1.440   13.694  1.00 28.71           C
ATOM   2785  O    PHE B 435      12.697    1.557   13.389  1.00 28.96           O
ATOM   2786  CB   PHE B 435      15.140    3.558   14.169  1.00 27.08           C
ATOM   2787  CG   PHE B 435      15.381    4.716   15.144  1.00 25.10           C
ATOM   2788  CD1  PHE B 435      14.324    5.372   15.755  1.00 27.67           C
ATOM   2789  CD2  PHE B 435      16.659    5.107   15.458  1.00 24.73           C
ATOM   2790  CE1  PHE B 435      14.541    6.418   16.628  1.00 23.09           C
ATOM   2791  CE2  PHE B 435      16.905    6.177   16.313  1.00 28.72           C
ATOM   2792  CZ   PHE B 435      15.844    6.840   16.893  1.00 24.31           C
ATOM   2793  N    ARG B 436      14.642    0.486   13.166  1.00 29.19           N
ATOM   2794  CA   ARG B 436      14.127   -0.445   12.165  1.00 30.07           C
ATOM   2795  C    ARG B 436      13.033   -1.316   12.792  1.00 31.36           C
ATOM   2796  O    ARG B 436      11.960   -1.486   12.193  1.00 29.11           O
ATOM   2797  CB   ARG B 436      15.241   -1.335   11.584  1.00 31.22           C
ATOM   2798  CG   ARG B 436      14.762   -2.349   10.513  1.00 31.92           C
ATOM   2799  CD   ARG B 436      15.848   -3.424   10.281  1.00 34.42           C
ATOM   2800  NE   ARG B 436      17.060   -2.694    9.959  1.00 41.51           N
ATOM   2801  CZ   ARG B 436      18.212   -2.827   10.627  1.00 39.46           C
ATOM   2802  NH1  ARG B 436      18.314   -3.685   11.621  1.00 36.97           N
ATOM   2803  NH2  ARG B 436      19.220   -2.051   10.264  1.00 40.73           N
ATOM   2804  N    GLU B 437      13.276   -1.754   14.024  1.00 32.14           N
ATOM   2805  CA   GLU B 437      12.273   -2.605   14.702  1.00 34.87           C
ATOM   2806  C    GLU B 437      10.983   -1.853   14.954  1.00 33.57           C
ATOM   2807  O    GLU B 437       9.862   -2.362   14.906  1.00 33.90           O
ATOM   2808  CB   GLU B 437      12.871   -3.185   15.973  1.00 40.30           C
ATOM   2809  CG   GLU B 437      13.862   -4.312   15.686  1.00 49.69           C
ATOM   2810  CD   GLU B 437      14.896   -4.501   16.779  1.00 57.75           C
ATOM   2811  OE1  GLU B 437      14.545   -4.433   17.989  1.00 58.57           O
ATOM   2812  OE2  GLU B 437      16.079   -4.729   16.401  1.00 58.23           O
ATOM   2813  N    LEU B 438      11.077   -0.550   15.238  1.00 29.78           N
ATOM   2814  CA   LEU B 438       9.938    0.307   15.445  1.00 29.52           C
ATOM   2815  C    LEU B 438       9.291    0.765   14.145  1.00 26.28           C
ATOM   2816  O    LEU B 438       8.235    1.397   14.169  1.00 27.56           O
ATOM   2817  CB   LEU B 438      10.391    1.566   16.229  1.00 33.11           C
ATOM   2818  CG   LEU B 438      10.412    1.409   17.743  1.00 39.39           C
ATOM   2819  CD1  LEU B 438      11.110    2.613   18.358  1.00 40.38           C
ATOM   2820  CD2  LEU B 438       8.982    1.266   18.276  1.00 37.45           C
ATOM   2821  N    LYS B 439       9.903    0.495   12.993  1.00 28.35           N
ATOM   2822  CA   LYS B 439       9.414    0.881   11.690  1.00 27.73           C
ATOM   2823  C    LYS B 439       9.217    2.408   11.606  1.00 25.44           C
ATOM   2824  O    LYS B 439       8.169    2.940   11.257  1.00 23.93           O
ATOM   2825  CB   LYS B 439       8.109    0.164   11.308  1.00 30.79           C
ATOM   2826  CG   LYS B 439       8.369   -1.324   10.989  1.00 36.88           C
ATOM   2827  CD   LYS B 439       7.060   -2.021   10.634  1.00 38.92           C
ATOM   2828  CE   LYS B 439       7.212   -3.540   10.639  1.00 44.57           C
ATOM   2829  NZ   LYS B 439       6.192   -4.182    9.749  1.00 50.78           N
ATOM   2830  N    LEU B 440      10.270    3.104   12.031  1.00 26.36           N
ATOM   2831  CA   LEU B 440      10.303    4.570   12.030  1.00 23.78           C
ATOM   2832  C    LEU B 440       9.932    5.079   10.654  1.00 24.55           C
ATOM   2833  O    LEU B 440      10.571    4.653    9.672  1.00 26.01           O
ATOM   2834  CB   LEU B 440      11.749    5.038   12.352  1.00 25.25           C
ATOM   2835  CG   LEU B 440      11.887    6.587   12.440  1.00 23.71           C
ATOM   2836  CD1  LEU B 440      11.161    7.175   13.632  1.00 19.69           C
ATOM   2837  CD2  LEU B 440      13.377    6.923   12.400  1.00 23.09           C
ATOM   2838  N    GLN B 441       8.957    5.976   10.586  1.00 20.88           N
ATOM   2839  CA   GLN B 441       8.526    6.530    9.294  1.00 27.60           C
ATOM   2840  C    GLN B 441       9.260    7.828    8.987  1.00 27.63           C
ATOM   2841  O    GLN B 441       9.778    8.510    9.885  1.00 23.77           O
ATOM   2842  CB   GLN B 441       7.025    6.818    9.355  1.00 24.97           C
```

FIG. 2KK

| | | | | | | | | | | |
|---|---|---|---|---|---|---|---|---|---|---|
| ATOM | 2843 | CG | GLN | B | 441 | 6.217 | 5.554 | 9.658 | 1.00 33.92 | C |
| ATOM | 2844 | CD | GLN | B | 441 | 6.418 | 4.515 | 8.568 | 1.00 42.79 | C |
| ATOM | 2845 | OE1 | GLN | B | 441 | 5.880 | 4.786 | 7.490 | 1.00 49.00 | O |
| ATOM | 2846 | NE2 | GLN | B | 441 | 7.165 | 3.441 | 8.802 | 1.00 47.31 | N |
| ATOM | 2847 | N | HIS | B | 442 | 9.306 | 8.219 | 7.731 | 1.00 26.50 | N |
| ATOM | 2848 | CA | HIS | B | 442 | 10.021 | 9.423 | 7.313 | 1.00 29.05 | C |
| ATOM | 2849 | C | HIS | B | 442 | 9.527 | 10.660 | 8.021 | 1.00 24.51 | C |
| ATOM | 2850 | O | HIS | B | 442 | 10.388 | 11.418 | 8.526 | 1.00 25.18 | O |
| ATOM | 2851 | CB | HIS | B | 442 | 9.996 | 9.539 | 5.768 | 1.00 31.83 | C |
| ATOM | 2852 | CG | HIS | B | 442 | 10.894 | 10.622 | 5.225 | 1.00 33.00 | C |
| ATOM | 2853 | ND1 | HIS | B | 442 | 12.242 | 10.727 | 5.455 | 1.00 34.94 | N |
| ATOM | 2854 | CD2 | HIS | B | 442 | 10.581 | 11.678 | 4.438 | 1.00 34.09 | C |
| ATOM | 2855 | CE1 | HIS | B | 442 | 12.715 | 11.799 | 4.844 | 1.00 34.42 | C |
| ATOM | 2856 | NE2 | HIS | B | 442 | 11.725 | 12.403 | 4.214 | 1.00 31.06 | N |
| ATOM | 2857 | N | LYS | B | 443 | 8.232 | 10.903 | 8.167 | 1.00 23.03 | N |
| ATOM | 2858 | CA | LYS | B | 443 | 7.739 | 12.085 | 8.832 | 1.00 23.66 | C |
| ATOM | 2859 | C | LYS | B | 443 | 8.036 | 12.057 | 10.336 | 1.00 22.88 | C |
| ATOM | 2860 | O | LYS | B | 443 | 8.109 | 13.134 | 10.934 | 1.00 19.97 | O |
| ATOM | 2861 | CB | LYS | B | 443 | 6.246 | 12.410 | 8.563 | 1.00 26.75 | C |
| ATOM | 2862 | CG | LYS | B | 443 | 6.009 | 12.667 | 7.064 | 1.00 31.03 | C |
| ATOM | 2863 | CD | LYS | B | 443 | 4.505 | 12.888 | 6.794 | 1.00 33.11 | C |
| ATOM | 2864 | CE | LYS | B | 443 | 4.304 | 13.255 | 5.318 | 1.00 45.60 | C |
| ATOM | 2865 | NZ | LYS | B | 443 | 2.834 | 13.347 | 4.991 | 1.00 46.60 | N |
| ATOM | 2866 | N | GLU | B | 444 | 8.115 | 10.869 | 10.920 | 1.00 21.21 | N |
| ATOM | 2867 | CA | GLU | B | 444 | 8.434 | 10.812 | 12.379 | 1.00 18.69 | C |
| ATOM | 2868 | C | GLU | B | 444 | 9.919 | 11.207 | 12.511 | 1.00 21.45 | C |
| ATOM | 2869 | O | GLU | B | 444 | 10.279 | 12.011 | 13.370 | 1.00 19.10 | O |
| ATOM | 2870 | CB | GLU | B | 444 | 8.275 | 9.389 | 12.932 | 1.00 21.53 | C |
| ATOM | 2871 | CG | GLU | B | 444 | 6.788 | 8.971 | 12.978 | 1.00 25.64 | C |
| ATOM | 2872 | CD | GLU | B | 444 | 6.612 | 7.492 | 13.273 | 1.00 24.94 | C |
| ATOM | 2873 | OE1 | GLU | B | 444 | 7.483 | 6.666 | 12.982 | 1.00 24.73 | O |
| ATOM | 2874 | OE2 | GLU | B | 444 | 5.585 | 7.165 | 13.884 | 1.00 26.20 | O |
| ATOM | 2875 | N | TYR | B | 445 | 10.776 | 10.716 | 11.656 | 1.00 20.35 | N |
| ATOM | 2876 | CA | TYR | B | 445 | 12.195 | 11.016 | 11.602 | 1.00 23.29 | C |
| ATOM | 2877 | C | TYR | B | 445 | 12.440 | 12.531 | 11.488 | 1.00 25.07 | C |
| ATOM | 2878 | O | TYR | B | 445 | 13.283 | 13.083 | 12.191 | 1.00 22.54 | O |
| ATOM | 2879 | CB | TYR | B | 445 | 12.905 | 10.299 | 10.462 | 1.00 23.22 | C |
| ATOM | 2880 | CG | TYR | B | 445 | 14.154 | 10.963 | 9.926 | 1.00 25.12 | C |
| ATOM | 2881 | CD1 | TYR | B | 445 | 15.329 | 10.898 | 10.683 | 1.00 26.68 | C |
| ATOM | 2882 | CD2 | TYR | B | 445 | 14.166 | 11.619 | 8.682 | 1.00 25.12 | C |
| ATOM | 2883 | CE1 | TYR | B | 445 | 16.486 | 11.480 | 10.236 | 1.00 26.30 | C |
| ATOM | 2884 | CE2 | TYR | B | 445 | 15.346 | 12.173 | 8.238 | 1.00 25.76 | C |
| ATOM | 2885 | CZ | TYR | B | 445 | 16.471 | 12.145 | 9.018 | 1.00 25.11 | C |
| ATOM | 2886 | OH | TYR | B | 445 | 17.680 | 12.652 | 8.602 | 1.00 32.57 | O |
| ATOM | 2887 | N | LEU | B | 446 | 11.689 | 13.181 | 10.602 | 1.00 22.15 | N |
| ATOM | 2888 | CA | LEU | B | 446 | 11.848 | 14.616 | 10.461 | 1.00 21.36 | C |
| ATOM | 2889 | C | LEU | B | 446 | 11.530 | 15.345 | 11.760 | 1.00 19.59 | C |
| ATOM | 2890 | O | LEU | B | 446 | 12.237 | 16.275 | 12.130 | 1.00 19.63 | O |
| ATOM | 2891 | CB | LEU | B | 446 | 10.902 | 15.194 | 9.383 | 1.00 24.06 | C |
| ATOM | 2892 | CG | LEU | B | 446 | 11.156 | 14.620 | 7.956 | 1.00 25.43 | C |
| ATOM | 2893 | CD1 | LEU | B | 446 | 10.056 | 15.081 | 6.999 | 1.00 29.92 | C |
| ATOM | 2894 | CD2 | LEU | B | 446 | 12.564 | 14.978 | 7.528 | 1.00 27.33 | C |
| ATOM | 2895 | N | CYS | B | 447 | 10.480 | 14.946 | 12.463 | 1.00 18.44 | N |
| ATOM | 2896 | CA | CYS | B | 447 | 10.110 | 15.624 | 13.696 | 1.00 16.12 | C |
| ATOM | 2897 | C | CYS | B | 447 | 11.221 | 15.376 | 14.748 | 1.00 18.28 | C |
| ATOM | 2898 | O | CYS | B | 447 | 11.512 | 16.262 | 15.514 | 1.00 17.67 | O |
| ATOM | 2899 | CB | CYS | B | 447 | 8.771 | 15.099 | 14.240 | 1.00 17.37 | C |
| ATOM | 2900 | SG | CYS | B | 447 | 7.391 | 15.722 | 13.134 | 1.00 21.76 | S |
| ATOM | 2901 | N | VAL | B | 448 | 11.621 | 14.089 | 14.879 | 1.00 19.27 | N |
| ATOM | 2902 | CA | VAL | B | 448 | 12.621 | 13.830 | 15.948 | 1.00 18.83 | C |
| ATOM | 2903 | C | VAL | B | 448 | 13.905 | 14.585 | 15.713 | 1.00 21.13 | C |
| ATOM | 2904 | O | VAL | B | 448 | 14.520 | 15.072 | 16.666 | 1.00 19.08 | O |
| ATOM | 2905 | CB | VAL | B | 448 | 12.846 | 12.292 | 15.982 | 1.00 25.15 | C |
| ATOM | 2906 | CG1 | VAL | B | 448 | 13.955 | 11.953 | 16.955 | 1.00 29.45 | C |
| ATOM | 2907 | CG2 | VAL | B | 448 | 11.498 | 11.659 | 16.336 | 1.00 21.83 | C |
| ATOM | 2908 | N | LYS | B | 449 | 14.355 | 14.647 | 14.437 | 1.00 18.13 | N |
| ATOM | 2909 | CA | LYS | B | 449 | 15.601 | 15.404 | 14.161 | 1.00 17.61 | C |
| ATOM | 2910 | C | LYS | B | 449 | 15.428 | 16.871 | 14.558 | 1.00 20.56 | C |
| ATOM | 2911 | O | LYS | B | 449 | 16.375 | 17.491 | 15.076 | 1.00 19.67 | O |
| ATOM | 2912 | CB | LYS | B | 449 | 16.004 | 15.195 | 12.699 | 1.00 17.60 | C |
| ATOM | 2913 | CG | LYS | B | 449 | 17.350 | 15.751 | 12.324 | 1.00 20.54 | C |
| ATOM | 2914 | CD | LYS | B | 449 | 17.812 | 15.029 | 11.026 | 1.00 24.11 | C |
| ATOM | 2915 | CE | LYS | B | 449 | 16.863 | 15.527 | 9.915 | 1.00 23.93 | C |
| ATOM | 2916 | NZ | LYS | B | 449 | 17.613 | 15.786 | 8.664 | 1.00 28.21 | N |
| ATOM | 2917 | N | ALA | B | 450 | 14.262 | 17.461 | 14.244 | 1.00 16.41 | N |
| ATOM | 2918 | CA | ALA | B | 450 | 14.037 | 18.851 | 14.648 | 1.00 18.74 | C |
| ATOM | 2919 | C | ALA | B | 450 | 14.000 | 18.929 | 16.174 | 1.00 18.63 | C |

FIG. 2LL

| ATOM | 2920 | O   | ALA B 450 | 14.510 | 19.892 | 16.771 | 1.00 | 20.03 | O |
|------|------|-----|-----------|--------|--------|--------|------|-------|---|
| ATOM | 2921 | CB  | ALA B 450 | 12.731 | 19.415 | 14.050 | 1.00 | 17.47 | C |
| ATOM | 2922 | N   | MET B 451 | 13.495 | 17.931 | 16.883 | 1.00 | 17.51 | N |
| ATOM | 2923 | CA  | MET B 451 | 13.502 | 17.947 | 18.329 | 1.00 | 18.37 | C |
| ATOM | 2924 | C   | MET B 451 | 14.924 | 17.871 | 18.885 | 1.00 | 17.64 | C |
| ATOM | 2925 | O   | MET B 451 | 15.198 | 18.573 | 19.865 | 1.00 | 20.15 | O |
| ATOM | 2926 | CB  | MET B 451 | 12.672 | 16.774 | 18.885 | 1.00 | 19.94 | C |
| ATOM | 2927 | CG  | MET B 451 | 11.204 | 17.051 | 18.498 | 1.00 | 27.03 | C |
| ATOM | 2928 | SD  | MET B 451 | 10.035 | 15.686 | 18.784 | 1.00 | 32.64 | S |
| ATOM | 2929 | CE  | MET B 451 | 10.922 | 14.995 | 20.161 | 1.00 | 27.86 | C |
| ATOM | 2930 | N   | ILE B 452 | 15.819 | 17.142 | 18.234 | 1.00 | 17.42 | N |
| ATOM | 2931 | CA  | ILE B 452 | 17.198 | 17.097 | 18.705 | 1.00 | 18.96 | C |
| ATOM | 2932 | C   | ILE B 452 | 17.806 | 18.479 | 18.667 | 1.00 | 21.80 | C |
| ATOM | 2933 | O   | ILE B 452 | 18.436 | 18.991 | 19.621 | 1.00 | 23.30 | O |
| ATOM | 2934 | CB  | ILE B 452 | 17.989 | 16.101 | 17.833 | 1.00 | 19.88 | C |
| ATOM | 2935 | CG1 | ILE B 452 | 17.450 | 14.701 | 18.126 | 1.00 | 21.76 | C |
| ATOM | 2936 | CG2 | ILE B 452 | 19.497 | 16.199 | 18.120 | 1.00 | 18.62 | C |
| ATOM | 2937 | CD1 | ILE B 452 | 18.112 | 13.672 | 17.197 | 1.00 | 22.87 | C |
| ATOM | 2938 | N   | LEU B 453 | 17.579 | 19.179 | 17.567 | 1.00 | 18.54 | N |
| ATOM | 2939 | CA  | LEU B 453 | 18.132 | 20.547 | 17.476 | 1.00 | 17.52 | C |
| ATOM | 2940 | C   | LEU B 453 | 17.574 | 21.466 | 18.543 | 1.00 | 22.82 | C |
| ATOM | 2941 | O   | LEU B 453 | 18.276 | 22.272 | 19.181 | 1.00 | 20.30 | O |
| ATOM | 2942 | CB  | LEU B 453 | 17.717 | 21.154 | 16.125 | 1.00 | 19.07 | C |
| ATOM | 2943 | CG  | LEU B 453 | 18.042 | 22.652 | 15.950 | 1.00 | 18.04 | C |
| ATOM | 2944 | CD1 | LEU B 453 | 19.517 | 23.012 | 15.887 | 1.00 | 22.50 | C |
| ATOM | 2945 | CD2 | LEU B 453 | 17.374 | 23.159 | 14.663 | 1.00 | 22.28 | C |
| ATOM | 2946 | N   | LEU B 454 | 16.234 | 21.381 | 18.711 | 1.00 | 17.98 | N |
| ATOM | 2947 | CA  | LEU B 454 | 15.634 | 22.323 | 19.641 | 1.00 | 21.35 | C |
| ATOM | 2948 | C   | LEU B 454 | 15.780 | 22.004 | 21.104 | 1.00 | 23.61 | C |
| ATOM | 2949 | O   | LEU B 454 | 15.595 | 22.945 | 21.897 | 1.00 | 25.52 | O |
| ATOM | 2950 | CB  | LEU B 454 | 14.140 | 22.453 | 19.270 | 1.00 | 20.71 | C |
| ATOM | 2951 | CG  | LEU B 454 | 13.833 | 22.975 | 17.887 | 1.00 | 20.30 | C |
| ATOM | 2952 | CD1 | LEU B 454 | 12.347 | 22.881 | 17.610 | 1.00 | 23.20 | C |
| ATOM | 2953 | CD2 | LEU B 454 | 14.317 | 24.430 | 17.695 | 1.00 | 21.88 | C |
| ATOM | 2954 | N   | ASN B 455 | 16.062 | 20.765 | 21.445 | 1.00 | 21.94 | N |
| ATOM | 2955 | CA  | ASN B 455 | 16.081 | 20.351 | 22.852 | 1.00 | 28.13 | C |
| ATOM | 2956 | C   | ASN B 455 | 17.425 | 19.900 | 23.406 | 1.00 | 27.63 | C |
| ATOM | 2957 | O   | ASN B 455 | 17.491 | 19.519 | 24.587 | 1.00 | 38.60 | O |
| ATOM | 2958 | CB  | ASN B 455 | 15.361 | 18.967 | 22.776 | 1.00 | 33.09 | C |
| ATOM | 2959 | CG  | ASN B 455 | 15.175 | 18.151 | 24.024 | 1.00 | 46.53 | C |
| ATOM | 2960 | OD1 | ASN B 455 | 15.470 | 16.948 | 24.077 | 1.00 | 43.08 | O |
| ATOM | 2961 | ND2 | ASN B 455 | 14.708 | 18.808 | 25.080 | 1.00 | 40.09 | N |
| ATOM | 2962 | N   | SER B 456 | 18.439 | 19.912 | 22.560 | 1.00 | 24.13 | N |
| ATOM | 2963 | CA  | SER B 456 | 19.638 | 19.252 | 23.128 | 1.00 | 30.74 | C |
| ATOM | 2964 | C   | SER B 456 | 20.506 | 20.033 | 24.059 | 1.00 | 31.89 | C |
| ATOM | 2965 | O   | SER B 456 | 21.250 | 19.391 | 24.818 | 1.00 | 29.82 | O |
| ATOM | 2966 | CB  | SER B 456 | 20.343 | 18.604 | 21.921 | 1.00 | 31.07 | C |
| ATOM | 2967 | OG  | SER B 456 | 19.446 | 17.466 | 21.649 | 1.00 | 29.71 | O |
| ATOM | 2968 | N   | ALA B 457 | 20.322 | 21.349 | 24.098 | 1.00 | 27.18 | N |
| ATOM | 2969 | CA  | ALA B 457 | 21.221 | 22.116 | 24.944 | 1.00 | 33.46 | C |
| ATOM | 2970 | C   | ALA B 457 | 21.155 | 21.687 | 26.401 | 1.00 | 35.06 | C |
| ATOM | 2971 | O   | ALA B 457 | 20.099 | 21.737 | 27.028 | 1.00 | 34.11 | O |
| ATOM | 2972 | CB  | ALA B 457 | 20.928 | 23.610 | 24.809 | 1.00 | 39.56 | C |
| ATOM | 2973 | N   | MET B 458 | 22.347 | 21.591 | 27.008 | 1.00 | 35.72 | N |
| ATOM | 2974 | CA  | MET B 458 | 22.393 | 21.244 | 28.430 | 1.00 | 29.71 | C |
| ATOM | 2975 | C   | MET B 458 | 22.393 | 22.505 | 29.298 | 1.00 | 42.19 | C |
| ATOM | 2976 | O   | MET B 458 | 22.691 | 23.569 | 28.725 | 1.00 | 41.34 | O |
| ATOM | 2977 | CB  | MET B 458 | 23.607 | 20.386 | 28.739 | 1.00 | 38.90 | C |
| ATOM | 2978 | CG  | MET B 458 | 23.552 | 18.990 | 28.158 | 1.00 | 35.74 | C |
| ATOM | 2979 | SD  | MET B 458 | 22.267 | 17.944 | 28.833 | 1.00 | 32.79 | S |
| ATOM | 2980 | CE  | MET B 458 | 22.653 | 17.715 | 30.567 | 1.00 | 35.81 | C |
| ATOM | 2981 | N   | ALA B 469 | 12.103 | 36.034 | 25.966 | 1.00 | 54.31 | N |
| ATOM | 2982 | CA  | ALA B 469 | 11.314 | 36.184 | 24.740 | 1.00 | 55.41 | C |
| ATOM | 2983 | C   | ALA B 469 | 11.762 | 35.123 | 23.727 | 1.00 | 54.41 | C |
| ATOM | 2984 | O   | ALA B 469 | 10.971 | 34.426 | 23.100 | 1.00 | 53.37 | O |
| ATOM | 2985 | CB  | ALA B 469 | 11.481 | 37.560 | 24.148 | 1.00 | 56.77 | C |
| ATOM | 2986 | N   | SER B 470 | 13.092 | 35.091 | 23.569 | 1.00 | 49.02 | N |
| ATOM | 2987 | CA  | SER B 470 | 13.677 | 34.082 | 22.669 | 1.00 | 46.55 | C |
| ATOM | 2988 | C   | SER B 470 | 13.409 | 32.747 | 23.368 | 1.00 | 43.33 | C |
| ATOM | 2989 | O   | SER B 470 | 12.951 | 31.791 | 22.750 | 1.00 | 43.16 | O |
| ATOM | 2990 | CB  | SER B 470 | 15.155 | 34.311 | 22.434 | 1.00 | 47.34 | C |
| ATOM | 2991 | OG  | SER B 470 | 15.760 | 33.317 | 21.622 | 1.00 | 44.03 | O |
| ATOM | 2992 | N   | SER B 471 | 13.697 | 32.727 | 24.670 | 1.00 | 43.18 | N |
| ATOM | 2993 | CA  | SER B 471 | 13.459 | 31.548 | 25.484 | 1.00 | 47.51 | C |
| ATOM | 2994 | C   | SER B 471 | 12.028 | 31.052 | 25.311 | 1.00 | 48.84 | C |
| ATOM | 2995 | O   | SER B 471 | 11.830 | 29.892 | 24.970 | 1.00 | 49.05 | O |
| ATOM | 2996 | CB  | SER B 471 | 13.659 | 31.871 | 26.972 | 1.00 | 50.06 | C |

FIG. 2MM

```
ATOM   2997  OG   SER B 471      13.172  30.756  27.719  1.00 53.89           O
ATOM   2998  N    ARG B 472      11.039  31.929  25.499  1.00 48.98           N
ATOM   2999  CA   ARG B 472       9.646  31.497  25.367  1.00 53.12           C
ATOM   3000  C    ARG B 472       9.241  31.130  23.951  1.00 47.16           C
ATOM   3001  O    ARG B 472       8.406  30.234  23.746  1.00 45.19           O
ATOM   3002  CB   ARG B 472       8.682  32.409  26.092  1.00 59.26           C
ATOM   3003  CG   ARG B 472       8.701  33.858  25.712  1.00 66.84           C
ATOM   3004  CD   ARG B 472       7.696  34.185  24.628  1.00 72.82           C
ATOM   3005  NE   ARG B 472       8.310  34.518  23.345  1.00 75.75           N
ATOM   3006  CZ   ARG B 472       7.902  35.580  22.643  1.00 78.82           C
ATOM   3007  NH1  ARG B 472       6.926  36.353  23.113  1.00 78.17           N
ATOM   3008  NH2  ARG B 472       8.489  35.858  21.486  1.00 79.34           N
ATOM   3009  N    LYS B 473       9.839  31.689  22.926  1.00 44.86           N
ATOM   3010  CA   LYS B 473       9.671  31.416  21.515  1.00 46.23           C
ATOM   3011  C    LYS B 473      10.197  30.019  21.128  1.00 42.00           C
ATOM   3012  O    LYS B 473       9.662  29.326  20.243  1.00 35.23           O
ATOM   3013  CB   LYS B 473      10.489  32.442  20.719  1.00 51.12           C
ATOM   3014  CG   LYS B 473      10.662  32.139  19.247  1.00 57.47           C
ATOM   3015  CD   LYS B 473       9.654  32.805  18.340  1.00 62.58           C
ATOM   3016  CE   LYS B 473       9.772  34.324  18.387  1.00 65.78           C
ATOM   3017  NZ   LYS B 473       9.434  34.906  17.052  1.00 69.85           N
ATOM   3018  N    LEU B 474      11.284  29.623  21.780  1.00 42.37           N
ATOM   3019  CA   LEU B 474      11.911  28.315  21.595  1.00 36.73           C
ATOM   3020  C    LEU B 474      10.996  27.226  22.136  1.00 38.16           C
ATOM   3021  O    LEU B 474      10.710  26.224  21.491  1.00 31.82           O
ATOM   3022  CB   LEU B 474      13.219  28.190  22.362  1.00 36.66           C
ATOM   3023  CG   LEU B 474      13.947  26.847  22.332  1.00 36.07           C
ATOM   3024  CD1  LEU B 474      14.091  26.373  20.883  1.00 28.80           C
ATOM   3025  CD2  LEU B 474      15.306  26.945  23.003  1.00 29.09           C
ATOM   3026  N    ALA B 475      10.549  27.399  23.382  1.00 37.80           N
ATOM   3027  CA   ALA B 475       9.639  26.426  24.016  1.00 35.34           C
ATOM   3028  C    ALA B 475       8.408  26.263  23.146  1.00 31.75           C
ATOM   3029  O    ALA B 475       7.818  25.186  22.971  1.00 35.23           O
ATOM   3030  CB   ALA B 475       9.254  27.052  25.357  1.00 37.48           C
ATOM   3031  N    HIS B 476       7.906  27.334  22.557  1.00 30.35           N
ATOM   3032  CA   HIS B 476       6.768  27.338  21.678  1.00 32.13           C
ATOM   3033  C    HIS B 476       7.044  26.567  20.382  1.00 34.39           C
ATOM   3034  O    HIS B 476       6.185  25.823  19.921  1.00 29.76           O
ATOM   3035  CB   HIS B 476       6.352  28.769  21.387  1.00 39.31           C
ATOM   3036  CG   HIS B 476       5.245  28.882  20.399  1.00 39.01           C
ATOM   3037  ND1  HIS B 476       3.911  28.701  20.707  1.00 42.30           N
ATOM   3038  CD2  HIS B 476       5.284  29.189  19.083  1.00 44.66           C
ATOM   3039  CE1  HIS B 476       3.193  28.884  19.612  1.00 45.07           C
ATOM   3040  NE2  HIS B 476       4.002  29.179  18.613  1.00 43.00           N
ATOM   3041  N    LEU B 477       8.207  26.755  19.761  1.00 31.57           N
ATOM   3042  CA   LEU B 477       8.506  26.025  18.508  1.00 30.52           C
ATOM   3043  C    LEU B 477       8.673  24.539  18.821  1.00 27.67           C
ATOM   3044  O    LEU B 477       8.225  23.646  18.100  1.00 29.59           O
ATOM   3045  CB   LEU B 477       9.725  26.692  17.874  1.00 30.28           C
ATOM   3046  CG   LEU B 477      10.411  25.953  16.725  1.00 34.16           C
ATOM   3047  CD1  LEU B 477       9.468  25.609  15.578  1.00 32.42           C
ATOM   3048  CD2  LEU B 477      11.599  26.793  16.232  1.00 35.60           C
ATOM   3049  N    LEU B 478       9.314  24.209  19.935  1.00 25.22           N
ATOM   3050  CA   LEU B 478       9.472  22.833  20.362  1.00 27.05           C
ATOM   3051  C    LEU B 478       8.133  22.133  20.616  1.00 30.54           C
ATOM   3052  O    LEU B 478       7.877  20.992  20.196  1.00 25.43           O
ATOM   3053  CB   LEU B 478      10.299  22.798  21.639  1.00 30.69           C
ATOM   3054  CG   LEU B 478      10.473  21.437  22.277  1.00 28.12           C
ATOM   3055  CD1  LEU B 478      10.964  20.403  21.245  1.00 33.21           C
ATOM   3056  CD2  LEU B 478      11.476  21.530  23.401  1.00 34.87           C
ATOM   3057  N    ASN B 479       7.226  22.877  21.250  1.00 28.17           N
ATOM   3058  CA   ASN B 479       5.867  22.367  21.472  1.00 30.21           C
ATOM   3059  C    ASN B 479       5.180  22.087  20.143  1.00 22.88           C
ATOM   3060  O    ASN B 479       4.440  21.106  20.025  1.00 24.27           O
ATOM   3061  CB   ASN B 479       5.035  23.378  22.286  1.00 32.73           C
ATOM   3062  CG   ASN B 479       5.534  23.365  23.736  1.00 40.31           C
ATOM   3063  OD1  ASN B 479       5.903  22.336  24.293  1.00 37.59           O
ATOM   3064  ND2  ASN B 479       5.552  24.558  24.327  1.00 44.28           N
ATOM   3065  N    ALA B 480       5.386  22.898  19.115  1.00 20.99           N
ATOM   3066  CA   ALA B 480       4.786  22.735  17.811  1.00 23.95           C
ATOM   3067  C    ALA B 480       5.353  21.489  17.156  1.00 21.66           C
ATOM   3068  O    ALA B 480       4.627  20.763  16.535  1.00 20.82           O
ATOM   3069  CB   ALA B 480       5.088  23.971  16.948  1.00 25.20           C
ATOM   3070  N    VAL B 481       6.694  21.289  17.289  1.00 20.53           N
ATOM   3071  CA   VAL B 481       7.239  20.054  16.694  1.00 17.55           C
ATOM   3072  C    VAL B 481       6.697  18.835  17.451  1.00 16.82           C
ATOM   3073  O    VAL B 481       6.442  17.849  16.773  1.00 22.41           O
```

FIG. 2NN

| | | | | | | | | | | |
|---|---|---|---|---|---|---|---|---|---|---|
| ATOM | 3074 | CB | VAL | B | 481 | 8.766 | 20.120 | 16.684 | 1.00 22.50 | C |
| ATOM | 3075 | CG1 | VAL | B | 481 | 9.356 | 18.798 | 16.125 | 1.00 23.47 | C |
| ATOM | 3076 | CG2 | VAL | B | 481 | 9.200 | 21.229 | 15.733 | 1.00 23.62 | C |
| ATOM | 3077 | N | THR | B | 482 | 6.556 | 18.883 | 18.786 | 1.00 18.00 | N |
| ATOM | 3078 | CA | THR | B | 482 | 5.949 | 17.738 | 19.474 | 1.00 22.76 | C |
| ATOM | 3079 | C | THR | B | 482 | 4.543 | 17.467 | 18.948 | 1.00 22.09 | C |
| ATOM | 3080 | O | THR | B | 482 | 4.166 | 16.328 | 18.642 | 1.00 19.49 | O |
| ATOM | 3081 | CB | THR | B | 482 | 5.970 | 17.975 | 21.000 | 1.00 29.51 | C |
| ATOM | 3082 | OG1 | THR | B | 482 | 7.324 | 18.198 | 21.397 | 1.00 27.76 | O |
| ATOM | 3083 | CG2 | THR | B | 482 | 5.430 | 16.809 | 21.810 | 1.00 27.12 | C |
| ATOM | 3084 | N | ASP | B | 483 | 3.725 | 18.508 | 18.826 | 1.00 20.17 | N |
| ATOM | 3085 | CA | ASP | B | 483 | 2.359 | 18.365 | 18.301 | 1.00 24.13 | C |
| ATOM | 3086 | C | ASP | B | 483 | 2.323 | 17.762 | 16.911 | 1.00 22.27 | C |
| ATOM | 3087 | O | ASP | B | 483 | 1.429 | 16.997 | 16.549 | 1.00 26.19 | O |
| ATOM | 3088 | CB | ASP | B | 483 | 1.611 | 19.702 | 18.199 | 1.00 29.71 | C |
| ATOM | 3089 | CG | ASP | B | 483 | 1.102 | 20.228 | 19.515 | 1.00 36.10 | C |
| ATOM | 3090 | OD1 | ASP | B | 483 | 0.857 | 19.405 | 20.430 | 1.00 31.63 | O |
| ATOM | 3091 | OD2 | ASP | B | 483 | 0.970 | 21.472 | 19.657 | 1.00 33.72 | O |
| ATOM | 3092 | N | ALA | B | 484 | 3.317 | 18.110 | 16.081 | 1.00 22.75 | N |
| ATOM | 3093 | CA | ALA | B | 484 | 3.439 | 17.595 | 14.734 | 1.00 22.22 | C |
| ATOM | 3094 | C | ALA | B | 484 | 3.709 | 16.095 | 14.756 | 1.00 22.87 | C |
| ATOM | 3095 | O | ALA | B | 484 | 3.131 | 15.295 | 14.011 | 1.00 21.02 | O |
| ATOM | 3096 | CB | ALA | B | 484 | 4.572 | 18.329 | 14.022 | 1.00 26.05 | C |
| ATOM | 3097 | N | LEU | B | 485 | 4.629 | 15.757 | 15.672 | 1.00 20.98 | N |
| ATOM | 3098 | CA | LEU | B | 485 | 4.955 | 14.327 | 15.808 | 1.00 19.83 | C |
| ATOM | 3099 | C | LEU | B | 485 | 3.731 | 13.511 | 16.168 | 1.00 19.13 | C |
| ATOM | 3100 | O | LEU | B | 485 | 3.436 | 12.430 | 15.633 | 1.00 22.33 | O |
| ATOM | 3101 | CB | LEU | B | 485 | 6.135 | 14.140 | 16.787 | 1.00 21.40 | C |
| ATOM | 3102 | CG | LEU | B | 485 | 6.506 | 12.662 | 16.981 | 1.00 18.67 | C |
| ATOM | 3103 | CD1 | LEU | B | 485 | 6.940 | 11.941 | 15.716 | 1.00 20.60 | C |
| ATOM | 3104 | CD2 | LEU | B | 485 | 7.640 | 12.520 | 18.044 | 1.00 19.57 | C |
| ATOM | 3105 | N | VAL | B | 486 | 3.024 | 13.929 | 17.192 | 1.00 21.56 | N |
| ATOM | 3106 | CA | VAL | B | 486 | 1.795 | 13.296 | 17.709 | 1.00 20.68 | C |
| ATOM | 3107 | C | VAL | B | 486 | 0.791 | 13.215 | 16.567 | 1.00 25.17 | C |
| ATOM | 3108 | O | VAL | B | 486 | 0.171 | 12.182 | 16.301 | 1.00 24.38 | O |
| ATOM | 3109 | CB | VAL | B | 486 | 1.220 | 14.149 | 18.845 | 1.00 23.66 | C |
| ATOM | 3110 | CG1 | VAL | B | 486 | -0.238 | 13.813 | 19.229 | 1.00 24.83 | C |
| ATOM | 3111 | CG2 | VAL | B | 486 | 2.045 | 14.002 | 20.124 | 1.00 21.63 | C |
| ATOM | 3112 | N | TRP | B | 487 | 0.674 | 14.343 | 15.830 | 1.00 21.96 | N |
| ATOM | 3113 | CA | TRP | B | 487 | -0.236 | 14.324 | 14.653 | 1.00 25.74 | C |
| ATOM | 3114 | C | TRP | B | 487 | 0.196 | 13.325 | 13.619 | 1.00 26.02 | C |
| ATOM | 3115 | O | TRP | B | 487 | -0.626 | 12.579 | 13.030 | 1.00 26.05 | O |
| ATOM | 3116 | CB | TRP | B | 487 | -0.264 | 15.750 | 14.059 | 1.00 25.93 | C |
| ATOM | 3117 | CG | TRP | B | 487 | -1.058 | 15.906 | 12.803 | 1.00 30.60 | C |
| ATOM | 3118 | CD1 | TRP | B | 487 | -2.409 | 16.096 | 12.721 | 1.00 37.56 | C |
| ATOM | 3119 | CD2 | TRP | B | 487 | -0.565 | 15.917 | 11.469 | 1.00 31.01 | C |
| ATOM | 3120 | NE1 | TRP | B | 487 | -2.779 | 16.218 | 11.394 | 1.00 40.01 | N |
| ATOM | 3121 | CE2 | TRP | B | 487 | -1.667 | 16.100 | 10.608 | 1.00 36.26 | C |
| ATOM | 3122 | CE3 | TRP | B | 487 | 0.697 | 15.745 | 10.903 | 1.00 29.94 | C |
| ATOM | 3123 | CZ2 | TRP | B | 487 | -1.528 | 16.157 | 9.222 | 1.00 32.52 | C |
| ATOM | 3124 | CZ3 | TRP | B | 487 | 0.838 | 15.816 | 9.534 | 1.00 37.87 | C |
| ATOM | 3125 | CH2 | TRP | B | 487 | -0.286 | 16.003 | 8.699 | 1.00 36.54 | C |
| ATOM | 3126 | N | VAL | B | 488 | 1.485 | 13.151 | 13.308 | 1.00 23.83 | N |
| ATOM | 3127 | CA | VAL | B | 488 | 2.006 | 12.204 | 12.360 | 1.00 21.03 | C |
| ATOM | 3128 | C | VAL | B | 488 | 1.740 | 10.761 | 12.832 | 1.00 26.30 | C |
| ATOM | 3129 | O | VAL | B | 488 | 1.293 | 9.887 | 12.075 | 1.00 25.72 | O |
| ATOM | 3130 | CB | VAL | B | 488 | 3.521 | 12.296 | 12.123 | 1.00 24.64 | C |
| ATOM | 3131 | CG1 | VAL | B | 488 | 4.070 | 11.047 | 11.443 | 1.00 26.89 | C |
| ATOM | 3132 | CG2 | VAL | B | 488 | 3.865 | 13.561 | 11.297 | 1.00 24.58 | C |
| ATOM | 3133 | N | ILE | B | 489 | 2.028 | 10.550 | 14.155 | 1.00 23.13 | N |
| ATOM | 3134 | CA | ILE | B | 489 | 1.765 | 9.180 | 14.666 | 1.00 22.06 | C |
| ATOM | 3135 | C | ILE | B | 489 | 0.256 | 8.881 | 14.538 | 1.00 24.87 | C |
| ATOM | 3136 | O | ILE | B | 489 | -0.098 | 7.719 | 14.264 | 1.00 24.99 | O |
| ATOM | 3137 | CB | ILE | B | 489 | 2.177 | 9.090 | 16.134 | 1.00 26.08 | C |
| ATOM | 3138 | CG1 | ILE | B | 489 | 3.734 | 9.132 | 16.232 | 1.00 22.32 | C |
| ATOM | 3139 | CG2 | ILE | B | 489 | 1.641 | 7.941 | 16.945 | 1.00 22.95 | C |
| ATOM | 3140 | CD1 | ILE | B | 489 | 4.210 | 9.443 | 17.653 | 1.00 20.14 | C |
| ATOM | 3141 | N | ALA | B | 490 | -0.617 | 9.831 | 14.685 | 1.00 27.34 | N |
| ATOM | 3142 | CA | ALA | B | 490 | -2.070 | 9.508 | 14.629 | 1.00 27.84 | C |
| ATOM | 3143 | C | ALA | B | 490 | -2.537 | 9.090 | 13.265 | 1.00 34.80 | C |
| ATOM | 3144 | O | ALA | B | 490 | -3.547 | 8.355 | 13.114 | 1.00 31.94 | O |
| ATOM | 3145 | CB | ALA | B | 490 | -2.880 | 10.619 | 15.276 | 1.00 28.91 | C |
| ATOM | 3146 | N | LYS | B | 491 | -1.803 | 9.380 | 12.183 | 1.00 32.12 | N |
| ATOM | 3147 | CA | LYS | B | 491 | -2.252 | 8.898 | 10.870 | 1.00 38.71 | C |
| ATOM | 3148 | C | LYS | B | 491 | -1.972 | 7.420 | 10.669 | 1.00 34.00 | C |
| ATOM | 3149 | O | LYS | B | 491 | -2.387 | 6.847 | 9.660 | 1.00 32.22 | O |
| ATOM | 3150 | CB | LYS | B | 491 | -1.719 | 9.752 | 9.735 | 1.00 44.36 | C |

FIG. 20O

| | | | | | | | | | | |
|---|---|---|---|---|---|---|---|---|---|---|
| ATOM | 3151 | CG | LYS | B | 491 | -0.239 | 9.800 | 9.522 | 1.00 48.41 | C |
| ATOM | 3152 | CD | LYS | B | 491 | 0.171 | 11.178 | 8.977 | 1.00 49.59 | C |
| ATOM | 3153 | CE | LYS | B | 491 | 0.188 | 11.102 | 7.466 | 1.00 53.70 | C |
| ATOM | 3154 | NZ | LYS | B | 491 | -0.254 | 12.384 | 6.856 | 1.00 55.43 | N |
| ATOM | 3155 | N | SER | B | 492 | -1.400 | 6.696 | 11.641 | 1.00 28.99 | N |
| ATOM | 3156 | CA | SER | B | 492 | -1.127 | 5.277 | 11.504 | 1.00 33.42 | C |
| ATOM | 3157 | C | SER | B | 492 | -2.366 | 4.456 | 11.835 | 1.00 28.23 | C |
| ATOM | 3158 | O | SER | B | 492 | -2.385 | 3.255 | 11.573 | 1.00 32.62 | O |
| ATOM | 3159 | CB | SER | B | 492 | 0.031 | 4.797 | 12.387 | 1.00 34.07 | C |
| ATOM | 3160 | OG | SER | B | 492 | -0.338 | 4.812 | 13.756 | 1.00 35.52 | O |
| ATOM | 3161 | N | GLY | B | 493 | -3.393 | 5.001 | 12.462 | 1.00 28.90 | N |
| ATOM | 3162 | CA | GLY | B | 493 | -4.592 | 4.264 | 12.783 | 1.00 26.51 | C |
| ATOM | 3163 | C | GLY | B | 493 | -4.559 | 3.393 | 14.015 | 1.00 31.70 | C |
| ATOM | 3164 | O | GLY | B | 493 | -5.500 | 2.653 | 14.347 | 1.00 29.72 | O |
| ATOM | 3165 | N | ILE | B | 494 | -3.498 | 3.487 | 14.799 | 1.00 30.49 | N |
| ATOM | 3166 | CA | ILE | B | 494 | -3.394 | 2.642 | 16.006 | 1.00 26.38 | C |
| ATOM | 3167 | C | ILE | B | 494 | -4.220 | 3.249 | 17.111 | 1.00 26.60 | C |
| ATOM | 3168 | O | ILE | B | 494 | -4.643 | 4.399 | 16.977 | 1.00 25.72 | O |
| ATOM | 3169 | CB | ILE | B | 494 | -1.928 | 2.494 | 16.410 | 1.00 29.64 | C |
| ATOM | 3170 | CG1 | ILE | B | 494 | -1.316 | 3.881 | 16.709 | 1.00 32.50 | C |
| ATOM | 3171 | CG2 | ILE | B | 494 | -1.153 | 1.759 | 15.340 | 1.00 29.24 | C |
| ATOM | 3172 | CD1 | ILE | B | 494 | 0.167 | 3.779 | 17.077 | 1.00 31.75 | C |
| ATOM | 3173 | N | SER | B | 495 | -4.533 | 2.484 | 18.155 | 1.00 22.01 | N |
| ATOM | 3174 | CA | SER | B | 495 | -5.322 | 2.960 | 19.268 | 1.00 28.60 | C |
| ATOM | 3175 | C | SER | B | 495 | -4.645 | 4.105 | 19.992 | 1.00 29.65 | C |
| ATOM | 3176 | O | SER | B | 495 | -3.426 | 4.270 | 19.872 | 1.00 29.51 | O |
| ATOM | 3177 | CB | SER | B | 495 | -5.519 | 1.793 | 20.264 | 1.00 28.32 | C |
| ATOM | 3178 | OG | SER | B | 495 | -4.309 | 1.556 | 20.995 | 1.00 29.30 | O |
| ATOM | 3179 | N | SER | B | 496 | -5.405 | 4.827 | 20.815 | 1.00 28.42 | N |
| ATOM | 3180 | CA | SER | B | 496 | -4.872 | 5.920 | 21.606 | 1.00 33.49 | C |
| ATOM | 3181 | C | SER | B | 496 | -3.787 | 5.454 | 22.560 | 1.00 31.99 | C |
| ATOM | 3182 | O | SER | B | 496 | -2.732 | 6.047 | 22.697 | 1.00 28.33 | O |
| ATOM | 3183 | CB | SER | B | 496 | -6.020 | 6.601 | 22.387 | 1.00 33.83 | C |
| ATOM | 3184 | OG | SER | B | 496 | -5.368 | 7.596 | 23.174 | 1.00 42.49 | O |
| ATOM | 3185 | N | GLN | B | 497 | -3.967 | 4.275 | 23.178 | 1.00 32.91 | N |
| ATOM | 3186 | CA | GLN | B | 497 | -2.957 | 3.707 | 24.062 | 1.00 33.88 | C |
| ATOM | 3187 | C | GLN | B | 497 | -1.693 | 3.419 | 23.254 | 1.00 29.03 | C |
| ATOM | 3188 | O | GLN | B | 497 | -0.586 | 3.672 | 23.743 | 1.00 30.75 | O |
| ATOM | 3189 | CB | GLN | B | 497 | -3.435 | 2.402 | 24.699 | 1.00 36.61 | C |
| ATOM | 3190 | CG | GLN | B | 497 | -2.540 | 1.791 | 25.748 | 1.00 37.77 | C |
| ATOM | 3191 | CD | GLN | B | 497 | -1.413 | 0.910 | 25.284 | 1.00 44.35 | C |
| ATOM | 3192 | OE1 | GLN | B | 497 | -1.374 | 0.429 | 24.150 | 1.00 47.20 | O |
| ATOM | 3193 | NE2 | GLN | B | 497 | -0.457 | 0.650 | 26.172 | 1.00 46.49 | N |
| ATOM | 3194 | N | GLN | B | 498 | -1.822 | 2.882 | 22.033 | 1.00 27.21 | N |
| ATOM | 3195 | CA | GLN | B | 498 | -0.667 | 2.636 | 21.202 | 1.00 25.33 | C |
| ATOM | 3196 | C | GLN | B | 498 | -0.065 | 3.975 | 20.730 | 1.00 26.83 | C |
| ATOM | 3197 | O | GLN | B | 498 | 1.167 | 3.907 | 20.578 | 1.00 26.30 | O |
| ATOM | 3198 | CB | GLN | B | 498 | -0.880 | 1.711 | 19.998 | 1.00 26.86 | C |
| ATOM | 3199 | CG | GLN | B | 498 | -1.241 | 0.323 | 20.549 | 1.00 27.39 | C |
| ATOM | 3200 | CD | GLN | B | 498 | 0.010 | -0.353 | 21.095 | 1.00 36.34 | C |
| ATOM | 3201 | OE1 | GLN | B | 498 | 0.947 | -0.562 | 20.310 | 1.00 40.62 | O |
| ATOM | 3202 | NE2 | GLN | B | 498 | 0.096 | -0.684 | 22.379 | 1.00 36.50 | N |
| ATOM | 3203 | N | GLN | B | 499 | -0.885 | 5.011 | 20.559 | 1.00 24.02 | N |
| ATOM | 3204 | CA | GLN | B | 499 | -0.308 | 6.296 | 20.125 | 1.00 22.80 | C |
| ATOM | 3205 | C | GLN | B | 499 | 0.661 | 6.807 | 21.224 | 1.00 23.57 | C |
| ATOM | 3206 | O | GLN | B | 499 | 1.774 | 7.246 | 20.920 | 1.00 23.90 | O |
| ATOM | 3207 | CB | GLN | B | 499 | -1.341 | 7.409 | 19.895 | 1.00 27.44 | C |
| ATOM | 3208 | CG | GLN | B | 499 | -2.178 | 7.291 | 18.606 | 1.00 32.73 | C |
| ATOM | 3209 | CD | GLN | B | 499 | -3.283 | 8.331 | 18.529 | 1.00 37.67 | C |
| ATOM | 3210 | OE1 | GLN | B | 499 | -3.993 | 8.430 | 17.520 | 1.00 39.66 | O |
| ATOM | 3211 | NE2 | GLN | B | 499 | -3.543 | 9.159 | 19.560 | 1.00 31.52 | N |
| ATOM | 3212 | N | SER | B | 500 | 0.224 | 6.765 | 22.474 | 1.00 25.59 | N |
| ATOM | 3213 | CA | SER | B | 500 | 1.070 | 7.206 | 23.598 | 1.00 25.90 | C |
| ATOM | 3214 | C | SER | B | 500 | 2.331 | 6.356 | 23.682 | 1.00 25.66 | C |
| ATOM | 3215 | O | SER | B | 500 | 3.458 | 6.835 | 23.980 | 1.00 22.82 | O |
| ATOM | 3216 | CB | SER | B | 500 | 0.290 | 7.061 | 24.907 | 1.00 31.89 | C |
| ATOM | 3217 | OG | SER | B | 500 | -0.676 | 8.089 | 25.040 | 1.00 36.59 | O |
| ATOM | 3218 | N | MET | B | 501 | 2.167 | 5.048 | 23.514 | 1.00 25.69 | N |
| ATOM | 3219 | CA | MET | B | 501 | 3.318 | 4.143 | 23.623 | 1.00 29.93 | C |
| ATOM | 3220 | C | MET | B | 501 | 4.360 | 4.391 | 22.538 | 1.00 28.16 | C |
| ATOM | 3221 | O | MET | B | 501 | 5.594 | 4.357 | 22.766 | 1.00 23.35 | O |
| ATOM | 3222 | CB | MET | B | 501 | 2.839 | 2.679 | 23.583 | 1.00 34.14 | C |
| ATOM | 3223 | CG | MET | B | 501 | 3.352 | 1.858 | 24.760 | 1.00 51.81 | C |
| ATOM | 3224 | SD | MET | B | 501 | 2.295 | 1.977 | 26.203 | 1.00 55.56 | S |
| ATOM | 3225 | CE | MET | B | 501 | 2.301 | 3.688 | 26.660 | 1.00 59.00 | C |
| ATOM | 3226 | N | ARG | B | 502 | 3.870 | 4.712 | 21.323 | 1.00 24.75 | N |
| ATOM | 3227 | CA | ARG | B | 502 | 4.763 | 4.948 | 20.191 | 1.00 22.72 | C |

FIG. 2PP

| | | | | | | | | | | |
|---|---|---|---|---|---|---|---|---|---|---|
| ATOM | 3228 | C | ARG | B | 502 | 5.566 | 6.239 | 20.402 | 1.00 20.84 | C |
| ATOM | 3229 | O | ARG | B | 502 | 6.783 | 6.283 | 20.126 | 1.00 22.79 | O |
| ATOM | 3230 | CB | ARG | B | 502 | 3.997 | 5.060 | 18.844 | 1.00 21.16 | C |
| ATOM | 3231 | CG | ARG | B | 502 | 4.991 | 5.295 | 17.692 | 1.00 25.92 | C |
| ATOM | 3232 | CD | ARG | B | 502 | 4.395 | 5.049 | 16.313 | 1.00 28.95 | C |
| ATOM | 3233 | NE | ARG | B | 502 | 5.357 | 5.004 | 15.238 | 1.00 23.66 | N |
| ATOM | 3234 | CZ | ARG | B | 502 | 6.164 | 4.003 | 14.897 | 1.00 27.73 | C |
| ATOM | 3235 | NH1 | ARG | B | 502 | 6.991 | 4.154 | 13.877 | 1.00 22.39 | N |
| ATOM | 3236 | NH2 | ARG | B | 502 | 6.231 | 2.829 | 15.534 | 1.00 30.80 | N |
| ATOM | 3237 | N | LEU | B | 503 | 4.858 | 7.238 | 20.884 | 1.00 18.40 | N |
| ATOM | 3238 | CA | LEU | B | 503 | 5.532 | 8.520 | 21.205 | 1.00 21.85 | C |
| ATOM | 3239 | C | LEU | B | 503 | 6.613 | 8.261 | 22.230 | 1.00 19.31 | C |
| ATOM | 3240 | O | LEU | B | 503 | 7.741 | 8.712 | 22.132 | 1.00 19.95 | O |
| ATOM | 3241 | CB | LEU | B | 503 | 4.485 | 9.527 | 21.670 | 1.00 20.32 | C |
| ATOM | 3242 | CG | LEU | B | 503 | 5.030 | 10.914 | 22.094 | 1.00 20.86 | C |
| ATOM | 3243 | CD1 | LEU | B | 503 | 5.669 | 11.650 | 20.932 | 1.00 22.23 | C |
| ATOM | 3244 | CD2 | LEU | B | 503 | 3.879 | 11.683 | 22.701 | 1.00 22.73 | C |
| ATOM | 3245 | N | ALA | B | 504 | 6.243 | 7.577 | 23.330 | 1.00 20.43 | N |
| ATOM | 3246 | CA | ALA | B | 504 | 7.227 | 7.276 | 24.372 | 1.00 23.26 | C |
| ATOM | 3247 | C | ALA | B | 504 | 8.379 | 6.431 | 23.864 | 1.00 23.81 | C |
| ATOM | 3248 | O | ALA | B | 504 | 9.581 | 6.708 | 24.146 | 1.00 22.74 | O |
| ATOM | 3249 | CB | ALA | B | 504 | 6.533 | 6.501 | 25.488 | 1.00 23.86 | C |
| ATOM | 3250 | N | ASN | B | 505 | 8.159 | 5.398 | 23.039 | 1.00 21.61 | N |
| ATOM | 3251 | CA | ASN | B | 505 | 9.259 | 4.578 | 22.525 | 1.00 22.57 | C |
| ATOM | 3252 | C | ASN | B | 505 | 10.180 | 5.384 | 21.611 | 1.00 23.21 | C |
| ATOM | 3253 | O | ASN | B | 505 | 11.424 | 5.219 | 21.617 | 1.00 22.51 | O |
| ATOM | 3254 | CB | ASN | B | 505 | 8.675 | 3.365 | 21.765 | 1.00 26.72 | C |
| ATOM | 3255 | CG | ASN | B | 505 | 8.271 | 2.267 | 22.745 | 1.00 34.58 | C |
| ATOM | 3256 | OD1 | ASN | B | 505 | 8.957 | 1.971 | 23.718 | 1.00 40.44 | O |
| ATOM | 3257 | ND2 | ASN | B | 505 | 7.152 | 1.635 | 22.496 | 1.00 33.99 | N |
| ATOM | 3258 | N | LEU | B | 506 | 9.602 | 6.259 | 20.763 | 1.00 21.36 | N |
| ATOM | 3259 | CA | LEU | B | 506 | 10.482 | 7.053 | 19.905 | 1.00 22.31 | C |
| ATOM | 3260 | C | LEU | B | 506 | 11.320 | 8.013 | 20.744 | 1.00 24.19 | C |
| ATOM | 3261 | O | LEU | B | 506 | 12.515 | 8.189 | 20.538 | 1.00 23.77 | O |
| ATOM | 3262 | CB | LEU | B | 506 | 9.658 | 7.870 | 18.898 | 1.00 22.24 | C |
| ATOM | 3263 | CG | LEU | B | 506 | 8.871 | 7.129 | 17.827 | 1.00 29.50 | C |
| ATOM | 3264 | CD1 | LEU | B | 506 | 8.068 | 8.166 | 17.036 | 1.00 33.79 | C |
| ATOM | 3265 | CD2 | LEU | B | 506 | 9.791 | 6.332 | 16.912 | 1.00 33.24 | C |
| ATOM | 3266 | N | LEU | B | 507 | 10.696 | 8.705 | 21.701 | 1.00 21.63 | N |
| ATOM | 3267 | CA | LEU | B | 507 | 11.471 | 9.694 | 22.481 | 1.00 25.03 | C |
| ATOM | 3268 | C | LEU | B | 507 | 12.444 | 8.987 | 23.394 | 1.00 23.77 | C |
| ATOM | 3269 | O | LEU | B | 507 | 13.501 | 9.548 | 23.706 | 1.00 26.25 | O |
| ATOM | 3270 | CB | LEU | B | 507 | 10.515 | 10.633 | 23.232 | 1.00 27.26 | C |
| ATOM | 3271 | CG | LEU | B | 507 | 9.592 | 11.371 | 22.233 | 1.00 29.67 | C |
| ATOM | 3272 | CD1 | LEU | B | 507 | 8.764 | 12.382 | 22.956 | 1.00 29.27 | C |
| ATOM | 3273 | CD2 | LEU | B | 507 | 10.372 | 12.022 | 21.097 | 1.00 31.99 | C |
| ATOM | 3274 | N | MET | B | 508 | 12.112 | 7.773 | 23.844 | 1.00 20.83 | N |
| ATOM | 3275 | CA | MET | B | 508 | 13.132 | 7.080 | 24.650 | 1.00 23.78 | C |
| ATOM | 3276 | C | MET | B | 508 | 14.390 | 6.726 | 23.848 | 1.00 29.09 | C |
| ATOM | 3277 | O | MET | B | 508 | 15.492 | 6.803 | 24.405 | 1.00 28.80 | O |
| ATOM | 3278 | CB | MET | B | 508 | 12.571 | 5.805 | 25.289 | 1.00 26.91 | C |
| ATOM | 3279 | CG | MET | B | 508 | 11.841 | 6.133 | 26.601 | 1.00 30.84 | C |
| ATOM | 3280 | SD | MET | B | 508 | 11.468 | 4.560 | 27.450 | 1.00 29.95 | S |
| ATOM | 3281 | CE | MET | B | 508 | 10.343 | 3.845 | 26.243 | 1.00 29.84 | C |
| ATOM | 3282 | N | LEU | B | 509 | 14.305 | 6.477 | 22.553 | 1.00 27.99 | N |
| ATOM | 3283 | CA | LEU | B | 509 | 15.424 | 6.228 | 21.679 | 1.00 29.96 | C |
| ATOM | 3284 | C | LEU | B | 509 | 16.285 | 7.458 | 21.470 | 1.00 30.52 | C |
| ATOM | 3285 | O | LEU | B | 509 | 17.483 | 7.306 | 21.166 | 1.00 27.74 | O |
| ATOM | 3286 | CB | LEU | B | 509 | 14.974 | 5.669 | 20.307 | 1.00 32.48 | C |
| ATOM | 3287 | CG | LEU | B | 509 | 14.638 | 4.173 | 20.309 | 1.00 33.77 | C |
| ATOM | 3288 | CD1 | LEU | B | 509 | 14.129 | 3.823 | 18.931 | 1.00 34.29 | C |
| ATOM | 3289 | CD2 | LEU | B | 509 | 15.854 | 3.403 | 20.830 | 1.00 37.61 | C |
| ATOM | 3290 | N | LEU | B | 510 | 15.836 | 8.680 | 21.726 | 1.00 26.40 | N |
| ATOM | 3291 | CA | LEU | B | 510 | 16.544 | 9.917 | 21.631 | 1.00 29.83 | C |
| ATOM | 3292 | C | LEU | B | 510 | 17.718 | 9.962 | 22.640 | 1.00 27.70 | C |
| ATOM | 3293 | O | LEU | B | 510 | 18.780 | 10.574 | 22.463 | 1.00 25.15 | O |
| ATOM | 3294 | CB | LEU | B | 510 | 15.679 | 11.127 | 21.928 | 1.00 37.31 | C |
| ATOM | 3295 | CG | LEU | B | 510 | 14.737 | 11.758 | 20.914 | 1.00 43.51 | C |
| ATOM | 3296 | CD1 | LEU | B | 510 | 13.671 | 12.521 | 21.714 | 1.00 47.22 | C |
| ATOM | 3297 | CD2 | LEU | B | 510 | 15.336 | 12.812 | 20.015 | 1.00 39.00 | C |
| ATOM | 3298 | N | SER | B | 511 | 17.483 | 9.251 | 23.788 | 1.00 25.53 | N |
| ATOM | 3299 | CA | SER | B | 511 | 18.540 | 9.158 | 24.767 | 1.00 22.45 | C |
| ATOM | 3300 | C | SER | B | 511 | 19.689 | 8.297 | 24.204 | 1.00 16.69 | C |
| ATOM | 3301 | O | SER | B | 511 | 20.855 | 8.465 | 24.528 | 1.00 21.23 | O |
| ATOM | 3302 | CB | SER | B | 511 | 18.121 | 8.283 | 25.975 | 1.00 25.55 | C |
| ATOM | 3303 | OG | SER | B | 511 | 19.264 | 8.432 | 26.827 | 1.00 37.78 | O |
| ATOM | 3304 | N | HIS | B | 512 | 19.300 | 7.293 | 23.385 | 1.00 18.67 | N |

FIG. 2QQ

```
ATOM  3305  CA   HIS B 512    20.289   6.421  22.761  1.00 20.94           C
ATOM  3306  C    HIS B 512    21.052   7.157  21.630  1.00 24.96           C
ATOM  3307  O    HIS B 512    22.260   6.952  21.469  1.00 17.72           O
ATOM  3308  CB   HIS B 512    19.656   5.159  22.182  1.00 21.42           C
ATOM  3309  CG   HIS B 512    18.936   4.371  23.266  1.00 26.29           C
ATOM  3310  ND1  HIS B 512    19.329   3.065  23.351  1.00 36.40           N
ATOM  3311  CD2  HIS B 512    17.948   4.525  24.167  1.00 31.77           C
ATOM  3312  CE1  HIS B 512    18.647   2.497  24.304  1.00 33.28           C
ATOM  3313  NE2  HIS B 512    17.777   3.303  24.816  1.00 28.54           N
ATOM  3314  N    VAL B 513    20.370   8.113  20.952  1.00 22.54           N
ATOM  3315  CA   VAL B 513    21.080   8.894  19.944  1.00 23.43           C
ATOM  3316  C    VAL B 513    22.010   9.865  20.659  1.00 25.90           C
ATOM  3317  O    VAL B 513    23.177  10.063  20.292  1.00 19.83           O
ATOM  3318  CB   VAL B 513    20.108   9.616  18.990  1.00 23.47           C
ATOM  3319  CG1  VAL B 513    20.981  10.300  17.923  1.00 24.99           C
ATOM  3320  CG2  VAL B 513    19.093   8.646  18.398  1.00 22.87           C
ATOM  3321  N    ARG B 514    21.601  10.431  21.820  1.00 20.20           N
ATOM  3322  CA   ARG B 514    22.454  11.311  22.586  1.00 19.38           C
ATOM  3323  C    ARG B 514    23.722  10.555  23.082  1.00 20.72           C
ATOM  3324  O    ARG B 514    24.780  11.111  23.070  1.00 19.22           O
ATOM  3325  CB   ARG B 514    21.775  11.826  23.891  1.00 20.64           C
ATOM  3326  CG   ARG B 514    22.723  12.689  24.724  1.00 25.83           C
ATOM  3327  CD   ARG B 514    23.204  13.947  24.011  1.00 35.37           C
ATOM  3328  NE   ARG B 514    22.455  15.060  24.415  1.00 43.69           N
ATOM  3329  CZ   ARG B 514    21.394  15.577  24.923  1.00 51.47           C
ATOM  3330  NH1  ARG B 514    20.304  15.017  25.392  1.00 60.27           N
ATOM  3331  NH2  ARG B 514    21.323  16.891  25.016  1.00 57.39           N
ATOM  3332  N    HIS B 515    23.484   9.350  23.563  1.00 17.72           N
ATOM  3333  CA   HIS B 515    24.641   8.527  24.041  1.00 19.41           C
ATOM  3334  C    HIS B 515    25.609   8.235  22.923  1.00 17.42           C
ATOM  3335  O    HIS B 515    26.833   8.352  23.105  1.00 18.81           O
ATOM  3336  CB   HIS B 515    23.964   7.245  24.547  1.00 19.53           C
ATOM  3337  CG   HIS B 515    24.967   6.484  25.347  1.00 24.48           C
ATOM  3338  ND1  HIS B 515    25.814   5.598  24.711  1.00 39.46           N
ATOM  3339  CD2  HIS B 515    25.237   6.457  26.665  1.00 28.08           C
ATOM  3340  CE1  HIS B 515    26.596   5.036  25.611  1.00 33.92           C
ATOM  3341  NE2  HIS B 515    26.258   5.525  26.792  1.00 34.27           N
ATOM  3342  N    ALA B 516    25.130   7.970  21.699  1.00 19.19           N
ATOM  3343  CA   ALA B 516    26.082   7.720  20.593  1.00 15.11           C
ATOM  3344  C    ALA B 516    26.867   8.947  20.257  1.00 16.34           C
ATOM  3345  O    ALA B 516    28.068   8.937  19.968  1.00 17.56           O
ATOM  3346  CB   ALA B 516    25.327   7.177  19.359  1.00 17.83           C
ATOM  3347  N    SER B 517    26.166  10.096  20.266  1.00 15.85           N
ATOM  3348  CA   SER B 517    26.891  11.347  19.977  1.00 15.27           C
ATOM  3349  C    SER B 517    27.920  11.649  21.051  1.00 18.02           C
ATOM  3350  O    SER B 517    29.050  12.088  20.754  1.00 17.13           O
ATOM  3351  CB   SER B 517    25.838  12.475  19.866  1.00 18.28           C
ATOM  3352  OG   SER B 517    25.189  12.747  21.054  1.00 29.75           O
ATOM  3353  N    ASN B 518    27.604  11.369  22.326  1.00 14.32           N
ATOM  3354  CA   ASN B 518    28.587  11.664  23.377  1.00 14.12           C
ATOM  3355  C    ASN B 518    29.805  10.730  23.197  1.00 15.89           C
ATOM  3356  O    ASN B 518    30.927  11.214  23.310  1.00 18.55           O
ATOM  3357  CB   ASN B 518    27.901  11.353  24.713  1.00 18.47           C
ATOM  3358  CG   ASN B 518    26.965  12.556  25.079  1.00 23.21           C
ATOM  3359  OD1  ASN B 518    27.007  13.650  24.599  1.00 33.02           O
ATOM  3360  ND2  ASN B 518    26.100  12.019  25.959  1.00 24.38           N
ATOM  3361  N    LYS B 519    29.461   9.465  22.896  1.00 16.87           N
ATOM  3362  CA   LYS B 519    30.631   8.547  22.734  1.00 20.10           C
ATOM  3363  C    LYS B 519    31.444   8.876  21.488  1.00 23.76           C
ATOM  3364  O    LYS B 519    32.691   8.723  21.474  1.00 16.66           O
ATOM  3365  CB   LYS B 519    30.172   7.094  22.727  1.00 18.89           C
ATOM  3366  CG   LYS B 519    29.394   6.586  23.923  1.00 31.80           C
ATOM  3367  CD   LYS B 519    29.724   7.102  25.286  1.00 43.98           C
ATOM  3368  CE   LYS B 519    31.035   6.723  25.916  1.00 48.07           C
ATOM  3369  NZ   LYS B 519    31.007   5.403  26.621  1.00 54.91           N
ATOM  3370  N    GLY B 520    30.769   9.348  20.435  1.00 19.42           N
ATOM  3371  CA   GLY B 520    31.438   9.749  19.198  1.00 18.51           C
ATOM  3372  C    GLY B 520    32.290  10.965  19.436  1.00 19.23           C
ATOM  3373  O    GLY B 520    33.426  11.046  18.973  1.00 18.96           O
ATOM  3374  N    MET B 521    31.831  11.961  20.208  1.00 16.60           N
ATOM  3375  CA   MET B 521    32.612  13.162  20.468  1.00 19.17           C
ATOM  3376  C    MET B 521    33.820  12.807  21.339  1.00 21.93           C
ATOM  3377  O    MET B 521    34.905  13.329  21.135  1.00 20.60           O
ATOM  3378  CB   MET B 521    31.747  14.198  21.220  1.00 21.74           C
ATOM  3379  CG   MET B 521    30.607  14.758  20.381  1.00 24.15           C
ATOM  3380  SD   MET B 521    31.265  15.823  19.049  1.00 26.04           S
ATOM  3381  CE   MET B 521    31.488  17.298  20.088  1.00 30.44           C
```

FIG. 2RR

```
ATOM   3382  N   GLU B 522      33.647  11.869  22.282  1.00 20.10           N
ATOM   3383  CA  GLU B 522      34.776  11.484  23.122  1.00 25.43           C
ATOM   3384  C   GLU B 522      35.885  10.863  22.260  1.00 26.45           C
ATOM   3385  O   GLU B 522      37.086  11.164  22.437  1.00 23.05           O
ATOM   3386  CB  GLU B 522      34.254  10.423  24.133  1.00 21.69           C
ATOM   3387  CG  GLU B 522      35.334  10.077  25.124  1.00 27.73           C
ATOM   3388  CD  GLU B 522      34.913   8.927  26.032  1.00 31.13           C
ATOM   3389  OE1 GLU B 522      33.872   8.299  25.821  1.00 29.63           O
ATOM   3390  OE2 GLU B 522      35.746   8.841  26.946  1.00 33.77           O
ATOM   3391  N   HIS B 523      35.416  10.025  21.357  1.00 20.32           N
ATOM   3392  CA  HIS B 523      36.313   9.360  20.391  1.00 20.93           C
ATOM   3393  C   HIS B 523      37.012  10.365  19.521  1.00 25.39           C
ATOM   3394  O   HIS B 523      38.227  10.290  19.395  1.00 23.10           O
ATOM   3395  CB  HIS B 523      35.544   8.328  19.575  1.00 23.46           C
ATOM   3396  CG  HIS B 523      36.478   7.584  18.642  1.00 25.84           C
ATOM   3397  ND1 HIS B 523      36.666   7.948  17.345  1.00 23.87           N
ATOM   3398  CD2 HIS B 523      37.273   6.518  18.889  1.00 29.69           C
ATOM   3399  CE1 HIS B 523      37.550   7.123  16.797  1.00 27.36           C
ATOM   3400  NE2 HIS B 523      37.934   6.238  17.708  1.00 27.67           N
ATOM   3401  N   LEU B 524      36.308  11.326  18.905  1.00 20.50           N
ATOM   3402  CA  LEU B 524      36.973  12.338  18.097  1.00 23.83           C
ATOM   3403  C   LEU B 524      37.994  13.140  18.887  1.00 25.77           C
ATOM   3404  O   LEU B 524      39.106  13.454  18.446  1.00 21.50           O
ATOM   3405  CB  LEU B 524      35.862  13.210  17.539  1.00 21.52           C
ATOM   3406  CG  LEU B 524      36.271  14.466  16.765  1.00 24.32           C
ATOM   3407  CD1 LEU B 524      37.110  14.051  15.556  1.00 19.83           C
ATOM   3408  CD2 LEU B 524      34.958  15.143  16.323  1.00 20.24           C
ATOM   3409  N   LEU B 525      37.635  13.523  20.113  1.00 20.25           N
ATOM   3410  CA  LEU B 525      38.625  14.289  20.896  1.00 25.69           C
ATOM   3411  C   LEU B 525      39.888  13.413  21.066  1.00 24.56           C
ATOM   3412  O   LEU B 525      41.035  13.864  20.924  1.00 25.34           O
ATOM   3413  CB  LEU B 525      38.020  14.641  22.256  1.00 23.20           C
ATOM   3414  CG  LEU B 525      38.942  15.434  23.191  1.00 25.59           C
ATOM   3415  CD1 LEU B 525      39.578  16.654  22.575  1.00 28.37           C
ATOM   3416  CD2 LEU B 525      38.141  15.921  24.409  1.00 33.64           C
ATOM   3417  N   ASN B 526      39.695  12.170  21.401  1.00 23.55           N
ATOM   3418  CA  ASN B 526      40.832  11.236  21.523  1.00 28.62           C
ATOM   3419  C   ASN B 526      41.638  11.161  20.235  1.00 29.46           C
ATOM   3420  O   ASN B 526      42.886  11.140  20.265  1.00 24.90           O
ATOM   3421  CB  ASN B 526      40.331   9.881  21.996  1.00 28.03           C
ATOM   3422  CG  ASN B 526      39.994   9.832  23.482  1.00 35.41           C
ATOM   3423  OD1 ASN B 526      40.551  10.585  24.281  1.00 33.77           O
ATOM   3424  ND2 ASN B 526      39.088   8.933  23.839  1.00 34.04           N
ATOM   3425  N   MET B 527      41.015  11.198  19.057  1.00 24.95           N
ATOM   3426  CA  MET B 527      41.708  11.174  17.769  1.00 25.60           C
ATOM   3427  C   MET B 527      42.488  12.460  17.537  1.00 26.85           C
ATOM   3428  O   MET B 527      43.626  12.425  17.038  1.00 29.13           O
ATOM   3429  CB  MET B 527      40.715  10.916  16.641  1.00 28.30           C
ATOM   3430  CG  MET B 527      40.079   9.529  16.527  1.00 22.52           C
ATOM   3431  SD  MET B 527      41.342   8.219  16.443  1.00 30.70           S
ATOM   3432  CE  MET B 527      41.422   7.830  18.188  1.00 31.91           C
ATOM   3433  N   LYS B 528      41.987  13.595  17.971  1.00 23.43           N
ATOM   3434  CA  LYS B 528      42.705  14.868  17.880  1.00 26.38           C
ATOM   3435  C   LYS B 528      43.913  14.849  18.816  1.00 31.70           C
ATOM   3436  O   LYS B 528      45.026  15.174  18.370  1.00 29.21           O
ATOM   3437  CB  LYS B 528      41.779  16.009  18.234  1.00 29.86           C
ATOM   3438  CG  LYS B 528      42.336  17.413  18.172  1.00 29.01           C
ATOM   3439  CD  LYS B 528      43.113  17.831  19.415  1.00 36.75           C
ATOM   3440  CE  LYS B 528      43.464  19.315  19.289  1.00 41.62           C
ATOM   3441  NZ  LYS B 528      43.763  19.878  20.650  1.00 47.99           N
ATOM   3442  N   CYS B 529      43.742  14.397  20.035  1.00 27.02           N
ATOM   3443  CA  CYS B 529      44.798  14.307  21.042  1.00 28.86           C
ATOM   3444  C   CYS B 529      45.901  13.362  20.645  1.00 30.53           C
ATOM   3445  O   CYS B 529      47.047  13.594  21.040  1.00 32.58           O
ATOM   3446  CB  CYS B 529      44.201  13.981  22.433  1.00 35.32           C
ATOM   3447  SG  CYS B 529      43.338  15.486  23.003  1.00 38.75           S
ATOM   3448  N   LYS B 530      45.614  12.388  19.802  1.00 28.29           N
ATOM   3449  CA  LYS B 530      46.511  11.398  19.246  1.00 31.42           C
ATOM   3450  C   LYS B 530      47.140  11.887  17.944  1.00 27.27           C
ATOM   3451  O   LYS B 530      47.942  11.204  17.314  1.00 31.67           O
ATOM   3452  CB  LYS B 530      45.654  10.141  18.988  1.00 33.17           C
ATOM   3453  CG  LYS B 530      46.422   8.905  18.632  1.00 41.59           C
ATOM   3454  CD  LYS B 530      45.471   7.761  18.253  1.00 29.36           C
ATOM   3455  CE  LYS B 530      46.310   6.765  17.488  1.00 35.55           C
ATOM   3456  NZ  LYS B 530      45.789   5.391  17.518  1.00 35.31           N
ATOM   3457  N   ASN B 531      46.811  13.118  17.528  1.00 25.91           N
ATOM   3458  CA  ASN B 531      47.347  13.713  16.304  1.00 30.46           C
```

FIG. 2SS

```
ATOM   3459  C    ASN B 531      46.902  13.034  15.022  1.00 31.27           C
ATOM   3460  O    ASN B 531      47.585  13.155  13.991  1.00 28.41           O
ATOM   3461  CB   ASN B 531      48.889  13.793  16.383  1.00 30.45           C
ATOM   3462  CG   ASN B 531      49.304  14.743  17.504  1.00 39.58           C
ATOM   3463  OD1  ASN B 531      49.678  14.366  18.623  1.00 36.05           O
ATOM   3464  ND2  ASN B 531      49.187  16.044  17.258  1.00 35.04           N
ATOM   3465  N    VAL B 532      45.734  12.377  15.020  1.00 28.01           N
ATOM   3466  CA   VAL B 532      45.186  11.714  13.840  1.00 29.98           C
ATOM   3467  C    VAL B 532      44.368  12.687  13.009  1.00 30.41           C
ATOM   3468  O    VAL B 532      44.263  12.574  11.785  1.00 28.60           O
ATOM   3469  CB   VAL B 532      44.390  10.454  14.257  1.00 29.00           C
ATOM   3470  CG1  VAL B 532      43.649   9.804  13.088  1.00 28.46           C
ATOM   3471  CG2  VAL B 532      45.415   9.473  14.831  1.00 30.80           C
ATOM   3472  N    VAL B 533      43.672  13.600  13.685  1.00 25.44           N
ATOM   3473  CA   VAL B 533      42.933  14.676  13.079  1.00 27.02           C
ATOM   3474  C    VAL B 533      43.376  15.979  13.765  1.00 25.40           C
ATOM   3475  O    VAL B 533      43.700  16.066  14.956  1.00 29.36           O
ATOM   3476  CB   VAL B 533      41.397  14.535  13.241  1.00 24.66           C
ATOM   3477  CG1  VAL B 533      40.874  13.320  12.485  1.00 26.45           C
ATOM   3478  CG2  VAL B 533      41.011  14.527  14.699  1.00 23.82           C
ATOM   3479  N    PRO B 534      43.251  17.087  13.047  1.00 27.85           N
ATOM   3480  CA   PRO B 534      43.681  18.366  13.555  1.00 32.15           C
ATOM   3481  C    PRO B 534      42.778  19.000  14.583  1.00 30.18           C
ATOM   3482  O    PRO B 534      43.262  19.800  15.358  1.00 30.62           O
ATOM   3483  CB   PRO B 534      43.653  19.283  12.316  1.00 32.15           C
ATOM   3484  CG   PRO B 534      42.778  18.627  11.320  1.00 29.14           C
ATOM   3485  CD   PRO B 534      42.893  17.136  11.607  1.00 29.21           C
ATOM   3486  N    VAL B 535      41.445  18.825  14.472  1.00 28.17           N
ATOM   3487  CA   VAL B 535      40.597  19.521  15.441  1.00 32.07           C
ATOM   3488  C    VAL B 535      39.468  18.630  15.932  1.00 30.10           C
ATOM   3489  O    VAL B 535      39.126  17.651  15.295  1.00 26.97           O
ATOM   3490  CB   VAL B 535      39.999  20.809  14.832  1.00 34.84           C
ATOM   3491  CG1  VAL B 535      41.032  21.890  14.529  1.00 36.98           C
ATOM   3492  CG2  VAL B 535      39.255  20.409  13.572  1.00 31.81           C
ATOM   3493  N    TYR B 536      38.831  19.062  17.003  1.00 30.00           N
ATOM   3494  CA   TYR B 536      37.724  18.337  17.616  1.00 28.84           C
ATOM   3495  C    TYR B 536      36.376  18.981  17.329  1.00 29.31           C
ATOM   3496  O    TYR B 536      35.403  18.246  17.047  1.00 27.74           O
ATOM   3497  CB   TYR B 536      38.008  18.489  19.142  1.00 34.32           C
ATOM   3498  CG   TYR B 536      36.918  18.169  20.108  1.00 35.17           C
ATOM   3499  CD1  TYR B 536      36.298  16.928  20.114  1.00 37.04           C
ATOM   3500  CD2  TYR B 536      36.522  19.088  21.077  1.00 36.24           C
ATOM   3501  CE1  TYR B 536      35.305  16.590  21.015  1.00 35.06           C
ATOM   3502  CE2  TYR B 536      35.542  18.775  22.004  1.00 38.43           C
ATOM   3503  CZ   TYR B 536      34.948  17.524  21.970  1.00 42.22           C
ATOM   3504  OH   TYR B 536      33.966  17.244  22.897  1.00 43.09           O
ATOM   3505  N    ASP B 537      36.287  20.310  17.501  1.00 27.59           N
ATOM   3506  CA   ASP B 537      35.014  20.990  17.261  1.00 26.75           C
ATOM   3507  C    ASP B 537      34.844  21.251  15.770  1.00 21.54           C
ATOM   3508  O    ASP B 537      35.245  22.251  15.172  1.00 25.75           O
ATOM   3509  CB   ASP B 537      34.935  22.260  18.124  1.00 34.07           C
ATOM   3510  CG   ASP B 537      33.646  23.015  17.986  1.00 37.10           C
ATOM   3511  OD1  ASP B 537      32.819  22.699  17.100  1.00 31.06           O
ATOM   3512  OD2  ASP B 537      33.377  23.965  18.764  1.00 41.65           O
ATOM   3513  N    LEU B 538      34.176  20.290  15.097  1.00 21.88           N
ATOM   3514  CA   LEU B 538      33.969  20.358  13.658  1.00 19.71           C
ATOM   3515  C    LEU B 538      33.040  21.491  13.255  1.00 22.91           C
ATOM   3516  O    LEU B 538      33.160  21.957  12.131  1.00 24.45           O
ATOM   3517  CB   LEU B 538      33.492  19.001  13.110  1.00 18.93           C
ATOM   3518  CG   LEU B 538      34.418  17.824  13.459  1.00 22.91           C
ATOM   3519  CD1  LEU B 538      33.920  16.505  12.794  1.00 20.69           C
ATOM   3520  CD2  LEU B 538      35.853  18.061  13.025  1.00 22.04           C
ATOM   3521  N    LEU B 539      32.091  21.876  14.108  1.00 22.95           N
ATOM   3522  CA   LEU B 539      31.189  22.953  13.701  1.00 21.70           C
ATOM   3523  C    LEU B 539      32.004  24.268  13.686  1.00 22.79           C
ATOM   3524  O    LEU B 539      31.823  24.990  12.726  1.00 22.25           O
ATOM   3525  CB   LEU B 539      30.050  23.045  14.708  1.00 21.40           C
ATOM   3526  CG   LEU B 539      29.106  24.243  14.530  1.00 23.23           C
ATOM   3527  CD1  LEU B 539      28.381  24.140  13.201  1.00 24.06           C
ATOM   3528  CD2  LEU B 539      28.166  24.276  15.738  1.00 26.44           C
ATOM   3529  N    LEU B 540      32.864  24.462  14.686  1.00 23.27           N
ATOM   3530  CA   LEU B 540      33.708  25.685  14.634  1.00 28.70           C
ATOM   3531  C    LEU B 540      34.663  25.717  13.455  1.00 28.37           C
ATOM   3532  O    LEU B 540      34.834  26.678  12.696  1.00 27.01           O
ATOM   3533  CB   LEU B 540      34.507  25.810  15.930  1.00 32.27           C
ATOM   3534  CG   LEU B 540      35.516  26.965  16.014  1.00 34.48           C
ATOM   3535  CD1  LEU B 540      34.820  28.314  16.024  1.00 36.62           C
```

FIG. 2TT

```
ATOM   3536  CD2 LEU B 540      36.392  26.787  17.238  1.00 33.58           C
ATOM   3537  N   GLU B 541      35.261  24.554  13.163  1.00 25.90           N
ATOM   3538  CA  GLU B 541      36.110  24.377  12.007  1.00 28.83           C
ATOM   3539  C   GLU B 541      35.353  24.677  10.716  1.00 26.71           C
ATOM   3540  O   GLU B 541      35.907  25.264   9.780  1.00 27.58           O
ATOM   3541  CB  GLU B 541      36.668  22.954  11.942  1.00 31.67           C
ATOM   3542  CG  GLU B 541      37.586  22.755  10.739  1.00 37.81           C
ATOM   3543  CD  GLU B 541      38.822  23.628  10.726  1.00 42.72           C
ATOM   3544  OE1 GLU B 541      39.328  24.080  11.773  1.00 41.96           O
ATOM   3545  OE2 GLU B 541      39.364  23.882   9.619  1.00 49.77           O
ATOM   3546  N   MET B 542      34.101  24.215  10.582  1.00 21.11           N
ATOM   3547  CA  MET B 542      33.361  24.549   9.369  1.00 21.46           C
ATOM   3548  C   MET B 542      33.144  26.074   9.333  1.00 22.23           C
ATOM   3549  O   MET B 542      33.300  26.628   8.239  1.00 25.20           O
ATOM   3550  CB  MET B 542      32.003  23.847   9.390  1.00 21.82           C
ATOM   3551  CG  MET B 542      31.146  23.993   8.154  1.00 27.74           C
ATOM   3552  SD  MET B 542      30.138  25.489   8.182  1.00 24.48           S
ATOM   3553  CE  MET B 542      29.030  25.202   9.538  1.00 23.74           C
ATOM   3554  N   LEU B 543      32.654  26.637  10.427  1.00 25.07           N
ATOM   3555  CA  LEU B 543      32.384  28.096  10.400  1.00 32.44           C
ATOM   3556  C   LEU B 543      33.648  28.931  10.186  1.00 32.47           C
ATOM   3557  O   LEU B 543      33.626  29.919   9.434  1.00 39.36           O
ATOM   3558  CB  LEU B 543      31.756  28.506  11.736  1.00 28.21           C
ATOM   3559  CG  LEU B 543      30.295  28.017  11.868  1.00 27.82           C
ATOM   3560  CD1 LEU B 543      29.856  28.264  13.307  1.00 30.68           C
ATOM   3561  CD2 LEU B 543      29.426  28.759  10.866  1.00 30.79           C
ATOM   3562  N   ASN B 544      34.734  28.558  10.811  1.00 33.87           N
ATOM   3563  CA  ASN B 544      36.008  29.257  10.626  1.00 39.63           C
ATOM   3564  C   ASN B 544      36.436  29.221   9.162  1.00 41.53           C
ATOM   3565  O   ASN B 544      36.977  30.193   8.636  1.00 42.20           O
ATOM   3566  CB  ASN B 544      37.102  28.607  11.477  1.00 36.92           C
ATOM   3567  CG  ASN B 544      37.112  28.924  12.951  1.00 39.12           C
ATOM   3568  OD1 ASN B 544      37.757  28.217  13.756  1.00 37.46           O
ATOM   3569  ND2 ASN B 544      36.493  29.972  13.428  1.00 29.53           N
ATOM   3570  N   ALA B 545      36.256  28.101   8.473  1.00 40.06           N
ATOM   3571  CA  ALA B 545      36.666  27.896   7.108  1.00 39.33           C
ATOM   3572  C   ALA B 545      35.732  28.432   6.039  1.00 39.87           C
ATOM   3573  O   ALA B 545      36.193  28.906   4.998  1.00 40.21           O
ATOM   3574  CB  ALA B 545      36.819  26.376   6.841  1.00 33.40           C
ATOM.  3575  N   HIS B 546      34.431  28.411   6.293  1.00 36.60           N
ATOM   3576  CA  HIS B 546      33.480  28.821   5.244  1.00 38.90           C
ATOM   3577  C   HIS B 546      33.205  30.297   5.338  1.00 39.14           C
ATOM   3578  O   HIS B 546      33.394  30.906   6.385  1.00 43.73           O
ATOM   3579  CB  HIS B 546      32.268  27.883   5.289  1.00 37.08           C
ATOM   3580  CG  HIS B 546      32.547  26.471   4.852  1.00 36.68           C
ATOM   3581  ND1 HIS B 546      32.182  25.966   3.629  1.00 36.35           N
ATOM   3582  CD2 HIS B 546      33.186  25.442   5.473  1.00 40.79           C
ATOM   3583  CE1 HIS B 546      32.561  24.716   3.497  1.00 35.39           C
ATOM   3584  NE2 HIS B 546      33.165  24.361   4.640  1.00 38.95           N
ATOM   3585  N   VAL B 547      33.003  30.981   4.208  1.00 42.53           N
ATOM   3586  CA  VAL B 547      32.780  32.419   4.181  1.00 40.61           C
ATOM   3587  C   VAL B 547      31.349  32.788   3.798  1.00 39.74           C
ATOM   3588  O   VAL B 547      30.740  32.127   2.957  1.00 46.40           O
ATOM   3589  CB  VAL B 547      33.726  33.076   3.154  1.00 42.18           C
ATOM   3590  CG1 VAL B 547      33.616  32.422   1.780  1.00 41.34           C
ATOM   3591  CG2 VAL B 547      33.495  34.575   3.040  1.00 43.99           C
ATOM   3592  N   LEU B 548      30.827  33.854   4.375  1.00 43.11           N
ATOM   3593  CA  LEU B 548      29.489  34.369   4.090  1.00 43.63           C
ATOM   3594  C   LEU B 548      29.417  34.918   2.660  1.00 48.73           C
ATOM   3595  O   LEU B 548      30.417  35.117   1.969  1.00 47.22           O
ATOM   3596  CB  LEU B 548      29.044  35.433   5.094  1.00 42.47           C
ATOM   3597  CG  LEU B 548      28.696  34.945   6.515  1.00 42.36           C
ATOM   3598  CD1 LEU B 548      28.361  36.107   7.435  1.00 39.25           C
ATOM   3599  CD2 LEU B 548      27.522  33.977   6.526  1.00 37.00           C
ATOM   3600  N   ALA B 549      28.184  35.165   2.229  1.00 53.29           N
ATOM   3601  CA  ALA B 549      27.801  35.658   0.924  1.00 57.20           C
ATOM   3602  C   ALA B 549      27.755  37.172   0.789  1.00 58.59           C
ATOM   3603  O   ALA B 549      27.504  37.897   1.766  1.00 60.47           O
ATOM   3604  CB  ALA B 549      26.397  35.104   0.615  1.00 58.47           C
ATOM   3605  C1  GEN C 601      32.490  11.892  39.227  1.00 23.90           C
ATOM   3606  C2  GEN C 601      32.091  10.767  39.973  1.00 23.88           C
ATOM   3607  C3  GEN C 601      30.791  10.807  40.540  1.00 21.97           C
ATOM   3608  C4  GEN C 601      29.974  11.941  40.273  1.00 20.22           C
ATOM   3609  C5  GEN C 601      30.407  13.070  39.515  1.00 22.71           C
ATOM   3610  C6  GEN C 601      31.687  13.016  38.980  1.00 24.29           C
ATOM   3611  O9  GEN C 601      30.434   9.701  41.275  1.00 23.58           O
ATOM   3612  C10 GEN C 601      29.135   9.720  41.824  1.00 20.60           C
```

FIG. 2UU

```
ATOM  3613  C11  GEN C 601    28.291  10.807  41.674  1.00 18.73           C
ATOM  3614  C12  GEN C 601    28.643  12.006  40.859  1.00 18.14           C
ATOM  3615  C14  GEN C 601    26.934  10.633  42.366  1.00 23.96           C
ATOM  3616  C15  GEN C 601    26.998  10.018  43.636  1.00 19.90           C
ATOM  3617  C16  GEN C 601    25.776   9.792  44.345  1.00 20.07           C
ATOM  3618  C17  GEN C 601    24.614  10.226  43.655  1.00 20.86           C
ATOM  3619  C18  GEN C 601    24.573  10.850  42.417  1.00 18.28           C
ATOM  3620  C19  GEN C 601    25.767  11.099  41.719  1.00 16.50           C
ATOM  3621  O24  GEN C 601    23.370  10.045  44.278  1.00 19.59           O
ATOM  3622  O25  GEN C 601    29.585  14.156  39.335  1.00 21.98           O
ATOM  3623  O26  GEN C 601    33.774  11.844  38.689  1.00 20.60           O
ATOM  3624  O27  GEN C 601    27.876  12.939  40.682  1.00 19.82           O
ATOM  3625  C1   GEN D 601    34.731  10.000  15.313  1.00 20.77           C
ATOM  3626  C2   GEN D 601    34.440  11.148  14.517  1.00 20.53           C
ATOM  3627  C3   GEN D 601    33.256  11.061  13.736  1.00 22.18           C
ATOM  3628  C4   GEN D 601    32.411   9.951  13.824  1.00 17.57           C
ATOM  3629  C5   GEN D 601    32.748   8.810  14.669  1.00 20.54           C
ATOM  3630  C6   GEN D 601    33.914   8.885  15.399  1.00 18.54           C
ATOM  3631  O9   GEN D 601    32.964  12.148  12.954  1.00 21.72           O
ATOM  3632  C10  GEN D 601    31.785  12.156  12.179  1.00 21.94           C
ATOM  3633  C11  GEN D 601    30.924  11.060  12.149  1.00 18.11           C
ATOM  3634  C12  GEN D 601    31.189   9.872  13.066  1.00 21.61           C
ATOM  3635  C14  GEN D 601    29.691  11.207  11.272  1.00 17.89           C
ATOM  3636  C15  GEN D 601    29.976  11.887  10.015  1.00 17.97           C
ATOM  3637  C16  GEN D 601    28.831  12.058   9.180  1.00 19.03           C
ATOM  3638  C17  GEN D 601    27.595  11.594   9.607  1.00 19.16           C
ATOM  3639  C18  GEN D 601    27.347  10.930  10.842  1.00 18.76           C
ATOM  3640  C19  GEN D 601    28.475  10.743  11.680  1.00 18.44           C
ATOM  3641  O24  GEN D 601    26.486  11.807   8.806  1.00 19.69           O
ATOM  3642  O25  GEN D 601    31.896   7.770  14.659  1.00 23.07           O
ATOM  3643  O26  GEN D 601    35.877  10.078  16.050  1.00 21.64           O
ATOM  3644  O27  GEN D 601    30.419   8.942  13.063  1.00 21.28           O
ATOM  3645  OW0  WAT W    1   20.594   8.842  43.843  1.00 18.37           O
ATOM  3646  OW0  WAT W    2   14.063  18.381   7.933  1.00 21.34           O
ATOM  3647  OW0  WAT W    3   34.441  20.788   9.936  1.00 22.98           O
ATOM  3648  OW0  WAT W    4   23.692  13.028   8.639  1.00 21.23           O
ATOM  3649  OW0  WAT W    5   19.222  22.147  42.611  1.00 23.71           O
ATOM  3650  OW0  WAT W    6   11.448   4.004  40.415  1.00 23.15           O
ATOM  3651  OW0  WAT W    7   23.203  15.680   5.742  1.00 23.89           O
ATOM  3652  OW0  WAT W    8   21.871  14.905   9.573  1.00 22.37           O
ATOM  3653  OW0  WAT W    9   27.959  17.792  18.999  1.00 27.12           O
ATOM  3654  OW0  WAT W   10   11.009   3.171  42.889  1.00 23.32           O
ATOM  3655  OW0  WAT W   11   14.021  17.668  10.521  1.00 23.54           O
ATOM  3656  OW0  WAT W   12   19.633   6.095  46.714  1.00 24.75           O
ATOM  3657  OW0  WAT W   13   21.902  17.659   9.044  1.00 27.81           O
ATOM  3658  OW0  WAT W   14   18.986   6.850  42.583  1.00 19.48           O
ATOM  3659  OW0  WAT W   15   25.651  16.524  19.584  1.00 20.56           O
ATOM  3660  OW0  WAT W   16   22.299  -0.256   9.519  1.00 29.51           O
ATOM  3661  OW0  WAT W   17   15.024  10.870  25.417  1.00 27.29           O
ATOM  3662  OW0  WAT W   18   23.250  18.239   6.810  1.00 25.22           O
ATOM  3663  OW0  WAT W   19   26.908   4.204  34.548  1.00 24.63           O
ATOM  3664  OW0  WAT W   20   18.354  28.175   4.814  1.00 33.17           O
ATOM  3665  OW0  WAT W   21   19.790   3.374  45.626  1.00 24.25           O
ATOM  3666  OW0  WAT W   22   18.007  22.841   3.919  1.00 27.68           O
ATOM  3667  OW0  WAT W   23   46.993   5.908   9.668  1.00 26.51           O
ATOM  3668  OW0  WAT W   24   24.507   5.376  33.461  1.00 21.53           O
ATOM  3669  OW0  WAT W   25   19.262  17.958   8.795  1.00 25.20           O
ATOM  3670  OW0  WAT W   26   35.957  18.589   9.557  1.00 27.11           O
ATOM  3671  OW0  WAT W   27   19.056   4.126  43.078  1.00 24.17           O
ATOM  3672  OW0  WAT W   28   13.848  30.071  10.671  1.00 30.60           O
ATOM  3673  OW0  WAT W   29   14.277  -1.107  47.634  1.00 29.57           O
ATOM  3674  OW0  WAT W   30    1.298  10.175  20.241  1.00 23.69           O
ATOM  3675  OW0  WAT W   31   31.050   8.239  29.186  1.00 30.83           O
ATOM  3676  OW0  WAT W   32   18.563  23.370  40.373  1.00 27.01           O
ATOM  3677  OW0  WAT W   33   20.290  21.874  20.963  1.00 33.27           O
ATOM  3678  OW0  WAT W   34   17.478   6.072  28.714  1.00 35.57           O
ATOM  3679  OW0  WAT W   35   50.053  12.647  12.109  1.00 37.72           O
ATOM  3680  OW0  WAT W   36   20.619   1.437  21.138  1.00 30.60           O
ATOM  3681  OW0  WAT W   37   21.302  -4.994  47.887  1.00 29.39           O
ATOM  3682  OW0  WAT W   38   28.170   9.720  -1.849  1.00 32.07           O
ATOM  3683  OW0  WAT W   39   31.362   1.220  44.700  1.00 29.94           O
ATOM  3684  OW0  WAT W   40   20.546  22.103   3.866  1.00 28.15           O
ATOM  3685  OW0  WAT W   41   46.350   2.724   9.952  1.00 30.93           O
ATOM  3686  OW0  WAT W   42   15.588  16.297  49.060  1.00 32.92           O
ATOM  3687  OW0  WAT W   43   39.739  17.212  12.409  1.00 28.98           O
ATOM  3688  OW0  WAT W   44   18.564  13.342  22.347  1.00 27.99           O
ATOM  3689  OW0  WAT W   45   11.265  -8.394  40.040  1.00 33.13           O
```

FIG. 2VV

```
ATOM  3690  OWO  WAT  W   46     3.123   12.261   42.568  1.00  28.66        O
ATOM  3691  OWO  WAT  W   47    31.354   13.280   25.163  1.00  28.87        O
ATOM  3692  OWO  WAT  W   48     0.658   11.369   28.091  1.00  31.71        O
ATOM  3693  OWO  WAT  W   49    38.712   22.250   18.051  1.00  40.44        O
ATOM  3694  OWO  WAT  W   50    43.645    4.572   40.510  1.00  41.82        O
ATOM  3695  OWO  WAT  W   51    38.532   18.730   10.324  1.00  34.38        O
ATOM  3696  OWO  WAT  W   52    -1.359   10.932   29.947  1.00  31.87        O
ATOM  3697  OWO  WAT  W   53    19.994    5.430    2.327  1.00  35.83        O
ATOM  3698  OWO  WAT  W   54    50.451   11.840   19.513  1.00  40.45        O
ATOM  3699  OWO  WAT  W   55     3.107   19.354   37.985  1.00  32.85        O
ATOM  3700  OWO  WAT  W   56    32.747    3.464   45.164  1.00  30.83        O
ATOM  3701  OWO  WAT  W   57    18.054    8.351   29.482  1.00  29.81        O
ATOM  3702  OWO  WAT  W   58    23.833   12.539    2.117  1.00  29.50        O
ATOM  3703  OWO  WAT  W   59    36.952    4.680   42.871  1.00  32.99        O
ATOM  3704  OWO  WAT  W   60    13.874   18.788   46.438  1.00  34.68        O
ATOM  3705  OWO  WAT  W   61    45.734    2.950   16.128  1.00  34.00        O
ATOM  3706  OWO  WAT  W   62    31.298    2.999   -0.169  1.00  32.57        O
ATOM  3707  OWO  WAT  W   63    46.735    3.167   23.449  1.00  34.81        O
ATOM  3708  OWO  WAT  W   64     5.146   15.414   44.002  1.00  36.81        O
ATOM  3709  OWO  WAT  W   65    19.618    9.333   50.357  1.00  37.68        O
ATOM  3710  OWO  WAT  W   66    21.594    9.697   48.584  1.00  32.45        O
ATOM  3711  OWO  WAT  W   67    20.632   14.698    7.174  1.00  33.83        O
ATOM  3712  OWO  WAT  W   68    28.617   19.529   20.885  1.00  33.83        O
ATOM  3713  OWO  WAT  W   69    16.831   -0.400   48.082  1.00  29.67        O
ATOM  3714  OWO  WAT  W   70     2.344   21.666   15.297  1.00  25.54        O
ATOM  3715  OWO  WAT  W   71     5.913   26.127    8.045  1.00  33.92        O
ATOM  3716  OWO  WAT  W   72    43.476   16.411   46.827  1.00  35.61        O
ATOM  3717  OWO  WAT  W   73    40.314   16.049    9.730  1.00  44.75        O
ATOM  3718  OWO  WAT  W   74    12.341    2.799   23.103  1.00  35.80        O
ATOM  3719  OWO  WAT  W   75     6.274    9.180    6.926  1.00  28.66        O
ATOM  3720  OWO  WAT  W   76    27.429   28.031   45.111  1.00  37.68        O
ATOM  3721  OWO  WAT  W   77    19.214   20.278   31.073  1.00  33.73        O
ATOM  3722  OWO  WAT  W   78    27.839    2.397   32.790  1.00  33.02        O
ATOM  3723  OWO  WAT  W   79    -2.391   20.534   10.657  1.00  33.99        O
ATOM  3724  OWO  WAT  W   80     3.501    6.274   12.553  1.00  34.23        O
ATOM  3725  OWO  WAT  W   81    23.056   16.556   21.213  1.00  35.55        O
ATOM  3726  OWO  WAT  W   82     1.730   19.909   29.262  1.00  29.41        O
ATOM  3727  OWO  WAT  W   83    21.402  -15.296   31.401  1.00  37.68        O
ATOM  3728  OWO  WAT  W   84    21.577   -1.704   11.851  1.00  29.83        O
ATOM  3729  OWO  WAT  W   85    31.911   11.942   53.219  1.00  42.18        O
ATOM  3730  OWO  WAT  W   86    -2.039    3.962   30.860  1.00  41.23        O
ATOM  3731  OWO  WAT  W   87    28.451   21.819    0.247  1.00  77.26        O
ATOM  3732  OWO  WAT  W   88    19.924   25.865   40.473  1.00  31.60        O
ATOM  3733  OWO  WAT  W   89    33.450    7.157   30.384  1.00  39.19        O
ATOM  3734  OWO  WAT  W   90    52.964   10.366   18.355  1.00  26.42        O
ATOM  3735  OWO  WAT  W   91    16.263    3.694   42.911  1.00  25.64        O
ATOM  3736  OWO  WAT  W   92    18.833    4.410   30.465  1.00  31.34        O
ATOM  3737  OWO  WAT  W   93    28.412   17.068   -2.056  1.00  29.02        O
ATOM  3738  OWO  WAT  W   94    14.490   23.651   24.369  1.00  34.47        O
ATOM  3739  OWO  WAT  W   95    30.926   -4.668   52.419  1.00  46.78        O
ATOM  3740  OWO  WAT  W   96    11.689   18.916   27.939  1.00  44.56        O
ATOM  3741  OWO  WAT  W   97    30.260    0.786   34.779  1.00  37.00        O
ATOM  3742  OWO  WAT  W   98    22.914   -4.010   11.910  1.00  39.16        O
ATOM  3743  OWO  WAT  W   99    20.013   15.557   -3.230  1.00  43.89        O
ATOM  3744  OWO  WAT  W  100    27.122   15.082   22.406  1.00  38.38        O
ATOM  3745  OWO  WAT  W  101    33.984    6.935   23.167  1.00  31.70        O
ATOM  3746  OWO  WAT  W  102    48.239   10.877   11.122  1.00  39.32        O
ATOM  3747  OWO  WAT  W  103    39.777   10.123   46.483  1.00  40.48        O
ATOM  3748  OWO  WAT  W  104    15.913    5.068    4.962  1.00  38.55        O
ATOM  3749  OWO  WAT  W  105     8.813   -9.674   40.078  1.00  53.32        O
ATOM  3750  OWO  WAT  W  106    47.605   16.487   21.063  1.00  40.23        O
ATOM  3751  OWO  WAT  W  107    35.602    3.446   44.927  1.00  39.85        O
ATOM  3752  OWO  WAT  W  108    31.129   -6.169    8.662  1.00  41.30        O
ATOM  3753  OWO  WAT  W  109    11.427   31.547   10.265  1.00  41.49        O
ATOM  3754  OWO  WAT  W  110    14.396   -1.879   26.658  1.00  36.77        O
ATOM  3755  OWO  WAT  W  111    46.762   18.021   19.152  1.00  46.85        O
ATOM  3756  OWO  WAT  W  112    43.398    5.319    2.222  1.00  52.48        O
ATOM  3757  OWO  WAT  W  113    34.516   20.702    2.758  1.00  45.48        O
ATOM  3758  OWO  WAT  W  114    36.231   -0.262   19.801  1.00  39.23        O
ATOM  3759  OWO  WAT  W  115    36.569   22.976    7.030  1.00  49.73        O
ATOM  3760  OWO  WAT  W  116    22.415   -4.926    4.527  1.00  38.24        O
ATOM  3761  OWO  WAT  W  117     4.372   25.938   10.233  1.00  39.24        O
ATOM  3762  OWO  WAT  W  118    52.348   17.172   17.310  1.00  34.24        O
ATOM  3763  OWO  WAT  W  119    40.416   21.290   54.111  1.00  49.71        O
ATOM  3764  OWO  WAT  W  120    34.032   14.639   24.790  1.00  40.57        O
ATOM  3765  OWO  WAT  W  121    40.309   20.591    9.258  1.00  42.56        O
ATOM  3766  OWO  WAT  W  122    31.232   12.395   27.555  1.00  44.52        O
```

FIG. 2WW

```
ATOM   3767  OW0  WAT  W  123      39.795   -0.317    2.652  1.00 44.68           O
ATOM   3768  OW0  WAT  W  124       5.610    2.009   11.401  1.00 38.29           O
ATOM   3769  OW0  WAT  W  125       7.529   32.075   12.842  1.00 64.16           O
ATOM   3770  OW0  WAT  W  126      17.920   15.784   23.067  1.00 43.06           O
ATOM   3771  OW0  WAT  W  127      14.136   21.143   25.527  1.00 38.04           O
ATOM   3772  OW0  WAT  W  128      38.574   15.873   54.803  1.00 51.81           O
ATOM   3773  OW0  WAT  W  129      -4.788    1.197   37.196  1.00 45.96           O
ATOM   3774  OW0  WAT  W  130      17.081    7.172   44.652  1.00 38.01           O
ATOM   3775  OW0  WAT  W  131      26.355    6.784   30.899  1.00 44.15           O
ATOM   3776  OW0  WAT  W  132      29.252  -12.936   48.056  1.00 35.90           O
ATOM   3777  OW0  WAT  W  133      19.871   11.775    5.475  1.00 40.56           O
ATOM   3778  OW0  WAT  W  134      36.006    3.305   21.918  1.00 48.65           O
ATOM   3779  OW0  WAT  W  135      22.954   -4.481    0.798  1.00 50.80           O
ATOM   3780  OW0  WAT  W  136      13.207   -6.171   24.730  1.00 43.42           O
ATOM   3781  OW0  WAT  W  137      -3.317    0.489   12.332  1.00 48.64           O
ATOM   3782  OW0  WAT  W  138      25.629   12.264    4.200  1.00 38.19           O
ATOM   3783  OW0  WAT  W  139      23.573   25.238   35.587  1.00 42.16           O
ATOM   3784  OW0  WAT  W  140      40.447   10.129    3.302  1.00 34.56           O
ATOM   3785  OW0  WAT  W  141       2.625   11.927   45.379  1.00 44.63           O
ATOM   3786  OW0  WAT  W  142      25.620   18.252   -1.548  1.00 45.28           O
ATOM   3787  OW0  WAT  W  143       4.689   19.820   29.824  1.00 39.35           O
ATOM   3788  OW0  WAT  W  144      -4.941   21.975   25.303  1.00 58.01           O
ATOM   3789  OW0  WAT  W  145      -0.643    4.350   26.309  1.00 54.33           O
ATOM   3790  OW0  WAT  W  146      38.573    1.533    1.090  1.00 44.32           O
ATOM   3791  OW0  WAT  W  147      18.132   24.827   32.593  1.00 37.08           O
ATOM   3792  OW0  WAT  W  148      20.278   25.946   36.703  1.00 44.49           O
ATOM   3793  OW0  WAT  W  149      -0.072   10.577   25.625  1.00 36.84           O
ATOM   3794  OW0  WAT  W  150      16.704   -5.369   13.610  1.00 53.67           O
ATOM   3795  OW0  WAT  W  151      25.510   -2.764   29.701  1.00 34.82           O
ATOM   3796  OW0  WAT  W  152       4.332   -5.544   25.984  1.00 65.27           O
ATOM   3797  OW0  WAT  W  153      40.847   21.215   18.492  1.00 42.39           O
ATOM   3798  OW0  WAT  W  154      16.209    9.997   46.118  1.00 45.45           O
ATOM   3799  OW0  WAT  W  155      18.045    2.761    4.686  1.00 42.06           O
ATOM   3800  OW0  WAT  W  156      29.533    6.085   29.934  1.00 43.67           O
ATOM   3801  OW0  WAT  W  157       0.620   22.763   17.036  1.00 43.19           O
ATOM   3802  OW0  WAT  W  158      22.171   14.826    3.381  1.00 39.74           O
ATOM   3803  OW0  WAT  W  159      26.060   19.294   54.077  1.00 46.68           O
ATOM   3804  OW0  WAT  W  160      45.733   17.018   16.481  1.00 30.83           O
ATOM   3805  OW0  WAT  W  161      37.760   10.259   30.385  1.00 41.55           O
ATOM   3806  OW0  WAT  W  162      34.451   22.116   34.910  1.00 41.24           O
ATOM   3807  OW0  WAT  W  163      26.582   17.904   23.043  1.00 40.64           O
ATOM   3808  OW0  WAT  W  164      42.978   12.211    9.438  1.00 40.50           O
ATOM   3809  OW0  WAT  W  165      34.042   19.067   54.737  1.00 55.40           O
ATOM   3810  OW0  WAT  W  166      47.826   18.320   16.788  1.00 36.84           O
ATOM   3811  OW0  WAT  W  167       2.635    1.607   19.768  1.00 40.36           O
ATOM   3812  OW0  WAT  W  168      42.706   15.702   51.168  1.00 53.73           O
ATOM   3813  OW0  WAT  W  169      29.444   -5.469   19.727  1.00 44.18           O
ATOM   3814  OW0  WAT  W  170       0.938    0.074   33.827  1.00 39.33           O
ATOM   3815  OW0  WAT  W  171       1.355   15.318   36.571  1.00 41.72           O
ATOM   3816  OW0  WAT  W  172      35.733   22.337   38.623  1.00 48.99           O
ATOM   3817  OW0  WAT  W  173      22.025  -16.840   54.098  1.00 60.26           O
ATOM   3818  OW0  WAT  W  174       8.180   19.230   41.714  1.00 50.71           O
ATOM   3819  OW0  WAT  W  175      15.073   10.349    3.405  1.00 41.40           O
ATOM   3820  OW0  WAT  W  176      18.275   26.866   47.583  1.00 43.95           O
ATOM   3821  OW0  WAT  W  177      26.149   22.604   52.505  1.00 52.87           O
ATOM   3822  OW0  WAT  W  178      36.628   10.191    1.537  1.00 43.41           O
ATOM   3823  OW0  WAT  W  179      -0.744   -7.200   35.515  1.00 58.15           O
ATOM   3824  OW0  WAT  W  180      10.690   11.744   47.602  1.00 50.01           O
ATOM   3825  OW0  WAT  W  181      27.869  -15.330   51.231  1.00 40.75           O
ATOM   3826  OW0  WAT  W  182      27.409   16.705   57.119  1.00 47.06           O
ATOM   3827  OW0  WAT  W  183      33.387   15.056   31.663  1.00 36.85           O
ATOM   3828  OW0  WAT  W  184      31.235   21.301   19.350  1.00 46.04           O
ATOM   3829  OW0  WAT  W  185      15.569   30.920    6.508  1.00 56.60           O
ATOM   3830  OW0  WAT  W  186      44.227   10.255   22.435  1.00 38.96           O
ATOM   3831  OW0  WAT  W  187      -4.537   19.107    8.733  1.00 53.62           O
ATOM   3832  OW0  WAT  W  188      34.122    2.662   52.345  1.00 65.45           O
ATOM   3833  OW0  WAT  W  189      28.450   19.016   27.150  1.00 54.11           O
END
```

METHOD USING CRYSTAL STRUCTURE OF ESTROGEN RECEPTOR-β COMPLEX

This application claims the benefit of U.S. Provisional Application No. 60/217,834 filed Jul. 12, 2000.

FIELD OF THE INVENTION

The present invention relates to the crystal structure of the Estrogen Receptor-β (ER-β) complexed with genistein. This structure is critical for the design and selection of potent and selective agents which interact with ER-β, and particularly, the design of novel chemotherapeutic agents.

BACKGROUND OF THE INVENTION

The beneficial effects of estrogen on bone maintenance, blood lipid profile, and the cardiovascular system are well known and account for the widespread use of hormone replacement therapy (HRT) in postmenopausal women (1). Estrogens and anti-estrogens affect several tissues, and the pattern of effects observed depends upon the particular ligand used (2). A major advance toward understanding the differential effects of various estrogenic compounds came with the recent discovery of an additional form of the estrogen receptor (3). The newly discovered receptor, named ER-β, is similar in sequence to the previously known form, now called ER-α. Mapping the distribution of ER-β and ER-α mRNA in normal and neoplastic tissues has provided an intriguing picture of differential expression patterns in different tissue types (4,5,6,7). The existence of clear-cut differences in receptor expression suggests that tissues could be targeted selectively with ligands selective for ER-α or ER-β.

Like all known nuclear receptors, estrogen receptors function as ligand-activated transcriptional factors and have a modular structure consisting of six discrete domains, named A-F. These domains mediate binding to DNA, ligands and co-activators (8,9,10,11). The E domain of ER-α binds ligands such as 17β-estradiol and the phytoestrogen, genistein. The E-domains of ER-α and ER-β are 59% identical in sequence and have a predicted mass of approximately 25 kD. The natural ligand, 17β-estradiol, binds both with similar affinity. In contrast, genistein is selective, having 30 fold greater affinity for ER-β than for ER-α ((3) and H. Harris, unpublished observations).

The ligand binding domains (LBDs) of all studied nuclear receptors change conformation substantially upon ligand binding (12,13,14,15), particularly in the positioning of helix 12 (H12). In the case of ER-α, the position of H12 induced by the ligand depends on whether the ligand is an agonist (estradiol or diethylstilbestrol (DES)) or antagonist (raloxifene or tamoxifen). In the agonist complex, H12 packs against helices H3, H5, H6 and H11, forming a lid over the ligand. In this complex, H12 forms a wall perpendicular with and at one end of the co-activator binding groove formed by residues in H3, H4, H5 and the turn between H3 and H4. Peptides derived from the NR box II region (16,17,18,19) of the co-activator, GRIP1 can bind in this groove (11), suggesting this is an important aspect of transcriptional regulation. In contrast, steric hindrance from a bound antagonist displaces H12 so that it now binds in a hydrophobic groove formed by residues from helices 3 and 5. In this position, H12 binds to and occludes the co-activator recognition site, mimicking the interactions formed by the NR box II with the LBD and probably preventing modulation by co-activators. From these results it is clear that the structure of the bound ligand affects the overall structure of ER-α and its interactions with co-activators.

SUMMARY OF THE INVENTION

The present invention provides a crystal of ER-β complexed with genistein, as well as the three dimensional structure of ER-β as derived by x-ray diffraction data of the ER-β/genistein crystal. Specifically, the three dimensional structure of ER-β is defined by the structural coordinates shown in FIGS. 2A-2XX, ± a root mean square deviation from the backbone atoms of the amino acids of not more than 1.5 Å. The structural coordinates of ER-β are useful for a number of applications, including, but not limited to, the visualization, identification and characterization of various active sites of ER-β, and the ER-β/genistein complex, including the genistein binding site. The active site structures may then be used to design various agents which interact with ER-β, as well as ER-β complexed with genistein or related molecules.

The present invention is also directed to an active site of a genistein binding protein or peptide, and preferably the genistein binding site of the ER-β, comprising the relative structural coordinates of amino acid residues MET343, LEU346, LEU349, GLU353, MET384, LEU387, MET388, ARG394, PHE404, ILE421, ILE424, GLY520, HIS523 and LEU524 according to FIGS. 2A-2XX for monomer A of ER-β, ± a root mean square deviation from the backbone atoms of said amino acids of not more than 1.5 Å. Alternatively, the active site may include, in addition to the structural coordinates define above, the relative structural coordinates of amino acid residues VAL328, MET342, SER345, THR347, LYS348, LEU349, ALA350, ASP351, LEU354, MET357, TRP383, GLU385, VAL386, MET389, GLY390, LEU391, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, VAL535, TYR536 and LEU538 according to FIGS. 2A-2XX for monomer A of ER-β, ± a root mean square deviation from the backbone atoms of said amino acids of not more than 1.5 Å. The genistein active site may correspond to the configuration of ER-β in its state of association with an agent, preferably, genistein, or in its unbound state.

In another embodiment, the active site of a genistein binding protein or peptide, and preferably the genistein binding site of the ER-β, comprises the relative structural coordinates of amino acid residues MET343, LEU346, LEU349, GLU353, MET384, LEU387, MET388, LEU391, ARG394, PHE404, ILE421, ILE424, GLY520, HIS523 and LEU524 according to FIGS. 2A-2XX for monomer B of ER-β, ± a root mean square deviation from the backbone atoms of said amino acids of not more than 1.5 Å. Alternatively, the active site may include, in addition to the structural coordinates define above, the relative structural coordinates of amino acid residues MET342, SER345, THR347, LYS348, ALA350, ASP351, MET357, TRP383, GLU385, VAL386, LEU387, MET389, GLY390, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, TYR536 and LEU538 according to FIGS. 2A-2XX for monomer B of ER-β, ± a root mean square deviation from the backbone atoms of said amino acids of not more than 1.5 Å. Here again, the genistein active site may correspond to the configuration of ER-β in its state of association with an agent, preferably, genistein, or in its unbound state.

In addition, the present invention provides a method for identifying an agent that interacts with ER-β, comprising the steps of: (a) generating a three dimensional model of ER-β using the relative structural coordinates according to FIGS. 2A-2XX, ± a root mean square deviation from the backbone atoms of said amino acids of not more than 1.5 Å; and (b) employing said three-dimensional model to design or select an agent that interacts with ER-β.

Still further the present invention provides a method for identifying an activator or inhibitor of a molecule or molecular complex comprising a genistein binding site, comprising the steps of: (a) generating a three dimensional model of said molecule or molecular complex comprising a genistein binding site using (i) the relative structural coordinates of amino acid residues MET343, LEU346, LEU349, GLU353, MET384, LEU387, MET388, ARG394, PHE404, ILE421, ILE424, GLY520, HIS523 and LEU524 according to FIGS. 2A-2XX for monomer A of ER-β, ± a root mean square deviation from the backbone atoms of said amino acids of not more than 1.5 Å, or (ii) the relative structural coordinates of amino acid residues MET343, LEU346, LEU349, GLU353, MET384, LEU387, MET388, LEU391, ARG394, PHE404, ILE421, ILE424, GLY520, HIS523 and LEU524 according to FIGS. 2A-2XX for monomer B of ER-β, ± a root mean square deviation from the backbone atoms of said amino acids of not more than 1.5 Å; and (b) selecting or designing a candidate activator or inhibitor by performing computer fitting analysis of the candidate activator or inhibitor with the three dimensional model generated in step (a). In another embodiment, the relative structural coordinates according to (i) further comprises the relative structural coordinates of amino acid residues VAL328, MET342, SER345, THR347, LYS348, LEU349, ALA350, ASP351, LEU354, MET357, TRP383, GLU385, VAL386, MET389, GLY390, LEU391, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, VAL535, TYR536 and LEU538 according to FIGS. 2A-2XX for monomer A of ER-β, ± a root mean square deviation from the backbone atoms of said amino acids of not more than 1.5 Å. In yet another embodiment, the relative structural coordinates according to (ii) further comprises the relative structural coordinates of amino acid residues MET342, SER345, THR347, LYS348, ALA350, ASP351, MET357, TRP383, GLU385, VAL386, LEU387, MET389, GLY390, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, TYR536 and LEU538 according to FIGS. 2A-2XX for monomer B of ER-β, ± a root mean square deviation from the backbone atoms of said amino acids of not more than 1.5 Å.

Finally, the present invention provides agents, activators or inhibitors identified using the foregoing methods. Small molecules or other agents which inhibit or otherwise interfere with ER-β may be useful in the treatment of diseases associated with ER-β such as cancer.

Additional objects of the present invention will be apparent from the description which follows.

BRIEF DESCRIPTION OF THE FIGURES

FIG. 1 provides a sequence alignment of ER-α with ER-β covering the ordered extent of ER-β. The numbering scheme used was chosen to be consistent with ER-α, such that the first ordered ER-β residue, 311 is residue 263 in the full length protein. Residues in helix 12 are underlined. The (*) symbols indicate the altered binding site residues.

FIGs. 2A-2XX provides the atomic structural coordinates for ER-β and genestein as derived by X-ray diffraction of an ER-β and genestein crystal complex. "Atom type" refers to the atom whose coordinates are being measured. "Residue" refers to the type of residue of which each measured atom is a part—i.e., amino acid, cofactor, ligand or solvent. The "x, y and z" coordinates indicate the Cartesian coordinates of each measured atom's location in the unit cell (Å). "Occ" indicates the occupancy factor. "B" indicates the "B-value", which is a measure of how mobile the atom is in the atomic structure ($Å^2$). Under "Residue type", "GEN C" refers to one molecule of genistein, "GEN D" refers to a second molecule of genistein, and "W" refers to water molecules.

DETAILED DESCRIPTION OF THE INVENTION

As used herein, the following terms and phrases shall have the meanings set forth below:

Unless otherwise noted, Estrogen Receptor-β (ER-β) comprises the amino acid sequence depicted in FIG. 1, including conservative substitutions.

"Genistein" is 4',5,7-trihydroxyisoflavone. A "genistein binding protein or peptide" is a protein or peptide that binds genistein and has a genistein binding site, and includes but is not limited to ER-β. A "molecule or molecular complex comprising a genistein binding site" includes ER-β and other molecules or molecular complexes having a genistein binding site.

Unless otherwise indicated, "protein" or "molecule" shall include a protein, protein domain, polypeptide or peptide.

"Structural coordinates" are the Cartesian coordinates corresponding to an atom's spatial relationship to other atoms in a molecule or molecular complex. Structural coordinates may be obtained using x-ray crystallography techniques or NMR techniques, or may be derived using molecular replacement analysis or homology modeling. Various software programs allow for the graphical representation of a set of structural coordinates to obtain a three dimensional representation of a molecule or molecular complex. The structural coordinates of the present invention may be modified from the original sets provided in FIGS. 2A-2XX by mathematical manipulation, such as by inversion or integer additions or subtractions. As such, it is recognized that the structural coordinates of the present invention are relative, and are in no way specifically limited by the actual x, y, z coordinates of FIGS. 2A-2XX.

An "agent" shall include a protein, polypeptide, peptide, nucleic acid, including DNA or RNA, molecule, compound or drug.

"Root mean square deviation" is the square root of the arithmetic mean of the squares of the deviations from the mean, and is a way of expressing deviation or variation from the structural coordinates described herein. The present invention includes all embodiments comprising conservative substitutions of the noted amino acid residues resulting in same structural coordinates within the stated root mean square deviation.

It will be obvious to the skilled practitioner that the numbering of the amino acid residues of ER-β may be different than that set forth herein, and may contain certain conservative amino acid substitutions that yield the same three dimensional structures as those defined by FIGS. 2A-2XX herein. Corresponding amino acids and conservative substitutions in other isoforms or analogues are easily identified by visual inspection of the relevant amino acid sequences or by using commercially available homology software programs (e.g., MODELLAR, MSI, San Diego, Calif.).

"Conservative substitutions" are those amino acid substitutions which are functionally equivalent to the substituted amino acid residue, either by way of having similar polarity, steric arrangement, or by belonging to the same class as the substituted residue (e.g., hydrophobic, acidic or basic), and includes substitutions having an inconsequential effect on the three dimensional structure of ER-β with respect to the use of said structures for the identification and design of agents which interact with ER-β and genistein, as well as other proteins, peptides, molecules or molecular complexes comprising a genistein or ER-β binding site, for molecular replacement analyses and/or for homology modeling.

An "active site" refers to a region of a molecule or molecular complex that, as a result of its shape and charge potential, favorably interacts or associates with another agent (including, without limitation, a protein, polypeptide, peptide, nucleic acid, including DNA or RNA, molecule, compound or drug) via various covalent and/or non-covalent binding forces. As such, an active site of the present invention may include, for example, the actual site of genistein binding with ER-β, as well as accessory binding sites adjacent or proximal to the actual site of genistein binding that nonetheless may affect ER-β activity upon interaction or association with a particular agent, either by direct interference with the actual site of genistein binding or by indirectly affecting the steric conformation or charge potential of the ER-β and thereby preventing or reducing binding of genistein to ER-β at the actual site of genistein binding. As used herein, an "active site" also includes analog residues of ER-β which exhibit observable NMR perturbations in the presence of a binding ligand, such as genistein. While such residues exhibiting observable NMR perturbations may not necessarily be in direct contact with or immediately proximate to ligand binding residues, they may be critical ER-β residues for rational drug design protocols.

The present invention first provides a crystallized complex comprising ER-β and genistein. In a particular embodiment, the amino acid sequence of ER-β is set forth in FIG. 1, and includes conservative substitutions. The crystal complex of the present invention effectively diffracts X-rays for the determination of the structural coordinates of the complex of ER-β and genistein, and is characterized as having space group $P2_12_12_1$, and unit cell parameters of a=53.49 Å, b=85.21 Å, c=107.07 Å. Further, the crystallized complex of the present invention consists of two molecules of ER-β each bound to a molecule of genistein.

Using a grown crystal complex of the present invention, X-ray diffraction data can be collected by a variety of means in order to obtain the atomic coordinates of the molecules in the crystallized complex. With the aid of specifically designed computer software, such crystallographic data can be used to generate a three dimensional structure of the molecules in the complex. Various methods used to generate and refine a three dimensional structure of a molecular structure are well known to those skilled in the art, and include, without limitation, multiwavelength anomalous dispersion (MAD), multiple isomorphous replacement, reciprocal space solvent flattening, molecular replacement, and single isomorphous replacement with anomalous scattering (SIRAS).

Accordingly, the present invention also provides the three dimensional structure of ER-β as derived by x-ray diffraction data of the ER-β/genistein crystal. Specifically, the three dimensional structure of ER-β is defined by the structural coordinates shown in FIGS. 2A-2XX, ± a root mean square deviation from the backbone atoms of the amino acids of not more than 1.5 Å, preferably not more than 1.0 Å, and most preferably not more than 0.5 Å. The structural coordinates of ER-β are useful for a number of applications, including, but not limited to, the visualization, identification and characterization of various active sites of ER-β, and the ER-β/genistein complex, including the genistein binding site. The active site structures may then be used to design agents with interact with ER-β, as well as ER-β complexed with genistein or related molecules.

The present invention is also directed to an active site of a genistein binding protein or peptide, and preferably the genistein binding site of the ER-β, comprising the relative structural coordinates of amino acid residues MET343, LEU346, LEU349, GLU353, MET384, LEU387, MET388, ARG394, PHE404, ILE421, ILE424, GLY520, HIS523 and LEU524 according to FIGS. 2A-2XX for monomer A of ER-β, ± a root mean square deviation from the backbone atoms of said amino acids of not more than 1.5 Å, preferably not more than 1.0 Å, and most preferably not more than 0.5 Å. Alternatively, the active site may include, in addition to the structural coordinates define above, the relative structural coordinates of amino acid residues VAL328, MET342, SER345, THR347, LYS348, LEU349, ALA350, ASP351, LEU354, MET357, TRP383, GLU385, VAL386, MET389, GLY390, LEU391, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, VAL535, TYR536 and LEU538 according to FIGS. 2A-2XX for monomer A of ER-β, ± a root mean square deviation from the backbone atoms of said amino acids of not more than 1.5 Å, preferably not more than 1.0 Å, and most preferably not more than 0.5 Å. The genistein active site may correspond to the configuration of ER-β in its state of association with an agent, preferably, genistein, or in its unbound state.

In another embodiment, the active site of a genistein binding protein or peptide, and preferably the genistein binding site of the ER-β, comprises the relative structural coordinates of amino acid residues MET343, LEU346, LEU349, GLU353, MET384, LEU387, MET388, LEU391, ARG394, PHE404, ILE421, ILE424, GLY520, HIS523 and LEU524 according to FIGS. 2A-2XX for monomer B of ER-β, ± a root mean square deviation from the backbone atoms of said amino acids of not more than 1.5 Å, preferably not more than 1.0 Å, and most preferably not more than 0.5 Å. Alternatively, the active site may include, in addition to the structural coordinates define above, the relative structural coordinates of amino acid residues MET342, SER345, THR347, LYS348, ALA350, ASP351, MET357, TRP383, GLU385, VAL386, LEU387, MET389, GLY390, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, TYR536 and LEU538 according to FIGS. 2A-2XX for monomer B of ER-β, ± a root mean square deviation from the backbone atoms of said amino acids of not more than 1.5 Å, preferably not more than 1.0 Å, and most preferably not more than 0.5 Å. Here again, the genistein active site may correspond to the configuration of ER-β in its state of association with an agent, preferably, genistein, or in its unbound state.

Another aspect of the present invention is directed to a method for identifying an agent that interacts with ER-β, comprising the steps of: (a) generating a three dimensional model of ER-β using the relative structural coordinates according to FIGS. 2A-2XX, ± a root mean square deviation from the backbone atoms of said amino acids of not more than 1.5 Å, preferably not more than 1.0 Å, and most preferably not more than 0.5 Å; and (b) employing said three-dimensional model to design or select an agent that interacts with ER-β. The agent may be identified using computer fitting analyses utilizing various computer software programs that evaluate the "fit" between the putative active site and the identified agent, by (a) generating a three dimensional model of the putative active site of a molecule or molecular complex using homology modeling or the atomic structural coordinates of the active site, and (b) determining the degree of association between the putative active site and the identified agent. Three dimensional models of the putative active site may be generated using any one of a number of methods known in the art, and include, but are not limited to, homology modeling as well as computer analysis of raw data generated using crystallographic or spectroscopy data. Computer programs used to generate such three dimensional models and/or perform the necessary fitting analyses include, but are not limited to: GRID (Oxford University, Oxford, UK), MCSS (Molecular Simulations, San Diego, Calif.), AUTODOCK (Scripps Research Institute, La Jolla, Calif.), DOCK (University of California, San Francisco, Calif.), Flo99 (Thistlesoft, Morris Township, N.J.), Ludi (Molecular Simulations, San Diego, Calif.), QUANTA (Molecular Simulations, San Diego, Calif.), Insight (Molecular Simulations, San Diego, Calif.), SYBYL (TRIPOS, Inc., St. Louis. Mo.) and LEAPFROG (TRIPOS, Inc., St. Louis, Mo.). The structural coordinates also may be used to visualize the three-dimensional structure of ER-β and the ER-β/genistein complex using MOLSCRIPT (28) and RASTER3D (29), for example.

The effect of such an agent identified by computer fitting analyses on ER-β activity may be further evaluated by contacting the identified agent with ER-β and measuring the effect of the agent on ER-β activity. Depending upon the action of the agent on the active site of ER-β, the agent may act either as an inhibitor or activator of ER-β activity. For example, enzymatic assays may be performed and the results analyzed to determine whether the agent is an inhibitor of ER-β and genistein (i.e., the agent may reduce or prevent binding affinity between ER-β and genistein) or an activator of ER-β and genistein (i.e., the agent may increase binding affinity between ER-β and genistein). Further tests may be performed to evaluate the potential therapeutic efficacy of the identified agent on conditions associated with ER-β such as cancer.

The present invention also provides a method for identifying an activator or inhibitor of a molecule or molecular complex comprising a genistein binding site, and preferably ER-β, comprising the steps of: (a) generating a three dimensional model of said molecule or molecular complex comprising a genistein binding site using (i) the relative structural coordinates of amino acid residues MET343, LEU346, LEU349, GLU353, MET384, LEU387, MET388, ARG394, PHE404, ILE421, ILE424, GLY520, HIS523 and LEU524 according to FIGS. 2A-2XX for monomer A of ER-β, ± a root mean square deviation from the backbone atoms of said amino acids of not more than 1.5 Å, preferably not more than 1.0 Å, and most preferably not more than 0.5 Å, or (ii) the relative structural coordinates of amino acid residues MET343, LEU346, LEU349, GLU353, MET384, LEU387, MET388, LEU391, ARG394, PHE404, ILE421, ILE424, GLY520, HIS523 and LEU524 according to FIGS. 2A-2XX for monomer B of ER-β, ± a root mean square deviation from the backbone atoms of said amino acids of not more than 1.5 Å, preferably not more than 1.0 Å, and most preferably not more than 0.5 Å; and (b) selecting or designing a candidate activator or inhibitor by performing computer fitting analysis of the candidate activator or inhibitor with the three dimensional model generated in step (a). In another embodiment, the structural coordinates according to (i) further comprises the relative structural coordinates of amino acid residues VAL328, MET342, SER345, THR347, LYS348, LEU349, ALA350, ASP351, LEU354, MET357, TRP383, GLU385, VAL386, MET389, GLY390, LEU391, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, VAL535, TYR536 and LEU538 according to FIGS. 2A-2XX for monomer A of ER-β, ± a root mean square deviation from the backbone atoms of said amino acids of not more than 1.5 Å, preferably not more than 1.0 Å, and most preferably not more than 0.5 Å. In yet another embodiment, the relative structural coordinates according to (ii) further comprises the relative structural coordinates of amino acid residues MET342, SER345, THR347, LYS348, ALA350, ASP351, MET357, TRP383, GLU385, VAL386, LEU387, MET389, GLY390, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, TYR536 and LEU538 according to FIG. 2 for monomer B of ER-β, ± a root mean square deviation from the backbone atoms of said amino acids of not more than 1.5 Å, preferably not more than 1.0 Å, and most preferably not more than 0.5 Å. Once the candidate activator or inhibitor is obtained or synthesized, the candidate activator or inhibitor may be contacted with the molecule or molecular complex, and the effect the candidate activator or inhibitor has on said molecule or molecular complex may be determined. Preferably, the candidate activator or inhibitor is contacted with the molecule or molecule complex in the presence of genistein (or a molecule or a molecular complex comprising genistein) in order to determine the effect the candidate activator or inhibitor has on binding of the molecule or molecular complex to genistein.

Various molecular analysis and rational drug design techniques are further disclosed in U.S. Pat. Nos. 5,834,228, 5,939,528 and 5,865,116, as well as in PCT Application No. PCT/US98/16879, published WO 99/09148, the contents of which are hereby incorporated by reference.

The present invention is also directed to the agents, activators or inhibitors identified using the foregoing methods. Such agents, activators or inhibitors may be a protein, polypeptide, peptide, nucleic acid, including DNA or RNA, molecule, compound, or drug. Small molecules or other agents which inhibit or otherwise interfere with ER-β and genistein may be useful in the treatment of diseases associated with ER-β such as cancer.

In addition, the present invention is directed to a method for determining the three dimensional structure of a molecule or molecular complex whose structure is unknown, comprising the steps of obtaining crystals of the molecule or molecular complex whose structure is unknown and generating X-ray diffraction data from the crystallized molecule or molecular complex. The X-ray diffraction data from the molecule or molecular complex is then compared with the known three dimensional structure determined from any of the aforementioned crystals of the present invention. Then, the known three dimensional structure determined from the crystals of the present invention is "conformed" using molecular replacement analysis to the X-ray diffraction data from the crystallized molecule or molecular complex. Alternatively, spectroscopic data or homology modeling may be used to generate a putative three dimensional structure for the molecule or molecular complex, and the putative structure is refined by conformation to the known three dimensional structure determined from any of the crystals of the present invention.

The present invention may be better understood by reference to the following non-limiting Example. The following Example is presented in order to more fully illustrate the preferred embodiments of the invention, and should in no way be construed as limiting the scope of the present invention.

EXAMPLE 1

We describe the 1.8 Å crystal structure of the recently discovered nuclear hormone receptor, ER-β, in complex with genistein, an agonistic phytoestrogen. The overall structure is similar to that of previously described ER-α complexes, with genistein occupying a central cavity similar to that of ER-α. Minor differences-between the two cavities account for genistein's 30 fold selectivity for ER-β over ER-α. Surprisingly, helix 12 in the complex of ER-β with genistein (an agonist) runs in the same direction, although in a different position, as helix 12 of ER-α bound to raloxifene (an antagonist). This suggests different mechanisms of agonism/antagonism for ER-α and ER-β.

1. Methods and Methods

Cloning, Expression and Purification. Human ER-β cDNA (21) was generated from human testis RNA by RT-PCR and cloned into the mammalian expression vector pcDNA3. The LBD of human ER-β was then PCR amplified from the cloned cDNA and inserted into the *E. coli* expression vector pET16b between the NcoI and XhoI restriction sites. The expressed LBD thus has the following sequence: $MD[D_{261}-L_{500}]DD$.

Frozen cells were lysed by two cycles in a French press (SLM Instruments). The protein was loaded on an estradiol-Sepharose column and the column was washed with 100 mL of 10 mM Tris-HCl, pH 7.5 containing 0.5 M NaCl, 5 mM dithiothreitol, and 1 mM EDTA. The column was then reequilibrated with 10 mM Tris-HCl, pH 7.5, 0.2M NaCl, 1 mM EDTA (buffer A), and accessible cysteines modified by 5 mM iodoacetic acid in the same buffer. The protein was eluted with 200 μM genistein and 5 mM DTT then passed over a G3000 SW TosoHaas size exclusion column equilibrated with buffer A. Mass spectroscopy (MALDI) showed that two cysteine residues had been modified by carboxymethylation.

Crystallization and Data Collection. The ERβ/genistein complex was concentrated to 12 mg/mL in 0.2M NaCl, 1 mM EDTA, 5 mM DTT, 10 mM Tris-HCl pH 7.5 buffer. Crystals were grown using vapor diffusion at 4° C. over wells containing 12% PEG2000 mono-methyl ether buffered with 0.1M MES (2-[N-morpholino] ethane sulphonic acid) at pH 6.0. Crystals were cooled to 100K in 8.5% PEG 2000, 3.6% PEG 8000, 5% glycerol, 0.13M MES pH 6.0, 0.02M sodium cacodylate pH 6.5, and 0.04M calcium acetate. The space group is $P2_12_12_1$ with cell parameters a=53.49 Å, b=85.21 Å, c=107.07 Å. Diffraction data were collected on station 5.0.2 at the Advanced Light Source, Berkeley, using a Quantum-4 CCD detector (Area Detector Systems), then reduced using DENZO/SCALEPACK (22), giving the statistics in Table 1.

Phasing and Refinement. The structure was solved using AMORE (23) molecular replacement with ER-αLBD (24) (without bound ligand, the loop H8-H9, C and N terminal helices) as a search model. The resulting 2Fo-Fc map showed clear density for the bound genistein not included in the phasing model.

BUSTER (25)/TNT (26) was used to generate maximum entropy omit maps to reduce model bias and generate a more detailed map for the bound ligand. REFMAC (27) was used for all further refinement of the model, giving the statistics in Table 1. The model consists of residues Leu311-Ala549, with the first ten residues, loop Tyr459-Ala468, and the last three residues in disordered regions. The dimer has two bound genistein molecules and 189 ordered water molecules. Electron density for the cysteine modifications was poor and was therefore not modeled.

2. Results

Like ER-α, ER-β has a predominantly globular structure formed by anti-parallel α helices arranged in three layers, and a short two-stranded β ribbon. A cavity is formed in the core of the protein which becomes occupied by ligand. In the structure reported here, the cavity is occupied by a molecule of genistein, which is completely buried and forms hydrogen bonds with a single buried water molecule. The protein forms a non-crystallographic dimer with a large interface formed by helices H9, H10 and H11 (not shown), consistent with size exclusion chromatography studies on the protein.

The overall structure of the ER-β-genistein complex is very similar to previously reported ER-α structures (10) (not shown). Superimposing 426 of 461 C-α coordinates of the dimer, the RMS differences with ER-α are only 0.53 Å and 0.57 Å for complexes with 17β-estradiol and raloxifene, respectively. There are, however, significant differences that may account for the selectivity of ER-β over ER-α when binding certain ligands and co-activator peptides (20). The most striking difference is in the position of H12. The position of this helix in ER-α has been found to vary depending upon the ligand bound. In the agonist (17β-estradiol) bound structure (not shown), H12 lies over the ligand and encapsulates it within the core of the protein. This conformation facilitates binding of co-activator peptides in a hydrophobic groove just below H12 (not shown), formed by residues from H3, H4 and H5. When ER-α binds an antagonist such as raloxifene, part of the ligand prevents H12 from occupying this location (not shown). Instead, H12 occupies the co-activator hydrophobic groove, thus preventing co-activation. The location of H12 in complexed ER-β is different from that of either ER-α-agonist or ER-α-antagonist complexes (not shown). H12 in ER-β runs in the same direction as H12 in ER-α-antagonist but does not cover the co-activator binding site. It occupies roughly the same space as H12 of the ER-α-agonist and buries the bound ligand. This unexpected position of H12 was observed in crystals of space group $P2_12_12_1$ (described here) and $P3_221$ (2.4 Å, refined to an R-value of 0.238 and a free R-value of 0.286, not described here). The equivalent position of H12 observed in two crystal forms suggests that this location is correct.

Genistein is bound in the hydrophobic core of the protein and is completely shielded from the bulk solvent by H3, H6, strand S1, H7, H8, H11 and H12. H12 appears to form a lid over the filled cavity. Bound genistein superimposes well with 17β-estradiol bound to ER-α (not shown) such that the phenolic moieties are in similar positions and the fused rings lie over the puckered C/D rings of the steroid. The position of the 70H hydroxyl group of genistein in the same as that of 17-OH of 17β-estradiol, allowing formation of similar hydrogen bonds. The phenolic hydroxyl (4'OH) of genistein hydrogen bonds with the OE2 of Glu353 (2.63 Å), the NH2 of Arg394 (2.93 Å) and a highly ordered water molecule (3.05 Å). This ordered water molecule was also found in ER-α when bound to agonist or antagonist and must therefore be considered part of the binding site. The last hydrogen bond genistein forms is between its 7-OH and the ND1 of His523 (2.62 Å). The position of His523 is stabilized by an interaction with the backbone carbonyl of Gly419 at the N-terminal end of H8.

There are very few differences between the binding cavities that can account for genistein's 30 fold preference for binding to ER-β. The substitution of Met421 to Ile in ER-β is likely the most significant. In the complex of ER-α with 17β-estradiol, the Met Sd lies 4.4 Å from the C16 atom in the puckered "D" ring. Upon superimposition of genistein into the ER-α binding cavity, the Met Sd would now appear to lie only 3.9 Å from genistein's 5-OH group, which is unable to move away due to the planarity of its ring. This close interaction is unfavorable not only sterically, but also electrostatically, due to close proximity of the small negative charges on the Sd and the 5-OH group. A superimposition of genistein against the ER-α/DES complex demonstrates a similar (and slightly more severe) steric and electrostatic clash. In contrast, ER-β places the Cg1 and Cd1 of Ile421 4.2 Å away from atoms in the ring thereby promoting more favorable van der Waals interactions. The other difference between the cavities that could affect selectivity is Leu384 to Met. The Met384 Ce of ER-β extends far into the binding cavity and provides favorable interactions with genistein, while placing the Met Sd of ER-β in the same position as the Leu Cd1 of ER-α. When looking down on the fused "B" ring from Met384, the Sd appears to be directly above the "B" ring at a distance of 4.2 Å, making favorable interactions. The Sd-Ce bond projects in the same plane as the B-C fused ring and places the terminal carbon 3.8 Å from the genistein O1 atom, making a good van der Waals interaction that would not be present in ER-α. Packing of Met Sd and Ce against the face of aromatic residues is common in protein structures and must therefore be considered as a stabilising interaction. The final difference between the binding cavities relates to the position of H12 and probably does not significantly impact the selectivity. In both forms of ER, leucines in H12 project down towards the bound ligand and seal the binding site. In ER-β Leu538 plays this role, whereas in ER-α it is Leu540. The difference is due to different direction of H12 in the two structures.

The position of H12 in ER-α has been used as the structural hallmark of a bound agonist versus antagonist (not shown). In ER-β, H12 runs in the opposite direction as in agonist ER-α H12.However, it has several non-equivalent, but superimposable side chains. Specifically, ER-α Met543 is replaced by ER-β Leu539 and ER-α Leu539 with ER-β Met542. Although the position of the ER-β helix can be roughly superimposed on ER-α H12, it does partially occlude the co-activator binding site. Co-activators may bind ER-β in a slightly different manner than ER-α, or ER-β's H12 may move upon binding of co-activators, to allow full access to the binding groove.

Why does H12 occupy a different location in agonist-bound ER-α versus ER-β? The only amino acid difference is Asp545 to Asn. This difference seems unlikely to explain the different positions of H12, as either residue is exposed to solvent and appears not to affect the positioning of H12. The key may lie in the residues just upstream of the helix which also move upon agonist/antagonist binding. Leu536 of ER-α, which makes favorable interactions in a hydrophobic cavity is replaced by Val in ER-β. Val cannot make comparable contacts. Two other differences, Gly344 to Met and Asn348 to Lys, influence the nature of the H12 binding surface in this same region and may affect the position of the loop just upstream of H12. Changes in the position of H12 could explain the selective binding of co-activators to ER-α and ER-β. Steroid receptor coactivator-3 (SRC-3) binds approximately 700 fold tighter to ER-α whereas SRC-1 preferentially activates ER-β (20).

The structure of ER-β in complex with genistein has enhanced our understanding of mechanisms of estrogen receptor agonism and co-activation. The structure has revealed the basis for the 30 fold selectivity of genistein for ER-β over ER-α and helps explain differences in co-activator binding. These insights should help in the design of more selective and therapeutically useful agonists or antagonists.

TABLE 1

Data Collection and Refinement Statistics.

| | |
|---|---|
| Resolution limits (Å) | 15.0–1.8(1.83–1.8) |
| Rmerge (%)[2] | 5.7(23.0) |
| Unique reflections | 45530(1977) |
| Total observations | 287034 |
| Completeness (%) | 98.8(88.1) |
| <I/sigma> | 26.2(4.1) |
| Refinement | |
| Refinement reflections | 43176 |
| R-value | 22.4 |
| Free reflections[3] | 2294 |
| Rfree | 26.4 |
| Average B - factor(Å2)[4] | 31.5 |
| R.m.s. differences[5] | |
| Main chain(Å2) | 1.94 |
| Side Chain(Å2) | 3.29 |
| R.m.s. deviations | |
| Bond lengths (Å) | 0.014 |
| Angles distance (Å) | 0.033 |
| Ramachandran Plot | |
| Most favored regions (%) | 96.7 |

[1]Values in parentheses refer to the highest resolution shell.
[2]Rmerge = S | I − <I> |/S<I> where I is the observed intensity and <I> is the average of the symmetry mates.
[3]5% of the data were randomly selected, not used in refinement and used for the calculation of the Free R-value.
[4]All atoms in the structure.
[5]R.m.s. differences in B factors between bonded atoms.

TABLE 2*

| Residues of ER-β That Interact With Genistein at 0-4 Å |
|---|
| From First Monomer of ER-β |
| MET343, LEU346, LEU349, GLU353, MET384, LEU387, MET388, ARG394, PHE404, ILE421, ILE424, GLY520, HIS523 and LEU524 |
| From Second Monomer of ER-β |
| MET343, LEU346, LEU349, GLU353, MET384, LEU387, MET388, LEU391, ARG394, PHE404, ILE421, ILE424, GLY520, HIS523 and LEU524 |

| Residues of ER-β That Interact With Genistein at 4-8 Å |
|---|
| From First Monomer of ER-β |
| VAL328, MET342, MET343, SER345, LEU346, THR347, LYS348, LEU349, ALA350, ASP351, GLU353, LEU354, MET357, TRP383, MET384, GLU385, VAL386, LEU387, MET388, MET389, GLY390, LEU391, MET392, ARG394, LEU402, ILE403, PHE404, ALA405, LEU408, VAL418, GLU419, GLY420, ILE421, LEU422, GLU423, |

TABLE 2*-continued

ILE424, PHE425, LEU428, ALA516, SER517, LYS519, GLY520, MET521, GLU522, HIS523, LEU524, LEU525, ASN526, MET527, LYS528, VAL533, VAL535, TYR536 and LEU538

From Second Monomer of ER-β

MET342, MET343, SER345, LEU346, THR347, LYS348, LEU349, ALA350, ASP351, GLU353, MET357, TRP383, MET384, GLU385, VAL386, LEU387, MET388, MET389, GLY390, LEU391, MET392, ARG394, LEU402, ILE403, PHE404, ALA405, LEU408, VAL418, GLU419, GLY420, ILE421, LEU422, GLU423, ILE424, PHE425, LEU428, ALA516, SER517, LYS519, GLY520, MET521, GLU522, HIS523, LEU524, LEU525, ASN526, MET527, LYS528, VAL533, TYR536 and LEU538

*The ER-β/genistein complex molecular structure is a dimer with each monomer of ER-β binding to one genistein molecule.

REFERENCES

1. Jenning, T. S., Creasman, W. T., Estrogens and Antiestrogens: Basic and Clinical Aspects; Lindsay, R.; Dempster, D. W., Jordan, V. C., Eds; Lippencott-Raven: Philadelphia, 1997, pp. 223.
2. Glasebrook, A. L., et al., Proc Natl Acad Sci (USA) 94:14105-14110 (1997).
3. Kuiper G G J M, et al. Proc Natl Acad Sci (USA) 93:5925-5930 (1996).
4. Couse J F, et al., Endocrinology 138(11):4613-4621 (1997).
5. Shughrue P J, et al., Steroids 61:678-681 (1996).
6. Lau K, et al., Endocrinology 139(1):424-427 (1998).
7. Enmark E, et al., J Clin Endocrinol Metab 82(12):4258-4265 (1997).
8. Tsai, M. J. and O'Malley, B. W., Annu. Rev. Biochem 63:451-486 (1994).
9. Evans, R. M., Science 240:889-895 (1988).
10. Horwitz, K. B., et al., Mol. Endocrinol. 10:1167-1177 (1996).
11. Glass, C. K., et al., Curr. Opin. Cell Biol. 9:222-232 (1997).
12. Brzozowski, A., et al., Nature 389:753-758 (1997).
13. Shiau, A., et al., Cell. 95: 927-937 (1998).
14. Bourguet, W., et al., Nature 375:377-382 (1995).
15. Renaud, J., et al., Nature 378:681-689 (1995).
16. Le Dourin, B. et al., EMBO J15:6701-6715 (1996).
17. Heery, D., et al., Nature 387:733-736 (1997).
18. Torchia, J. et al., Nature 387:677-684 (1997).
19. Ding, S., et al., Mol. Endocrinol. 12:302-313 (1998).
20. Suen, C-S., et al., J. Biol. Chem. 273:27645-27653 (1998).
21. Mosselman, S., et al., FEBS letters 392:49-53 (1996).
22. Otwinowski, Z. & Minor, W., Methods Enzymol., 276: 307-326 (1997).
23. Collaborative Computational Project, Number 4. (1994). Acta Cryst. D50.
24. D. M. Tanenbaum, et al., PNAS 95:5998-6003 (1998).
25. Bricogne, G., Acta Cryst. D49:37-60 (1993).
26. Tronrud, D. E., (1997) Methods in Enzymology. 277B eds. Charlie Carter and Robert Sweet.
27. Murshudov, G. N., et al., Acta. Cryst. D53:240-255 (1997).
28. Kraulis, P J, J. Appl. Crystallogr. 24:946-950 (1991).
29. Bacon, D. J. and Anderson, W. F., J. Mol. Graph. 6:219-220 (1998).

All publications mentioned herein above, whether to issued patents, pending applications, published articles, or otherwise, are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A method for identifying an agent that interacts with ER-β, the method comprising:
 (a) providing a crystal structure of ER-β, having a resolution of 1.83 Å or less;
 (b) generating a three dimensional model of ER-β using the relative structural coordinates according to FIGS. 2A-2XX, ±a root mean square deviation from the backbone atoms of the amino acids of not more than 1.5 Å, the relative structural coordinates being based on the crystal structure of ER-β; and
 (c) employing the three-dimensional model to design or select an agent that interacts with ER-β.

2. The method of claim 1, further comprising:
 (d) obtaining the agent; and
 (e) contacting the agent with ER-β in order to determine the effect the agent has on ER-β activity.

3. A method for identifying an activator or inhibitor of ER-β, the method comprising:
 (a) providing a crystal structure of ER-β having a resolution of 1.83 Å or less;
 (b) generating a three dimensional model of ER-β using (i) the relative structural coordinates of amino acid residues MET343, LEU346, LEU349, GLU353, MET384, LEU387, MET388, ARG394, PHE404, ILE421, ILE424, GLY520, HIS523 and LEU524 according to FIGS. 2A-2XX for monomer A of ER-β, ± a root mean square deviation from the backbone atoms of the amino acids of not more than 1.5 ÅA, the relative structural coordinates of the amino acid residues for monomer A of ER-β being based on the crystal structure of ER-β or (ii) the relative structural coordinates of amino acid residues MET343, LEU346, LEU349, GLU353, MET384, LEU387, MET388, LEU391, ARG394, PHE404, ILE421, ILE424, GLY520, HIS523 and LEU524 according to FIG. 2 for monomer B of ER-β±, a root mean square deviation from the backbone atoms of the amino acids of not more than 1.5 Å, the relative structural coordinates of the amino acid residues for monomer B of ER-β being based on the crystal structure of ER-β; and
 (c) selecting or designing a candidate activator or inhibitor by performing computer fitting analysis of the candidate activator or inhibitor with the three dimensional model generated in step (b).

4. The method of claim 3, wherein the structural coordinates according to (i) further comprise the relative structural coordinates of amino acid residues VAL328, MET342, SER345, THR347, LYS348, LEU349, ALA350, ASP351, LEU354, MET357, TRP383, GLU385, VAL386, MET389, GLY390, LEU391, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, VAL535, TYR536 and LEU538 according to FIGS. 2A-2XX for monomer A of ER-β, ± a root mean square deviation from the backbone atoms of the amino acids of not more than 1.5 Å, the relative structural coordinates of the amino acid residues for monomer A of ER-β being based on the crystal structure of ER-β.

5. The method of claim 3, wherein the relative structural coordinates according to (ii) further comprise the relative structural coordinates of amino acid residues MET342, SER345, THR347, LYS348, ALA350, ASP351, MET357, TRP383, GLU385, VAL386, LEU387, MET389, GLY390, MET392, LEU402, ILE403, ALA405, LEU408, VAL418, GLU419, GLY420, LEU422, GLU423, PHE425, LEU428, ALA516, SER517, LYS519, MET521, GLU522, LEU525, ASN526, MET527, LYS528, VAL533, TYR536 and LEU538 according to FIGS. 2A-2XX for monomer B of ER-β, ± a root mean square deviation from the backbone atoms of the amino acids of not more than 1.5 Å, the relative structural coordinates of the amino acid residues for monomer B of ER-β being based on the crystal structure of ER-β.

6. The method of claim 3, further comprising the steps of:
 (d) obtaining the candidate activator or inhibitor; and
 (e) contacting the candidate activator or inhibitor with the molecule or molecular complex and determining the effect the candidate activator or inhibitor has on the molecule or molecular complex.

7. The method of claim 6, wherein the candidate activator or inhibitor is contacted with the molecule or molecular complex in the presence of genistein to determine the effect the candidate activator or inhibitor has on binding of the molecule or molecular complex to genistein.

8. The method of claim 1, wherein the crystal structure of ER-62 has a resolution of 1.8 Å.

9. The method of claim 3, wherein the crystal structure of ER-β has a resolution of 1.8 Å.

* * * * *

SEQUENCE LISTING

```
<160> NUMBER OF SEQ ID NOS: 2

<210> SEQ ID NO 1
<211> LENGTH: 243
<212> TYPE: PRT
<213> ORGANISM: Homo sapiens

<400> SEQUENCE: 1

Ala Leu Ser Leu Thr Ala Asp Gln Met Val Ser Ala Leu Leu Asp Ala
1               5                   10                  15

Glu Pro Pro Ile Leu Tyr Ser Glu Tyr Asp Pro Thr Arg Pro Phe Ser
            20                  25                  30

Glu Ala Ser Met Met Gly Leu Leu Thr Asn Leu Ala Asp Arg Glu Leu
        35                  40                  45

Val His Met Ile Asn Trp Ala Lys Arg Val Pro Gly Phe Val Asp Leu
    50                  55                  60

Thr Leu His Asp Gln Val His Leu Leu Glu Cys Ala Trp Leu Glu Ile
65                  70                  75                  80
```

-continued

```
Leu Met Ile Gly Leu Val Trp Arg Ser Met Glu His Pro Val Lys Leu
                85                  90                  95

Leu Phe Ala Pro Asn Leu Leu Asp Arg Asn Gln Gly Lys Cys Val
            100                 105                 110

Glu Gly Met Val Glu Ile Phe Asp Met Leu Leu Ala Thr Ser Ser Arg
        115                 120                 125

Phe Arg Met Met Asn Leu Gln Gly Glu Glu Phe Val Cys Leu Lys Ser
130                 135                 140

Ile Ile Leu Leu Asn Ser Gly Val Tyr Thr Phe Leu Ser Ser Thr Leu
145                 150                 155                 160

Lys Ser Leu Glu Glu Lys Asp His Ile His Arg Val Leu Asp Lys Ile
                165                 170                 175

Thr Asp Thr Leu Ile His Leu Met Ala Lys Ala Gly Leu Thr Leu Gln
            180                 185                 190

Gln Gln His Gln Arg Leu Ala Gln Leu Leu Ile Leu Ser His Ile
        195                 200                 205

Arg His Met Ser Asn Lys Gly Met Glu His Leu Tyr Ser Met Lys Cys
210                 215                 220

Lys Asn Val Val Pro Leu Tyr Asp Leu Leu Leu Glu Met Leu Asp Ala
225                 230                 235                 240

His Arg Leu

<210> SEQ ID NO 2
<211> LENGTH: 239
<212> TYPE: PRT
<213> ORGANISM: Homo sapiens

<400> SEQUENCE: 2

Leu Asp Ala Leu Ser Pro Glu Gln Leu Val Leu Thr Leu Leu Glu Ala
1               5                   10                  15

Glu Pro Pro His Val Leu Ile Ser Arg Pro Ser Ala Pro Phe Thr Glu
                20                  25                  30

Ala Ser Met Met Met Ser Leu Thr Lys Leu Ala Asp Lys Glu Leu Val
            35                  40                  45

His Met Ile Ser Trp Ala Lys Lys Ile Pro Gly Phe Val Glu Leu Ser
        50                  55                  60

Leu Phe Asp Gln Val Arg Leu Leu Glu Ser Cys Trp Met Glu Val Leu
65                  70                  75                  80

Met Met Gly Leu Met Trp Arg Ser Ile Asp His Pro Gly Lys Leu Ile
                85                  90                  95

Phe Ala Pro Asp Leu Val Leu Asp Arg Asp Glu Gly Lys Cys Val Glu
            100                 105                 110

Gly Ile Leu Glu Ile Phe Asp Met Leu Leu Ala Thr Thr Ser Arg Phe
        115                 120                 125

Arg Glu Leu Lys Leu Gln His Lys Glu Tyr Leu Cys Val Lys Ala Met
130                 135                 140

Ile Leu Leu Asn Ser Ser Met Tyr Pro Leu Val Thr Ala Gln Asp Ala
145                 150                 155                 160

Asp Ser Ser Arg Lys Leu Ala His Leu Leu Asn Ala Val Thr Asp Ala
                165                 170                 175

Leu Val Trp Val Ile Ala Lys Ser Gly Ile Ser Ser Gln Gln Gln Ser
            180                 185                 190

Met Arg Leu Ala Asn Leu Leu Met Leu Ser His Val Arg His Ala Ser
        195                 200                 205
```

```
-continued

Asn Lys Gly Met Glu His Leu Leu Asn Met Lys Cys Lys Asn Val Val
    210             215             220

Pro Val Tyr Asp Leu Leu Leu Glu Met Leu Asn Ala His Val Leu
225             230             235
```